US011253605B2

(12) United States Patent
Dias et al.

(10) Patent No.: US 11,253,605 B2
(45) Date of Patent: *Feb. 22, 2022

(54) CODON-OPTIMIZED CFTR MRNA

(71) Applicant: Translate Bio, Inc., Cambridge, MA (US)

(72) Inventors: Anusha Dias, Cambridge, MA (US); Jonathan Abysalh, Cambridge, MA (US); Brian Bettencourt, Cambridge, MA (US); Frank DeRosa, Cambridge, MA (US); Michael Heartlein, Cambridge, MA (US)

(73) Assignee: Translate Bio, Inc., Lexington, MA (US)

( * ) Notice: Subject to any disclaimer, the term of this patent is extended or adjusted under 35 U.S.C. 154(b) by 1033 days.

This patent is subject to a terminal disclaimer.

(21) Appl. No.: 15/907,131

(22) Filed: Feb. 27, 2018

(65) Prior Publication Data

US 2018/0256741 A1 Sep. 13, 2018

Related U.S. Application Data

(60) Provisional application No. 62/464,215, filed on Feb. 27, 2017.

(51) Int. Cl.

| | |
|---|---|
| ***A61K 47/69*** | (2017.01) |
| ***A61K 47/64*** | (2017.01) |
| ***A61K 9/127*** | (2006.01) |
| ***C12N 15/10*** | (2006.01) |
| ***A61K 38/17*** | (2006.01) |
| ***C07K 14/47*** | (2006.01) |
| ***A61P 11/00*** | (2006.01) |
| ***A61K 9/00*** | (2006.01) |
| ***A61K 31/7105*** | (2006.01) |

(52) U.S. Cl.

CPC ........ *A61K 47/6455* (2017.08); *A61K 9/0075* (2013.01); *A61K 9/1272* (2013.01); *A61K 31/7105* (2013.01); *A61K 38/1709* (2013.01); *A61K 47/6911* (2017.08); *A61P 11/00* (2018.01); *C07K 14/4712* (2013.01); *C12N 15/10* (2013.01)

(58) Field of Classification Search

None

See application file for complete search history.

(56) References Cited

U.S. PATENT DOCUMENTS 2,647,121 A 7/1953 Jacoby
2,717,909 A 9/1955 Kosmin
2,819,718 A 1/1958 Goldman
2,844,629 A 7/1958 William et al.
3,096,560 A 7/1963 Liebig
3,535,289 A 10/1970 Yoshihara et al.
3,614,954 A 10/1971 Mirowski et al.
3,614,955 A 10/1971 Mirowski
3,656,185 A 4/1972 Carpentier
3,805,301 A 4/1974 Liebig
3,945,052 A 3/1976 Liebig
3,995,623 A 12/1976 Blake et al.
4,013,507 A 3/1977 Rembaum
4,072,146 A 2/1978 Howes
4,096,860 A 6/1978 McLaughlin
4,099,528 A 7/1978 Sorenson et al.
4,106,129 A 8/1978 Carpentier et al.
4,134,402 A 1/1979 Mahurkar
4,140,126 A 2/1979 Choudhury
4,180,068 A 12/1979 Jacobsen et al.
4,182,833 A 1/1980 Hicks
4,227,533 A 10/1980 Godfrey
4,284,459 A 8/1981 Patel et al.
4,308,085 A 12/1981 Horhold et al.
4,323,525 A 4/1982 Bornat
4,335,723 A 6/1982 Patel
4,339,369 A 7/1982 Hicks et al.
4,355,426 A 10/1982 MacGregor
4,375,817 A 3/1983 Engle et al.
4,385,631 A 5/1983 Uthmann
4,401,472 A 8/1983 Gerber
4,406,656 A 9/1983 Hattler et al.
4,475,972 A 10/1984 Wong
4,530,113 A 7/1985 Matterson
4,550,447 A 11/1985 Seiler, Jr. et al.
4,562,596 A 1/1986 Kornberg
4,568,329 A 2/1986 Mahurkar
4,571,241 A 2/1986 Christopher
4,601,718 A 7/1986 Possis et al.
4,647,416 A 3/1987 Seiler, Jr. et al.
4,662,382 A 5/1987 Sluetz et al.

(Continued)

FOREIGN PATENT DOCUMENTS

CA 2518132 A1 3/2006
CA 2807552 A1 2/2012

(Continued)

OTHER PUBLICATIONS

U.S. Appl. No. 60/083,294, filed Apr. 28, 1998, Chen et al.
U.S. Appl. No. 61/494,714, filed Jun. 8, 2011, Guild.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).

(Continued)

*Primary Examiner* — Michael D Burkhart
(74) *Attorney, Agent, or Firm* — Proskauer Rose LLP; Fangli Chen

(57) ABSTRACT

The present invention provides, among other things, improved methods and pharmaceutical compositions for treating cystic fibrosis based on codon optimized mRNA encoding a Cystic Fibrosis Transmembrane Conductance Regulator (CFTR) protein.

14 Claims, 1 Drawing Sheet

Specification includes a Sequence Listing.

(56) References Cited

U.S. PATENT DOCUMENTS 4,701,162 A 10/1987 Rosenberg
4,710,169 A 12/1987 Christopher
4,720,517 A 1/1988 Ravichandran et al.
4,737,323 A 4/1988 Martin et al.
4,762,915 A 8/1988 Kung et al.
4,782,836 A 11/1988 Alt
4,856,521 A 8/1989 Irnich
4,860,751 A 8/1989 Callaghan
4,878,908 A 11/1989 Martin et al.
4,892,540 A 1/1990 Vallana
4,897,355 A 1/1990 Eppstein et al.
4,920,016 A 4/1990 Allen et al.
4,946,683 A 8/1990 Forssen
4,946,857 A 8/1990 Kanehira et al.
4,960,409 A 10/1990 Catalano
4,966,945 A 10/1990 Drawer et al.
5,024,671 A 6/1991 Tu et al.
5,025,005 A 6/1991 Nomura et al.
5,047,540 A 9/1991 Kamata et al.
5,101,824 A 4/1992 Lekholm
5,104,399 A 4/1992 Lazarus
5,116,360 A 5/1992 Pinchuk et al.
5,138,067 A 8/1992 Kamata et al.
5,151,105 A 9/1992 Kwan-Gett
5,171,678 A 12/1992 Behr et al.
5,176,661 A 1/1993 Evard et al.
5,194,654 A 3/1993 Hostetler et al.
5,200,395 A 4/1993 Eto et al.
5,223,263 A 6/1993 Hostetler et al.
5,261,419 A 11/1993 Osypka
5,264,618 A 11/1993 Felgner et al.
5,279,833 A 1/1994 Rose
5,282,824 A 2/1994 Gianturco
5,284,491 A 2/1994 Sutton et al.
5,300,022 A 4/1994 Klapper et al.
5,314,430 A 5/1994 Bardy
5,330,768 A 7/1994 Park et al.
5,334,761 A 8/1994 Gebeyehu et al.
5,395,619 A 3/1995 Zalipsky et al.
5,405,363 A 4/1995 Kroll et al.
5,405,379 A 4/1995 Lane
5,455,352 A 10/1995 Huellmann et al.
5,464,924 A 11/1995 Silvis et al.
5,503,852 A 4/1996 Steiner et al.
5,528,023 A 6/1996 Butturini et al.
5,552,155 A 9/1996 Bailey et al.
5,595,756 A 1/1997 Bally et al.
5,607,385 A 3/1997 Francischelli et al.
5,609,624 A 3/1997 Kalis
5,610,283 A 3/1997 Buechler
5,614,548 A 3/1997 Piantadosi et al.
5,626,869 A 5/1997 Nyqvist et al.
5,631,018 A 5/1997 Zalipsky et al.
5,677,124 A 10/1997 DuBois et al.
5,693,088 A 12/1997 Lazarus
5,697,953 A 12/1997 Kroll et al.
5,700,437 A 12/1997 Fujii et al.
5,705,188 A 1/1998 Junichi et al.
5,705,385 A 1/1998 Bally et al.
5,736,573 A 4/1998 Galat
5,744,335 A 4/1998 Wolff et al.
5,772,694 A 6/1998 Bokros et al.
5,776,165 A 7/1998 Ripart
5,776,747 A 7/1998 Schinstine et al.
5,783,383 A 7/1998 Kondo et al.
5,844,107 A 12/1998 Hanson et al.
5,874,105 A 2/1999 Watkins et al.
5,885,613 A 3/1999 Holland et al.
5,910,168 A 6/1999 Myers et al.
5,916,208 A 6/1999 Luther et al.
5,965,434 A 10/1999 Wolff et al.
5,976,567 A 11/1999 Wheeler et al.
5,976,569 A 11/1999 Milstein
5,981,501 A 11/1999 Wheeler et al.
6,055,454 A 4/2000 Heemels
6,067,471 A 5/2000 Warren
6,090,384 A 7/2000 Ra et al.
6,096,070 A 8/2000 Ragheb et al.
6,096,075 A 8/2000 Bokros et al.
6,120,799 A 9/2000 McDonald et al.
6,147,055 A 11/2000 Hobart et al.
6,152,955 A 11/2000 KenKnight et al.
6,165,763 A 12/2000 Brown et al.
6,169,923 B1 1/2001 Kroll
6,176,877 B1 1/2001 Buchanan et al.
6,204,297 B1 3/2001 Tracy et al.
6,210,892 B1 4/2001 Bennett et al.
6,214,804 B1 4/2001 Felgner et al.
6,271,208 B1 8/2001 Bischoff
6,271,209 B1 8/2001 Smith et al.
6,287,591 B1 9/2001 Semple et al.
6,299,604 B1 10/2001 Ragheb et al.
6,335,199 B1 1/2002 Bischoff et al.
6,358,278 B1 3/2002 Brendzel et al.
6,370,434 B1 4/2002 Zhang et al.
6,371,983 B1 4/2002 Lane
6,417,326 B1 7/2002 Cullis et al.
6,485,726 B1 11/2002 Blumberg et al.
6,534,484 B1 3/2003 Wheeler et al.
6,585,410 B1 7/2003 Ryan
6,586,410 B1 7/2003 Wheeler et al.
6,670,178 B1 12/2003 Selden et al.
6,696,424 B1 2/2004 Wheeler
6,733,777 B2 5/2004 Erbacher et al.
6,743,823 B1 6/2004 Summar et al.
6,756,055 B2 6/2004 McDonald et al.
6,790,838 B2 9/2004 Alison et al.
6,815,432 B2 11/2004 Wheeler et al.
6,821,530 B2 11/2004 Koob et al.
6,835,395 B1 12/2004 Semple et al.
6,858,224 B2 2/2005 Wheeler et al.
6,858,225 B2 2/2005 Semple et al.
6,887,665 B2 5/2005 Trulson et al.
6,998,115 B2 2/2006 Langer et al.
7,022,214 B2 4/2006 Olech
7,067,697 B2 6/2006 Gao
7,084,303 B2 8/2006 Watanabe et al.
7,341,738 B2 3/2008 Semple et al.
7,422,902 B1 9/2008 Wheeler et al.
7,427,394 B2 9/2008 Anderson et al.
7,507,859 B2 3/2009 Grinstaff et al.
7,556,684 B2 7/2009 Bury et al.
7,745,651 B2 6/2010 Heyes et al.
7,799,565 B2 9/2010 MacLachlan et al.
7,803,397 B2 9/2010 Heyes et al.
7,901,708 B2 3/2011 MacLachlan et al.
7,972,435 B2 7/2011 Bury et al.
8,021,686 B2 9/2011 Semple et al.
8,071,082 B2 12/2011 Zugates et al.
8,101,741 B2 1/2012 MacLachlan et al.
8,106,022 B2 1/2012 Manoharan et al.
8,158,601 B2 4/2012 Chen et al.
8,188,263 B2 5/2012 MacLachlan et al.
RE43,612 E 8/2012 Anderson et al.
8,236,943 B2 8/2012 Lee et al.
8,278,036 B2 10/2012 Kariko et al.
8,287,849 B2 10/2012 Langer et al.
8,329,070 B2 12/2012 MacLachlan et al.
8,389,238 B2 3/2013 Cooper et al.
8,450,298 B2 5/2013 Mahon et al.
8,450,467 B2 5/2013 Manoharan et al.
8,513,403 B2 8/2013 MacLachlan et al.
8,557,231 B2 10/2013 Langer et al.
8,562,966 B2 10/2013 Zugates et al.
8,569,256 B2 10/2013 Heyes et al.
8,652,512 B2 2/2014 Schmehl et al.
8,691,966 B2 4/2014 Kariko et al.
8,710,200 B2 4/2014 Schrum et al.
8,748,089 B2 6/2014 Kariko et al.
8,802,644 B2 8/2014 Chen et al.
8,808,681 B2 8/2014 Anderson et al.
8,808,982 B2 8/2014 Dahl et al.
8,822,663 B2 9/2014 Schrum et al.
8,828,956 B2 9/2014 Manoharan et al.

(56) References Cited

U.S. PATENT DOCUMENTS

| | | | |
|---|---|---|---|
| 8,835,108 | B2 | 9/2014 | Kariko et al. |
| 8,846,348 | B2 | 9/2014 | Jendrisak et al. |
| 8,853,377 | B2 | 10/2014 | Guild et al. |
| 8,859,229 | B2 | 10/2014 | Rabinovich et al. |
| 8,883,202 | B2 | 11/2014 | Manoharan et al. |
| 8,936,942 | B2 | 1/2015 | Heyes et al. |
| 8,969,353 | B2 | 3/2015 | Mahon et al. |
| 8,980,864 | B2 | 3/2015 | Hoge et al. |
| 8,999,351 | B2 | 4/2015 | Manoharan et al. |
| 8,999,950 | B2 | 4/2015 | MacLachlan et al. |
| 9,005,930 | B2 | 4/2015 | Jendrisak et al. |
| 9,012,219 | B2 | 4/2015 | Kariko et al. |
| 9,012,498 | B2 | 4/2015 | Manoharan et al. |
| 9,018,187 | B2 | 4/2015 | Heyes et al. |
| 9,040,256 | B2 | 5/2015 | Grunenwald et al. |
| 9,051,567 | B2 | 6/2015 | Fitzgerald et al. |
| 9,061,021 | B2 | 6/2015 | Guild et al. |
| 9,061,059 | B2 | 6/2015 | Chakraborty et al. |
| 9,074,208 | B2 | 7/2015 | MacLachlan et al. |
| 9,080,211 | B2 | 7/2015 | Grunenwald et al. |
| 9,085,801 | B2 | 7/2015 | Grunenwald et al. |
| 9,089,604 | B2 | 7/2015 | Chakraborty et al. |
| 9,095,552 | B2 | 8/2015 | Chakraborty et al. |
| 9,107,886 | B2 | 8/2015 | Chakraborty et al. |
| 9,114,113 | B2 | 8/2015 | Chakraborty et al. |
| 9,181,319 | B2 | 11/2015 | Schrum et al. |
| 9,181,321 | B2 | 11/2015 | Heartlein et al. |
| 9,186,325 | B2 | 11/2015 | Manoharan et al. |
| 9,186,372 | B2 | 11/2015 | De Fougerolles et al. |
| 9,187,748 | B2 | 11/2015 | Geisbert et al. |
| 9,192,651 | B2 | 11/2015 | Chakraborty et al. |
| 9,220,682 | B2 | 12/2015 | Manoharan et al. |
| 9,220,683 | B2 | 12/2015 | Manoharan et al. |
| 9,220,755 | B2 | 12/2015 | Chakraborty et al. |
| 9,220,792 | B2 | 12/2015 | Chakraborty et al. |
| 9,233,141 | B2 | 1/2016 | Chakraborty et al. |
| 9,254,311 | B2 | 2/2016 | Bancel et al. |
| 9,295,689 | B2 | 3/2016 | de Fougerolles et al. |
| 9,301,993 | B2 | 4/2016 | Chakraborty et al. |
| 9,303,079 | B2 | 4/2016 | Chakraborty et al. |
| 9,334,328 | B2 | 5/2016 | Schrum et al. |
| 9,345,780 | B2 | 5/2016 | Manoharan et al. |
| 9,352,042 | B2 | 5/2016 | Heyes et al. |
| 9,352,048 | B2 | 5/2016 | Manoharan et al. |
| 9,364,435 | B2 | 6/2016 | Yaworski et al. |
| 9,394,234 | B2 | 7/2016 | Chen et al. |
| 9,404,127 | B2 | 8/2016 | Yaworski et al. |
| 9,428,751 | B2 | 8/2016 | MacDonald et al. |
| 9,464,124 | B2 | 10/2016 | Bancel et al. |
| 9,492,386 | B2 | 11/2016 | MacLachlan et al. |
| 9,504,651 | B2 | 11/2016 | MacLachlan et al. |
| 9,504,734 | B2 | 11/2016 | Bancel et al. |
| 9,518,272 | B2 | 12/2016 | Yaworksi et al. |
| 9,572,874 | B2 | 2/2017 | Fotin-Mleczek et al. |
| 9,587,003 | B2 | 3/2017 | Bancel et al. |
| 9,616,084 | B2 | 4/2017 | Mutzke |
| 2002/0022721 | A1 | 2/2002 | Trulson et al. |
| 2002/0094528 | A1 | 7/2002 | Salafsky |
| 2002/0192651 | A1 | 12/2002 | Wheeler et al. |
| 2002/0192721 | A1 | 12/2002 | Rizzuto et al. |
| 2002/0193622 | A1 | 12/2002 | Watanabe et al. |
| 2003/0082154 | A1 | 5/2003 | Leamon |
| 2003/0083272 | A1 | 5/2003 | Wiederholt et al. |
| 2003/0104044 | A1 | 6/2003 | Semple et al. |
| 2003/0181410 | A1 | 9/2003 | Wheeler et al. |
| 2003/0215395 | A1 | 11/2003 | Yu et al. |
| 2004/0110709 | A1 | 6/2004 | Li et al. |
| 2004/0132683 | A1 | 7/2004 | Feigner et al. |
| 2004/0142025 | A1 | 7/2004 | MacLachlan et al. |
| 2004/0224912 | A1 | 11/2004 | Dobie et al. |
| 2004/0235982 | A1 | 11/2004 | Rabasco et al. |
| 2005/0004058 | A1 | 1/2005 | Benoit et al. |
| 2005/0008689 | A1 | 1/2005 | Semple et al. |
| 2005/0032730 | A1 | 2/2005 | Von Der Mulbe et al. |
| 2005/0054026 | A1 | 3/2005 | Atsushi et al. |
| 2005/0059005 | A1 | 3/2005 | Tuschl et al. |
| 2005/0059624 | A1 | 3/2005 | Hoerr et al. |
| 2005/0065107 | A1 | 3/2005 | Hobart et al. |
| 2005/0069590 | A1 | 3/2005 | Buehler et al. |
| 2005/0079212 | A1 | 4/2005 | Wheeler et al. |
| 2005/0143332 | A1 | 6/2005 | Monahan et al. |
| 2005/0148786 | A1 | 7/2005 | Ikeda et al. |
| 2005/0158302 | A1 | 7/2005 | Faustman et al. |
| 2005/0244961 | A1 | 11/2005 | Short et al. |
| 2005/0250723 | A1 | 11/2005 | Hoerr et al. |
| 2006/0008910 | A1 | 1/2006 | MacLachlan et al. |
| 2006/0059576 | A1 | 3/2006 | Pasinetti et al. |
| 2006/0069225 | A1 | 3/2006 | Wintermantel et al. |
| 2006/0083780 | A1 | 4/2006 | Heyes et al. |
| 2006/0172003 | A1 | 8/2006 | Meers et al. |
| 2006/0204566 | A1 | 9/2006 | Smyth-Templeton et al. |
| 2006/0216343 | A1 | 9/2006 | Panzner et al. |
| 2006/0223939 | A1 | 10/2006 | Lange et al. |
| 2006/0228404 | A1 | 10/2006 | Anderson et al. |
| 2006/0241071 | A1 | 10/2006 | Grinstaff et al. |
| 2007/0135372 | A1 | 6/2007 | MacLachlan et al. |
| 2007/0142628 | A1 | 6/2007 | Ghoshal et al. |
| 2007/0172950 | A1 | 7/2007 | Wheeler et al. |
| 2007/0252295 | A1 | 11/2007 | Panzner et al. |
| 2007/0275923 | A1 | 11/2007 | Chen et al. |
| 2007/0281336 | A1 | 12/2007 | Jendrisak et al. |
| 2008/0145338 | A1 | 6/2008 | Anderson et al. |
| 2008/0160048 | A1 | 7/2008 | Fuller |
| 2008/0242626 | A1 | 10/2008 | Zugates et al. |
| 2008/0260706 | A1 | 10/2008 | Rabinovich et al. |
| 2009/0023673 | A1 | 1/2009 | Manoharan et al. |
| 2009/0093433 | A1 | 4/2009 | Woolf et al. |
| 2009/0163705 | A1 | 6/2009 | Manoharan et al. |
| 2009/0186805 | A1 | 7/2009 | Tabor et al. |
| 2009/0221684 | A1 | 9/2009 | Grinstaff et al. |
| 2009/0263407 | A1 | 10/2009 | Dande et al. |
| 2009/0270481 | A1 | 10/2009 | MacLachlan et al. |
| 2009/0286852 | A1 | 11/2009 | Kariko et al. |
| 2009/0326051 | A1 | 12/2009 | Corey et al. |
| 2010/0028943 | A1 | 2/2010 | Thomas et al. |
| 2010/0035249 | A1 | 2/2010 | Hayashizaki et al. |
| 2010/0036084 | A1 | 2/2010 | Langer et al. |
| 2010/0041152 | A1 | 2/2010 | Wheeler et al. |
| 2010/0047261 | A1 | 2/2010 | Hoerr et al. |
| 2010/0120129 | A1 | 5/2010 | Amshey et al. |
| 2010/0178699 | A1 | 7/2010 | Gao et al. |
| 2010/0189729 | A1 | 7/2010 | Hoerr et al. |
| 2010/0267806 | A1 | 10/2010 | Bumcrot et al. |
| 2010/0323356 | A1 | 12/2010 | Inoue et al. |
| 2010/0331234 | A1 | 12/2010 | Mahon et al. |
| 2011/0009641 | A1 | 1/2011 | Anderson et al. |
| 2011/0035819 | A1 | 2/2011 | Cooper et al. |
| 2011/0038941 | A1 | 2/2011 | Lee et al. |
| 2011/0092739 | A1 | 4/2011 | Chen et al. |
| 2011/0143397 | A1 | 6/2011 | Kariko et al. |
| 2011/0200582 | A1 | 8/2011 | Baryza et al. |
| 2011/0244026 | A1 | 10/2011 | Guild et al. |
| 2011/0256175 | A1 | 10/2011 | Hope et al. |
| 2011/0287435 | A1 | 11/2011 | Grunenwald et al. |
| 2011/0293703 | A1 | 12/2011 | Mahon et al. |
| 2011/0311583 | A1 | 12/2011 | Manoharan et al. |
| 2012/0007803 | A1 | 1/2012 | Takatsuka |
| 2012/0009222 | A1 | 1/2012 | Nguyen et al. |
| 2012/0065252 | A1 | 3/2012 | Schrum et al. |
| 2012/0065358 | A1 | 3/2012 | Langer et al. |
| 2012/0114831 | A1 | 5/2012 | Semple et al. |
| 2012/0128760 | A1 | 5/2012 | Manoharan et al. |
| 2012/0129910 | A1 | 5/2012 | Thompson et al. |
| 2012/0142756 | A1 | 6/2012 | Guild et al. |
| 2012/0195936 | A1 | 8/2012 | Rudolph et al. |
| 2012/0202871 | A1 | 8/2012 | Heyes et al. |
| 2012/0237975 | A1 | 9/2012 | Schrum et al. |
| 2012/0251560 | A1 | 10/2012 | Dahlman et al. |
| 2012/0251618 | A1 | 10/2012 | Schrum et al. |
| 2012/0328668 | A1 | 12/2012 | MacLachlan et al. |
| 2013/0017223 | A1 | 1/2013 | Hope et al. |
| 2013/0158021 | A1 | 6/2013 | Dong et al. |
| 2013/0195967 | A1 | 8/2013 | Guild et al. |
| 2013/0237594 | A1 | 9/2013 | de Fougerolles et al. |

(56) References Cited

U.S. PATENT DOCUMENTS

| | | | |
|---|---|---|---|
| 2013/0259923 | A1 | 10/2013 | Bancel et al. |
| 2013/0259924 | A1 | 10/2013 | Bancel et al. |
| 2013/0266640 | A1 | 10/2013 | de Fougerolles et al. |
| 2013/0302401 | A1 | 11/2013 | Ma et al. |
| 2014/0010861 | A1 | 1/2014 | Bancel et al. |
| 2014/0044772 | A1 | 2/2014 | MacLachlan et al. |
| 2014/0094399 | A1 | 4/2014 | Langer et al. |
| 2014/0105964 | A1 | 4/2014 | Bancel et al. |
| 2014/0105965 | A1 | 4/2014 | Bancel et al. |
| 2014/0147432 | A1 | 5/2014 | Bancel et al. |
| 2014/0147454 | A1 | 5/2014 | Chakraborty et al. |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2014/0155474 | A1 | 6/2014 | Bancel et al. |
| 2014/0155475 | A1 | 6/2014 | Bancel et al. |
| 2014/0161830 | A1 | 6/2014 | Anderson et al. |
| 2014/0162897 | A1 | 6/2014 | Grunenwald et al. |
| 2014/0171485 | A1 | 6/2014 | Bancel et al. |
| 2014/0179756 | A1 | 6/2014 | MacLachlan et al. |
| 2014/0179771 | A1 | 6/2014 | Bancel et al. |
| 2014/0186432 | A1 | 7/2014 | Bancel et al. |
| 2014/0193482 | A1 | 7/2014 | Bancel et al. |
| 2014/0194494 | A1 | 7/2014 | Bancel et al. |
| 2014/0199371 | A1 | 7/2014 | Bancel et al. |
| 2014/0200163 | A1 | 7/2014 | Mikkelsen et al. |
| 2014/0200261 | A1 | 7/2014 | Hoge et al. |
| 2014/0200262 | A1 | 7/2014 | Bancel et al. |
| 2014/0200263 | A1 | 7/2014 | Bancel et al. |
| 2014/0200264 | A1 | 7/2014 | Bancel et al. |
| 2014/0206752 | A1 | 7/2014 | Afeyan et al. |
| 2014/0206753 | A1 | 7/2014 | Guild et al. |
| 2014/0206755 | A1 | 7/2014 | Bancel et al. |
| 2014/0206852 | A1 | 7/2014 | Hoge et al. |
| 2014/0221248 | A1 | 8/2014 | Jendrisak et al. |
| 2014/0221465 | A1 | 8/2014 | Bancel et al. |
| 2014/0227300 | A1 | 8/2014 | Chin et al. |
| 2014/0243399 | A1 | 8/2014 | Schrum et al. |
| 2014/0249208 | A1 | 9/2014 | Bancel et al. |
| 2014/0255467 | A1 | 9/2014 | Bancel et al. |
| 2014/0255468 | A1 | 9/2014 | Bancel et al. |
| 2014/0275227 | A1 | 9/2014 | Hoge et al. |
| 2014/0275229 | A1 | 9/2014 | Bancel et al. |
| 2014/0288160 | A1 | 9/2014 | Guild et al. |
| 2014/0294937 | A1 | 10/2014 | MacLachlan et al. |
| 2014/0294938 | A1 | 10/2014 | Guild et al. |
| 2014/0294939 | A1 | 10/2014 | Guild et al. |
| 2014/0294940 | A1 | 10/2014 | Guild et al. |
| 2014/0329884 | A1 | 11/2014 | Dong et al. |
| 2014/0343129 | A1 | 11/2014 | de Fougerolles et al. |
| 2014/0363876 | A1 | 12/2014 | Jendrisak et al. |
| 2015/0004217 | A1 | 1/2015 | Guild et al. |
| 2015/0005372 | A1 | 1/2015 | Hoge et al. |
| 2015/0011615 | A1 | 1/2015 | Manoharan et al. |
| 2015/0011633 | A1 | 1/2015 | Shorr et al. |
| 2015/0017211 | A1 | 1/2015 | de Fougerolles et al. |
| 2015/0038556 | A1 | 2/2015 | Heartlein et al. |
| 2015/0038558 | A1 | 2/2015 | Kariko et al. |
| 2015/0044277 | A1 | 2/2015 | Bancel et al. |
| 2015/0050354 | A1 | 2/2015 | Bouchon et al. |
| 2015/0051268 | A1 | 2/2015 | Bancel et al. |
| 2015/0056253 | A1 | 2/2015 | Bancel et al. |
| 2015/0064235 | A1 | 3/2015 | Bancel et al. |
| 2015/0064236 | A1 | 3/2015 | Bancel et al. |
| 2015/0064242 | A1 | 3/2015 | Heyes et al. |
| 2015/0064725 | A1 | 3/2015 | Schrum et al. |
| 2015/0086614 | A1 | 3/2015 | Bancel et al. |
| 2015/0110857 | A1 | 4/2015 | DeRosa et al. |
| 2015/0110858 | A1 | 4/2015 | DeRosa et al. |
| 2015/0110859 | A1 | 4/2015 | Heartlein et al. |
| 2015/0111248 | A1 | 4/2015 | Bancel et al. |
| 2015/0111945 | A1 | 4/2015 | Geisbert et al. |
| 2015/0119444 | A1 | 4/2015 | Manoharan et al. |
| 2015/0119445 | A1 | 4/2015 | Manoharan et al. |
| 2015/0157565 | A1 | 6/2015 | Heartlein et al. |
| 2015/0166465 | A1 | 6/2015 | Chen et al. |
| 2015/0190515 | A1 | 7/2015 | Manoharan et al. |
| 2015/0191760 | A1 | 7/2015 | Jendrisak et al. |
| 2015/0265708 | A1 | 9/2015 | Manoharan et al. |
| 2015/0267192 | A1 | 9/2015 | Heartlein et al. |
| 2015/0315541 | A1 | 11/2015 | Bancel et al. |
| 2015/0315584 | A1 | 11/2015 | MacDonald et al. |
| 2015/0366997 | A1 | 12/2015 | Guild et al. |
| 2016/0095924 | A1 | 4/2016 | Hope et al. |
| 2016/0114011 | A1 | 4/2016 | Bancel et al. |
| 2016/0115477 | A1 | 4/2016 | MacLachlan et al. |
| 2016/0115483 | A1 | 4/2016 | MacLachlan et al. |
| 2016/0136236 | A1 | 5/2016 | Hoge et al. |
| 2016/0151284 | A1 | 6/2016 | Heyes et al. |
| 2016/0158385 | A1 | 6/2016 | Bancel et al. |
| 2016/0193299 | A1 | 7/2016 | de Fougerolles et al. |
| 2016/0194368 | A1 | 7/2016 | Hoge et al. |
| 2016/0194625 | A1 | 7/2016 | Hoge et al. |
| 2016/0199485 | A1 | 7/2016 | Manoharan et al. |
| 2016/0213785 | A1 | 7/2016 | Manoharan et al. |
| 2016/0237108 | A1 | 8/2016 | Fraley et al. |
| 2016/0237134 | A1 | 8/2016 | Hoge et al. |
| 2016/0250354 | A1 | 9/2016 | Manoharan et al. |
| 2016/0251681 | A1 | 9/2016 | Yaworski et al. |
| 2016/0256567 | A1 | 9/2016 | Heyes et al. |
| 2016/0256568 | A1 | 9/2016 | Heyes et al. |
| 2016/0256573 | A1 | 9/2016 | de Fougerolles et al. |
| 2016/0264971 | A1 | 9/2016 | Geisbert et al. |
| 2016/0264975 | A1 | 9/2016 | Schrum et al. |
| 2016/0274089 | A1 | 9/2016 | Ciufolini et al. |
| 2016/0304552 | A1 | 10/2016 | Roy et al. |
| 2016/0317647 | A1 | 11/2016 | Ciaramella et al. |
| 2016/0317676 | A1 | 11/2016 | Hope et al. |
| 2016/0331828 | A1 | 11/2016 | Ciaramella et al. |
| 2016/0348099 | A1 | 12/2016 | Roy et al. |
| 2016/0354490 | A1 | 12/2016 | Roy et al. |
| 2016/0354491 | A1 | 12/2016 | Roy et al. |
| 2016/0354492 | A1 | 12/2016 | Roy et al. |
| 2016/0354493 | A1 | 12/2016 | Roy et al. |
| 2016/0367687 | A1 | 12/2016 | Manoharan et al. |
| 2016/0367702 | A1 | 12/2016 | Hoge et al. |
| 2016/0375134 | A1 | 12/2016 | Bancel et al. |
| 2016/0375137 | A9 | 12/2016 | Manoharan et al. |
| 2017/0000858 | A1 | 1/2017 | Fotin-Mleczek et al. |
| 2017/0000870 | A1 | 1/2017 | Hoerr et al. |
| 2017/0000871 | A1 | 1/2017 | Probst et al. |
| 2017/0002060 | A1 | 1/2017 | Bolen et al. |
| 2017/0007702 | A1 | 1/2017 | Heyes et al. |
| 2017/0014496 | A1 | 1/2017 | Fotin-Mleczek et al. |
| 2017/0028059 | A1 | 2/2017 | Baumhoff et al. |
| 2017/0029847 | A1 | 2/2017 | Thess |
| 2017/0056528 | A1 | 3/2017 | De Fougerolles et al. |
| 2017/0056529 | A1 | 3/2017 | Thess et al. |
| 2017/0065727 | A1 | 3/2017 | Fotin-Mleczek et al. |

FOREIGN PATENT DOCUMENTS

| | | | |
|---|---|---|---|
| CN | 100569877 | C | 12/2009 |
| CN | 101863544 | A | 10/2010 |
| DE | 24 30 998 | A1 | 1/1975 |
| DE | 2520814 | A1 | 11/1976 |
| DE | 3728917 | A1 | 3/1989 |
| EP | 6 73 637 | A1 | 9/1995 |
| EP | 0783297 | A1 | 7/1997 |
| EP | 0853123 | A1 | 7/1998 |
| EP | 0959092 | A1 | 11/1999 |
| EP | 1519714 | B1 | 4/2005 |
| EP | 1979364 | A2 | 10/2008 |
| EP | 2045251 | A1 | 4/2009 |
| EP | 2338478 | B1 | 6/2011 |
| EP | 2338520 | A1 | 6/2011 |
| EP | 2449106 | A1 | 5/2012 |
| EP | 2532649 | A1 | 12/2012 |
| EP | 2578685 | A2 | 4/2013 |
| EP | 2823809 | A1 | 1/2015 |
| FR | 1 378 382 | A | 11/1964 |
| FR | 2 235 112 | A1 | 1/1975 |
| GB | 1072118 | A | 6/1967 |
| GB | 1602085 | A | 11/1981 |

(56) References Cited

FOREIGN PATENT DOCUMENTS

| | | | |
|---|---|---|---|
| JP | H07-053535 | | 2/1955 |
| JP | S48-022365 | | 3/1973 |
| JP | S49-127908 | A | 12/1974 |
| JP | S51-023537 | | 2/1976 |
| JP | 51-125144 | | 11/1976 |
| JP | S52-010847 | | 1/1977 |
| JP | S63125144 | A | 5/1988 |
| JP | 63-154788 | | 6/1988 |
| JP | H09-505593 | A | 6/1997 |
| JP | H10-197978 | A | 7/1998 |
| JP | 11-005786 | A | 1/1999 |
| JP | 11-080142 | | 3/1999 |
| JP | 2001-523215 | A | 11/2001 |
| JP | 2002-167368 | A | 6/2002 |
| JP | 2003-519199 | A | 6/2003 |
| JP | 4-108173 | B2 | 6/2008 |
| JP | 2008-247749 | A | 10/2008 |
| JP | 50-24216 | B2 | 9/2012 |
| WO | WO-90/11092 | A1 | 10/1990 |
| WO | WO-93/18229 | A1 | 9/1993 |
| WO | WO-93/18754 | A1 | 9/1993 |
| WO | WO-95/11004 | A1 | 4/1995 |
| WO | WO-95/14651 | A1 | 6/1995 |
| WO | WO-95/27478 | A1 | 10/1995 |
| WO | WO-96/18372 | A2 | 6/1996 |
| WO | WO-96/26179 | A1 | 8/1996 |
| WO | WO-96/37211 | A1 | 11/1996 |
| WO | WO-96/40964 | A2 | 12/1996 |
| WO | WO-97/46223 | A1 | 12/1997 |
| WO | WO-98/10748 | A1 | 3/1998 |
| WO | WO-98/16202 | A2 | 4/1998 |
| WO | WO-98/51278 | A2 | 11/1998 |
| WO | WO-99/14346 | A2 | 3/1999 |
| WO | WO-00/03044 | A1 | 1/2000 |
| WO | WO-00/62813 | A2 | 10/2000 |
| WO | WO-00/64484 | A2 | 11/2000 |
| WO | WO-00/69913 | A1 | 11/2000 |
| WO | WO-01/05375 | A1 | 1/2001 |
| WO | WO-01/07599 | A1 | 2/2001 |
| WO | WO-02/00870 | A2 | 1/2002 |
| WO | WO-02/22709 | A1 | 3/2002 |
| WO | WO-02/31025 | A2 | 4/2002 |
| WO | WO-02/34236 | A2 | 5/2002 |
| WO | WO-02/42317 | A2 | 5/2002 |
| WO | WO-03/040288 | A2 | 5/2003 |
| WO | WO-03/070735 | A2 | 8/2003 |
| WO | WO-2004/043588 | A2 | 5/2004 |
| WO | WO-2004/048345 | A2 | 6/2004 |
| WO | WO-2004/106411 | A2 | 12/2004 |
| WO | WO-2005/026372 | A1 | 3/2005 |
| WO | WO-2005/028619 | A2 | 3/2005 |
| WO | WO-2005/037226 | A2 | 4/2005 |
| WO | WO-2005/121348 | A1 | 12/2005 |
| WO | WO-2006/000448 | A2 | 1/2006 |
| WO | WO-2006/016097 | A2 | 2/2006 |
| WO | WO-2006/082088 | A1 | 8/2006 |
| WO | WO-2006/105043 | A2 | 10/2006 |
| WO | WO-2006/138380 | A2 | 12/2006 |
| WO | WO-2007/024708 | A2 | 3/2007 |
| WO | WO-2007/031091 | A2 | 3/2007 |
| WO | WO-2007/120863 | A2 | 10/2007 |
| WO | WO-2007/126386 | A1 | 11/2007 |
| WO | WO-2007/143659 | A2 | 12/2007 |
| WO | WO-2008/011561 | A2 | 1/2008 |
| WO | WO-2008/042973 | A2 | 4/2008 |
| WO | WO-2008/045548 | A2 | 4/2008 |
| WO | WO-2008/083949 | A2 | 7/2008 |
| WO | WO-2008/113364 | A2 | 9/2008 |
| WO | WO-2009/046220 | A2 | 4/2009 |
| WO | WO-2009/127060 | A1 | 10/2009 |
| WO | WO-2009/127230 | A1 | 10/2009 |
| WO | WO-2010/037408 | A1 | 4/2010 |
| WO | WO-2010/042877 | A1 | 4/2010 |
| WO | WO-2010/045512 | A2 | 4/2010 |
| WO | WO-2010/053572 | A2 | 5/2010 |
| WO | WO-2010/054401 | A1 | 5/2010 |
| WO | WO-2010/054405 | A1 | 5/2010 |
| WO | WO-2010/056403 | A1 | 5/2010 |
| WO | WO-2010/099387 | A1 | 9/2010 |
| WO | WO-2010/114789 | A1 | 10/2010 |
| WO | WO-2010/119256 | A1 | 10/2010 |
| WO | WO-2010/129709 | A1 | 11/2010 |
| WO | WO-2010/144740 | A1 | 12/2010 |
| WO | WO-2010/147992 | A1 | 12/2010 |
| WO | WO-2010/148013 | A2 | 12/2010 |
| WO | WO-2011/012316 | A2 | 2/2011 |
| WO | WO-2011/012746 | A2 | 2/2011 |
| WO | WO-2011/039144 | A1 | 4/2011 |
| WO | WO-2011/068810 | A1 | 6/2011 |
| WO | WO-2011/075656 | A1 | 6/2011 |
| WO | WO-2011/141705 | A1 | 11/2011 |
| WO | WO-2012/019168 | A2 | 2/2012 |
| WO | WO-2012/019630 | A1 | 2/2012 |
| WO | WO-2012/019780 | A1 | 2/2012 |
| WO | WO-2012/027675 | A2 | 3/2012 |
| WO | WO-2012/045075 | A1 | 4/2012 |
| WO | WO-2012/045082 | A2 | 4/2012 |
| WO | WO-2012/075040 | A2 | 6/2012 |
| WO | WO-2012/133737 | A1 | 10/2012 |
| WO | WO-2012/135025 | A2 | 10/2012 |
| WO | WO-2012/135805 | A2 | 10/2012 |
| WO | WO-2012/170889 | A1 | 12/2012 |
| WO | WO-2012/170930 | A1 | 12/2012 |
| WO | WO-2013/039857 | A1 | 3/2013 |
| WO | WO-2013/039861 | A2 | 3/2013 |
| WO | WO-2013/063468 | A1 | 5/2013 |
| WO | WO2013/090186 | | 6/2013 |
| WO | WO-2013/101690 | A1 | 7/2013 |
| WO | WO-2013/102203 | A1 | 7/2013 |
| WO | WO-2013/126803 | A1 | 8/2013 |
| WO | WO-2013/130161 | A1 | 9/2013 |
| WO | WO-2013/149140 | A1 | 10/2013 |
| WO | WO-2013/149141 | A1 | 10/2013 |
| WO | WO-2013/151663 | A1 | 10/2013 |
| WO | WO-2013/151664 | A1 | 10/2013 |
| WO | WO-2013/151666 | A2 | 10/2013 |
| WO | WO-2013/151667 | A1 | 10/2013 |
| WO | WO-2013/151668 | A2 | 10/2013 |
| WO | WO-2013/151670 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2013/182683 | A1 | 12/2013 |
| WO | WO-2013/185067 | A1 | 12/2013 |
| WO | WO-2013/185069 | A1 | 12/2013 |
| WO | WO-2014/028487 | A1 | 2/2014 |
| WO | WO-2014/089486 | A1 | 6/2014 |
| WO | WO-2014/113089 | A2 | 7/2014 |
| WO | WO-2014/144039 | A1 | 9/2014 |
| WO | WO-2014/144196 | A1 | 9/2014 |
| WO | WO-2014/144711 | A1 | 9/2014 |
| WO | WO-2014/144767 | A1 | 9/2014 |
| WO | WO-2014/152027 | A1 | 9/2014 |
| WO | WO-2014/152030 | A1 | 9/2014 |
| WO | WO-2014/152031 | A1 | 9/2014 |
| WO | WO-2014/152211 | A1 | 9/2014 |
| WO | WO-2014/152513 | A1 | 9/2014 |
| WO | WO-2014/152540 | A1 | 9/2014 |
| WO | WO-2014/152659 | A1 | 9/2014 |
| WO | WO-2014/152673 | A1 | 9/2014 |
| WO | WO-2014/152774 | A1 | 9/2014 |
| WO | WO-2014/152940 | A1 | 9/2014 |
| WO | WO-2014/152966 | A1 | 9/2014 |
| WO | WO-2014/153052 | A2 | 9/2014 |
| WO | WO-2014/158795 | A1 | 10/2014 |
| WO | WO-2014/159813 | A1 | 10/2014 |
| WO | WO-2014/179562 | A1 | 11/2014 |
| WO | WO-2014/210356 | A1 | 12/2014 |
| WO | WO-2015/006747 | A2 | 1/2015 |
| WO | WO-2015/011633 | A1 | 1/2015 |
| WO | WO-2015/048744 | A2 | 4/2015 |
| WO | WO-2015/051169 | A2 | 4/2015 |
| WO | WO-2015/051173 | A2 | 4/2015 |
| WO | WO-2015/058069 | A1 | 4/2015 |

(56) References Cited

FOREIGN PATENT DOCUMENTS

| | | | |
|---|---|---|---|
| WO | WO 2015/061467 | | 4/2015 |
| WO | WO2015/085318 | | 6/2015 |
| WO | WO2015/089511 | | 6/2015 |
| WO | WO2016/054421 | | 4/2016 |
| WO | WO2016/071857 | | 5/2016 |
| WO | WO2016/077123 | | 5/2016 |
| WO | WO2016/077125 | | 5/2016 |
| WO | WO2016/118724 | | 7/2016 |
| WO | WO2016/118725 | | 7/2016 |
| WO | WO2016/154127 | | 9/2016 |
| WO | WO2016/164762 | | 10/2016 |
| WO | WO2016/183366 | A2 | 11/2016 |
| WO | WO2016/197132 | A1 | 12/2016 |
| WO | WO2016/197133 | A1 | 12/2016 |
| WO | WO2016/201377 | A1 | 12/2016 |
| WO | WO2017/019891 | A2 | 2/2017 |
| WO | WO2017/049074 | A1 | 3/2017 |
| WO | WO2017/049275 | A2 | 3/2017 |
| WO | WO2017/049286 | A1 | 3/2017 |
| WO | WO 2017/177169 | | 10/2017 |
| WO | WO 2018/089790 | | 5/2018 |
| WO | WO 2018/089801 | | 5/2018 |
| WO | WO 2018/213476 | | 11/2018 |

OTHER PUBLICATIONS

Akinc, A. et al., Development of lipidoid-siRNA formulations for systemic delivery to the liver. Molecular Therapy 17(5):872-879 (2009).

Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).

Anderson, D.G. et al., Structure/property studies of polymeric gene delivery using a library of poly(beta-amino esters). Molecular Therapy 11(3):426-434 (2005).

Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).

Anderson, J. Biological Responses to Materials. Annual Review of Materials Research 31:81-110 (2001).

Anderson, W. French, Human gene therapy, Nature, 392, 25-30 (1998).

Andries, O. et al., Comparison of the Gene Transfer Efficiency of mRNA/GL67 and pDNA/GL67 Complexes in Respiratory Cells, Mol. Pharmaceut., 9: 2136-2145 (2012).

Auffray, C. et al., Purification of Mouse Immunoglubulin Heavy-Chain Messenger RNAs from Total Myeloma Tumor RNA, European Journal of Biochemistry, 107(2):303-314 (1980).

Author Unknown, Blood Proteins, published by WikiPedia, San Francisco, CA, 2 pages, <http://en.wikipedia.org/wiki/Biood_proteins> downloaded May 17, 2015.

Bajaj, A. et al., Synthesis and gene transfection efficacies of PEI-cholesterol-based lipopolymers. Bioconjugate Chemistry 19(8):1640-516511 (2008).

Barreau, C. et al., Liposome-mediated RNA transfection should be used with caution, RNA, 12:1790-1793 (2006).

Behlke, M. A. et al., Progress towards in vivo use of siRNAs, Molecular Therapy, 13:644-670 (2006).

Behr, J. et al., Efficient Gene Transfer into Mammalian Primary Endocrine Cells with Lipo Polyamine-Coated DNA, Proc. Nat.'l Acad. Sci., 86: 6982-6986 (1989).

Bennett, J. Immune response following intraocular delivery of recombinant viral vectors, Gene Therapy, 10: 977-982 (2003).

Bhaduri, S. et al., Procedure for the preparation of milligram quantities of adenovirus messenger ribonucleic acid, J. Virol., 10(6): 1126-1129 (1972).

Bloomfield, V.A., Quasi-Elastic Light Scattering Applications in Biochemistry and Biology, Ann. Rev. Biophys. Bioeng. 10:421-450 (1981).

Boussif, O. et al., A versatile vector for gene and oligonucleotide transfer into cells in culture and in vivo: polyethylenimine. Proceedings of the National Academy of Sciences of the USA. 92(16):7297-7301 (1995).

Braun, C.S. et al., ucture/function relationships of polyamidoamine/DNA dendrimers as gene delivery vehicles. Journal of Pharmaceutical Sciences 94(2):423-436 (2005).

Breunig, M. et al., Breaking up the correlation between efficacy and toxicity for nonviral gene delivery. Proceedings of the National Academy of Sciences of the U S A. 104(36):14454-14459 (2007).

Breunig, M. et al., Mechanistic investigation of poly(ethylene imine)-based siRNA delivery: disulfide bonds boost intracellular release of the cargo. Journal of Controlled Release 130(1):57-63 (2008).

Brey, D.M. et al., Controlling poly(beta-amino ester) network properties through macromer branching. Acta Biomaterialia 4(2):207-217 (2008).

Brey, D.M. et al., Influence of macromer molecular weight and chemistry on poly(beta-amino ester) network properties and initial cell interactions. Journal of Biomedical Materials Research Part A 85(3):731-741 (2007).

Budker, V. et al., Protein/Amphipathic Polyamine Complexes Enable Highly Efficient Transfection with Minimal Toxicity, BioTechniques, 23: 139-147 (1997).

Burger, G. et al., Sequencing complete mitochondrial and plastid genomes, Nature Protocols, 2: 603-614 (2007).

Burnett, J.C. et al., Current progress of siRNA/shRNA therapeutics in clinical trials. Biotechnology Journal 6(9):1130-1146 (2011).

Byk, G. et al., Synthesis, activity, and structure-activity relationship studies of novel cationic lipids for DNA transfer. Journal of Medical Chemistry 41(2):224-235 (1998).

Caplen, N.J. et al., In vitro liposome-mediated DNA transfection of epithelial cell lines using the cationic liposome DC-Chol/DOPE, Gene Therapy, 2:603-613 (1995).

Cassiman, D. Gene transfer for inborn errors of metabolism of the liver: the clinical perspective, Current Pharmaceutical Design, 17(24):2550-2557 (2011).

Castanotto, D. et al., The promises and pitfalls of RNA-interference-based therapeutics. Nature 457(7228):426-433 (2009).

Chakraborty, C. Potentiality of Small Interfering RNAs (siRNA) as Recent Therapeutic Targets for Gene-Silencing. Current Drug Targets 8(3):469-82 (2007).

Chandler, R. et al., Liver-directed adeno-associated virus serotype 8 gene transfer rescues a lethal murine model of citrullinemmiatype 1, Gene Therapy, 20:1188-1191 (2013).

Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).

Chen, D. et al., Rapid discovery of potent siRNA-containing lipid nanoparticles enabled by controlled microfluidic formulation. Journal of the American Chemical Society 134(16):6948-6951 (2012).

Chen, Y. and Huang, L., Tumor-targeted delivery of siRNA by non-viral vector: safe and effective cancer therapy. Expert Opinion on Drug Delivery 5(12):1301-1311 (2008).

Chiou, H.C. et al., Enhanced resistance to nuclease degradation of nucleic acids complexed to; asialoglycoprotein-polylysine carriers, Nucleic Acids Research, 22(24):5439-5446 (1994).

Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).

Conese, M. et al., Gene and Cell Therapy for Cystic Fibrosis: From Bench to Bedside, J. Cyst. Fibros., 10 Suppl 2:S114-s128 (2011).

Cotten, M. et al., Receptor-mediated transport of DNA into eukaryotic cells. Methods in Enzymology 217 (H):618-644 (1993).

Cowling, V.H., Regulation of mRNA cap methylation, Biochemical Journal, 425:295-302 (2010).

Creusat, G. et al., Proton sponge trick for pH-sensitive disassembly of polyethylenimine-based siRNA delivery systems. Bioconjugate Chemistry 21 (5):994-1002 (2010).

Crooke, S.T. Molecular mechanisms of action of antisense drugs. Biochimica et Biophysica Acta 1489(1):31-44. Review (1999).

(56) References Cited

OTHER PUBLICATIONS

Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N",N'"-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Driscoll, K.E. et al., Intratracheal instillation as an exposure technique for the evaluation of respiratory tract toxicity: uses and limitations, Toxicol. Sci., 55(1): 24-35 (2000).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Galipon, J. et al., Stress-induced lncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).

(56) References Cited

OTHER PUBLICATIONS

Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy-pharmacokinetics and in vivo; gene transfer, Gene Therapy, 9(6):407-414 (2002).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA/ Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (dated Jun. 14, 2012).
International Search Report for PCT/US15/27563, 5 pages (dated Sep. 18, 2015).
International Search Report for PCT/US2010/058457, 4 pages (dated May 6, 2011).
International Search Report for PCT/US2011/062459, 3 pages (dated Apr. 11, 2012).
International Search Report for PCT/US2012/041663, 4 pages (dated Oct. 8, 2012).
International Search Report for PCT/US2012/041724, 5 pages (dated Oct. 25, 2012).
International Search Report for PCT/US2013/034602, 2 pages (dated Jun. 17, 2013).
International Search Report for PCT/US2013/034604, 4 pages (dated Jun. 17, 2013).
International Search Report for PCT/US2013/044769, 4 pages (dated Nov. 12, 2013).
International Search Report for PCT/US2013/044771, 6 pages (dated Nov. 1, 2013).
International Search Report for PCT/US2013/073672, 6 pages (dated Mar. 3, 2014).
International Search Report for PCT/US2014/027422, 5 pages (dated Jul. 31, 2014).
International Search Report for PCT/US2014/027585, 3 pages (dated Jul. 14, 2014).
International Search Report for PCT/US2014/027587, 6 pages (dated Jul. 24, 2014).
International Search Report for PCT/US2014/027602, 6 pages (dated Jul. 28, 2014).
International Search Report for PCT/US2014/027717, 5 pages (dated Jul. 16, 2014).
International Search Report for PCT/US2014/028330, 5 pages (dated Jul. 22, 2014).
International Search Report for PCT/US2014/028441, 6 pages (dated Jul. 22, 2014).
International Search Report for PCT/US2014/028498, 5 pages (dated Jul. 28, 2014).
International Search Report for PCT/US2014/028849, 6 pages (dated Jul. 17, 2015).
International Search Report for PCT/US2014/061786, 6 pages (dated Feb. 6, 2015).
International Search Report for PCT/US2014/061793, 4 pages (dated Feb. 6, 2015).
International Search Report for PCT/US2014/061830, 5 pages (dated Feb. 4, 2015).
International Search Report for PCT/US2014/061841, 6 pages (dated Feb. 24, 2015).
International Search Report for PCT/US2015/039004, 4 pages (dated Oct. 6, 2015).
International Search Report for PCT/US2015/21403 (4 pages) dated Jun. 15, 2015.
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).

(56) References Cited

OTHER PUBLICATIONS

Jemielity, J. et al., Novel "anti-reverse" cap analogs with superior translational properties, Cold Spring Harbor Laboratory Press, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21 (5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic& Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying Phaseolus vulgaris Agglutinin-L4 Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kore, A. and Charles, I., Synthesis and evaluation of 2'-O-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).
Lu, D. et al., Optimization of methods to achieve mRNA-mediated transfection of tumor cells in vitro and in vivo employing cationic liposome vectors, Cancer Gene Therapy, 1 (4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123 (33): 8155-8156 (2001).

(56) References Cited

OTHER PUBLICATIONS

Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Developlment of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences USA, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72:5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5:13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37:1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al.. The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications fordrug delivery: nasal and pulmonary routes, Nanomaterials and Nanosystems for Biomedical Applications, M.R. Mozafari (ed.): 99-112 (2007).
Painter, H. et al., Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Pearson, H. One Gene, Twenty Years, Nature 460:165-169 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).

(56) References Cited

OTHER PUBLICATIONS

Putnam, D. and Langer, R., Poly(4-hydroxy-l-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).
Rudolph, C. et al., Methodological optimization of polyethylenimine (PEI)-based gene delivery to the lungs of mice via aerosol application, Journal of Gene Medicine, 7(1): 59-66 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145:182-195 (2010).
Sakiyama-Elbert, S.E. and Hubbell, J.A., Functional Biomaterials: Design of Novel Biomaterials. Annual Review of Materials Research 31:183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings ofthe National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21 (6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway ofthe Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA To Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al.. Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).

(56) References Cited

OTHER PUBLICATIONS

Van De Wetering, P. et al.. Structure-activity relationships of water-soluble cationic methacrylate/methacrylamide polymers for nonviral gene delivery. Bioconjugate Chemistry 10(4): 589-597 (1999).
Van Der Gun, B.T.F. et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al.. Gene therapy for liver diseases using non-viral minicircle-DNA vector, Human Gene Therapy, 23(10):A145 (2012).
Viecelli, H. et al.. Gene therapy for liver diseases using non-viral minicircle-DNA vector, Molecular Therapy, 21 (1):S136 (2013).
Vomelova, I. et al.. Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al.. Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al.. Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al.. Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US15/27563, 12 pages (dated Sep. 18, 2015).
Written Opinion for PCT/US2010/058457, 14 pages (dated May 6, 2011).
Written Opinion for PCT/US2011/062459, 9 pages (dated Apr. 11, 2012).
Written Opinion for PCT/US2012/041663, 7 pages (dated Oct. 8, 2012).
Written Opinion for PCT/US2012/041724, 11 pages (dated Oct. 25, 2012).
Written Opinion for PCT/US2013/034602, 4 pages (dated Jun. 17, 2013).
Written Opinion for PCT/US2013/034604, 9 pages (dated Jun. 17, 2013).
Written Opinion for PCT/US2013/044769, 8 pages (dated Nov. 12, 2013).
Written Opinion for PCT/US2013/044771,7 pages (dated Nov. 1, 2013).
Written Opinion for PCT/US2013/073672, 7 pages (dated Mar. 3, 2014).
Written Opinion for PCT/US2014/027422, 6 pages (dated Jul. 31, 2014).
Written Opinion for PCT/US2014/027587, 5 pages (dated Jul. 24, 2014).
Written Opinion for PCT/US2014/027602, 7 pages (dated Jul. 28, 2014).
Written Opinion for PCT/US2014/027717, 5 pages (dated Jul. 16, 2014).
Written Opinion for PCT/US2014/028330, 7 pages (dated Jul. 22, 2014).
Written Opinion for PCT/US2014/028441,6 pages (dated Jul. 22, 2014).
Written Opinion for PCT/US2014/028498, 6 pages (dated Jul. 28, 2014).
Written Opinion for PCT/US2014/028849, 7 pages (dated Jul. 17, 2015).
Written Opinion for PCT/US2014/061786, 5 pages (dated Feb. 6, 2015).
Written Opinion for PCT/US2014/061793, 4 pages (dated Feb. 6, 2015).
Written Opinion for PCT/US2014/061830, 7 pages (dated Feb. 4, 2015).
Written Opinion for PCT/US2014/061841, 8 pages (dated Feb. 24, 2015).
Written Opinion for PCT/US2015/039004, 8 pages (dated Oct. 6, 2015).
Written Opinion for PCT/US2015/21403 (7 pages) dated Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chern. Lett., 18(5): 1632-1636 (2008).

(56) References Cited

OTHER PUBLICATIONS

Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry, 26(1):184-88. Russian (1990).
Zaugg, H.E. et al., 3-Carboxy-2,5-piperazinedione and Derivatives. Journal of American Chemical Society 78(11 ):2626-2631 (1956).
Zauner, W. et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).
Brown, M.D. et al., Gene Delivery with synthetic (non viral) carriers, Int. J. Pharm., 1-21 (2001).
Eck, et al., Goodman & Gilman's The Pharmacological Basis of Therapeutics, McGraw-Hill, New York, 77-101 (1996).
Gorecki, et al., Prospects and problems of gene therapy: an update, Expert Opin. Emerging Drugs, 6(2): 187- 198 (2001).
Lechardeur, et al., Metabolic instability of plasmid DNA in the cytosol: a potential barrier to gene transfer, Gene Therapy, 6: 482-497 (1999).
Matsumura, Yoshihiro et al., "In vitro methods for CFTR biogenesis." In *Cystic Fibrosis*, pp. 233-253. Humana Press, 2011.

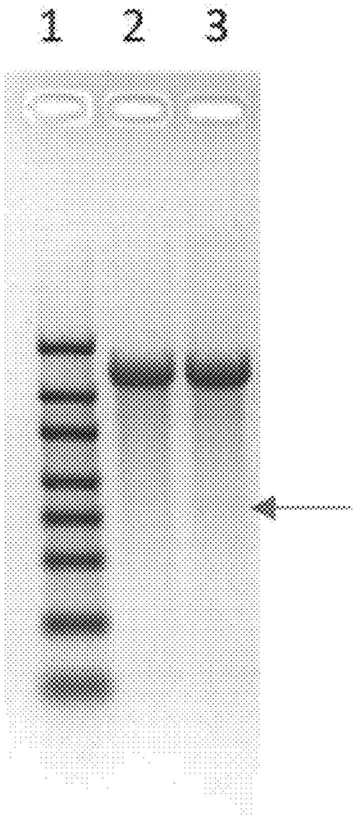
1 2 3

SEQUENCE LISTING

```
<160> NUMBER OF SEQ ID NOS: 40

<210> SEQ ID NO 1
<211> LENGTH: 4443
<212> TYPE: RNA
<213> ORGANISM: Artificial Sequence
<220> FEATURE:
<223> OTHER INFORMATION: chemically synthesized oligonucleotide
<220> FEATURE:
<221> NAME/KEY: mRNA
<222> LOCATION: (1)..(4443)
<223> OTHER INFORMATION: Coding Sequence
<220> FEATURE:
<221> NAME/KEY: mRNA
<222> LOCATION: (1)..(4443)

<400> SEQUENCE: 1

augcaacgcu cuccucuuga aaaggccucg guggugucca agcucuucuu cucguggacu      60
```

-continued agacccaucc ugagaaaggg guacagacag cgcuuggagc uguccgauau cuaucaaauc 120
ccuuccgugg acuccgcgga caaccugucc gagaagcucg agagagaaug ggacagagaa 180
cucgccucaa agaagaaccc gaagcugauu aaugcgcuua ggcggugcuu uuucuggcgg 240
uucauguucu acggcaucuu ccucuaccug ggagagguca ccaaggccgu gcagccccug 300
uugcugggac ggauuauugc cuccuacgac cccgacaaca aggaagaaag aagcaucgcu 360
aucuacuugg gcaucggucu gugccugcuu uucaucgucc ggacccucuu guugcauccu 420
gcuauuuucg gccugcauca cauuggcaug cagaugagaa uugccauguu uucccugauc 480
uacaagaaaa cucugaagcu cucgagccgc gugcuugaca agauuuccau cggccagcuc 540
gugucccugc ucuccaacaa ucugaacaag uucgacgagg gccucgcccu ggcccacuuc 600
guguggaucg ccccucugca aguggcgcuu cugaugggcc ugaucuggga gcugcugcaa 660
gccucggcau ucugugggcu uggauuccug aucgugcugg cacuguucca ggccggacug 720
gggcggauga ugaugaagua cagggaccag agagccggaa agauuuccga acggcuggug 780
aucacuucgg aaaugaucga aaacauccag ucagugaagg ccuacugcug ggaagaggcc 840
auggaaaaga ugauugaaaa ccuccggcaa accgagcuga agcugacccg caaggccgcu 900
uacgugcgcu auuucaacuc guccgcuuuc uucuucuccg gguucuucgu gguguuucuc 960
uccgugcucc ccuacgcccu gauuaaggga aucauccuca ggaagaucuu caccaccauu 1020
uccuucugua ucgugcuccg cauggccgug acccggcagu ucccaugggc cgugcagacu 1080
ugguacgacu cccugggagc cauuaacaag auccaggacu uccuucaaaa gcaggaguac 1140
aagacccucg aguacaaccu gacuacuacc gaggucguga uggaaaacgu caccgccuuu 1200
ugggaggagg gauuuggcga acuguucgag aaggccaagc agaacaacaa caaccgcaag 1260
accucgaacg gugacgacuc ccucuucuuu ucaaacuuca gccugcucgg gacgcccgug 1320
cugaaggaca uuaacuucaa gaucgaaaga ggacagcucc uggcggugge cggaucgacc 1380
ggagccggaa agacuucccu gcugauggug aucaugggag agcuugaacc uagcgaggga 1440
aagaucaagc acuccggccg caucagcuuc uguagccagu uuuccuggau caugcccgga 1500
accauuaagg aaaacaucau cuucggcgug uccuacgaug aauaccgcua ccgguccgug 1560
aucaaagccu gccagcugga agaggauauu ucaaaguucg cggagaaaga uaacaucgug 1620
cugggcgaag gggguauuac cuugucgggg ggccagcggg cuagaaucuc gcuggccaga 1680
gccguguaua aggacgccga ccuguaucuc cuggacuccc ccuucggaua ccuggacguc 1740
cugaccgaaa aggagaucuu cgaaucgugc gugugcaagc ugauggcuaa caagacucgc 1800
auccucguga ccuccaaaau ggagcaccug aagaaggcag acaagauucu gauucugcau 1860
gaggggucu ccuacuuuua cggcaccuuc ucggaguugc agaacuugca gcccgacuuc 1920
ucaucgaagc ugaugggug cgacagcuuc gaccaguucu ccgccgaaag aaggaacucg 1980
auccugacgg aaaccuugca ccgcuucucu uuggaaggcg acgccccugu gucauggacc 2040
gagacuaaga agcagagcuu caagcagacc ggggaauucg gcgaaaagag gaagaacagc 2100
aucuugaacc ccauuaacuc cauccgcaag uucucaaucg ugcaaaagac gccacugcag 2160
augaacggca uugaggagga cuccgacgaa ccccuugaga ggcgccuguc ccuggugccg 2220
gacagcgagc agggagaagc cauccugccu cggauuuccg ugaucuccac ugguccgacg 2280
cuccaagccc ggcggcggca guccgugcug aaccugauga cccacagcgu gaaccagggc 2340
caaaacauuc accgcaagac uaccgcaucc acccggaaag ugucccuggc accucaagcg 2400
aaucuuaccg agcucgacau cuacucccgg agacugucgc aggaaaccgg gcucgaaauu 2460
uccgaagaaa ucaacgagga ggaucugaaa gagugcuucu ucgacgauau ggagucgaua 2520
cccgccguga cgacuuggaa cacuuaucug cgguacauca cugugcacaa gucauugauc 2580
uucgugcuga uuuggugccu ggugauuuuc cuggccgagg ucgcggccuc acuggugug 2640 cucuggcugu ugggaaacac gccucugcaa gacaagggaa acuccacgca cucgagaaac 2700
aacagcuaug ccgugauuau cacuuccacc uccucuuauu acguguucua caucuacguc 2760
ggaguggcgg auacccugcu cgcgaugggu uucuucagag gacugccgcu gguccacacc 2820
uugaucaccg ucagcaagau ucuucaccac aagauguugc auagcgugcu gcaggccccc 2880
auguccaccc ucaacacucu gaaggccgga ggcauucuga acagauucuc caaggacauc 2940
gcuauccugg acgaucuccu gccgcuuacc aucuuugacu ucauccagcu gcugcugauc 3000
gugauuggag caaucgcagu gguggcggug cugcagccuu acauuuucgu ggccacugug 3060
ccggucauug uggcguucau caugcugcgg gccuacuucc uccaaaccag ccagcagcug 3120
aagcaacugg aauccgaggg acgauccccc aucuucacuc accuugugac gucguugaag 3180
ggacugugga cccuccgggc uuucggacgg cagcccuacu ucgaaacccu cuuccacaag 3240
gcccugaacc uccacaccgc caauugguuc cuguaccugu ccacccugcg gugguuccag 3300
augcgcaucg agaugauuuu cgucaucuuc uucaucgcgg ucacauucau cagcauccug 3360
acuaccggag agggagaggg acgggucgga auaauccuga cccucgccau gaacauuaug 3420
agcacccugc agugggcagu gaacagcucg aucgacgugg acagccugau gcgaagcguc 3480
agccgcgugu ucaaguucau cgacaugccu acugagggaa aacccacuaa guccacuaag 3540
cccuacaaaa auggccagcu gagcaagguc augaucaucg aaaacuccca cgugaagaag 3600
gacgauauuu ggcccuccgg aggucaaaug accgugaagg accugaccgc aaaguacacc 3660
gagggaggaa acgccauucu cgaaaacauc agcuucucca uuucgccggg acagcggguc 3720
ggccuucucg ggcggaccgg uuccgggaag ucaacucugc ugucggcuuu ccuccggcug 3780
cugaauaccg agggggaaau ccaaauugac ggcgugucuu gggauuccau uacucugcag 3840
caguggcgga aggccuucgg cgugaucccc cagaaggugu ucaucuucuc ggguaccuuc 3900
cggaagaacc uggauccuua cgagcagugg agcgaccaag aaaucuggaa ggucgccgac 3960
gaggucggcc ugcgcuccgu gauugaacaa uuuccuggaa agcuggacuu cgugcucguc 4020
gacgggggau guguccuguc gcacggacau aagcagcuca ugugccucgc acgguccgug 4080
cucuccaagg ccaagauucu gcugcuggac gaaccuucgg cccaccugga uccggucacc 4140
uaccagauca ucaggaggac ccugaagcag gccuuugccg auugcaccgu gauucucugc 4200
gagcaccgca ucgaggccau gcuggagugc cagcaguucc uggucaucga ggagaacaag 4260
guccgccaau acgacuccau ucaaaagcuc cucaacgagc ggucgcuguu cagacaagcu 4320
auuucaccgu ccgauagagu gaagcucuuc ccgcaucgga acagcucaaa gugcaaaucg 4380
aagccgcaga ucgcagccuu gaaggaagag acugaggaag aggugcagga cacccggcuu 4440
uaa 4443

<210> SEQ ID NO 2
<211> LENGTH: 4443
<212> TYPE: RNA
<213> ORGANISM: Artificial Sequence
<220> FEATURE:
<223> OTHER INFORMATION: chemically synthesized oligonucleotide

<400> SEQUENCE: 2

-continued

```
augcagcggu ccccgcucga aaaggccagu gucgugucca aacucuucuu cucauggacu      60
cggccuaucc uuagaaaggg guaucggcag aggcuugagu ugucugacau cuaccagauc     120
cccucgguag auucggcgga uaaccucucg gagaagcucg aacgggaaug ggaccgcgaa     180
cucgcgucua agaaaaaccc gaagcucauc aacgcacuga gaaggugcuu cuucuggcgg     240
uucauguucu acgguaucuu cuuguaucuc ggggagguca caaaagcagu ccaaccccug     300
uuguugggug gcauuaucgc cucguacgac cccgauaaca aagaagaacg gagcaucgcg     360
aucuaccucg ggaucggacu guguuugcuu uucaucguca gaacacuuuu guugcaucca     420
gcaaucuucg gccuccauca caucgguaug cagaugcgaa ucgcuauguu uagcuugauc     480
uacaaaaaga cacugaaacu cucgucgcgg guguuggaua agauuuccau cggucaguug     540
guguccccugc uuaguaauaa ccucaacaaa uucgaugagg gacuggcgcu ggcacauuuc    600
guguggauug ccccguugca agucgcccuu uugaugggcc uuauuuggga gcuguugcag     660
gcaucugccu uuguggccu gggauuucug auuguguugg cauuguuuca ggcugggcuu      720
gggcggauga ugaugaagua ucgcgaccag agagcgggua aaaucucgga aagacucguc     780
aucacuucgg aaaugaucga aaacauccag ucggucaaag ccuauugcug ggaagaagcu     840
auggagaaga ugauugaaaa ccuccgccaa acugagcuga aacugacccg caaggcggcg     900
uauguccggu auuucaauuc gucagcguuc uucuuuuccg gguucuucgu ugucuuucuc     960
ucgguuuugc cuuaugccuu gauuaagggg auuauccucc gcaagauuuu caccacgauu    1020
ucguucugca uuguauugcg cauggcagug acacggcaau uuccgugggc cgugcagaca    1080
ugguaugacu cgcuuggagc gaucaacaaa auccaagacu ucuugcaaaa gcaagaguac    1140
aagacccugg aguacaaucu uacuacuacg gagguaguaa uggagaaugu gacggcuuuu    1200
ugggaagagg guuuuggaga acuguuugag aaagcaaagc agaauaacaa caaccgcaag    1260
accucaaaug ggacgauuc ccuguuuuuc ucgaacuucu cccugcucgg aacacccgug     1320
uugaaggaca ucaauuucaa gauugagagg ggacagcuuc ucgcgguagc gggaagcacu    1380
ggugcgggaa aaacuagccu cuugauggug auuauggggg agcuugagcc cagcgagggg    1440
aagauuaaac acuccgggcg uaucucauuc uguagccagu uuucauggau caugcccgga    1500
accauuaaag agaacaucau uuucggagua uccuaugaug aguaccgaua cagaucgguc    1560
auuaaggcgu gccaguugga agaggacauu ucuaaguucg ccgagaagga uaacaucguc    1620
uugggagaag gggguauuac auugucggga gggcagcgag cgcggaucag ccucgcgaga    1680
gcgguauaca aagaugcaga uuuguaucug cuugauucac cguuuggaua ccucgacgua    1740
uugacagaaa aagaaaucuu cgagucgugc guguguaaac uuauggcuaa uaagacgaga    1800
auccugguga caucaaaaau ggaacaccuu aagaaggcgg acaagauccu gauccuccac    1860
gaaggaucgu ccuacuuuua cggcacuuuc ucagaguugc aaaacuugca gccggacuuc    1920
ucaagcaaac ucauggggug ugacucauuc gaccaguuca gcgcggaacg gcggaacucg    1980
aucuugacgg aaacgcugca ccgauucucg cuugagggug augccccggu aucgugggacc   2040
gagacaaaga agcagucguu uaagcagaca ggagaauuug gugagaaaag aaagaacagu    2100
aucuugaauc cuauuaacuc aauucgcaag uucucaaucg uccagaaaac uccacugcag    2160
augaauggaa uugaagagga uucggacgaa ccccuggagc gcaggcuuag ccucgugccg    2220
gauucagagc aaggggaggc cauucuuccc cggauuucgg ugauuucaac cggaccuaca    2280
cuucaggcga ggcgaaggca auccgugcuc aaccucauga cgcauucggu aaaccagggg    2340
caaaacauuc accgcaaaac gacggccuca acgagaaaag ugucacuugc accccaggcg    2400
```

```
aauuugacug aacucgacau cuacagccgu aggcuuucgc aagaaaccgg acuugagauc   2460

agcgaagaaa ucaaugaaga agauuugaaa gaguguuucu uugaugacau ggaaucaauc   2520

ccagcgguga caacguggaa cacauacuug cguuacauca cggugcacaa guccuugauu   2580

uucguccuca ucuggugucu cgugaucuuu cucgcugagg ucgcagcguc acuuguggus   2640

cucuggcugc uugguaauac gcccuugcaa gacaaaggca auucuacaca cucaagaaac   2700

aauuccuaug ccgugauuau cacuucuaca agcucguauu acguguuuua caucuacgua   2760

ggaguggccg acacucugcu cgcgaugggu uucuuccgag gacucccacu cguucacacg   2820

cuuaucacug ucuccaagau ucuccaccau aagaugcuuc auagcguacu gcaggcuccc   2880

auguccaccu ugaauacgcu caaggcggga gguauuuuga aucgcuucuc aaaagauauu   2940

gcaauuuugg augaccuucu gccccugacg aucuucgacu ucauccaguu guugcugauc   3000

gugauugggg cuauugcagu agucgcuguc cuccagccuu acauuuuugu cgcgaccguu   3060

ccggugaucg uggcguuuau caugcugcgg gccuauuucu ugcagacguc acagcagcuu   3120

aagcaacugg agucugaagg gaggucgccu aucuuuacgc aucuugugac caguuugaag   3180

ggauugugga cguugcgcgc cuuuggcagg cagcccuacu uugaaacacu guuccacaaa   3240

gcgcugaauc uccauacggc aaauugguuu uuguauuuga guacccuccg augguuucag   3300

augcgcauug agaugauuuu ugugaucuuc uuuaucgcgg ugacuuuuau cuccaucuug   3360

accacgggag agggcgaggg acgggucggu auuauccuga cacucgccau gaacauuaug   3420

agcacuuugc agugggcagu gaacagcucg auugaugugg auagccugau gagguccguu   3480

ucgagggucu uuaaguucau cgacaugccg acggagggaa agcccacaaa aaguacgaaa   3540

cccuauaaga augggcaauu gaguaaggua augaucaucg agaacaguca cgugaagaag   3600

gaugacaucu ggccuagcgg gggucagaug accgugaagg accugacggc aaaauacacc   3660

gagggaggga acgcaauccu ugaaaacauc ucguucagca uuagccccgg ucagcgugug   3720

ggguugcucg ggaggaccgg gucaggaaaa ucgacguugc ugucggccuu cuugagacuu   3780

cugaauacag agggugagau ccagaucgac ggcguuucgu gggauagcau caccuugcag   3840

caguggcgga aagcguuugg aguaaucccc caaaaggucu uuaucuuuag cggaaccuuc   3900

cgaaagaauc ucgauccuua ugaacagugg ucagaucaag agauuuggaa agucgcggac   3960

gagguuggcc uucggagugu aaucgagcag uuuccgggaa aacucgacuu uguccuugua   4020

gaugggggau gcguccuguc gcaugggcac aagcagcuca ugugccuggc gcgauccguc   4080

cucucuaaag cgaaaauucu ucucuuggau gaaccuucgg cccaucugga cccgguaacg   4140

uaucagauca ucagaaggac acuuaagcag gcguuugccg acugcacggu gauucucugu   4200

gagcaucgua ucgaggccau gcucgaaugc cagcaauuuc uugucaucga agagaauaag   4260

guccgccagu acgacuccau ccagaagcug cuuaaugaga gaucauuguu ccggcaggcg   4320

auuucaccau ccgauagggu gaaacuuuuu ccacacagaa auucgucgaa gugcaagucc   4380

aaaccgcaga ucgcggccuu gaaagaagag acugaagaag aaguucaaga cacgcgucuu   4440

uaa                                                                 4443
```

<210> SEQ ID NO 3
<211> LENGTH: 1480
<212> TYPE: PRT
<213> ORGANISM: Homo sapiens

<400> SEQUENCE: 3

-continued

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
```

```
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845
```

-continued

```
Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                1005

Ala Val  Leu Gln Pro Tyr Ile  Phe Val Ala Thr Val  Pro Val Ile
    1010                1015                1020

Val Ala  Phe Ile Met Leu Arg  Ala Tyr Phe Leu Gln  Thr Ser Gln
    1025                1030                1035

Gln Leu  Lys Gln Leu Glu Ser  Glu Gly Arg Ser Pro  Ile Phe Thr
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095

Phe Gln  Met Arg Ile Glu Met  Ile Phe Val Ile Phe  Phe Ile Ala
    1100                1105                1110

Val Thr  Phe Ile Ser Ile Leu  Thr Thr Gly Glu Gly  Glu Gly Arg
    1115                1120                1125

Val Gly  Ile Ile Leu Thr Leu  Ala Met Asn Ile Met  Ser Thr Leu
    1130                1135                1140

Gln Trp  Ala Val Asn Ser Ser  Ile Asp Val Asp Ser  Leu Met Arg
    1145                1150                1155

Ser Val  Ser Arg Val Phe Lys  Phe Ile Asp Met Pro  Thr Glu Gly
    1160                1165                1170

Lys Pro  Thr Lys Ser Thr Lys  Pro Tyr Lys Asn Gly  Gln Leu Ser
    1175                1180                1185

Lys Val  Met Ile Ile Glu Asn  Ser His Val Lys Lys  Asp Asp Ile
    1190                1195                1200

Trp Pro  Ser Gly Gly Gln Met  Thr Val Lys Asp Leu  Thr Ala Lys
    1205                1210                1215

Tyr Thr  Glu Gly Gly Asn Ala  Ile Leu Glu Asn Ile  Ser Phe Ser
    1220                1225                1230

Ile Ser  Pro Gly Gln Arg Val  Gly Leu Leu Gly Arg  Thr Gly Ser
    1235                1240                1245
```

```
Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 4
<211> LENGTH: 140
<212> TYPE: RNA
<213> ORGANISM: Artificial Sequence
<220> FEATURE:
<223> OTHER INFORMATION: chemically synthesized oligonucleotide

<400> SEQUENCE: 4

```
ggacagaucg ccuggagacg ccauccacgc uguuuugacc uccauagaag acaccgggac     60

cgauccagcc uccgcggccg ggaacggugc auuggaacgc ggauuccccg ugccaagagu    120

gacucaccgu ccuugacacg                                                140
```

<210> SEQ ID NO 5
<211> LENGTH: 105
<212> TYPE: RNA
<213> ORGANISM: Artificial Sequence
<220> FEATURE:
<223> OTHER INFORMATION: chemically synthesized oligonucleotide

<400> SEQUENCE: 5

```
cggguggcau cccugugacc ccuccccagu gccucuccug gcccuggaag uugccacucc     60

agugcccacc agccuugucc uaauaaaauu aaguugcauc aagcu                    105
```

<210> SEQ ID NO 6
<211> LENGTH: 105
<212> TYPE: RNA
<213> ORGANISM: Artificial Sequence
<220> FEATURE:
<223> OTHER INFORMATION: chemically synthesized oligonucleotide

<400> SEQUENCE: 6 gggugggcauc ccugugaccc cuccccagug ccucuccugg cccuggaagu ugccacucca 60
gugcccacca gccuuguccu aauaaaauua aguugcauca aagcu 105

<210> SEQ ID NO 7
<211> LENGTH: 4688
<212> TYPE: RNA
<213> ORGANISM: Artificial Sequence
<220> FEATURE:
<223> OTHER INFORMATION: chemically synthesized oligonucleotide

<400> SEQUENCE: 7
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcaacgcu cuccucuuga aaaggccucg guggugucca 180
agcucuucuu cucguggacu agacccaucc ugagaaaggg guacagacag cgcuuggagc 240
uguccgauau cuaucaaauc ccuuccgugg acuccgcgga caaccugucc gagaagcucg 300
agagagaaug ggacagagaa cucgccucaa agaagaaccc gaagcugauu aaugcgcuua 360
ggcggugcuu uuucuggcgg uucauguucu acggcaucuu ccucuaccug ggagagguca 420
ccaaggccgu gcagccccug uugcugggac ggauuauugc cuccuacgac cccgacaaca 480
aggaagaaag aagcaucgcu aucuacuugg gcaucggucu gugccugcuu uucaucgucc 540
ggacccucuu guugcauccu gcuauuuucg gccugcauca cauuggcaug cagaugagaa 600
uugccauguu uucccugauc uacaagaaaa cucugaagcu cucgagccgc gugcuugaca 660
agauuuccau cggccagcuc guguccccugc ucuccaacaa ucugaacaag uucgacgagg 720
gccucgcccu ggcccacuuc guguggaucg ccccucugca aguggcgcuu cugaugggcc 780
ugaucuggga gcugcugcaa gccucggcau ucugugggcu uggauuccug aucgugcugg 840
cacuguucca ggccggacug ggcggaauga ugaugaagua cagggaccag agagccggaa 900
agauuuccga acggcuggug aucacuucgg aaaugaucga aaacauccag ucagugaagg 960
ccuacugcug ggaagaggcc auggaaaaga ugauugaaaa ccuccggcaa accgagcuga 1020
agcugacccg caaggccgcu uacgugcgcu auuucaacuc guccgcuuuc uucuucuccg 1080
gguucuucgu gguguuucuc uccgugcucc ccuacgcccu gauuaaggga aucauccuca 1140
ggaagaucuu caccaccauu uccuucugua ucgugcuccg cauggccgug acccggcagu 1200
ucccaugggc cgugcagacu ugguacgacu cccugggagc cauuaacaag auccaggacu 1260
uccuucaaaa gcaggaguac aagacccucg aguacaaccu gacuacuacc gaggucguga 1320
uggaaaacgu caccgccuuu ugggaggagg gauuuggcga acuguucgag aaggccaagc 1380
agaacaacaa caaccgcaag accucgaacg gugacgacuc ccucuucuuu ucaaacuuca 1440
gccugcucgg gacgcccgug cugaaggaca uuaacuucaa gaucgaaaga ggacagcucc 1500 uggcggugggc cggaucgacc ggagccggaa agacuucccu gcugauggug aucaugggag 1560
agcuugaacc uagcgaggga aagaucaagc acuccggccg caucagcuuc uguagccagu 1620
uuuccuggau caugcccgga accauuaagg aaaacaucau cuucggcgug uccuacgaug 1680

-continued

```
aauaccgcua ccgguccgug aucaaagccu gccagcugga agaggauauu ucaaaguucg   1740
cggagaaaga uaacaucgug cugggcgaag gggguauuac cuugucgggg ggccagcggg   1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gaggggcucu ccuacuuuua cggcaccuuc ucggaguugc   2040
agaacuugca gcccgacuuc ucaucgaagc ugauggguug cgacagcuuc gaccaguucu   2100
ccgccgaaag aaggaacucg auccugacgg aaaccuugca ccgcuucucu uuggaaggcg   2160
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuuccg   2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520
ugucccuggc accucaagcg aaucuuaccg agcucgacau cuacucccgg agacugucgc   2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acuggugguug cucuggcugu ugggaaacac gccucugcaa gacaagggaa   2820
acuccacgca cucgagaaac aacagcuaug ccgugauuau cacuuccacc uccucuuauu   2880
acguguucua caucuacguc ggaguggcgg auacccugcu cgcgaugggu uucuucagag   2940
gacugccgcu gguccacacc uugaucaccg ucagcaagau ucuucaccac aagauguugc   3000
auagcgugcu gcaggccccc auguccaccc ucaacacucu gaaggccgga ggcauucuga   3060
acagauucuc caaggacauc gcuauccugg acgaucuccu gccgcuuacc aucuuugacu   3120
ucauccagcu gcugcugauc gugauuggag caaucgcagu gguggcggug cugcagccuu   3180
acauuuucgu ggccacugug ccggucauug uggcguucau caugcugcgg gccuacuucc   3240
uccaaaccag ccagcagcug aagcaacugg aauccgaggg acgauccccc aucuucacuc   3300
accuugugac gucguugaag ggacugugga cccuccgggc uuucggacgg cagcccuacu   3360
ucgaaacccu cuuccacaag gcccugaacc uccacaccgc caauugguuc cuguaccugu   3420
ccacccugcg gugguuccag augcgcaucg agaugauuuu cgucaucuuc uucaucgcgg   3480
ucacauucau cagcauccug acuaccggag agggagaggg acgggucgga auaauccuga   3540
cccucgccau gaacauuaug agcacccugc agugggcagu gaacagcucg aucgacgugg   3600
acagccugau gcgaagcguc agccgcgugu ucaaguucau cgacaugccu acugagggaa   3660
aacccacuaa guccacuaag cccuacaaaa auggccagcu gagcaagguc augaucaucg   3720
aaaacuccca cgugaagaag gacgauauuu ggcccuccgg aggucaaaug accgugaagg   3780
accugaccgc aaaguacacc gagggaggaa acgccauucu cgaaaacauc agcuucucca   3840
uuucgccggg acagcggguc ggccuucucg ggcggaccgg uuccgggaag ucaacucugc   3900
ugucggcuuu ccuccggcug cugaauaccg agggggaaau ccaaauugac ggcgugucuu   3960
gggauuccau uacucugcag caguggcgga aggccuucgg cgugaucccc cagaaggugu   4020
ucaucuucuc ggguaccuuc cggaagaacc uggauccuua cgagcagugg agcgaccaag   4080
```

```
aaaucuggaa ggucgccgac gaggucggcc ugcgcuccgu gauugaacaa uuuccuggaa   4140

agcuggacuu cgugcucguc gacgggggau guguccuguc gcacggacau aagcagcuca   4200

ugugccucgc acgguccgug cucuccaagg ccaagauucu gcugcuggac gaaccuucgg   4260

cccaccugga uccggucacc uaccagauca ucaggaggac ccugaagcag gccuuugccg   4320

auugcaccgu gauucucugc gagcaccgca ucgaggccau gcuggagugc cagcaguucc   4380

uggucaucga ggagaacaag guccgccaau acgacuccau ucaaaagcuc cucaacgagc   4440

ggucgcuguu cagacaagcu auuucaccgu ccgauagagu gaagcucuuc ccgcaucgga   4500

acagcucaaa gugcaaaucg aagccgcaga ucgcagccuu gaaggaagag acugaggaag   4560

aggugcagga cacccggcuu uaacgggugg caucccugug accccucccc agugccucuc   4620

cuggcccugg aaguugccac uccagugccc accagccuug uccuaauaaa auuaaguugc   4680

aucaagcu                                                            4688
```

<210> SEQ ID NO 8
<211> LENGTH: 4688
<212> TYPE: RNA
<213> ORGANISM: Artificial Sequence
<220> FEATURE:
<223> OTHER INFORMATION: chemically synthesized oligonucleotide

<400> SEQUENCE: 8

```
ggacagaucg ccuggagacg ccauccacgc uguuuugacc uccauagaag acaccgggac     60

cgauccagcc uccgcggccg ggaacggugc auuggaacgc ggauuccccg ugccaagagu    120

gacucaccgu ccuugacacg augcaacgcu cuccucuuga aaaggccucg guggugucca    180

agcucuucuu cucguggacu agacccaucc ugagaaaggg guacagacag cgcuuggagc    240

uguccgauau cuaucaaauc ccuuccgugg acuccgcgga caaccugucc gagaagcucg    300

agagagaaug ggacagagaa cucgccucaa agaagaaccc gaagcugauu aaugcgcuua    360

ggcggugcuu uuucuggcgg uucauguucu acggcaucuu ccucuaccug ggagagguca    420

ccaaggccgu gcagccccug uugcugggac ggauuauugc cuccuacgac cccgacaaca    480

aggaagaaag aagcaucgcu aucuacuugg gcaucggucu gugccugcuu uucaucgucc    540

ggacccucuu guugcauccu gcuauuuucg gccugcauca cauuggcaug cagaugagaa    600

uugccauguu uucccugauc uacaagaaaa cucugaagcu cucgagccgc gugcuugaca    660

agauuuccau cggccagcuc guguccugc ucuccaacaa ucugaacaag uucgacgagg    720

gccucgcccu ggcccacuuc guguggaucg ccccucugca aguggcgcuu cugaugggcc    780

ugaucuggga gcugcugcaa gccucggcau ucugugggcu uggauuccug aucgugcugg    840

cacuguucca ggccggacug ggcggaauga ugaugaagua cagggaccag agagccggaa    900

agauuuccga acggcuggug aucacuucgg aaaugaucga aaacauccag ucagugaagg    960

ccuacugcug ggaagaggcc auggaaaaga ugauugaaaa ccuccggcaa accgagcuga   1020

agcugacccg caaggccgcu uacgugcgcu auuucaacuc guccgcuuuc uucuucuccg   1080

gguucuucgu gguguuucuc uccgugcucc ccuacgcccu gauuaaggga aucauccuca   1140

ggaagaucuu caccaccauu uccuucugua ucgugcuccg cauggccgug acccggcagu   1200

ucccaugggc cgugcagacu ugguacgacu cccugggagc cauuaacaag auccaggacu   1260

uccuucaaaa gcaggaguac aagacccucg aguacaaccu gacuacuacc gaggucguga   1320

uggaaaacgu caccgccuuu ugggaggagg gauuuggcga acuguucgag aaggccaagc   1380
```

-continued agaacaacaa caaccgcaag accucgaacg gugacgacuc ccucuucuuu ucaaacuuca 1440
gccugcucgg gacgcccgug cugaaggaca uuaacuucaa gaucgaaaga ggacagcucc 1500
uggcggugge cggaucgacc ggagccggaa agacuucccu gcugauggug aucaugggag 1560
agcuugaacc uagcgaggga aagaucaagc acuccggccg caucagcuuc uguagccagu 1620
uuuccuggau caugcccgga accauuaagg aaaacaucau cuucggcgug uccuacgaug 1680
aauaccgcua ccgguccgug aucaaagccu gccagcugga agaggauauu ucaaaguucg 1740
cggagaaaga uaacaucgug cugggcgaag ggggauauac cuugucgggg ggccagcggg 1800
cuagaaucuc gcuggccaga gccguguaua aggacgccga ccuguaucuc cuggacuccc 1860
ccuucggaua ccuggacguc cugaccgaaa aggagaucuu cgaaucgugc gugugcaagc 1920
ugauggcuaa caagacucgc auccucguga ccuccaaaau ggagcaccug aagaaggcag 1980
acaagauucu gauucugcau gagggggucc ccuacuuuua cggcaccuuc ucggaguugc 2040
agaacuugca gcccgacuuc ucaucgaagc ugaugggguug cgacagcuuc gaccaguucu 2100
ccgccgaaag aaggaacucg auccugacgg aaaccuugca ccgcuucucu uuggaaggcg 2160
acgccccugu gucauggacc gagacuaaga agcagagcuu caagcagacc ggggaauucg 2220
gcgaaaagag gaagaacagc aucuugaacc ccauuaacuc cauccgcaag uucucaaucg 2280
ugcaaaagac gccacugcag augaacggca uugaggagga cuccgacgaa ccccuugaga 2340
ggcgccuguc ccuggugccg gacagcgagc agggagaagc cauccugccu cggauuuccg 2400
ugaucuccac ugguccgacg cuccaagccc ggcggcggca guccgugcug aaccugauga 2460
cccacagcgu gaaccagggc caaaacauuc accgcaagac uaccgcaucc acccggaaag 2520
ugucccuggc accucaagcg aaucuuaccg agcucgacau cuacucccgg agacugucgc 2580
aggaaaccgg gcucgaaauu uccgaagaaa ucaacgagga ggaucugaaa gagugcuucu 2640
ucgacgauau ggagucgaua cccgccguga cgacuuggaa cacuuaucug cgguacauca 2700
cugugcacaa gucauugauc uucgugcuga uuuggugccu ggugauuuuc cuggccgagg 2760
ucgcggccuc acugguggug cucuggcugu ugggaaacac gccucugcaa gacaagggaa 2820
acuccacgca cucgagaaac aacagcuaug ccgugauuau cacuuccacc uccucuuauu 2880
acguguucua caucuacguc ggaguggcgg auacccugcu cgcgaugggu uucuucagag 2940
gacugccgcu gguccacacc uugaucaccg ucagcaagau ucuucaccac aagauguugc 3000
auagcgugcu gcaggccccc auguccaccc ucaacacucu gaaggccgga ggcauucuga 3060
acagauucuc caaggacauc gcuauccugg acgaucuccu gccgcuuacc aucuuugacu 3120
ucauccagcu gcugcugauc gugauuggag caaucgcagu gguggcggug cugcagccuu 3180
acauuuucgu ggccacugug ccggucauug uggcguucau caugcugcgg gccuacuucc 3240
uccaaaccag ccagcagcug aagcaacugg aauccgaggg acgaucccccc aucuucacuc 3300
accuugugac gucguugaag ggacugugga cccuccgggc uuucggacgg cagcccuacu 3360
ucgaaacccu cuuccacaag gcccugaacc uccacaccgc caauugguuc cuguaccugu 3420
ccacccugcg gugguuccag augcgcaucg agaugauuuu cgucaucuuc uucaucgcgg 3480
ucacauucau cagcauccug acuaccggag agggagaggg acgggucgga auaauccuga 3540
cccucgccau gaacauuaug agcacccugc agugggcagu gaacagcucg aucgacgugg 3600
acagccugau gcgaagcguc agccgcgugu ucaaguucau cgacaugccu acugagggaa 3660
aacccacuaa guccacuaag cccuacaaaa auggccagcu gagcaagguc augaucaucg 3720
aaaacuccca cgugaagaag gacgauauuu ggcccuccgg aggucaaaug accgugaagg 3780

-continued

```
accugaccgc aaaguacacc gagggaggaa acgccauucu cgaaaacauc agcuucucca   3840

uuucgccggg acagcggguc ggccuucucg ggcggaccgg uuccgggaag ucaacucugc   3900

ugucggcuuu ccuccggcug cugaauaccg agggggaaau ccaaauugac ggcgugucuu   3960

gggauuccau uacucugcag caguggcgga aggccuucgg cgugaucccc cagaaggugu   4020

ucaucuucuc ggguaccuuc cggaagaacc uggauccuua cgagcagugg agcgaccaag   4080

aaaucuggaa ggucgccgac gaggucggcc ugcgcuccgu gauugaacaa uuuccuggaa   4140

agcuggacuu cgugcucguc gacgggggau guguccuguc gcacggacau aagcagcuca   4200

ugugccucgc acgguccgug cucuccaagg ccaagauucu gcugcuggac gaaccuucgg   4260

cccaccugga uccggucacc uaccagauca ucaggaggac ccugaagcag gccuuugccg   4320

auugcaccgu gauucucugc gagcaccgca ucgaggccau gcuggagugc cagcaguucc   4380

uggucaucga ggagaacaag guccgccaau acgacuccau ucaaaagcuc cucaacgagc   4440

ggucgcuguu cagacaagcu auuucaccgu ccgauagagu gaagcucuuc ccgcaucgga   4500

acagcucaaa gugcaaaucg aagccgcaga ucgcagccuu gaaggaagag acugaggaag   4560

aggugcagga cacccggcuu uaagggugge aucccuguga ccccuccccca gugccucucc   4620

uggcccugga aguugccacu ccagugccca ccagccuugu ccuaauaaaa uuaaguugca   4680

ucaaagcu                                                            4688
```

<210> SEQ ID NO 9
<211> LENGTH: 874
<212> TYPE: PRT
<213> ORGANISM: Bacteriophage SP6

<400> SEQUENCE: 9

```
Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
            20                  25                  30

Ala Gly Ser Glu Ser Asp Thr Ala Trp Asn Arg Arg Leu Leu Ser Glu
        35                  40                  45

Leu Ile Ala Pro Met Ala Glu Gly Ile Gln Ala Tyr Lys Glu Glu Tyr
    50                  55                  60

Glu Gly Lys Lys Gly Arg Ala Pro Arg Ala Leu Ala Phe Leu Gln Cys
65                  70                  75                  80

Val Glu Asn Glu Val Ala Ala Tyr Ile Thr Met Lys Val Val Met Asp
                85                  90                  95

Met Leu Asn Thr Asp Ala Thr Leu Gln Ala Ile Ala Met Ser Val Ala
            100                 105                 110

Glu Arg Ile Glu Asp Gln Val Arg Phe Ser Lys Leu Glu Gly His Ala
        115                 120                 125

Ala Lys Tyr Phe Glu Lys Val Lys Lys Ser Leu Lys Ala Ser Arg Thr
    130                 135                 140

Lys Ser Tyr Arg His Ala His Asn Val Ala Val Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205
```

-continued

```
Tyr Gly Gly Lys Thr Ile Tyr Tyr Leu Gln Thr Ser Glu Ser Val Gly
    210                 215                 220

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
            260                 265                 270

Gly Asn Arg Glu His Val Arg Lys Leu Thr Gln Lys Gln Met Pro Lys
        275                 280                 285

Val Tyr Lys Ala Ile Asn Ala Leu Gln Asn Thr Gln Trp Gln Ile Asn
    290                 295                 300

Lys Asp Val Leu Ala Val Ile Glu Glu Val Ile Arg Leu Asp Leu Gly
305                 310                 315                 320

Tyr Gly Val Pro Ser Phe Lys Pro Leu Ile Asp Lys Glu Asn Lys Pro
                325                 330                 335

Ala Asn Pro Val Pro Val Glu Phe Gln His Leu Arg Gly Arg Glu Leu
            340                 345                 350

Lys Glu Met Leu Ser Pro Glu Gln Trp Gln Gln Phe Ile Asn Trp Lys
        355                 360                 365

Gly Glu Cys Ala Arg Leu Tyr Thr Ala Glu Thr Lys Arg Gly Ser Lys
    370                 375                 380

Ser Ala Ala Val Val Arg Met Val Gly Gln Ala Arg Lys Tyr Ser Ala
385                 390                 395                 400

Phe Glu Ser Ile Tyr Phe Val Tyr Ala Met Asp Ser Arg Ser Arg Val
                405                 410                 415

Tyr Val Gln Ser Ser Thr Leu Ser Pro Gln Ser Asn Asp Leu Gly Lys
            420                 425                 430

Ala Leu Leu Arg Phe Thr Glu Gly Arg Pro Val Asn Gly Val Glu Ala
        435                 440                 445

Leu Lys Trp Phe Cys Ile Asn Gly Ala Asn Leu Trp Gly Trp Asp Lys
    450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Glu Phe Leu Ala Trp Cys Phe Glu Tyr
            500                 505                 510

Ala Gln Tyr Leu Asp Leu Val Asp Glu Gly Arg Ala Asp Glu Phe Arg
        515                 520                 525

Thr His Leu Pro Val His Gln Asp Gly Ser Cys Ser Gly Ile Gln His
    530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Lys Lys Asn Ala Leu Tyr Met Asp Ala Asp Asp Ala Thr Thr
            580                 585                 590

Phe Thr Ser Gly Ser Val Thr Leu Ser Gly Thr Glu Leu Arg Ala Met
        595                 600                 605

Ala Ser Ala Trp Asp Ser Ile Gly Ile Thr Arg Ser Leu Thr Lys Lys
    610                 615                 620
```

-continued

```
Pro Val Met Thr Leu Pro Tyr Gly Ser Thr Arg Leu Thr Cys Arg Glu
625                 630                 635                 640

Ser Val Ile Asp Tyr Ile Val Asp Leu Glu Glu Lys Glu Ala Gln Lys
                645                 650                 655

Ala Val Ala Glu Gly Arg Thr Ala Asn Lys Val His Pro Phe Glu Asp
            660                 665                 670

Asp Arg Gln Asp Tyr Leu Thr Pro Gly Ala Ala Tyr Asn Tyr Met Thr
        675                 680                 685

Ala Leu Ile Trp Pro Ser Ile Ser Glu Val Val Lys Ala Pro Ile Val
    690                 695                 700

Ala Met Lys Met Ile Arg Gln Leu Ala Arg Phe Ala Ala Lys Arg Asn
705                 710                 715                 720

Glu Gly Leu Met Tyr Thr Leu Pro Thr Gly Phe Ile Leu Glu Gln Lys
                725                 730                 735

Ile Met Ala Thr Glu Met Leu Arg Val Arg Thr Cys Leu Met Gly Asp
            740                 745                 750

Ile Lys Met Ser Leu Gln Val Glu Thr Asp Ile Val Asp Glu Ala Ala
        755                 760                 765

Met Met Gly Ala Ala Ala Pro Asn Phe Val His Gly His Asp Ala Ser
    770                 775                 780

His Leu Ile Leu Thr Val Cys Glu Leu Val Asp Lys Gly Val Thr Ser
785                 790                 795                 800

Ile Ala Val Ile His Asp Ser Phe Gly Thr His Ala Asp Asn Thr Leu
                805                 810                 815

Thr Leu Arg Val Ala Leu Lys Gly Gln Met Val Ala Met Tyr Ile Asp
            820                 825                 830

Gly Asn Ala Leu Gln Lys Leu Leu Glu Glu His Glu Val Arg Trp Met
        835                 840                 845

Val Asp Thr Gly Ile Glu Val Pro Glu Gln Gly Glu Phe Asp Leu Asn
    850                 855                 860

Glu Ile Met Asp Ser Glu Tyr Val Phe Ala
865                 870


<210> SEQ ID NO 10
<211> LENGTH: 18
<212> TYPE: DNA
<213> ORGANISM: Artificial Sequence
<220> FEATURE:
<223> OTHER INFORMATION: chemically synthesized oligonucleotide

<400> SEQUENCE: 10

atttaggtga cactatag                                                   18


<210> SEQ ID NO 11
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 11

atttagggga cactatagaa gag                                             23


<210> SEQ ID NO 12
<211> LENGTH: 22
<212> TYPE: DNA
<213> ORGANISM: Artificial Sequence
<220> FEATURE:
<223> OTHER INFORMATION: chemically synthesized oligonucleotide
```

-continued

<400> SEQUENCE: 12
atttagggga cactatagaa gg 22

<210> SEQ ID NO 13
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 13
atttagggga cactatagaa ggg 23

<210> SEQ ID NO 14
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 14
atttaggtga cactatagaa 20

<210> SEQ ID NO 15
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 15
atttaggtga cactatagaa ga 22

<210> SEQ ID NO 16
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 16
atttaggtga cactatagaa gag 23

<210> SEQ ID NO 17
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 17
atttaggtga cactatagaa gg 22

<210> SEQ ID NO 18
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 18
atttaggtga cactatagaa ggg 23

<210> SEQ ID NO 19

<211> LENGTH: 23
<212> TYPE: DNA
<213> ORGANISM: Artificial Sequence
<220> FEATURE:
<223> OTHER INFORMATION: chemically synthesized oligonucleotide
<220> FEATURE:
<221> NAME/KEY: misc_feature
<222> LOCATION: (22)..(22)
<223> OTHER INFORMATION: n is a, c, g, or t

<400> SEQUENCE: 19
atttaggtga cactatagaa gng 23

<210> SEQ ID NO 20
<211> LENGTH: 24
<212> TYPE: DNA
<213> ORGANISM: Artificial Sequence
<220> FEATURE:
<223> OTHER INFORMATION: chemically synthesized oligonucleotide

<400> SEQUENCE: 20
catacgattt aggtgacact atag 24

<210> SEQ ID NO 21
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 21
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg ggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc caattaacag tattcgcaag ttcagcattg tccagaagac acccctccag 2160
atgaatggca tcgaagaaga tagtgacgag ccgctggaga gacggctgag tctggtgcca 2220
gattcagaac agggggaggc catcctgccc cggatcagcg tcatttccac aggccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gctggaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttattttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct cccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 22
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 22
atgcagagga gcccactgga gaaagcctcc gtggtgagta aactcttttt tagttggacc 60
agacccatcc tgcgaaaagg atacaggcag cgcctcgagt tgtctgatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggcaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggcttttttg attgtactgg cactttttca ggctgggctc 720
ggaagaatga tgatgaaata cagagatcag cgggccggga agatttcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg gggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc caattaacag tattcgcaag ttcagcattg tccagaagac acccctccag 2160
atgaatggca tcgaagaaga tagtgacgag ccgctggaga gacggctgag tctggtgcca 2220
gattcagaac agggggaggc catcctgccc cggatcagcg tcatttccac aggccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gctggaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttattttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct cccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600

-continued

```
gatgacattt ggcccagcgg gggccagatg actgtgaagg acctgacggc caagtacacc   3660

gaaggtggaa atgccatttt ggaaaacatc agcttctcaa tctctcctgg gcagagagtt   3720

ggattgctgg gtcgcacggg cagcggcaaa tcaaccctgc tcagtgcctt ccttcggctc   3780

ctgaatacag aaggcgaaat ccaaattgac ggggtgagct gggacagcat caccctgcag   3840

cagtggagaa aagcatttgg ggtcattcca cagaaagttt tcatcttctc tggcactttc   3900

agaaagaacc tggaccccta tgagcagtgg agcgaccagg agatctggaa ggttgcagat   3960

gaagttggcc tgcggagtgt gatagaacaa tttcctggca agctggattt tgtgctggta   4020

gatggaggct gcgtgctgtc ccacggccac aaacagctga tgtgcctcgc ccgctccgtt   4080

ctttcaaagg ccaaaatctt gcttttggat gagcccagtg ctcaccttga cccagtgacc   4140

tatcagataa tccgcaggac cttaaagcaa gcttttgccg actgcaccgt catactgtgt   4200

gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

<210> SEQ ID NO 23
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 23

```
atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg ggggaggtca ccaaagctgt tcagccgctc    300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggctttttg attgtactgg cactttttca ggctgggctc    720

ggaagaatga tgatgaaata cagagatcag cgggccggga agatatcaga gcgacttgtg    780

atcaccagtg aaatgattga aaatattcag agcgtgaaag cctactgctg ggaagaagcc    840

atggagaaga tgattgagaa cctgaggcag acagagctca agctcactcg gaaggctgct    900

tatgttcgct atttcaacag cagcgccttc ttcttcagtg gcttctttgt tgtcttcctg    960

tctgttctgc catatgcact gataaaaggc attattttac gaaagatctt caccaccatc   1020

agtttttgca tcgttctcag gatggccgtc acaagacagt tcccctgggc tgtgcagacc   1080

tggtacgatt ccttgggggc catcaacaag attcaagatt tcttgcaaaa acaagaatat   1140

aaaactttag aatacaacct caccaccact gaagtggtca tggaaaatgt gacagccttt   1200
```

-continued

```
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtacaca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct cccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
```

```
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcaccttga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                 4443
```

<210> SEQ ID NO 24
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 24

```
atgcagagga gcccactgga gaaagcctcc gtggtgagta aactcttttt tagttggacc     60
agacccatcc tgcgaaaagg atacaggcag cgcctcgagt tgtcagatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
```

-continued

```
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg    1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct cccccctgaca atctttgact ttatccagct tctgctgatc  3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
```

```
tcccgggtgt ttaaattcat tgatatgcca actgagggga aacccaccaa gtcaacaaaa   3540

ccttataaga atggacagct gagcaaggtg atgataattg agaacagcca cgtgaagaag   3600

gatgacattt ggcccagcgg gggccagatg actgtgaagg acctgacggc caagtacacc   3660

gaaggtggaa atgccatttt ggaaaacatc agcttctcaa tctctcctgg gcagagagtt   3720

ggattgctgg gtcgcacggg cagcggcaaa tcaaccctgc tcagtgcctt ccttcggctc   3780

ctgaatacag aaggcgaaat ccaaattgac ggggtgagct gggacagcat caccctgcag   3840

cagtggagaa aagcatttgg ggtcattcca cagaaagttt tcatcttctc tggcactttc   3900

agaaagaacc tggaccccta tgagcagtgg agcgaccagg agatctggaa ggttgcagat   3960

gaagttggcc tgcggagtgt gatagaacaa tttcctggca agctggattt tgtgctggta   4020

gatggaggct gcgtgctgtc ccacggccac aaacagctga tgtgcctcgc ccgctccgtt   4080

ctttcaaagg ccaaaatctt gcttttggat gagcccagtg ctcacctcga cccagtgacc   4140

tatcagataa tccgcaggac cttaaagcaa gcttttgccg actgcaccgt catactgtgt   4200

gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

<210> SEQ ID NO 25
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 25

```
atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg ggggaggtca ccaaagctgt tcagccgctc    300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggctttttg attgtactgg cactttttca ggctgggctc    720

ggaagaatga tgatgaaata cagagatcag cgggccggga agatatcaga gcgacttgtg    780

atcaccagtg aaatgattga aaatattcag agcgtgaaag cctactgctg ggaagaagcc    840

atggagaaga tgattgagaa cctgaggcag acagagctca agctcactcg gaaggctgct    900

tatgttcgct atttcaacag cagcgccttc ttcttcagtg gcttctttgt tgtcttcctg    960

tctgttctgc catatgcact gataaaaggc attattttac gaaagatctt caccaccatc   1020

agtttttgca tcgttctcag gatggccgtc acaagacagt tcccctgggc tgtgcagacc   1080
```

-continued tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg ggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc ctattaacag tattcgcaag ttcagcattg tccagaagac accccctccag 2160
atgaatggca tcgaagaaga tagtgacgag ccgctggaga gacggctgag tctggtgcca 2220
gattcagaac agggggaggc catcctgccc cggatcagcg tcatttccac aggccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gcttgaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttatttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420

-continued

```
tccaccttgc agtgggccgt gaattccagt atagatgtgg attctctaat gaggagtgtc   3480

tcccgggtgt ttaaattcat tgatatgcct actgagggga aacccaccaa gtcaacaaaa   3540

ccttataaga atggacagct gagcaaggtg atgataattg agaacagcca cgtgaagaag   3600

gatgacattt ggcccagcgg gggccagatg actgtgaagg acctgacggc caagtacacc   3660

gaaggtggaa atgccatttt ggaaaacatc agcttctcaa tctctcctgg gcagagagtt   3720

ggattgctgg gtcgcacggg cagcggcaaa tcaaccctgc tcagtgcctt ccttcggctc   3780

ctgaatacag aaggcgaaat ccaaattgac ggggtgagct gggacagcat caccctgcag   3840

cagtggagaa aagcatttgg ggtcattcca cagaaagttt tcatcttctc tggcactttc   3900

agaaagaacc tggaccccta tgagcagtgg agcgaccagg agatctggaa ggttgcagat   3960

gaagttggcc tgcggagtgt gatagaacaa tttcctggca agctggattt tgtgctggta   4020

gatggaggct gcgtgctgtc ccacggccac aaacagctga tgtgcctcgc ccgctccgtt   4080

ctttcaaagg ccaaaatctt gcttttggat gagcccagtg ctcacctcga cccagtgacc   4140

tatcagataa tccgcaggac cttaaagcaa gcttttgccg actgcaccgt catactgtgt   4200

gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

```
<210> SEQ ID NO 26
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 26

atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg gggggaggtca ccaaagctgt tcagccgctc    300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggctttttg attgtactgg cactttttca ggctgggctc    720

ggaagaatga tgatgaaata cagagatcag cgggccggga agatttcaga gcgacttgtg    780

atcaccagtg aaatgattga aaatattcag agcgtgaaag cctactgctg ggaagaagcc    840

atggagaaga tgattgagaa cctgaggcag acagagctca agctcactcg gaaggctgct    900

tatgttcgct atttcaacag cagcgccttc ttcttcagtg gcttctttgt tgtcttcctg    960

tctgttctgc catatgcact gataaaaggc attattttac gaaagatctt caccaccatc   1020
```

-continued

```
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acattttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
```

```
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcca actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                4443
```

<210> SEQ ID NO 27
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 27

```
atgcagagga gcccactgga gaaagcctcc gtggtgagta aactcttttt tagttggacc     60
agacccatcc tgcgaaaagg atacaggcag cgcctcgagt tgtctgatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggGaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
```

```
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtccgtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac accccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttatttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct cccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
```

-continued atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaag 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 28
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 28
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900

```
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc ctattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtacaca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
```

```
gccctgaact tgcacactgc caactggttt ctttacctga gcacactccg ctggttccag   3300

atgcggatag agatgatctt cgtcatcttt tttatagctg taaccttcat ttctatcctt   3360

acaacaggag aaggagaggg cagggtggga atcatcctca cgctggctat gaacataatg   3420

tccaccttgc agtgggccgt gaattccagt atagatgtgg attctctaat gaggagtgtc   3480

tcccgggtgt ttaaattcat tgatatgcct actgagggga aacccaccaa gtcaacaaaa   3540

ccttataaga atggacagct gagcaaggtg atgataattg agaacagcca cgtgaagaag   3600

gatgacattt ggcccagcgg gggccagatg actgtgaagg acctgacggc caagtacacc   3660

gaaggtggaa atgccatttt ggaaaacatc agcttctcaa tctctcctgg gcagagagtt   3720

ggattgctgg gtcgcacggg cagcggcaaa tcaaccctgc tcagtgcctt ccttcggctc   3780

ctgaatacag aaggcgaaat ccaaattgac ggggtgagct gggacagcat caccctgcag   3840

cagtggagaa aagcatttgg ggtcattcca cagaaagttt tcatcttctc tggcactttc   3900

agaaagaacc tggaccccta tgagcagtgg agcgaccagg agatctggaa ggttgcagat   3960

gaagttggcc tgcggagtgt gatagaacaa tttcctggca agctggattt tgtgctggta   4020

gatggaggct gcgtgctgtc ccacggccac aaacagctga tgtgcctcgc ccgctccgtt   4080

ctttcaaagg ccaaaatctt gcttttggat gagcccagtg ctcacctcga cccagtgacc   4140

tatcagataa tccgcaggac cttaaagcaa gcttttgccg actgcaccgt catactgtgt   4200

gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

<210> SEQ ID NO 29
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 29

```
atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg gggg aggtca ccaaagctgt tcagccgctc    300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggctttttg attgtactgg cactttttca ggctgggctc    720

ggaagaatga tgatgaaata cagagatcag cgggccggga agatatcaga gcgacttgtg    780

atcaccagtg aaatgattga aaatattcag agcgtgaaag cctactgctg ggaagaagcc    840
```

atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg gggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtccgtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc caattaacag tattcgcaag ttcagcattg tccagaagac acccctccag 2160
atgaatggca tcgaagaaga tagtgacgag ccgctggaga gacggctgag tctggtgcca 2220
gattcagaac agggggaggc catcctgccc cggatcagcg tcatttccac aggccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gctggaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttattttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag agtctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 30
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 30
atgcagagga gcccactgga gaaagcctcc gtggtgagta aactcttttt tagttggacc 60
agacccatcc tgcgaaaagg atacaggcag cgcctcgagt tgtctgatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggagaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggcttttttg attgtactgg cactttttca ggctgggctc 720
ggaagaatga tgatgaaata cagagatcag cgggccggga agatttcaga gcgacttgtg 780

-continued atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg gggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc ctattaacag tattcgcaag ttcagcattg tccagaagac acccctccag 2160
atgaatggca tcgaagaaga tagtgacgag ccgctggaga gacggctgag tctggtgcca 2220
gattcagaac agggggaggc catcctgccc cggatcagcg tcatttccac aggccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gctggaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttatttc ctcgctgagg tggcggccag tcttgttgtg 2640
ctctggctgc tgggcaacac tcctctccag gacaagggca atagtacaca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 31
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 31
atgcagagaa gcccccctgga gaaggcctct gtggtgagca agctgttctt cagctggacc 60
agacccatcc tgagaaaggg ctacagacag agactggagc tgtctgacat ctaccagatc 120
ccctctgtgg actctgccga caacctgtct gagaagctgg agagagagtg ggacagagag 180
ctggccagca agaagaaccc caagctgatc aatgccctga gaagatgctt cttctggaga 240
ttcatgttct atggcatctt cctgtacctg ggagaggtga ccaaggccgt gcagcccctg 300
ctgctgggca ggatcattgc cagctatgac cctgacaaca aggaggagag aagcattgcc 360
atctacctgg gcattggcct gtgcctgctg ttcattgtga gaaccctgct gctgcaccct 420
gccatctttg gcctgcacca cattggcatg cagatgagaa ttgccatgtt cagcctgatc 480
tacaagaaga ccctgaagct gagcagcaga gtgctggaca agatcagcat tggccagctg 540
gtgagcctgc tgagcaacaa cctgaacaag tttgatgagg gcctggccct ggcccacttt 600
gtgtggattg ccccccctgca ggtggccctg ctgatgggcc tgatctggga gctgctgcag 660
gcctctgcct tctgtggcct gggcttcctg attgtgctgg ccctgttcca ggccggcctg 720
ggcagaatga tgatgaagta cagagaccag agagccggca agatctctga gagactggtg 780
atcacctctg agatgattga gaacatccag tctgtgaagg cctactgctg ggaggaggcc 840
atggagaaga tgattgagaa cctgagacag acagagctga agctgaccag gaaggccgcc 900
tatgtgagat acttcaacag ctctgccttc ttcttctctg gcttctttgt ggtgttcctg 960
tctgtgctgc cctatgccct gatcaagggc atcatcctga ggaagatctt caccaccatc 1020
agcttctgca ttgtgctgag gatggccgtg accaggcagt tcccctgggc cgtgcagacc 1080
tggtatgaca gcctgggggc catcaacaag atccaggact tcctgcagaa gcaggagtac 1140
aagaccctgg agtacaacct gaccaccaca gaggtggtga tggagaatgt gacagccttc 1200
tgggaggagg gctttggaga gctgtttgag aaggccaagc agaacaacaa caacagaaag 1260
accagcaatg gagatgacag cctgttcttc agcaacttca gcctgctggg cacccctgtg 1320
ctgaaggaca tcaacttcaa gattgagagg ggccagctgc tggccgtggc cggcagcaca 1380
ggagccggca agaccagcct gctgatggtg atcatgggag agctggagcc ctctgagggc 1440
aagatcaagc actctggcag aatcagcttc tgcagccagt tcagctggat catgcctggc 1500
accatcaagg agaacatcat ctttggggtg agctatgatg agtacaggta cagatctgtg 1560
atcaaggcct gccagctgga ggaggacatc tccaagtttg ccgagaagga caacattgtg 1620
ctgggggagg gaggcatcac cctgtctggg ggccagagag ccagaatcag cctggccaga 1680
gccgtgtaca aggatgccga cctgtacctg ctggacagcc cctttggcta cctggatgtg 1740
ctgacagaga aggagatctt tgagagctgt gtgtgcaagc tgatggccaa caagaccagg 1800
atcctggtga ccagcaagat ggagcacctg aagaaggccg acaagatcct gatcctgcat 1860
gagggcagca gctacttcta tggcaccttc tctgagctgc agaacctgca gcctgacttc 1920
agcagcaagc tgatgggctg tgacagcttt gaccagttct ctgctgagag aagaaacagc 1980
atcctgacag agaccctgca caggttcagc ctggaggggg atgcccctgt gagctggaca 2040
gagaccaaga agcagagctt caagcagaca ggagagtttg ggagaagagg gaagaacagc 2100
atcctgaacc ccatcaacag catcaggaag ttcagcattg tgcagaagac ccccctgcag 2160
atgaatggca ttgaggagga ctctgatgag cccctggaga gaagactgag cctggtgcca 2220
gactctgagc agggagaggc catcctgccc aggatctctg tgatcagcac aggccccacc 2280
ctgcaggcca gaagaagaca gtctgtgctg aacctgatga cccactctgt gaaccagggc 2340
cagaatatcc acagaaagac cacagccagc accagaaagg tgagcctggc cccccaggcc 2400
aacctgacag agctggacat ctacagcaga aggctgagcc aggagacagg cctggagatc 2460
tctgaggaga tcaatgagga ggacctgaag gagtgcttct ttgatgacat ggagagcatc 2520
cctgccgtga ccacctggaa cacctacctg agatacatca cagtgcacaa gagcctgatc 2580
tttgtgctga tctggtgcct ggtgatcttc ctggccgagg tggccgccag cctggtggtg 2640
ctgtggctgc tgggcaacac ccccctgcag gacaagggca acagcaccca cagcagaaac 2700
aacagctatg ctgtgatcat caccagcacc agcagctact atgtgttcta catctatgtg 2760
ggagtggctg acaccctgct ggccatgggc ttcttcagag gcctgcccct ggtgcacacc 2820
ctgatcacag tgagcaagat cctgcaccac aagatgctgc actctgtgct gcaggccccc 2880
atgagcaccc tgaacaccct gaaggctgga ggcatcctga acagattcag caaggacatt 2940
gccatcctgg atgacctgct gcccctgacc atctttgact tcatccagct gctgctgatt 3000
gtgattggag ccattgccgt ggtggccgtg ctgcagccct acatctttgt ggccacagtg 3060

-continued cctgtgattg tggccttcat catgctgagg gcctacttcc tgcagaccag ccagcagctg 3120
aagcagctgg agtctgaggg cagaagcccc atcttcaccc acctggtgac cagcctgaag 3180
ggcctgtgga ccctgagggc ctttggcaga cagccctact ttgagaccct gttccacaag 3240
gccctgaacc tgcacacagc caactggttc ctgtacctga gcaccctgag atggttccag 3300
atgaggattg agatgatctt tgtgatcttc ttcattgccg tgaccttcat cagcatcctg 3360
accacagggg agggcgaggg cagagtgggc atcatcctga ccctggccat gaacatcatg 3420
agcaccctgc agtgggccgt gaacagcagc attgatgtgg acagcctgat gagatctgtg 3480
agcagagtgt tcaagttcat tgacatgccc acagagggca agcccaccaa gagcaccaag 3540
ccctacaaga atggccagct gagcaaggtg atgatcattg agaacagcca tgtgaagaag 3600
gatgacatct ggccctctgg aggccagatg acagtgaagg acctgacagc caagtacaca 3660
gaggggggca atgccatcct ggagaacatc agcttcagca tcagccctgg ccagagggtg 3720
ggcctgctgg gcagaacagg ctctggcaag agcaccctgc tgtctgcctt cctgaggctg 3780
ctgaacacag agggagagat ccagattgat ggggtgagct gggacagcat caccctgcag 3840
cagtggagga aggcctttgg ggtgatcccc cagaaggtgt tcatcttctc tggcaccttc 3900
aggaagaacc tggaccccta tgagcagtgg tctgaccagg agatctggaa ggtggccgat 3960
gaggtgggcc tgagatctgt gattgagcag ttccctggca agctggactt tgtgctggtg 4020
gatggaggct gtgtgctgag ccatggccac aagcagctga tgtgcctggc cagatctgtg 4080
ctgagcaagg ccaagatcct gctgctggat gagccctctg cccacctgga ccctgtgacc 4140
taccagatca tcagaagaac cctgaagcag gcctttgccg actgcacagt gatcctgtgt 4200
gagcacagaa ttgaggccat gctggagtgc cagcagttcc tggtgattga ggagaacaag 4260
gtgaggcagt atgacagcat ccagaagctg ctgaatgaga gaagcctgtt cagacaggcc 4320
atcagcccct ctgacagagt gaagctgttc ccccacagga acagcagcaa gtgcaagagc 4380
aagccccaga ttgccgccct gaaggaggag acagaggagg aggtgcagga caccagactg 4440
tga 4443

<210> SEQ ID NO 32
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 32
atgcagagga gcccccctgga gaaggccagc gtggtgagca agctgttctt cagctggacc 60
aggcccatcc tgaggaaggg ctacaggcag aggctggagc tgagcgacat ctaccagatc 120
cccagcgtgg acagcgccga caacctgagc gagaagctgg agagggagtg ggacagggag 180
ctggccagca agaagaaccc caagctgatc aacgccctga ggaggtgctt cttctggagg 240
ttcatgttct acggcatctt cctgtacctg ggcgaggtga ccaaggccgt gcagcccctg 300
ctgctgggca ggatcatcgc cagctacgac cccgacaaca aggaggagag gagcatcgcc 360
atctacctgg gcatcggcct gtgcctgctg ttcatcgtga ggaccctgct gctgcacccc 420
gccatcttcg gcctgcacca catcggcatg cagatgagga tcgccatgtt cagcctgatc 480
tacaagaaga ccctgaagct gagcagcagg gtgctggaca agatcagcat cggccagctg 540
gtgagcctgc tgagcaacaa cctgaacaag ttcgacgagg gcctggccct ggcccacttc 600
gtgtggatcg ccccccctgca ggtggccctg ctgatgggcc tgatctggga gctgctgcag 660

```
gccagcgcct tctgcggcct gggcttcctg atcgtgctgg ccctgttcca ggccggcctg    720
ggcaggatga tgatgaagta cagggaccag agggccggca agatcagcga gaggctggtg    780
atcaccagcg agatgatcga gaacatccag agcgtgaagg cctactgctg ggaggaggcc    840
atggagaaga tgatcgagaa cctgaggcag accgagctga agctgaccag gaaggccgcc    900
tacgtgaggt acttcaacag cagcgccttc ttcttcagcg gcttcttcgt ggtgttcctg    960
agcgtgctgc cctacgccct gatcaagggc atcatcctga ggaagatctt caccaccatc   1020
agcttctgca tcgtgctgag gatggccgtg accaggcagt tcccctgggc cgtgcagacc   1080
tggtacgaca gcctgggcgc catcaacaag atccaggact tcctgcagaa gcaggagtac   1140
aagaccctgg agtacaacct gaccaccacc gaggtggtga tggagaacgt gaccgccttc   1200
tgggaggagg gcttcggcga gctgttcgag aaggccaagc agaacaacaa caacaggaag   1260
accagcaacg gcgacgacag cctgttcttc agcaacttca gcctgctggg cacccccgtg   1320
ctgaaggaca tcaacttcaa gatcgagagg ggccagctgc tggccgtggc cggcagcacc   1380
ggcgccggca agaccagcct gctgatggtg atcatgggcg agctggagcc cagcgagggc   1440
aagatcaagc acagcggcag gatcagcttc tgcagccagt tcagctggat catgcccggc   1500
accatcaagg agaacatcat cttcggcgtg agctacgacg agtacaggta caggagcgtg   1560
atcaaggcct gccagctgga ggaggacatc agcaagttcg ccgagaagga caacatcgtg   1620
ctgggcgagg gcggcatcac cctgagcggc ggccagaggg ccaggatcag cctggccagg   1680
gccgtgtaca aggacgccga cctgtacctg ctggacagcc ccttcggcta cctggacgtg   1740
ctgaccgaga aggagatctt cgagagctgc gtgtgcaagc tgatggccaa caagaccagg   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag gaggaacagc   1980
atcctgaccg agaccctgca caggttcagc ctggagggcg acgcccccgt gagctggacc   2040
gagaccaaga agcagagctt caagcagacc ggcgagttcg gcgagaagag gaagaacagc   2100
atcctgaacc ccatcaacag catcaggaag ttcagcatcg tgcagaagac cccccctgcag   2160
atgaacggca tcgaggagga cagcgacgag cccctggaga ggaggctgag cctggtgccc   2220
gacagcgagc agggcgaggc catcctgccc aggatcagcg tgatcagcac cggccccacc   2280
ctgcaggcca ggaggaggca gagcgtgctg aacctgatga cccacagcgt gaaccagggc   2340
cagaacatcc acaggaagac caccgccagc accaggaagg tgagcctggc cccccaggcc   2400
aacctgaccg agctggacat ctacagcagg aggctgagcc aggagaccgg cctggagatc   2460
agcgaggaga tcaacgagga ggacctgaag gagtgcttct tcgacgacat ggagagcatc   2520
cccgccgtga ccacctggaa cacctacctg aggtacatca ccgtgcacaa gagcctgatc   2580
ttcgtgctga tctggtgcct ggtgatcttc ctggccgagg tggccgccag cctggtggtg   2640
ctgtggctgc tgggcaacac ccccctgcag gacaagggca acagcaccca cagcaggaac   2700
aacagctacg ccgtgatcat caccagcacc agcagctact acgtgttcta catctacgtg   2760
ggcgtggccg acaccctgct ggccatgggc ttcttcaggg gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga acaggttcag caaggacatc   2940
gccatcctgg acgacctgct gcccctgacc atcttcgact tcatccagct gctgctgatc   3000
```

-continued

```
gtgatcggcg ccatcgccgt ggtggccgtg ctgcagccct acatcttcgt ggccaccgtg   3060

cccgtgatcg tggccttcat catgctgagg gcctacttcc tgcagaccag ccagcagctg   3120

aagcagctgg agagcgaggg caggagcccc atcttcaccc acctggtgac cagcctgaag   3180

ggcctgtgga ccctgagggc cttcggcagg cagccctact tcgagaccct gttccacaag   3240

gccctgaacc tgcacaccgc caactggttc ctgtacctga gcaccctgag gtggttccag   3300

atgaggatcg agatgatctt cgtgatcttc ttcatcgccg tgaccttcat cagcatcctg   3360

accaccggcg agggcgaggg cagggtgggc atcatcctga ccctggccat gaacatcatg   3420

agcaccctgc agtgggccgt gaacagcagc atcgacgtgg acagcctgat gaggagcgtg   3480

agcagggtgt tcaagttcat cgacatgccc accgagggca agcccaccaa gagcaccaag   3540

ccctacaaga acggccagct gagcaaggtg atgatcatcg agaacagcca cgtgaagaag   3600

gacgacatct ggcccagcgg cggccagatg accgtgaagg acctgaccgc caagtacacc   3660

gagggcggca acgccatcct ggagaacatc agcttcagca tcagccccgg ccagagggtg   3720

ggcctgctgg gcaggaccgg cagcggcaag agcaccctgc tgagcgcctt cctgaggctg   3780

ctgaacaccg agggcgagat ccagatcgac ggcgtgagct gggacagcat caccctgcag   3840

cagtggagga aggccttcgg cgtgatcccc cagaaggtgt tcatcttcag cggcaccttc   3900

aggaagaacc tggaccccta cgagcagtgg agcgaccagg agatctggaa ggtggccgac   3960

gaggtgggcc tgaggagcgt gatcgagcag ttccccggca agctggactt cgtgctggtg   4020

gacggcggct gcgtgctgag ccacggccac aagcagctga tgtgcctggc caggagcgtg   4080

ctgagcaagg ccaagatcct gctgctggac gagcccagcg cccacctgga ccccgtgacc   4140

taccagatca tcaggaggac cctgaagcag gccttcgccg actgcaccgt gatcctgtgc   4200

gagcacagga tcgaggccat gctggagtgc cagcagttcc tggtgatcga ggagaacaag   4260

gtgaggcagt acgacagcat ccagaagctg ctgaacgaga ggagcctgtt caggcaggcc   4320

atcagcccca gcgacagggt gaagctgttc ccccacagga acagcagcaa gtgcaagagc   4380

aagccccaga tcgccgccct gaaggaggag accgaggagg aggtgcagga caccaggctg   4440

tga                                                                 4443
```

<210> SEQ ID NO 33
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 33

```
atgcagagat cccctctgga gaaggcctca gtggtgtcca agcttttctt ctcctggacc     60

aggcccattt taagaaaggg ctacaggcag agacttgagc tgtctgacat ctatcagatc    120

ccttctgtgg attctgctga caatcttagt gaaaaattgg aaagggagtg ggacagagag    180

ctggcaagta aaaagaaccc caagctgatt aatgccctga ggcgctgctt tttttggaga    240

ttcatgttct atggcatatt cctctacctt ggagaagtaa ccaaagctgt acagcctctc    300

ctccttggca gaatcattgc ctcctatgat cctgataaca aggaggagag aagcatagcc    360

atctacctgg gcattgggct gtgcctcttg tttattgtga ggacccttct cttgcaccct    420

gccatctttg gccttcatca cattggcatg caaatgagaa tagcaatgtt tagtcttatt    480

tacaaaaaaa cattaaaact ctcttccagg gtgttggaca agatcagtat tggacaactg    540

gtcagcctgc tgagcaacaa cctgaacaag tttgatgaag gactggccct ggcccacttt    600
```

```
gtctggattg ccccccttca ggtggctctt ttgatgggcc tgatctggga actcctgcag    660
gcctctgcct tctgtgggtt aggcttcctg atagtgctag ctctctttca ggcagggttg    720
ggtagaatga tgatgaagta cagagaccag agggctggga agatatctga gaggctggtc    780
attacttctg aaatgataga aaacatccag tctgttaaag cttactgctg ggaggaggct    840
atggaaaaga tgattgagaa cttgaggcaa acagagctca agctgactag gaaggcagcc    900
tatgtcaggt atttcaacag cagtgctttc ttcttctcag gctttttcgt ggtcttcttg    960
agtgttctgc cctatgccct catcaagggg ataattttga gaaagatttt caccactatt   1020
tccttttgca ttgtcctgag gatggctgtc accaggcaat tcccctgggc tgtgcagaca   1080
tggtatgact ctctgggggc catcaacaaa atccaagatt tcctgcagaa gcaggagtac   1140
aagaccctgg aatacaacct caccaccaca gaagttgtga tggagaatgt gactgcattc   1200
tgggaggaag gatttgggga gctgtttgag aaagcaaaac aaaacaataa taacaggaaa   1260
accagcaatg gagatgactc cctgttcttt tccaacttct ctttgttggg cacccctgtc   1320
ctgaaagata taaactttaa aattgaaaga gggcagctgt tggcagttgc tggctccaca   1380
ggagctggaa aaacttcact actgatggtg atcatggggg agttagaacc ctctgaaggg   1440
aaaataaaac attctgggag gattagtttc tgcagccagt tcagctggat catgcctggg   1500
accattaaag aaaatattat atttggagtg agctatgatg aatatagata taggagtgtc   1560
atcaaagcct gtcagttgga ggaagacatc agcaaatttg cagagaaaga caacattgtt   1620
ctgggtgaag gtggcatcac cctgtcagga gggcaaaggg ccaggatcag cttggccaga   1680
gcagtctata aagatgctga tctgtacctc ctggatagcc cttttggcta tctggatgtt   1740
ttgacagaga aggaaatttt tgagtcctgt gtctgcaagt taatggcaaa taaaacaagg   1800
atacttgtga cctcaaaaat ggaacacctg aagaaggctg acaaaattct gatcctgcat   1860
gagggcagca gctactttta tggaacattt tctgaactgc agaatttgca accagacttt   1920
tcatcaaagc tcatgggatg tgacagtttt gatcagtttt ctgcagaaag gagaaactcc   1980
attttgactg agaccctgca caggttcagt ctggaggggg atgccccagt gagttggact   2040
gagacaaaga aacagagctt caagcagact ggagagtttg gagaaaagag gaaaaactca   2100
attctcaatc ccatcaatag catcaggaag ttcagcatag ttcagaagac tcctttgcag   2160
atgaatggga ttgaagagga ctcagatgag cccctggaaa ggagactctc cttggtgcca   2220
gattcagagc agggggaagc catactgcca aggatctctg tgatttctac agggcccacc   2280
ctccaagcaa gaaggagaca gtcagtttta aacctgatga cccactctgt caaccaggga   2340
cagaacattc atagaaagac aacagcatct acaagaaaag tttcactggc ccctcaagcc   2400
aatttaactg aactagatat ctacagcagg aggctcagcc aagaaacagg cctggagatc   2460
tcagaagaaa taaatgagga ggatttgaag gaatgcttct ttgatgatat ggagagcatc   2520
ccagctgtca caacctggaa cacctacctg agatacatca cagtgcacaa atccctcatc   2580
tttgtactta tatggtgcct tgtcatcttc ttagctgagg tggctgcttc cctggtggtg   2640
ctgtggctgc tgggaaacac acccctccag gataaaggga actctactca cagcaggaac   2700
aacagttatg ctgtgatcat caccagtacc tcctcctact atgtgttcta catttatgtt   2760
ggagttgcag acacattgct tgccatgggt ttttttagag gactcccccct ggtgcatact   2820
ctcatcactg tttccaaaat ccttcaccac aagatgctgc acagtgtact acaggctccc   2880
atgagcaccc tcaacactct taaagcagga ggaatcttga acagatttag caaggacatt   2940
```

gcaattcttg atgacctgct tccactgacc atctttgact tcatccagct tctgctcatt 3000
gtaattggtg ccattgctgt ggtagcagtg ctccagccat atatttttgt ggccactgtg 3060
cctgttattg tggccttcat tatgttgaga gcctacttcc tgcagacctc tcagcagctc 3120
aagcaacttg aaagtgaggg caggagcccc atatttacac acttggtcac ttccctcaaa 3180
ggcctctgga cactcagagc ttttggaaga caaccttatt ttgaaactct cttccacaag 3240
gctctgaatc tccacacagc caactggttt ctgtatcttt caacactgcg ctggttccag 3300
atgaggattg agatgatctt tgttatcttc ttcatagctg ttaccttcat ctctattctg 3360
acaactggtg agggggaagg gagagtaggc atcatcctca cactagccat gaacataatg 3420
tctaccttac aatgggccgt gaacagctcc atagatgtgg acagcctcat gagaagtgtg 3480
tcaagagttt tcaaattcat tgacatgccc acagaaggca aaccaaccaa gagcacaaaa 3540
ccctacaaga atggccagct gagtaaggtc atgatcattg aaaattctca tgtgaagaag 3600
gatgatattt ggcccagtgg gggccagatg acagtcaagg acctcactgc caaatacaca 3660
gagggtggaa atgctatcct agagaacatc tccttctcca tctccccagg ccaaagagtt 3720
ggcttgctgg gcaggactgg cagtggcaag tccaccttgc tctcagcatt tctcaggctt 3780
ttaaatacag agggagagat tcaaattgat ggggtgtctt gggatagtat aacacttcaa 3840
cagtggagga aagcctttgg tgtgattcct cagaaagtgt ttatcttctc tggcactttc 3900
agaaaaaatc tggaccccta tgaacagtgg agtgaccagg aaatctggaa ggtggcagat 3960
gaagtgggcc taagatcagt catagagcag tttcctggaa agttggattt tgtgcttgta 4020
gatggaggct gtgtgctgtc ccatggccat aaacagctaa tgtgcctggc taggtcagtg 4080
ctgagcaagg ccaagatcct gctgttagat gagccttcag cccatctgga ccctgtgaca 4140
taccagatta tcagaagaac tctgaagcag gcctttgctg actgcactgt catcctgtgt 4200
gagcacagaa ttgaggccat gctggagtgc cagcagttcc ttgttataga agagaataag 4260
gttaggcagt atgacagcat tcagaaactg ctaaatgaaa gatctctctt caggcaagct 4320
atttcaccat ctgatagagt gaaacttttt ccccacagaa attcctctaa atgtaaatct 4380
aagccccaga tagctgcctt gaaagaggag actgaagaag aagtccagga caccagactg 4440
tga 4443

<210> SEQ ID NO 34
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 34
atgcagagat ccccgctgga gaaggcatct gtggtgtcaa aactgttctt tagctggaca 60
aggcccatcc ttaggaaagg gtacagacag aggttggagc tgtcagacat atatcagatc 120
ccttcagtgg actctgcaga caacctctct gaaaagctgg agagggaatg ggacagggaa 180
ctggccagca aaaaaaaccc taaactgatt aatgccctga ggaggtgctt cttttggaga 240
ttcatgttct atgggatctt cctttacctg ggggaggtga ctaaagctgt tcagcctctt 300
cttctgggga ggattattgc ctcctatgac ccagacaaca aagaagaaag aagcatagcc 360
atttacttag gcataggcct ctgcttgctc ttcatagtta gaaccctcct actccaccca 420
gccatctttg gtctccacca cataggtatg cagatgagaa tagcaatgtt ctccttgatc 480
tacaagaaga ccctcaagct gtccagcagg gtgctggaca agatctccat aggccagtta 540
gtcagtctac tgtccaataa cttaaataag tttgatgagg gactggcact ggcacatttt 600
gtgtggattg ccccctcca agtggccctt cttatgggcc ttatctggga gctgttgcag 660
gcctctgctt tctgtggcct gggtttcctc atagtcctag ccttattcca ggctggactg 720
ggcagaatga tgatgaagta tagggaccaa agagcaggga agatttctga aaggctggtt 780
ataacttctg agatgattga gaacattcag tcagtgaaag cttactgctg ggaagaagct 840
atggaaaaaa tgattgaaaa tctcagacag actgaattaa agttgaccag gaaagctgct 900
tatgtcagat acttcaactc ctcagccttc tttttttctg gcttctttgt tgtattcctt 960
tcagtcctcc cctatgccct gattaagggc attatcttga ggaaaatttt cacaaccatc 1020
tccttttgta ttgtcctcag gatggctgtt acaaggcaat ttccttgggc tgtgcaaact 1080
tggtatgata gccttggagc aatcaacaag atccaggatt tcctgcaaaa gcaggagtac 1140
aagacattgg aatacaacct taccaccact gaggtggtga tggaaaatgt gactgccttc 1200
tgggaggagg ggtttggaga gctgtttgag aaagccaaac agaacaacaa caatagaaag 1260
acctctaatg gtgatgattc cctgttcttt tctaacttta gtcttctggg gaccccagtt 1320
ctgaaagata ttaactttaa aattgaaagg ggacagttgc tggctgtggc tgggtccact 1380
ggggctggga agacaagcct gctcatggtg atcatgggag agctggaacc cagtgaagga 1440
aagatcaaac actcaggcag gatctccttc tgcagccagt tctcatggat tatgccaggc 1500
actattaaag aaaatatcat ctttggtgta agctatgatg agtacaggta tagatctgta 1560
attaaagcct gccagctgga ggaagacatc tctaagtttg ctgagaagga taacattgtg 1620
ttgggggaag gggcatcac cctttctggt gggcagaggg ctaggatctc ccttgctagg 1680
gcagtataca aggatgctga cttgtacctc ttggatagtc cttttggcta cctagatgtg 1740
ctgacagaga aagaaatatt tgaaagctgt gtgtgtaagc tcatggctaa caagaccagg 1800
atcctggtca ccagtaaaat ggaacacctc aaaaaagcag acaagatcct tattctccat 1860
gagggctcct cctacttcta tgggaccttc agtgagctgc agaatctgca gccagacttc 1920
tcctcaaaac ttatgggctg tgactccttt gaccaattct ctgcagaaag aaggaatagc 1980
atactgacag aaacactgca tagattctcc ctggaaggag atgccccagt gagttggaca 2040
gaaaccaaaa agcagagctt caagcagact ggtgagtttg gtgaaaagag gaagaattct 2100
atcctgaacc ccatcaatag catcaggaaa tttagcatag tccaaaagac cccccctccag 2160 atgaatggaa tagaggagga tagtgatgag cctcttgaga gaaggctgtc cctggttcca 2220
gacagtgaac agggtgaagc cattcttccg aggatcagtg tcatctccac tgggcccaca 2280
ttgcaggcca gaagaagaca gtctgttctg aatttgatga cacattctgt gaatcaaggc 2340
cagaatatcc atagaaaaac cactgccagc accagaaaag tttctctagc cccccaggct 2400
aacctgactg agttagacat ctacagcaga aggctgagcc aagagactgg cttggaaata 2460
tctgaggaga tcaatgagga ggacctcaag gagtgcttct ttgatgacat ggagtcaatc 2520
cctgcagtca ctacatggaa cacttaccta aggtacatca cagttcataa gagcctcatc 2580
tttgtcctca tatggtgtct ggtcatcttt ttagcagaag tggctgccag cctagttgtg 2640
ctgtggttac tgggcaatac acctcttcag gacaaaggca atagcacaca cagcagaaac 2700
aactcctatg cagtgatcat cacctctaca agctcttact atgtattcta tatatatgtg 2760
ggagtggcag atactctcct ggccatggga ttcttcaggg gattacctct agttcacaca 2820
ttgatcacag tgtcaaaaat tctccaccac aagatgttac acagtgtcct gcaagcccca 2880

```
atgtctactc tgaacacact taaggcaggt ggaattttga ataggtttag caaggacata   2940

gctatcctgg atgatctcct ccctctgacc atctttgact tcatccagtt actgctcatt   3000

gtaattggag ccattgcagt ggtagcagtc ctacagcctt acatttttgt ggctactgtt   3060

cctgttattg tggccttcat tatgctaaga gcttacttcc tgcaaacaag ccaacagttg   3120

aaacagctag aaagtgaggg aaggtccccc atcttcaccc acctggtgac atcactcaag   3180

gggctatgga ctcttagggc ttttgggaga cagccgtact ttgagacctt attccataag   3240

gcccttaacc tccatacagc aaactggttc ttatacctga gtactctgag gtggtttcaa   3300

atgaggattg aaatgatttt tgtgatcttc ttcattgctg tgaccttcat ctcaatcttg   3360

accacaggag agggggaggg cagggtgggc atcatactga ccttggccat gaacattatg   3420

tcaaccctgc agtgggctgt caatagctcc attgatgtgg acagtctgat gaggagtgtc   3480

tccagggtct tcaagtttat tgacatgcca actgagggca aacccaccaa aagcactaag   3540

ccatataaaa atggccaact gtccaaagtg atgatcattg aaaattcaca tgtaaagaag   3600

gatgatatct ggccctctgg aggacagatg acagtgaaag acctgactgc caagtacaca   3660

gagggtggta atgccattct tgagaacatt agtttcagta tttccccggg gcaaagggtg   3720

ggcctccttg gcagaacagg ctctggcaag agtaccctgc tgtcagcctt tttaagactg   3780

ttgaacactg agggagaaat tcagattgat ggtgtctcct gggatagcat caccctccag   3840

cagtggagaa aagcttttgg agtgatcccg caaaaggttt tcatcttttc aggcaccttc   3900

cggaagaacc tggaccccta tgagcagtgg tctgaccagg aaatatggaa ggtagctgat   3960

gaagttgggc ttaggtcagt catagagcag ttcccaggca aactggactt tgtcctggtg   4020

gatggtggat gtgtactgag tcatgggcac aaacagctga tgtgcctagc caggtctgtg   4080

ctcagcaagg caaagatatt gctgcttgat gaacccagtg cccatctgga cccagtcaca   4140

tatcagatca tcagaagaac attgaagcag gcctttgctg attgcacagt tatcctctgt   4200

gagcacagga ttgaggccat gctggagtgc cagcagtttc tggtgattga ggagaataaa   4260

gtaaggcagt atgactccat ccagaagctg ctcaatgaaa gaagcctctt tagacaagct   4320

atctccccct cagacagggt caaattgttc cctcacagaa acagcagcaa gtgcaagagc   4380

aagccccaaa ttgcagcctt gaaagaggag acagaggaag aggtgcagga caccagactc   4440

tga                                                                 4443
```

```
<210> SEQ ID NO 35
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 35
```

```
atgcagagaa gcccccctgga gaaggccagc gtggtgagca agctgttctt cagctggacc     60

agacccatcc tgagaaaggg ctacagacag agactggagc tgagcgacat ctaccagatc    120

cccagcgtgg acagcgccga caacctgagc gagaagctgg agagagagtg ggacagagag    180

ctggccagca agaagaaccc caagctgatc aacgccctga gaagatgctt cttctggaga    240

ttcatgttct acggcatctt cctgtacctg ggcgaggtga ccaaggccgt gcagcccctg    300

ctgctgggca gaatcatcgc cagctacgac cccgacaaca aggaggagag aagcatcgcc    360

atctacctgg gcatcggcct gtgcctgctg ttcatcgtga gaaccctgct gctgcacccc    420

gccatcttcg gcctgcacca catcggcatg cagatgagaa tcgccatgtt cagcctgatc    480
```

-continued

```
tacaagaaga ccctgaagct gagcagcaga gtgctggaca agatcagcat cggccagctg    540
gtgagcctgc tgagcaacaa cctgaacaag ttcgacgagg gcctggccct ggcccacttc    600
gtgtggatcg ccccccctgca ggtggccctg ctgatgggcc tgatctggga gctgctgcag    660
gccagcgcct tctgcggcct gggcttcctg atcgtgctgg ccctgttcca ggccggcctg    720
ggcagaatga tgatgaagta cagagaccag agagccggca agatcagcga gagactggtg    780
atcaccagcg agatgatcga gaacatccag agcgtgaagg cctactgctg ggaggaggcc    840
atggagaaga tgatcgagaa cctgagacag accgagctga agctgaccag aaaggccgcc    900
tacgtgagat acttcaacag cagcgccttc ttcttcagcg gcttcttcgt ggtgttcctg    960
agcgtgctgc cctacgccct gatcaagggc atcatcctga gaaagatctt caccaccatc   1020
agcttctgca tcgtgctgag aatggccgtg accagacagt tcccctgggc cgtgcagacc   1080
tggtacgaca gcctgggcgc catcaacaag atccaggact tcctgcagaa gcaggagtac   1140
aagaccctgg agtacaacct gaccaccacc gaggtggtga tggagaacgt gaccgccttc   1200
tgggaggagg gcttcggcga gctgttcgag aaggccaagc agaacaacaa caacagaaag   1260
accagcaacg gcgacgacag cctgttcttc agcaacttca gcctgctggg cacccccgtg   1320
ctgaaggaca tcaacttcaa gatcgagaga ggccagctgc tggccgtggc cggcagcacc   1380
ggcgccggca agaccagcct gctgatggtg atcatgggcg agctggagcc cagcgagggc   1440
aagatcaagc acagcggcag aatcagcttc tgcagccagt tcagctggat catgcccggc   1500
accatcaagg agaacatcat cttcggcgtg agctacgacg agtacagata cagaagcgtg   1560
atcaaggcct gccagctgga ggaggacatc agcaagttcg ccgagaagga caacatcgtg   1620
ctgggcgagg gcggcatcac cctgagcggc ggccagagag ccagaatcag cctggccaga   1680
gccgtgtaca aggacgccga cctgtacctg ctggacagcc ccttcggcta cctggacgtg   1740
ctgaccgaga aggagatctt cgagagctgc gtgtgcaagc tgatggccaa caagaccaga   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag aagaaacagc   1980
atcctgaccg agaccctgca cagattcagc ctggagggcg acgcccccgt gagctggacc   2040
gagaccaaga agcagagctt caagcagacc ggcgagttcg gcgagaagag aaagaacagc   2100
atcctgaacc ccatcaacag catcagaaag ttcagcatcg tgcagaagac cccccctgcag   2160
atgaacggca tcgaggagga cagcgacgag cccctggaga gaagactgag cctggtgccc   2220
gacagcgagc agggcgaggc catcctgccc agaatcagcg tgatcagcac cggccccacc   2280
ctgcaggcca gaagaagaca gagcgtgctg aacctgatga cccacagcgt gaaccagggc   2340
cagaacatcc acagaaagac caccgccagc accagaaagg tgagcctggc cccccaggcc   2400
aacctgaccg agctggacat ctacagcaga agactgagcc aggagaccgg cctggagatc   2460
agcgaggaga tcaacgagga ggacctgaag gagtgcttct tcgacgacat ggagagcatc   2520
cccgccgtga ccacctggaa cacctacctg agatacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagcagaaac   2700
aacagctacg ccgtgatcat caccagcacc agcagctact acgtgttcta catctacgtg   2760
ggcgtggccg acaccctgct ggccatgggc ttcttcagag gcctgcccct ggtgcacacc   2820
```

```
ctgatcaccg tgagcaagat cctgcaccac aagatgctgc acagcgtgct gcaggccccc   2880
atgagcaccc tgaacaccct gaaggccggc ggcatcctga acagattcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgaga gcctacttcc tgcagaccag ccagcagctg   3120
aagcagctgg agagcgaggg cagaagcccc atcttcaccc acctggtgac cagcctgaag   3180
ggcctgtgga ccctgagagc cttcggcaga cagccctact tcgagaccct gttccacaag   3240
gccctgaacc tgcacaccgc caactggttc ctgtacctga gcaccctgag atggttccag   3300
atgagaatcg agatgatctt cgtgatcttc ttcatcgccg tgaccttcat cagcatcctg   3360
accaccggcg agggcgaggg cagagtgggc atcatcctga ccctggccat gaacatcatg   3420
agcaccctgc agtgggccgt gaacagcagc atcgacgtgg acagcctgat gagaagcgtg   3480
agcagagtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagagagtg   3720
ggcctgctgg gcagaaccgg cagcggcaag agcaccctgc tgagcgcctt cctgagactg   3780
ctgaacaccg agggcgagat ccagatcgac ggcgtgagct gggacagcat caccctgcag   3840
cagtggagaa aggccttcgg cgtgatcccc cagaaggtgt tcatcttcag cggcaccttc   3900
agaaagaacc tggaccccta cgagcagtgg agcgaccagg agatctggaa ggtggccgac   3960
gaggtgggcc tgagaagcgt gatcgagcag ttccccggca agctggactt cgtgctggtg   4020
gacggcggct gcgtgctgag ccacggccac aagcagctga tgtgcctggc cagaagcgtg   4080
ctgagcaagg ccaagatcct gctgctggac gagcccagcg cccacctgga ccccgtgacc   4140
taccagatca tcagaagaac cctgaagcag gccttcgccg actgcaccgt gatcctgtgc   4200
gagcacagaa tcgaggccat gctggagtgc cagcagttcc tggtgatcga ggagaacaag   4260
gtgagacagt acgacagcat ccagaagctg ctgaacgaga gaagcctgtt cagacaggcc   4320
atcagcccca gcgacagagt gaagctgttc cccacagaa acagcagcaa gtgcaagagc   4380
aagccccaga tcgccgccct gaaggaggag accgaggagg aggtgcagga caccagactg   4440
tga                                                                 4443
```

<210> SEQ ID NO 36
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 36

```
atgcagcgca gcccccctgga gaaggccagc gtggtgagca agctgttctt cagctggacc    60
cgccccatcc tgcgcaaggg ctaccgccag cgcctggagc tgagcgacat ctaccagatc   120
cccagcgtgg acagcgccga caacctgagc gagaagctgg agcgcgagtg ggaccgcgag   180
ctggccagca agaagaaccc caagctgatc aacgccctgc gccgctgctt cttctggcgc   240
ttcatgttct acggcatctt cctgtacctg ggcgaggtga ccaaggccgt gcagcccctg   300
ctgctgggcc gcatcatcgc cagctacgac cccgacaaca aggaggagcg cagcatcgcc   360
atctacctgg gcatcggcct gtgcctgctg ttcatcgtgc gcaccctgct gctgcacccc   420
```

-continued

```
gccatcttcg gcctgcacca catcggcatg cagatgcgca tcgccatgtt cagcctgatc    480
tacaagaaga ccctgaagct gagcagccgc gtgctggaca agatcagcat cggccagctg    540
gtgagcctgc tgagcaacaa cctgaacaag ttcgacgagg gcctggccct ggcccacttc    600
gtgtggatcg ccccccctgca ggtggccctg ctgatgggcc tgatctggga gctgctgcag    660
gccagcgcct tctgcggcct gggcttcctg atcgtgctgg ccctgttcca ggccggcctg    720
ggccgcatga tgatgaagta ccgcgaccag cgcgccggca agatcagcga gcgcctggtg    780
atcaccagcg agatgatcga gaacatccag agcgtgaagg cctactgctg ggaggaggcc    840
atggagaaga tgatcgagaa cctgcgccag accgagctga agctgacccg caaggccgcc    900
tacgtgcgct acttcaacag cagcgccttc ttcttcagcg gcttcttcgt ggtgttcctg    960
agcgtgctgc cctacgccct gatcaagggc atcatcctgc gcaagatctt caccaccatc   1020
agcttctgca tcgtgctgcg catggccgtg acccgccagt tcccctgggc cgtgcagacc   1080
tggtacgaca gcctgggcgc catcaacaag atccaggact tcctgcagaa gcaggagtac   1140
aagaccctgg agtacaacct gaccaccacc gaggtggtga tggagaacgt gaccgccttc   1200
tgggaggagg gcttcggcga gctgttcgag aaggccaagc agaacaacaa caaccgcaag   1260
accagcaacg gcgacgacag cctgttcttc agcaacttca gcctgctggg cacccccgtg   1320
ctgaaggaca tcaacttcaa gatcgagcgc ggccagctgc tggccgtggc cggcagcacc   1380
ggcgccggca agaccagcct gctgatggtg atcatgggcg agctggagcc cagcgagggc   1440
aagatcaagc acagcggccg catcagcttc tgcagccagt tcagctggat catgcccggc   1500
accatcaagg agaacatcat cttcggcgtg agctacgacg agtaccgcta ccgcagcgtg   1560
atcaaggcct gccagctgga ggaggacatc agcaagttcg ccgagaagga caacatcgtg   1620
ctgggcgagg gcggcatcac cctgagcggc ggccagcgcg cccgcatcag cctggcccgc   1680
gccgtgtaca aggacgccga cctgtacctg ctggacagcc ccttcggcta cctggacgtg   1740
ctgaccgaga aggagatctt cgagagctgc gtgtgcaagc tgatggccaa caagacccgc   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagcg ccgcaacagc   1980
atcctgaccg agaccctgca ccgcttcagc ctggagggcg acgcccccgt gagctggacc   2040
gagaccaaga agcagagctt caagcagacc ggcgagttcg gcgagaagcg caagaacagc   2100
atcctgaacc ccatcaacag catccgcaag ttcagcatcg tgcagaagac cccctgcag    2160
atgaacggca tcgaggagga cagcgacgag cccctggagc gccgcctgag cctggtgccc   2220
gacagcgagc agggcgaggc catcctgccc cgcatcagcg tgatcagcac cggccccacc   2280
ctgcaggccc gccgccgcca gagcgtgctg aacctgatga cccacagcgt gaaccagggc   2340
cagaacatcc accgcaagac caccgccagc acccgcaagg tgagcctggc cccccaggcc   2400
aacctgaccg agctggacat ctacagccgc cgcctgagcc aggagaccgg cctggagatc   2460
agcgaggaga tcaacgagga ggacctgaag gagtgcttct tcgacgacat ggagagcatc   2520
cccgccgtga ccacctggaa cacctacctg cgctacatca ccgtgcacaa gagcctgatc   2580
ttcgtgctga tctggtgcct ggtgatcttc ctggccgagg tggccgccag cctggtggtg   2640
ctgtggctgc tgggcaacac ccccctgcag gacaagggca acagcaccca cagccgcaac   2700
aacagctacg ccgtgatcat caccagcacc agcagctact acgtgttcta catctacgtg   2760
```

-continued

```
ggcgtggccg acaccctgct ggccatgggc ttcttccgcg gcctgcccct ggtgcacacc   2820

ctgatcaccg tgagcaagat cctgcaccac aagatgctgc acagcgtgct gcaggccccc   2880

atgagcaccc tgaacaccct gaaggccggc ggcatcctga accgcttcag caaggacatc   2940

gccatcctgg acgacctgct gcccctgacc atcttcgact tcatccagct gctgctgatc   3000

gtgatcggcg ccatcgccgt ggtggccgtg ctgcagccct acatcttcgt ggccaccgtg   3060

cccgtgatcg tggccttcat catgctgcgc gcctacttcc tgcagaccag ccagcagctg   3120

aagcagctgg agagcgaggg ccgcagcccc atcttcaccc acctggtgac cagcctgaag   3180

ggcctgtgga ccctgcgcgc cttcggccgc cagccctact tcgagaccct gttccacaag   3240

gccctgaacc tgcacaccgc caactggttc ctgtacctga gcaccctgcg ctggttccag   3300

atgcgcatcg agatgatctt cgtgatcttc ttcatcgccg tgaccttcat cagcatcctg   3360

accaccggcg agggcgaggg ccgcgtgggc atcatcctga ccctggccat gaacatcatg   3420

agcaccctgc agtgggccgt gaacagcagc atcgacgtgg acagcctgat gcgcagcgtg   3480

agccgcgtgt tcaagttcat cgacatgccc accgagggca agcccaccaa gagcaccaag   3540

ccctacaaga acggccagct gagcaaggtg atgatcatcg agaacagcca cgtgaagaag   3600

gacgacatct ggcccagcgg cggccagatg accgtgaagg acctgaccgc caagtacacc   3660

gagggcggca acgccatcct ggagaacatc agcttcagca tcagccccgg ccagcgcgtg   3720

ggcctgctgg gccgcaccgg cagcggcaag agcaccctgc tgagcgcctt cctgcgcctg   3780

ctgaacaccg agggcgagat ccagatcgac ggcgtgagct gggacagcat caccctgcag   3840

cagtggcgca aggccttcgg cgtgatcccc cagaaggtgt tcatcttcag cggcaccttc   3900

cgcaagaacc tggaccccta cgagcagtgg agcgaccagg agatctggaa ggtggccgac   3960

gaggtgggcc tgcgcagcgt gatcgagcag ttccccggca agctggactt cgtgctggtg   4020

gacggcggct gcgtgctgag ccacggccac aagcagctga tgtgcctggc ccgcagcgtg   4080

ctgagcaagg ccaagatcct gctgctggac gagcccagcg cccacctgga ccccgtgacc   4140

taccagatca tccgccgcac cctgaagcag gccttcgccg actgcaccgt gatcctgtgc   4200

gagcaccgca tcgaggccat gctggagtgc cagcagttcc tggtgatcga ggagaacaag   4260

gtgcgccagt acgacagcat ccagaagctg ctgaacgagc gcagcctgtt ccgccaggcc   4320

atcagcccca gcgaccgcgt gaagctgttc ccccaccgca acagcagcaa gtgcaagagc   4380

aagccccaga tcgccgccct gaaggaggag accgaggagg aggtgcagga cacccgcctg   4440

taa                                                                 4443
```

<210> SEQ ID NO 37
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 37

```
atgcagagaa gcccccctgga gaaggccagc gtggtgagca agctgttctt cagctggacc     60

agacccatcc tgagaaaggg ctacagacag agactggagc tgagcgacat ctaccagatc    120

cccagcgtgg acagcgccga caacctgagc gagaagctgg agagagagtg ggacagagag    180

ctggccagca agaagaaccc caagctgatc aacgccctga gaagatgctt cttctggaga    240

ttcatgttct acggcatctt cctgtacctg ggcgaggtga ccaaggccgt gcagcccctg    300

ctgctgggca gaatcatcgc cagctacgac cccgacaaca aggaggagag aagcatcgcc    360
```

```
atctacctgg gcatcggcct gtgcctgctg ttcatcgtga gaaccctgct gctgcacccc    420
gccatcttcg gcctgcacca catcggcatg cagatgagaa tcgccatgtt cagcctgatc    480
tacaagaaga ccctgaagct gagcagcaga gtgctggaca agatcagcat cggccagctg    540
gtgagcctgc tgagcaacaa cctgaacaag ttcgacgagg gcctggccct ggcccacttc    600
gtgtggatcg ccccccctgca ggtggccctg ctgatgggcc tgatctggga gctgctgcag    660
gccagcgcct tctgcggcct gggcttcctg atcgtgctgg ccctgttcca ggccggcctg    720
ggcagaatga tgatgaagta cagggaccag agagccggca agatcagcga gagactggtg    780
atcaccagcg agatgatcga gaacatccag agcgtgaagg cctactgctg ggaggaggcc    840
atggagaaga tgatcgagaa cctgagacag accgagctga agctgaccag aaaggccgcc    900
tacgtgagat acttcaacag cagcgccttc ttcttcagcg gcttcttcgt ggtgttcctg    960
agcgtgctgc cctacgccct gatcaagggc atcatcctga gaaagatctt caccaccatc   1020
agcttctgca tcgtgctgag aatggccgtg accagacagt tcccctgggc cgtgcagacc   1080
tggtacgaca gcctgggcgc catcaacaag atccaggact tcctgcagaa gcaggagtac   1140
aagaccctgg agtacaacct gaccaccacc gaggtggtga tggagaacgt gaccgccttc   1200
tgggaggagg gcttcggcga gctgttcgag aaggccaagc agaacaacaa caacagaaag   1260
accagcaacg gcgacgacag cctgttcttc agcaacttca gcctgctggg cacccccgtg   1320
ctgaaggaca tcaacttcaa gatcgagaga ggccagctgc tggccgtggc cggcagcacc   1380
ggcgccggca agaccagcct gctgatggtg atcatgggcg agctggagcc cagcgagggc   1440
aagatcaagc acagcggcag aatcagcttc tgcagccagt tcagctggat catgcccggc   1500
accatcaagg agaacatcat cttcggcgtg agctacgacg agtacagata cagaagcgtg   1560
atcaaggcct gccagctgga ggaggacatc agcaagttcg ccgagaagga caacatcgtg   1620
ctgggcgagg gcggcatcac cctgagcggc ggccagagag ccagaatcag cctggccaga   1680
gccgtgtaca aggacgccga cctgtacctg ctggacagcc ccttcggcta cctggacgtg   1740
ctgaccgaga aggagatctt cgagagctgc gtgtgcaagc tgatggccaa caagaccaga   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag aagaaacagc   1980
atcctgaccg agaccctgca cagattcagc ctggagggcg acgcccccgt gagctggacc   2040
gagaccaaga agcagagctt caagcagacc ggcgagttcg gcgagaagag aaagaacagc   2100
atcctgaacc ccatcaacag catcagaaag ttcagcatcg tgcagaagac ccccctgcag   2160
atgaacggca tcgaggagga cagcgacgag cccctggaga gaagactgag cctggtgccc   2220
gacagcgagc agggcgaggc catcctgccc agaatcagcg tgatcagcac cggccccacc   2280
ctgcaggcca gaagaagaca gagcgtgctg aacctgatga cccacagcgt gaaccagggc   2340
cagaacatcc acagaaagac caccgccagc accagaaagg tgagcctggc cccccaggcc   2400
aacctgaccg agctggacat ctacagcaga agactgagcc aggagaccgg cctggagatc   2460
agcgaggaga tcaacgagga ggacctgaag gagtgcttct tcgacgacat ggagagcatc   2520
cccgccgtga ccacctggaa cacctacctg agatacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagcagaaac   2700
```

```
aacagctacg ccgtgatcat caccagcacc agcagctact acgtgttcta catctacgtg   2760

ggcgtggccg acaccctgct ggccatgggc ttcttcagag gcctgcccct ggtgcacacc   2820

ctgatcaccg tgagcaagat cctgcaccac aagatgctgc acagcgtgct gcaggccccc   2880

atgagcaccc tgaacaccct gaaggccggc ggcatcctga acagattcag caaggacatc   2940

gccatcctgg acgacctgct gcccctgacc atcttcgact tcatccagct gctgctgatc   3000

gtgatcggcg ccatcgccgt ggtggccgtg ctgcagccct acatcttcgt ggccaccgtg   3060

cccgtgatcg tggccttcat catgctgaga gcctacttcc tgcagaccag ccagcagctg   3120

aagcagctgg agagcgaggg caggagcccc atcttcaccc acctggtgac cagcctgaag   3180

ggcctgtgga ccctgagagc cttcggcaga cagccctact tcgagaccct gttccacaag   3240

gccctgaacc tgcacaccgc caactggttc ctgtacctga gcaccctgag atggttccag   3300

atgagaatcg agatgatctt cgtgatcttc ttcatcgccg tgaccttcat cagcatcctg   3360

accaccggcg agggcgaggg cagagtgggc atcatcctga ccctggccat gaacatcatg   3420

agcaccctgc agtgggccgt gaacagcagc atcgacgtgg acagcctgat gagaagcgtg   3480

agcagagtgt tcaagttcat cgacatgccc accgagggca agcccaccaa gagcaccaag   3540

ccctacaaga acggccagct gagcaaggtg atgatcatcg agaacagcca cgtgaagaag   3600

gacgacatct ggcccagcgg cggccagatg accgtgaagg acctgaccgc caagtacacc   3660

gagggcggca acgccatcct ggagaacatc agcttcagca tcagccccgg ccagagagtg   3720

ggcctgctgg gcagaaccgg cagcggcaag agcaccctgc tgagcgcctt cctgagactg   3780

ctgaacaccg agggcgagat ccagatcgac ggcgtgagct gggacagcat caccctgcag   3840

cagtggagaa aggccttcgg cgtgatcccc cagaaggtgt tcatcttcag cggcaccttc   3900

agaaagaacc tggaccccta cgagcagtgg agcgaccagg agatctggaa ggtggccgac   3960

gaggtgggcc tgagaagcgt gatcgagcag ttccccggca agctggactt cgtgctggtg   4020

gacggcggct gcgtgctgag ccacggccac aagcagctga tgtgcctggc cagaagcgtg   4080

ctgagcaagg ccaagatcct gctgctggac gagcccagcg cccacctgga ccccgtgacc   4140

taccagatca tcagaagaac cctgaagcag gccttcgccg actgcaccgt gatcctgtgc   4200

gagcacagaa tcgaggccat gctggagtgc cagcagttcc tggtgatcga ggagaacaag   4260

gtgagacagt acgacagcat ccagaagctg ctgaacgaga gaagcctgtt cagacaggcc   4320

atcagcccca gcgacagagt gaagctgttc cccccacagaa acagcagcaa gtgcaagagc   4380

aagccccaga tcgccgccct gaaggaggag accgaggagg aggtgcagga caccagactg   4440

tga                                                                  4443
```

<210> SEQ ID NO 38
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 38

```
atgcagaggt cacctctgga aaaggctagc gtggtcagca agctattttt ttcctggacc     60

cgcccgatac tcaggaaggg ctaccgacag cggctggagc tgagtgacat ttatcagatt    120

ccctccgtcg attccgctga caacctgtct gagaaactgg agcgggaatg ggatagggaa    180

ctggcgtcca aaaaaaaccc caaactcatc aatgcactcc gcagatgctt cttctggcgg    240

tttatgtttt atggcatatt cctgtatctg ggggaggtga cgaaagccgt gcagccgctg    300
```

```
ctgcttggtc gcattatcgc gtcatacgat ccagataaca aggaggaaag aagtatcgct    360
atctatctcg ggatagggct gtgcctgctc ttcattgtgc ggactcttct cttgcacccc    420
gccattttcg gtctgcatca tataggtatg cagatgagaa ttgcgatgtt ctcattgatt    480
tacaaaaaaa cgcttaagct aagttcaagg gtgctagata agatatcgat cggccagctg    540
gtgtctctgc ttagcaacaa cctcaataaa ttcgacgaag gccttgcact ggcccacttc    600
gtgtggatcg cccctctgca ggtggctctg ctgatggggt taatatggga gctgttgcag    660
gcctccgctt tttgtggcct ggggtttctc atcgtgttgg ccttgtttca ggcagggctg    720
ggacgtatga tgatgaaata tagggatcag agggctggca aaatctctga gcgcctggtt    780
attacgagtg aaatgattga gaacatccag tcagtgaagg cctattgctg ggaggaggcc    840
atggaaaaaa tgattgagaa cctacgccag actgagctga agttaaccag aaaagccgcc    900
tatgtgcgct actttaacag tagcgcattt ttcttctccg gtttttttcgt ggtgtttctt    960
agtgtgttgc cgtatgcctt aatcaaggga ataatactcc ggaagatttt cactaccatc   1020
agcttctgta tcgtgttgcg gatggccgtc acccggcagt ttccctgggc agtacagact   1080
tggtacgatt ctctcggagc aattaacaaa atccaagact ttctacaaaa gcaggagtac   1140
aagaccctgg agtacaatct gaccaccaca gaagtcgtaa tggagaatgt aactgccttc   1200
tgggaagagg gctttggcga actctttgaa aaggccaagc agaacaataa caaccggaag   1260
acctccaacg gggacgacag cttatttttc agcaattttt ctttgctcgg gacccctgta   1320
ctgaaagata ttaactttaa gatcgagcgc ggacaactcc tggctgtcgc cggcagcact   1380
ggagctggaa aaacatcact gcttatggtg ataatgggag aactcgaacc aagcgaggga   1440
aaaataaagc actctggacg gattagtttt tgctcccagt tctcgtggat aatgcctggc   1500
accattaagg agaatatcat ctttggagtg agttacgacg aataccggta ccggtccgtt   1560
atcaaggctt gtcaactcga ggaggacatt tctaaattcg ccgaaaaaga taatatagtg   1620
ctgggcgaag gaggcattac actgagcggg ggtcagagag ctcgaattag cctcgcccga   1680
gcagtctata aagacgccga tctttacctg ctggattccc cttttgggta tttggatgtt   1740
ctgacagaga aggaaatctt tgaatcatgt gtctgtaaac tgatggccaa taagactagg   1800
attctagtga cttcgaaaat ggagcacctg aaaaaagcgg acaaaattct gatactccat   1860
gaagggtctt cctacttcta cggcaccttc tcagagttgc agaacttaca acctgatttt   1920
tcatctaagc ttatggggtg cgactcgttt gaccagttct ccgctgaaag acgaaacagc   1980
atcttaacgg aaactcttca caggttctca ttagagggag atgcgccggt gtcctggaca   2040
gagacaaaaa aacagtcttt caaacagaca ggagagtttg gcgagaagag aaaaaactca   2100
atcctcaatc ccatcaattc tattagaaag tttagcatcg tccaaaaaac accattgcag   2160
atgaatggga ttgaggagga cagtgatgag cctttggaac gaagactgtc cctggtaccc   2220
gatagcgaac agggtgaggc catccttcct aggatctcgg tcataagtac agggcccaca   2280
ctgcaggcca ggcgacgtca aagtgtcctc aatcttatga cgcacagtgt gaatcagggg   2340
cagaacatcc atcgtaagac gacagcttca actcgaaagg tcagtctagc tccacaagcc   2400
aatcttacag agctggacat ttattcccgc cgcctcagtc aggagaccgg attggaaata   2460
tcagaggaaa ttaatgaaga ggatctgaag gaatgcttct ttgatgacat ggaatcgatc   2520
cccgctgtta ctacctggaa cacatatctg agatatatta ccgtccataa gagcttaatc   2580
tttgtactga tatggtgctt ggtgattttc ctggcagagg ttgcggcgag tttggtcgtg   2640
```

ctatggctcc ttggaaacac tcccctgcag gataaggga actccactca tagcaggaat 2700
aacagctatg ccgtgatcat cacctctacc tcctcttatt acgtgtttta catatacgtc 2760
ggtgttgcgg ataccctgtt ggcaatgggg ttctttagag gactacccct agttcacacc 2820
ctgatcaccg tttcgaagat cttgcaccac aagatgcttc atagcgttct ccaagctcct 2880
atgagcaccc ttaatacact gaaagcagga ggtatcctta accgcttttc caaagacatc 2940
gctatactcg acgatttgct cccattgacc atcttcgact tcattcagct gctcctcatt 3000
gtgatcggcg ccattgccgt ggtcgcagtg ttacagccat atattttcgt agccaccgtg 3060
cccgtcatcg tggcatttat catgctgcgc gcatatttct tacagacatc tcagcaactg 3120
aagcagctgg aatctgaggg cagatctcct atttttacac acctggttac cagcctgaag 3180
ggcctgtgga ccctgcgtgc tttcggtcgc caaccctact ttgagactct cttccataag 3240
gctctgaatt tacatactgc caattggttc ctatacctta gtacccttcg gtggttccag 3300
atgcggatag aaatgatctt cgtgattttc ttcatcgcag tcactttcat ctctattttg 3360
acgaccggtg agggcgaggg cagggtgggc atcattctga ctttggccat gaacattatg 3420
tcaacactcc agtgggccgt taattcaagc attgatgtgg attccttgat gcgttccgtc 3480
agcagggtat ttaaattcat agacatgccc accgagggca agccaacaaa atctaccaag 3540
ccatacaaaa atggccaact aagcaaggtc atgattatcg agaattctca tgtgaaaaag 3600
gacgacattt ggccttccgg gggtcaaatg actgtaaagg acctgacggc taaatacact 3660
gagggcggta atgctatctt ggagaacatc tctttcagca tctcccctgg ccagagagtg 3720
ggactgctcg ggcggacagg ctccggaaag tctacgctcc tttcagcatt ccttagactt 3780
ctgaacaccg aaggtgagat tcagattgac ggggtctctt gggactccat cacacttcag 3840
caatggagga aggcattcgg tgtaatcccc caaaaggttt ttatcttctc cggaacattt 3900
cgtaagaatc tggacccgta cgagcagtgg tcagatcagg agatctggaa agtagcagac 3960
gaggtcgggc tacggagcgt tattgaacag tttcctggca aactggactt cgttttggtg 4020
gacggaggct gtgtgctgag tcacggccat aaacaactga tgtgcttagc taggtctgtt 4080
ctcagcaagg caaagatttt actgctggat gaaccaagcg cccaccttga tccagtgaca 4140
tatcaaatca tcagaagaac tcttaaacag gcgttcgccg actgcacagt gatcctgtgt 4200
gagcacagaa tagaagccat gctggaatgt caacagtttc tcgtgattga ggagaacaag 4260
gtgcgccagt acgatagcat ccagaagtta ctcaatgaaa ggtcactctt caggcaggcc 4320
atctcaccca gcgaccgcgt taagctgttt ccacaccgaa acagttccaa gtgcaaaagt 4380
aagccacaga ttgctgcact gaaggaagag acagaagaag aagttcagga cactcggctc 4440
tga 4443

<210> SEQ ID NO 39
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 39
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240

```
ttcatgtttt atgggatctt cctgtacctg ggggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac accccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
```

tttgtcctca tctggtgcct ggttattttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct cccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 40
<211> LENGTH: 4443
<212> TYPE: DNA
<213> ORGANISM: Artificial Sequence
<220> FEATURE:
<223> OTHER INFORMATION: chemically synthesized oligonucleotide

<400> SEQUENCE: 40
atgcaacgga gtcctctgga aaaagcctct gtcgtatcta agcttttctt cagttggaca 60
cgcccgattt tgagaaaggg ttatcggcaa cgcttggaac ttagtgacat ctaccaaatt 120
ccaagtgtag actcagccga taacttgagc gaaaagctcg aacgagagtg ggatcgagaa 180

```
ctggctagca aaaaaaatcc caaactcata aatgccctgc gacgctgttt cttttggcga    240
tttatgtttt acggtatttt cctttatttg ggtgaggtca cgaaggctgt acagccactg    300
ctgctgggtc gcatcattgc ctcttacgac cctgacaaca aagaggagcg gtcaatagct    360
atctaccttg gtataggact ttgcttgctc ttcatagtcc gcacgttgct tctccaccct    420
gctatatttg gtctccatca cattgggatg caaatgcgga tcgcgatgtt cagtcttata    480
tataaaaaga ctcttaaact ttccagccgg gttctggata agatctctat tggtcaactg    540
gtatctcttt tgtctaacaa cctgaataag ttcgacgagg gccttgcatt ggcccatttt    600
gtatggattg cccctttgca agtcgccctc ctgatgggat tgatctggga actcctgcaa    660
gctagtgctt tttgcggatt gggattcctc atagtccttg cgctctttca ggcgggactt    720
ggacgcatga tgatgaagta tcgcgaccaa cgagctggca agatcagtga acggcttgta    780
ataaccagtg aaatgataga gaacatccag agcgtaaaag cttactgttg ggaagaagcg    840
atggaaaaga tgattgagaa ccttcgccag acagaactta aacttacacg aaaggccgct    900
tatgtccggt acttcaactc ttcagcattt ttttttagtg gcttctttgt agtgttcctg    960
tccgtccttc cgtatgcact tatcaagggt ataatactta ggaaaatctt cacaacaatc   1020
agtttttgca tagtccttcg catggcagta actcgccaat ttccctgggc agttcagacg   1080
tggtacgact cacttggcgc aattaacaaa attcaagatt tcctccaaaa gcaagagtat   1140
aaaaccttgg aatacaacct taccaccaca gaagttgtaa tggaaaatgt cacagccttc   1200
tgggaggaag gtttcggcga actttttgag aaggcgaagc aaaataacaa taatcggaaa   1260
acatcaaacg gtgacgattc actgttcttt tctaacttta gccttcttgg gacgcccgtc   1320
ctgaaggaca taaactttaa gattgaacgg ggtcaacttc tcgcggtcgc agggagtact   1380
ggagcgggga aaacgagcct gctgatggtg ataatggggg agttggagcc ctcagaaggc   1440
aagatcaagc atagtggtag aattagcttc tgcagtcaat ttagttggat tatgccgggc   1500
acgatcaaag aaaatataat ctttggggta tcctacgatg aatacaggta ccgatcagtg   1560
ataaaagcgt gccagcttga agaagacatt tcaaagtttg ctgagaagga taatatcgta   1620
cttggagaag gaggtatcac cctgtctggg ggtcaacgag cgaggatctc cctggcacgc   1680
gccgtctaca aggacgcgga cctctatctg ttggattcac cgttcggata tttggacgtg   1740
cttacggaga aagaaatatt tgagagctgt gtttgcaagc tcatggcaaa taaaaccaga   1800
atattggtta caagcaagat ggagcatctt aagaaagcag ataaaatcct gatattgcac   1860
gagggctctt catacttcta cgggacgttt tctgagttgc agaacctcca gccggatttc   1920
agctctaagc tgatgggctg tgattccttt gatcagttta gtgcggaaag acgaaacagt   1980
atactcaccg aaacactgca caggttctct ctggagggcg acgccccggt ttcctggaca   2040
gagacgaaga agcagtcctt caaacagaca ggcgagtttg gggagaaaag gaaaaatagc   2100
atactcaacc cgattaacag cattcgcaag ttcagtatag tacaaaagac cccgttgcag   2160
atgaacggta tagaggaaga ttctgatgag ccactggaaa gacggctttc tctcgttccg   2220
gacagtgaac agggagaggc aatactgcct cggatcagcg ttatctctac aggacctact   2280
ttgcaagctc ggcgccgaca gtcagtcttg aatcttatga ctcatagtgt taatcaaggc   2340
cagaatatcc atcgcaagac caccgcaagt acaaggaaag tgagcttggc acctcaagca   2400
aaccttactg aacttgatat ctactcacgg cgactttcac aggagaccgg acttgaaatt   2460
agtgaagaaa ttaacgagga ggacctcaag gagtgcttct tcgatgacat ggaatcaatc   2520
```

-continued

```
cccgcagtca caacctggaa cacttatctg aggtatataa cagttcacaa gagcctcatt   2580
tttgtactta tttggtgttt ggtaattttc ctggcggagg ttgctgcttc tttggtcgtc   2640
ctttggctcc tcgggaatac accgctccaa gacaaaggca actctaccca tagtaggaac   2700
aattcatatg cagtgattat aaccagtaca tcatcttatt acgttttcta tatttatgtc   2760
ggggtagctg acacgctgtt ggcgatgggc ttctttaggg gcctcccctt ggtacacacc   2820
cttatcacgg tgagtaaaat cctgcatcac aaaatgcttc attctgtact ccaagcgccg   2880
atgagtacgc ttaatacgct gaaagcagga gggatactga atcggttcag caaggacatc   2940
gccattctgg atgacctgct tccattgaca atatttgatt tcattcagct ccttctcata   3000
gttattggag ccatagcggt ggtggctgtg cttcagcctt atatattcgt tgccacagtt   3060
cccgttatag tggcatttat aatgctcagg gcctactttc tccagacttc ccagcagttg   3120
aagcaactcg aatcagaagg aaggtcacct attttcacac atcttgtgac ttccttgaag   3180
ggcttgtgga cgctgcgggc cttcggaaga caaccatatt ttgaaactct cttccacaaa   3240
gctttgaatc ttcatactgc gaactggttc ctgtatttga gtactttgcg ctggttccag   3300
atgaggatag aaatgatatt cgttatcttc tttatcgcgg ttacgttcat aagtatcctc   3360
actacggggg agggtgaggg tagagtgggc ataatactga ccctcgccat gaacattatg   3420
tccaccctgc agtgggcggt aaacagcagc atagatgtgg attctttgat gcgcagtgtg   3480
agcagggttt ttaagtttat cgatatgccg acggaaggaa agcccactaa aagcacgaaa   3540
ccctataaaa atggacagct tagcaaagta atgataatcg agaatagcca tgtgaaaaag   3600
gatgacatat ggccttccgg aggccaaatg actgttaaag atctgaccgc taaatatacc   3660
gagggcggca acgcaatact cgaaaacata agcttttcca taagccccgg ccaacgcgtg   3720
ggtcttctgg ggaggactgg ctccggaaaa tcaacgttgc ttagcgcgtt tttgcggctc   3780
cttaacactg aaggtgagat ccaaatagat ggcgttagtt gggactctat aacactgcaa   3840
caatggcgga aagctttcgg cgtcatacct cagaaggtgt tcatctttag cggaacgttc   3900
aggaagaact tggatcccta cgaacaatgg agtgatcaag aaatatggaa agtggcagat   3960
gaggtaggct tgcgcagtgt cattgaacaa ttcccaggga aactcgactt tgtactggtg   4020
gacggcggtt gcgtcttgtc acacgggcac aaacagttga tgtgtttggc ccgcagtgtt   4080
ttgtctaagg cgaagattct gttgctcgac gaaccgagtg ctcatcttga tcccgtcacc   4140
taccaaatca tcagaaggac gttgaagcaa gctttcgccg actgcactgt aatcctttgt   4200
gagcatagga tcgaagcaat gctcgagtgc caacagttct tggttataga ggagaataag   4260
gttcggcaat acgactcaat acagaaactg cttaatgagc ggtcactctt tcgacaagct   4320
atctctccta gtgacagggt aaagcttttt cctcatcgga attccagcaa gtgtaagagt   4380
aaaccacaga tcgccgccct taaagaggag accgaagaag aggtgcagga tacgagactt   4440
tag                                                                 4443
```

CODON-OPTIMIZED CFTR MRNA

RELATED APPLICATIONS

This application claims priority to U.S. Provisional Application Ser. No. 62/464,215, filed Feb. 27, 2017, the disclosures of which are hereby incorporated by reference.

SEQUENCE LISTING

The present specification makes reference to a Sequence Listing (submitted electronically as a .txt file named MRT-2001 US_ST25 on Feb. 27, 2018). The .txt file was generated on date and is 166,293 bytes in size. The entire contents of the sequence are herein incorporated by reference.

BACKGROUND

Cystic fibrosis is an autosomal inherited disorder resulting from mutation of the CFTR gene, which encodes a chloride ion channel believed to be involved in regulation of multiple other ion channels and transport systems in epithelial cells. Loss of function of CFTR results in chronic lung disease, aberrant mucus production, and dramatically reduced life expectancy. See generally Rowe et al., New Engl. J. Med. 352, 1992-2001 (2005).

Currently there is no cure for cystic fibrosis. The literature has documented numerous difficulties encountered in attempting to induce expression of CFTR in the lung. For example, viral vectors comprising CFTR DNA triggered immune responses and CF symptoms persisted after administration. Conese et al., J. Cyst. Fibros. 10 Suppl 2, S114-28 (2011); Rosenecker et al., Curr. Opin. Mol. Ther. 8, 439-45 (2006). Non-viral delivery of DNA, including CFTR DNA, has also been reported to trigger immune responses. Alton et al., Lancet 353, 947-54 (1999); Rosenecker et al., J Gene Med. 5, 49-60 (2003). Furthermore, non-viral DNA vectors encounter the additional problem that the machinery of the nuclear pore complex does not ordinarily import DNA into the nucleus, where transcription would occur. Pearson, Nature 460, 164-69 (2009).

SUMMARY OF THE INVENTION

The present invention provides, among other things, pharmaceutical compositions comprising messenger RNA (mRNA) encoding a Cystic Fibrosis Transmembrane Conductance Regulator (CFTR) protein and methods of making and using thereof. These pharmaceutical compositions can be used for improved treatment of cystic fibrosis.

In one aspect, the present invention provides pharmaceutical compositions for treating cystic fibrosis, comprising an mRNA encoding a Cystic Fibrosis Transmembrane Conductance Regulator (CFTR) protein and wherein the mRNA encoding the CFTR protein comprises a polynucleotide sequence at least 85% identical to SEQ ID NO: 1. In some embodiments, the mRNA encoding the CFTR protein comprises SEQ ID NO: 1. In some embodiments, the mRNA further comprises a 5' untranslated region (UTR) sequence of SEQ ID NO: 4. In some embodiments, the mRNA further comprises a 3' untranslated region (UTR) sequence of SEQ ID NO: 5 or SEQ ID NO: 6.

In some embodiments, the mRNA encoding the CFTR protein is encapsulated within a nanoparticle. In some embodiments, the nanoparticle is a liposome. In some embodiments, the liposome comprises one or more cationic lipids, one or more non-cationic lipids, one or more cholesterol-based lipids and one or more PEG-modified lipids. In some embodiments, the liposome comprises no more than three distinct lipid components. In some embodiments, one distinct lipid component is a sterol-based cationic lipid. In some embodiments, the liposome has a size less than about 100 nm. In another aspect, the present invention provides methods for large scale production of mRNA encoding Cystic Fibrosis Transmembrane Conductance Regulator (CFTR). In some embodiments, a method according to the present invention comprises in vitro synthesizing mRNA encoding a CFTR protein using a SP6 RNA polymerase, wherein at least 80% of the synthesized mRNA molecules are full-length and wherein at least 100 mg of mRNA is synthesized at a single batch.

In some embodiments, the in vitro synthesized mRNA encoding CFTR is substantially free of a secondary polynucleotide species of approximately 1800 nucleotides in length. In some embodiments, the in vitro synthesis of mRNA results in a secondary polynucleotide species that constitutes less than 10%, 5%, 4%, 3%, 2%, 1%, 0.5%, 0.4%, 0.3%, 0.2% or 0.1% of the total mRNA synthesized.

In some embodiments, at least 85%, 90%, 95%, 96%, 97%, 98%, or 99% of the synthesized mRNA molecules are full-length. In some embodiments, the synthesized mRNA molecules are substantially full-length.

In some embodiments, at least 200 mg, 300 mg, 400 mg, 500 mg, 600 mg, 700 mg, 800 mg, 900 mg, 1 g, 5 g, 10 g, 25 g, 50 g, 75 g, 100 g, 150 g, 200 g, 250 g, 500 g, 750 g, 1 kg, 5 kg, 10 kg, 50 kg, 100 kg, 1000 kg, or more of mRNA is synthesized at a single batch.

In some embodiments, the CFTR protein comprises the amino acid sequence of SEQ ID NO: 3. In some embodiments, the mRNA comprises a polynucleotide sequence at least 85% identical to SEQ ID NO: 1. In some embodiments, the mRNA further comprises a 5' untranslated region (UTR) sequence of SEQ ID NO: 4. In some embodiments, the mRNA further comprises a 3' untranslated region (UTR) sequence of SEQ ID NO: 5 or SEQ ID NO: 6.

In some embodiments, the method further comprises a step of capping and/or tailing of the synthesized CFTR mRNA.

Among other things, the present invention provides mRNA encoding Cystic Fibrosis Transmembrane Conductance Regulator (CFTR) synthesized using various methods described herein and pharmaceutical compositions containing the same.

In yet another aspect, the present invention provides methods of delivering mRNA encoding CFTR described herein for in vivo protein expression and/or for treatment of Cystic Fibrosis. In some embodiments, the present invention provides methods of treating cystic fibrosis, comprising administering to a subject in need of treatment a composition comprising an mRNA encoding an Cystic Fibrosis Transmembrane Conductance Regulator (CFTR) protein wherein the mRNA comprises a polynucleotide sequence at least 85% (e.g., at least 90%, 92%, 94%, 95%, 96%, 97%, 98%, or 99%) identical to SEQ ID NO: 1.

In some embodiments, the mRNA encoding the CFTR protein comprises SEQ ID NO: 1. In some embodiments, the mRNA further comprises a 5' untranslated region (UTR) sequence of SEQ ID NO: 4. In some embodiments, the mRNA further comprises a 3' untranslated region (UTR) sequence of SEQ ID NO: 5 or SEQ ID NO: 6.

In some embodiments, the mRNA encoding the CFTR protein is encapsulated within a nanoparticle. In some embodiments, the nanoparticle is a liposome. In some embodiments, the liposome comprises one or more cationic lipids, one or more non-cationic lipids, one or more cholesterol-based lipids and one or more PEG-modified lipids. In some embodiments, the liposome comprises no more than three distinct lipid components. In some embodiments, one distinct lipid component is a sterol-based cationic lipid. In some embodiments, the sterol-based cationic lipid is the imidazole cholesterol ester "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate. In some embodiments, the liposome has a size less than about 100 nm.

In some embodiments, the mRNA is administered to the subject via pulmonary delivery. In some embodiments, the pulmonary delivery is nebulization.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

FIG. 1 depicts an exemplary gel showing that synthesis of the novel codon-optimized Cystic Fibrosis Transmembrane Conductance Regulator (CFTR) sequence using an SP6 promoter eliminated the secondary polynucleotide species (lane 2), as compared to a previous codon-optimized CFTR sequence (lane 3). Arrow indicates a secondary polynucleotide species approximately 1800 nucleotides in length.

DEFINITIONS

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "not in a single batch" would not mean mRNA synthesized at different times that are combined to achieve the desired amount.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery). In some embodiments, delivery is pulmonary delivery, e.g., comprising nebulization.

Encapsulation: As used herein, the term "encapsulation," or grammatical equivalent, refers to the process of confining an mRNA molecule within a nanoparticle.

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalents, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguano sine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, improved methods and pharmaceutical compositions for treating cystic fibrosis based on codon optimized messenger RNA (mRNA) encoding a Cystic Fibrosis Transmembrane Conductance Regulator (CFTR) protein. In particular, these codon optimized mRNA may be synthesized efficiently at a large scale by, e.g., SP6 RNA polymerase. Certain codon optimized mRNA may be particularly useful for producing homogenous, safe and efficacious clinical product.

In some embodiments, the present invention provides methods of producing a pharmaceutical composition comprising an mRNA, wherein the mRNA is an in vitro transcribed mRNA encoding a Cystic Fibrosis Transmembrane Conductance Regulator (CFTR) protein, wherein the in vitro transcribed mRNA is synthesized from a DNA template using an SP6 RNA polymerase, and wherein the synthesis of the in vitro transcribed mRNA does not result in the production of a secondary polynucleotide species of approximately 1800 nucleotides in length.

Cystic Fibrosis

The present invention may be used to treat a subject who is suffering from or susceptible to cystic fibrosis. Cystic fibrosis is a genetic disorder characterized by mutations in the gene for Cystic Fibrosis Transmembrane Conductance Regulator (CFTR). The CFTR protein functions as a channel across the membrane of cells that produce mucus, sweat, saliva, tears, and digestive enzymes. The channel transports negatively charged particles called chloride ions into and out of cells. The transport of chloride ions helps control the movement of water in tissues, which is necessary for the production of thin, freely flowing mucus. Mucus is a slippery substance that lubricates and protects the lining of the airways, digestive system, reproductive system, and other organs and tissues.

Respiratory symptoms of cystic fibrosis include: a persistent cough that produces thick mucus (sputum), wheezing, breathlessness, exercise intolerance, repeated lung infections and inflamed nasal passages or a stuffy nose. Digestive symptoms of cystic fibrosis include: foul-smelling, greasy stools, poor weight gain and growth, intestinal blockage, particularly in newborns (meconium ileus), and severe constipation.

Codon Optimized mRNA Encoding CFTR

In some embodiments, the present invention provides methods and compositions for delivering codon optimized mRNA encoding CFTR to a subject for the treatment of cystic fibrosis. A suitable codon optimized CFTR mRNA encodes any full length, fragment or portion of a CFTR protein which can be substituted for naturally-occurring CFTR protein activity and/or reduce the intensity, severity, and/or frequency of one or more symptoms associated with cystic fibrosis.

In some embodiments, a suitable codon optimized mRNA sequence is an mRNA sequence encoding a human CFTR (hCFTR) protein. Exemplary codon optimized CFTR mRNA coding sequence and the corresponding amino acid sequence are shown in Table 1:

TABLE 1

| Exemplary Codon-Optimized Human CFTR | |
|---|---|
| SEQ ID NO: 1 | **AUG**CAACGCUCUCCUCUUGAAAAGGCCUCGGUGGUGUCCAAGCUCUU<br>CUUCUCGUGGACUAGACCCAUCCUGAGAAAGGGGUACAGACAGCGCU<br>UGGAGCUGUCCGAUAUCUAUCAAAUCCCUUCCGUGGACUCCGCGGAC<br>AACCUGUCCGAGAAGCUCGAGAGAGAAUGGGACAGAGAACUCGCCUC<br>AAAGAAGAACCCGAAGCUGAUUAAUGCGCUUAGGCGGUGCUUUUUC<br>UGGCGGUUCAUGUUCUACGGCAUCUUCCUCUACCUGGGAGAGGUCAC<br>CAAGGCCGUGCAGCCCCUGUUGCUGGGACGGAUUAUUGCCUCCUACG<br>ACCCCGACAACAAGGAAGAAAGAAGCAUCGCUAUCUACUUGGGCAUC<br>GGUCUGUGCCUGCUUUUCAUCGUCCGGACCCUCUUGUUGCAUCCUGC<br>UAUUUUCGGCCUGCAUCACAUUGGCAUGCAGAUGAGAAUUGCCAUG<br>UUUUCCCUGAUCUACAAGAAAACUCUGAAGCUCUCGAGCCGCGUGCU<br>UGACAAGAUUUCCAUCGGCCAGCUCGUGUCCCUGCUCUCCAACAAUC<br>UGAACAAGUUCGACGAGGGCCUCGCCCUGGCCCACUUCGUGUGGAUC<br>GCCCCUCUGCAAGUGGCGCUUCUGAUGGGCCUGAUCUGGGAGCUGCU<br>GCAAGCCUCGGCAUUCUGUGGGCUUGGAUUCCUGAUCGUGCUGGCAC<br>UGUUCCAGGCCGGACUGGGGCGGAUGAUGAUGAAGUACAGGGACCA<br>GAGAGCCGGAAAGAUUUCCGAACGGCUGGUGAUCACUUCGGAAAUG<br>AUCGAAAACAUCCAGUCAGUGAAGGCCUACUGCUGGGAAGAGGCCAU<br>GGAAAAGAUGAUUGAAAACCUCCGGCAAACCGAGCUGAAGCUGACCC<br>GCAAGGCCGCUUACGUGCGCUAUUUCAACUCGUCCGCUUUCUUCUUC<br>UCCGGGUUCUUCGUGGUGUUUCUCUCCGUGCUCCCCUACGCCCUGAU<br>UAAGGGAAUCAUCCUCAGGAAGAUCUUCACCACCAUUUCCUUCUGUA<br>UCGUGCUCCGCAUGGCCGUGACCCGGCAGUUCCCAUGGGCCGUGCAG<br>ACUUGGUACGACUCCCUGGGAGCCAUUAACAAGAUCCAGGACUUCCU<br>UCAAAAGCAGGAGUACAAGACCCUCGAGUACAACCUGACUACUACCG<br>AGGUCGUGAUGGAAAACGUCACCGCCUUUUGGGAGGAGGGAUUUGG<br>CGAACUGUUCGAGAAGGCCAAGCAGAACAACAACAACCGCAAGACCU<br>CGAACGGUGACGACUCCCUCUUCUUUUCAAACUUCAGCCUGCUCGGG<br>ACGCCCGUGCUGAAGGACAUUAACUUCAAGAUCGAAAGAGGACAGCU<br>CCUGGCGGUGGCCGGAUCGACCGGAGCCGGAAAGACUUCCCUGCUGA<br>UGGUGAUCAUGGGAGAGCUUGAACCUAGCGAGGGAAAGAUCAAGCA<br>CUCCGGCCGCAUCAGCUUCUGUAGCCAGUUUUCCUGGAUCAUGCCCG<br>GAACCAUUAAGGAAAACAUCAUCUUCGGCGUGUCCUACGAUGAAUAC<br>CGCUACCGGUCCGUGAUCAAAGCCUGCCAGCUGGAAGAGGAUAUUUC<br>AAAGUUCGCGGAGAAAGAUAACAUCGUGCUGGGCGAAGGGGGUAUU<br>ACCUUGUCGGGGGGCCAGCGGGCUAGAAUCUCGCUGGCCAGAGCCGU<br>GUAUAAGGACGCCGACCUGUAUCUCCUGGACUCCCCCUUCGGAUACC<br>UGGACGUCCUGACCGAAAAGGAGAUCUUCGAAUCGUGCGUGUGCAA<br>GCUGAUGGCUAACAAGACUCGCAUCCUCGUGACCUCCAAAAUGGAGC<br>ACCUGAAGAAGGCAGACAAGAUUCUGAUUCUGCAUGAGGGGUCCUCC<br>UACUUUUACGGCACCUUCUCGGAGUUGCAGAACUUGCAGCCCGACUU<br>CUCAUCGAAGCUGAUGGGUUGCGACAGCUUCGACCAGUUCUCCGCCG<br>AAAGAAGGAACUCGAUCCUGACGGAAACCUUGCACCGCUUCUCUUUG<br>GAAGGCGACGCCCCUGUGUCAUGGACCGAGACUAAGAAGCAGAGCUU<br>CAAGCAGACCGGGGAAUUCGGCGAAAAGAGGAAGAACAGCAUCUUG |

TABLE 1-continued

| Exemplary Codon-Optimized Human CFTR | |
|---|---|
| | AACCCCAUUAACUCCAUCCGCAAGUUCUCAAUCGUGCAAAAGACGCC |
| | ACUGCAGAUGAACGGCAUUGAGGAGGACUCCGACGAACCCCUUGAGA |
| | GGCGCCUGUCCCUGGUGCCGGACAGCGAGCAGGGAGAAGCCAUCCUG |
| | CCUCGGAUUUCCGUGAUCUCCACUGGUCCGACGCUCCAAGCCCGGCG |
| | GCGGCAGUCCGUGCUGAACCUGAUGACCCACAGCGUGAACCAGGGCC |
| | AAAACAUUCACCGCAAGACUACCGCAUCCACCCGGAAAGUGUCCCUG |
| | GCACCUCAAGCGAAUCUUACCGAGCUCGACAUCUACUCCCGGAGACU |
| | GUCGCAGGAAACCGGGCUCGAAAUUUCCGAAGAAAUCAACGAGGAG |
| | GAUCUGAAAGAGUGCUUCUUCGACGAUAUGGAGUCGAUACCCGCCGU |
| | GACGACUUGGAACACUUAUCUGCGGUACAUCACUGUGCACAAGUCAU |
| | UGAUCUUCGUGCUGAUUUGGUGCCUGGUGAUUUUCCUGGCCGAGGU |
| | CGCGGCCUCACUGGUGGUGCUCUGGCUGUUGGGAAACACGCCUCUGC |
| | AAGACAAGGGAAACUCCACGCACUCGAGAAACAACAGCUAUGCCGUG |
| | AUUAUCACUUCCACCUCCUCUUAUUACGUGUUCUACAUCUACGUCGG |
| | AGUGGCGGAUACCCUGCUCGCGAUGGGUUUCUUCAGAGGACUGCCGC |
| | UGGUCCACACCUUGAUCACCGUCAGCAAGAUUCUUCACCACAAGAUG |
| | UUGCAUAGCGUGCUGCAGGCCCCCAUGUCCACCCUCAACACUCUGAA |
| | GGCCGGAGGCAUUCUGAACAGAUUCUCCAAGGACAUCGCUAUCCUGG |
| | ACGAUCUCCUGCCGCUUACCAUCUUUGACUUCAUCCAGCUGCUGCUG |
| | AUCGUGAUUGGAGCAAUCGCAGUGGUGGCGGUGCUGCAGCCUUACA |
| | UUUUCGUGGCCACUGUGCCGGUCAUUGUGGCGUUCAUCAUGCUGCGG |
| | GCCUACUUCCUCCAAACCAGCCAGCAGCUGAAGCAACUGGAAUCCGA |
| | GGGACGAUCCCCCAUCUUCACUCACCUUGUGACGUCGUUGAAGGGAC |
| | UGUGGACCCUCCGGGCUUUCGGACGGCAGCCCUACUUCGAAACCCUC |
| | UUCCACAAGGCCCUGAACCUCCACACCGCCAAUUGGUUCCUGUACCU |
| | GUCCACCCUGCGGUGGUUCCAGAUGCGCAUCGAGAUGAUUUUCGUCA |
| | UCUUCUUCAUCGCGGUCACAUUCAUCAGCAUCCUGACUACCGGAGAG |
| | GGAGAGGGACGGGUCGGAAUAAUCCUGACCCUCGCCAUGAACAUUAU |
| | GAGCACCCUGCAGUGGGCAGUGAACAGCUCGAUCGACGUGGACAGCC |
| | UGAUGCGAAGCGUCAGCCGCGUGUUCAAGUUCAUCGACAUGCCUACU |
| | GAGGGAAAACCCACUAAGUCCACUAAGCCCUACAAAAAUGGCCAGCU |
| | GAGCAAGGUCAUGAUCAUCGAAAACUCCCACGUGAAGAAGGACGAU |
| | AUUUGGCCCUCCGGAGGUCAAAUGACCGUGAAGGACCUGACCGCAAA |
| | GUACACCGAGGGAGGAAACGCCAUUCUCGAAAACAUCAGCUUCUCCA |
| | UUUCGCCGGGACAGCGGGUCGGCCUUCUCGGGCGGACCGGUUCCGGG |
| | AAGUCAACUCUGCUGUCGGCUUUCCUCCGGCUGCUGAAUACCGAGGG |
| | GGAAAUCCAAAUUGACGGCGUGUCUUGGGAUUCCAUUACUCUGCAGC |
| | AGUGGCGGAAGGCCUUCGGCGUGAUCCCCCAGAAGGUGUUCAUCUUC |
| | UCGGGUACCUUCCGGAAGAACCUGGAUCCUUACGAGCAGUGGAGCGA |
| | CCAAGAAAUCUGGAAGGUCGCCGACGAGGUCGGCCUGCGCUCCGUGA |
| | UUGAACAAUUUCCUGGAAAGCUGGACUUCGUGCUCGUCGACGGGGG |
| | AUGUGUCCUGUCGCACGGACAUAAGCAGCUCAUGUGCCUCGCACGGU |
| | CCGUGCUCUCCAAGGCCAAGAUUCUGCUGCUGGACGAACCUUCGGCC |
| | CACCUGGAUCCGGUCACCUACCAGAUCAUCAGGAGGACCCUGAAGCA |
| | GGCCUUUGCCGAUUGCACCGUGAUUCUCUGCGAGCACCGCAUCGAGG |
| | CCAUGCUGGAGUGCCAGCAGUUCCUGGUCAUCGAGGAGAACAAGGUC |
| | CGCCAAUACGACUCCAUUCAAAAGCUCCUCAACGAGCGGUCGCUGUU |
| | CAGACAAGCUAUUUCACCGUCCGAUAGAGUGAAGCUCUUCCCGCAUC |
| | GGAACAGCUCAAAGUGCAAAUCGAAGCCGCAGAUCGCAGCCUUGAAG |
| | GAAGAGACUGAGGAAGAGGUGCAGGACACCCGGCUU**UAA** |
| SEQ ID | **AUG**CAGCGGUCCCCGCUCGAAAAGGCCAGUGUCGUGUCCAAACUCUU |
| NO: 2 | CUUCUCAUGGACUCGGCCUAUCCUUAGAAAGGGGUAUCGGCAGAGGC |
| | UUGAGUUGUCUGACAUCUACCAGAUCCCCUCGGUAGAUUCGGCGGAU |
| | AACCUCUCGGAGAAGCUCGAACGGGAAUGGGACCGCGAACUCGCGUC |
| | UAAGAAAAACCCGAAGCUCAUCAACGCACUGAGAAGGUGCUUCUUCU |
| | GGCGGUUCAUGUUCUACGGUAUCUUCUUGUAUCUCGGGGAGGUCAC |
| | AAAAGCAGUCCAACCCCUGUUGUUGGGUCGCAUUAUCGCCUCGUACG |
| | ACCCCGAUAACAAAGAAGAACGGAGCAUCGCGAUCUACCUCGGGAUC |
| | GGACUGUGUUUGCUUUUCAUCGUCAGAACACUUUUGUUGCAUCCAGC |
| | AAUCUUCGGCCUCCAUCACAUCGGUAUGCAGAUGCGAAUCGCUAUGU |
| | UUAGCUUGAUCUACAAAAAGACACUGAAACUCUCGUCGCGGGUGUU |
| | GGAUAAGAUUUCCAUCGGUCAGUUGGUGUCCCUGCUUAGUAAUAAC |
| | CUCAACAAAUUCGAUGAGGGACUGGCGCUGGCACAUUUCGUGUGGA |
| | UUGCCCCGUUGCAAGUCGCCCUUUUGAUGGGCCUUAUUUGGGAGCUG |
| | UUGCAGGCAUCUGCCUUUUGUGGCCUGGGAUUUCUGAUUGUGUUGG |
| | CAUUGUUUCAGGCUGGGCUUGGGCGGAUGAUGAUGAAGUAUCGCGA |
| | CCAGAGAGCGGGUAAAAUCUCGGAAAGACUCGUCAUCACUUCGGAAA |
| | UGAUCGAAAACAUCCAGUCGGUCAAAGCCUAUUGCUGGGAAGAAGC |
| | UAUGGAGAAGAUGAUUGAAAACCUCCGCCAAACUGAGCUGAAACUG |
| | ACCCGCAAGGCGGCGUAUGUCCGGUAUUUCAAUUCGUCAGCGUUCUU |
| | CUUUUCCGGGUUCUUCGUUGUCUUUCUCUCGGUUUUGCCUUAUGCCU |
| | UGAUUAAGGGGAUUAUCCUCCGCAAGAUUUUCACCACGAUUUCGUUC |
| | UGCAUUGUAUUGCGCAUGGCAGUGACACGGCAAUUUCCGUGGGCCGU |
| | GCAGACAUGGUAUGACUCGCUUGGAGCGAUCAACAAAAUCCAAGACU |
| | UCUUGCAAAAGCAAGAGUACAAGACCCUGGAGUACAAUCUUACUACU |
| | ACGGAGGUAGUAAUGGAGAAUGUGACGGCUUUUUGGGAAGAGGGUU |
| | UUGGAGAACUGUUUGAGAAAGCAAAGCAGAAUAACAACAACCGCAA |

TABLE 1-continued

| Exemplary Codon-Optimized Human CFTR | |
|---|---|
| | GACCUCAAAUGGGGACGAUUCCCUGUUUUUCUCGAACUUCUCCCUGC<br>UCGGAACACCCGUGUUGAAGGACAUCAAUUUCAAGAUUGAGAGGGG<br>ACAGCUUCUCGCGGUAGCGGGAAGCACUGGUGCGGGAAAAACUAGCC<br>UCUUGAUGGUGAUUAUGGGGGAGCUUGAGCCCAGCGAGGGGAAGAU<br>UAAACACUCCGGGCGUAUCUCAUUCUGUAGCCAGUUUUCAUGGAUCA<br>UGCCCGGAACCAUUAAAGAGAACAUCAUUUUCGGAGUAUCCUAUGA<br>UGAGUACCGAUACAGAUCGGUCAUUAAGGCGUGCCAGUUGGAAGAG<br>GACAUUUCUAAGUUCGCCGAGAAGGAUAACAUCGUCUUGGGAGAAG<br>GGGGUAUUACAUUGUCGGGAGGGCAGCGAGCGCGGAUCAGCCUCGCG<br>AGAGCGGUAUACAAAGAUGCAGAUUUGUAUCUGCUUGAUUCACCGU<br>UUGGAUACCUCGACGUAUUGACAGAAAAAGAAAUCUUCGAGUCGUG<br>CGUGUGUAAACUUAUGGCUAAUAAGACGAGAAUCCUGGUGACAUCA<br>AAAAUGGAACACCUUAAGAAGGCGGACAAGAUCCUGAUCCUCCACGA<br>AGGAUCGUCCUACUUUUACGGCACUUUCUCAGAGUUGCAAAACUUGC<br>AGCCGGACUUCUCAAGCAAACUCAUGGGGUGUGACUCAUUCGACCAG<br>UUCAGCGCGGAACGGCGGAACUCGAUCUUGACGGAAACGCUGCACCG<br>AUUCUCGCUUGAGGGUGAUGCCCCGGUAUCGUGGACCGAGACAAAGA<br>AGCAGUCGUUUAAGCAGACAGGAGAAUUUGGUGAGAAAAGAAAGAA<br>CAGUAUCUUGAAUCCUAUUAACUCAAUUCGCAAGUUCUCAAUCGUCC<br>AGAAAACUCCACUGCAGAUGAAUGGAAUUGAAGAGGAUUCGGACGA<br>ACCCCUGGAGCGCAGGCUUAGCCUCGUGCCGGAUUCAGAGCAAGGGG<br>AGGCCAUUCUUCCCCGGAUUUCGGUGAUUUCAACCGGACCUACACUU<br>CAGGCGAGGCGAAGGCAAUCCGUGCUCAACCUCAUGACGCAUUCGGU<br>AAACCAGGGGCAAAACAUUCACCGCAAAACGACGGCCUCAACGAGAA<br>AAGUGUCACUUGCACCCCAGGCGAAUUUGACUGAACUCGACAUCUAC<br>AGCCGUAGGCUUUCGCAAGAAACCGGACUUGAGAUCAGCGAAGAAA<br>UCAAUGAAGAAGAUUUGAAAGAGUGUUUCUUUGAUGACAUGGAAUC<br>AAUCCCAGCGGUGACAACGUGGAACACAUACUUGCGUUACAUCACGG<br>UGCACAAGUCCUUGAUUUUCGUCCUCAUCUGGUGUCUCGUGAUCUUU<br>CUCGCUGAGGUCGCAGCGUCACUUGUGGUCCUCUGGCUGCUUGGUAA<br>UACGCCCUUGCAAGACAAAGGCAAUUCUACACACUCAAGAAACAAUU<br>CCUAUGCCGUGAUUAUCACUUCUACAAGCUCGUAUUACGUGUUUUAC<br>AUCUACGUAGGAGUGGCCGACACUCUGCUCGCGAUGGGUUUCUUCCG<br>AGGACUCCCACUCGUUCACACGCUUAUCACUGUCUCCAAGAUUCUCC<br>ACCAUAAGAUGCUUCAUAGCGUACUGCAGGCUCCCAUGUCCACCUUG<br>AAUACGCUCAAGGCGGGAGGUAUUUUGAAUCGCUUCUCAAAAGAUA<br>UUGCAAUUUUGGAUGACCUUCUGCCCCUGACGAUCUUCGACUUCAUC<br>CAGUUGUUGCUGAUCGUGAUUGGGGCUAUUGCAGUAGUCGCUGUCC<br>UCCAGCCUUACAUUUUUGUCGCGACCGUUCCGGUGAUCGUGGCGUUU<br>AUCAUGCUGCGGGCCUAUUUCUUGCAGACGUCACAGCAGCUUAAGCA<br>ACUGGAGUCUGAAGGGAGGUCGCCUAUCUUUACGCAUCUUGUGACCA<br>GUUUGAAGGGAUUGUGGACGUUGCGCGCCUUUGGCAGGCAGCCCUAC<br>UUUGAAACACUGUUCCACAAAGCGCUGAAUCUCCAUACGGCAAAUUG<br>GUUUUUGUAUUUGAGUACCCUCCGAUGGUUUCAGAUGCGCAUUGAG<br>AUGAUUUUUGUGAUCUUCUUUAUCGCGGUGACUUUUAUCUCCAUCU<br>UGACCACGGGAGAGGGCGAGGGACGGGUCGGUAUUAUCCUGACACUC<br>GCCAUGAACAUUAUGAGCACUUUGCAGUGGGCAGUGAACAGCUCGA<br>UUGAUGUGGAUAGCCUGAUGAGGUCCGUUUCGAGGGUCUUUAAGUU<br>CAUCGACAUGCCGACGGAGGGAAAGCCCACAAAAAGUACGAAACCCU<br>AUAAGAAUGGGCAAUUGAGUAAGGUAAUGAUCAUCGAGAACAGUCA<br>CGUGAAGAAGGAUGACAUCUGGCCUAGCGGGGGUCAGAUGACCGUG<br>AAGGACCUGACGGCAAAAUACACCGAGGGAGGGAACGCAAUCCUUGA<br>AAACAUCUCGUUCAGCAUUAGCCCCGGUCAGCGUGUGGGGUUGCUCG<br>GGAGGACCGGGUCAGGAAAAUCGACGUUGCUGUCGGCCUUCUUGAG<br>ACUUCUGAAUACAGAGGGUGAGAUCCAGAUCGACGGCGUUUCGUGG<br>GAUAGCAUCACCUUGCAGCAGUGGCGGAAAGCGUUUGGAGUAAUCCC<br>CCAAAAGGUCUUUAUCUUUAGCGGAACCUUCCGAAAGAAUCUCGAUC<br>CUUAUGAACAGUGGUCAGAUCAAGAGAUUUGGAAAGUCGCGGACGA<br>GGUUGGCCUUCGGAGUGUAAUCGAGCAGUUUCCGGGAAAACUCGAC<br>UUUGUCCUUGUAGAUGGGGGAUGCGUCCUGUCGCAUGGGCACAAGC<br>AGCUCAUGUGCCUGGCGCGAUCCGUCCUCUCUAAAGCGAAAAUUCUU<br>CUCUUGGAUGAACCUUCGGCCCAUCUGGACCCGGUAACGUAUCAGAU<br>CAUCAGAAGGACACUUAAGCAGGCGUUUGCCGACUGCACGGUGAUUC<br>UCUGUGAGCAUCGUAUCGAGGCCAUGCUCGAAUGCCAGCAAUUUCUU<br>GUCAUCGAAGAGAAUAAGGUCCGCCAGUACGACUCCAUCCAGAAGCU<br>GCUUAAUGAGAGAUCAUUGUUCCGGCAGGCGAUUUCACCAUCCGAUA<br>GGGUGAAACUUUUUCCACACAGAAAUUCGUCGAAGUGCAAGUCCAA<br>ACCGCAGAUCGCGGCCUUGAAAGAAGAGACUGAAGAAGAAGUUCAA<br>GACACGCGUCUU**UAA** |
| Human CFTR Protein Sequence | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE |

TABLE 1-continued

| Exemplary Codon-Optimized Human CFTR |
| --- |
| KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNSILTETLHR<br>FSLEGDAPVSWTETKKQSFKQTGEFGEKRKNSILNPINSIRKFSIVQKTPLQ<br>MNGIEEDSDEPLERRLSLVPDSEQGEAILPRISVISTGPTLQARRRQSVLNL<br>MTHSVNQGQNIHRKTTASTRKVSLAPQANLTELDIYSRRLSQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDEPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 3) |

Additional exemplary codon optimized mRNA sequences are described in the Examples section below, for example, SEQ ID NO: 7 and SEQ ID NO: 8, both of which include 5' and 3' untranslated regions framing a codon-optimized hCFTR-encoding mRNA and SEQ ID NO: 27 to SEQ ID NO: 40.

In some embodiments, a suitable mRNA sequence may be an mRNA sequence encoding a homolog or an analog of human CFTR (hCFTR) protein. For example, a homolog or an analog of hCFTR protein may be a modified hCFTR protein containing one or more amino acid substitutions, deletions, and/or insertions as compared to a wild-type or naturally-occurring hCFTR protein while retaining substantial hCFTR protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 3. In some embodiments, an mRNA suitable for the present invention encodes a protein substantially identical to hCFTR protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 3. In some embodiments, an mRNA suitable for the present invention encodes a fragment or a portion of hCFTR protein. In some embodiments, an mRNA suitable for the present invention encodes a fragment or a portion of hCFTR protein, wherein the fragment or portion of the protein still maintains CFTR activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 7 or SEQ ID NO: 8.

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to any one of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39 or SEQ ID NO: 40.

In some embodiments, a suitable mRNA encodes a fusion protein comprising a full length, fragment or portion of an hCFTR protein fused to another protein (e.g., an N or C terminal fusion). In some embodiments, the protein fused to the mRNA encoding a full length, fragment or portion of an hCFTR protein encodes a signal or a cellular targeting sequence.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Synthesis of mRNA Using SP6 RNA Polymerase

In some embodiments, CFTR mRNA is produced using SP6 RNA Polymerase. SP6 RNA Polymerase is a DNA-dependent RNA polymerase with high sequence specificity for SP6 promoter sequences. The SP6 polymerase catalyzes the 5'→3' in vitro synthesis of RNA on either single-stranded DNA or double-stranded DNA downstream from its promoter; it incorporates native ribonucleotides and/or modified ribonucleotides and/or labeled ribonucleotides into the polymerized transcript. Examples of such labeled ribonucleotides include biotin-, fluorescein-, digoxigenin-, aminoallyl-, and isotope-labeled nucleotides.

The sequence for bacteriophage SP6 RNA polymerase was initially described (GenBank: Y00105.1) as having the following amino acid sequence:

```
                                        (SEQ ID NO: 9)
MQDLHAIQLQLEEEMFNGGIRRFEADQQRQIAAGSESDTAWNRRLLSELI
APMAEGIQAYKEEYEGKKGRAPRALAFLQCVENEVAAYITMKVVMDMLNT
DATLQAIAMSVAERIEDQVRFSKLEGHAAKYFEKVKKSLKASRTKSYRHA
HNVAVVAEKSVAEKDADFDRWEAWPKETQLQIGTTLLEILEGSVFYNGEP
VFMRAMRTYGGKTIYYLQTSESVGQWISAFKEHVAQLSPAYAPCVIPPRP
WRTPFNGGFHTEKVASR1RLVKGNREHVRKLTQKQMPKVYKAINALQNTQ
WQINKDVLAVIEEVIRLDLGYGVPSFKPLIDKENKPANPVPVEFQHLRGR
ELKEMLSPEQWQQFINWKGECARLYTAETKRGSKSAAVVRMVGQARKYSA
FESIYFVYAMDSRSRVYVQSSTLSPQSNDLGKALLRFTEGRPVNGVEALK
WFCINGANLWGWDKKTFDVRVSNVLDEEFQDMCRDIAADPLTFTQWAKAD
APYEFLAWCFEYAQYLDLVDEGRADEFRTHLPVHQDGSCSGIQHYSAMLR
DEVGAKAVNLKPSDAPQDIYGAVAQVVIKKNALYMDADDATTFTSGSVTL
SGTELRAMASAWDSIGITRSLTKKPVMTLPYGSTRLTCRESVIDYIVDLE
EKEAQKAVAEGRTANKVHPFEDDRQDYLTPGAAYNYMTALIWPSISEVVK
APIVAMKMIRQLARFAAKRNEGLMYTLPTGFILEQKIMATEMLRVRTCLM
GDIKMSLQVETDIVDEAAMMGAAAPNFVHGHDASHLILTVCELVDKGVTS
IAVIHDSFGTHADNTLTLRVALKGQMVAMYIDGNALQKLLEEHEVRWMVD
TGIEVPEQGEFDLNEIMDSEYVFA.
```

An SP6 RNA polymerase suitable for the present invention can be any enzyme having substantially the same polymerase activity as bacteriophage SP6 RNA polymerase. Thus, in some embodiments, an SP6 RNA polymerase suitable for the present invention may be modified from SEQ ID NO: 9. For example, a suitable SP6 RNA polymerase may contain one or more amino acid substitutions, deletions, or additions. In some embodiments, a suitable SP6 RNA polymerase has an amino acid sequence about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% identical or homologous to SEQ ID NO: 9. In some embodiments, a suitable SP6 RNA polymerase may be a truncated protein (from N-terminus, C-terminus, or internally) but retain the polymerase activity. In some embodiments, a suitable SP6 RNA polymerase is a fusion protein.

An SP6 RNA polymerase suitable for the invention may be a commercially-available product, e.g., from Aldevron, Ambion, New England Biolabs (NEB), Promega, and Roche. The SP6 may be ordered and/or custom designed from a commercial source or a non-commercial source according to the amino acid sequence of SEQ ID NO: 9 or a variant of SEQ ID NO: 9 as described herein. The SP6 may be a standard-fidelity polymerase or may be a high-fidelity/high-efficiency/high-capacity which has been modified to promote RNA polymerase activities, e.g., mutations in the SP6 RNA polymerase gene or post-translational modifications of the SP6 RNA polymerase itself. Examples of such modified SP6 include SP6 RNA Polymerase-Plus™ from Ambion, HiScribe SP6 from NEB, and RiboMAX™ and Riboprobe® Systems from Promega.

In some embodiments, a suitable SP6 RNA polymerase is a fusion protein. For example, an SP6 RNA polymerase may include one or more tags to promote isolation, purification, or solubility of the enzyme. A suitable tag may be located at the N-terminus, C-terminus, and/or internally. Non-limiting examples of a suitable tag include Calmodulin-binding protein (CBP); *Fasciola hepatica* 8-kDa antigen (Fh8); FLAG tag peptide; glutathione-S-transferase (GST); Histidine tag (e.g., hexahistidine tag (His6)); maltose-binding protein (MBP); N-utilization substance (NusA); small ubiquitin related modifier (SUMO) fusion tag; Streptavidin binding peptide (STREP); Tandem affinity purification (TAP); and thioredoxin (TrxA). Other tags may be used in the present invention. These and other fusion tags have been described, e.g., Costa et al. Frontiers in Microbiology 5 (2014): 63 and in PCT/US16/57044, the contents of which are incorporated herein by reference in their entireties. In certain embodiments, a His tag is located at SP6's N-terminus.

SP6 Promoter

Any promoter that can be recognized by an SP6 RNA polymerase may be used in the present invention. Typically, an SP6 promoter comprises 5' ATTTAGGTGACACTATAG-3' (SEQ ID NO: 10). Variants of the SP6 promoter have been discovered and/or created to optimize recognition and/or binding of SP6 to its promoter. Non-limiting variants include but are not limited to: 5'-ATTTAGGGGACACTATAGAAGAG-3'; 5'-ATTTAGGGGACACTATAGAAGG-3'; 5'-ATTTAGGGGACACTATAGAAGGG-3'; 5'-ATTTAGGTGACACTATAGAA-3'; 5'-ATTTAGGTGACACTATAGAAGA-3'; 5'-ATTTAGGTGACACTATAGAAGAG-3'; 5'-ATTTAGGTGACACTATAGAAGG-3'; 5'-ATTTAGGTGACACTATAGAAGGG-3'; 5'-ATTTAGGTGACACTATAGAAGNG-3'; and 5'-CATACGATTTAGGTGACACTATAG-3' (SEQ ID NO: 11 to SEQ ID NO: 20).

In addition, a suitable SP6 promoter for the present invention may be about 95%, 90%, 85%, 80%, 75%, or 70% identical or homologous to any one of SEQ ID NO: 10 to SEQ ID NO: 20. Moreover, an SP6 promoter useful in the present invention may include one or more additional nucleotides 5' and/or 3' to any of the promoter sequences described herein.

DNA Template

Typically, a CFTR DNA template is either entirely double-stranded or mostly single-stranded with a double-stranded SP6 promoter sequence.

Linearized plasmid DNA (linearized via one or more restriction enzymes), linearized genomic DNA fragments (via restriction enzyme and/or physical means), PCR products, and/or synthetic DNA oligonucleotides can be used as templates for in vitro transcription with SP6, provided that they contain a double-stranded SP6 promoter upstream (and in the correct orientation) of the DNA sequence to be transcribed.

In some embodiments, the linearized DNA template has a blunt-end.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which are described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Large-Scale mRNA Synthesis

The present invention relates to large-scale production of codon optimized CFTR mRNA. In some embodiments, a method according to the invention synthesizes mRNA at least 100 mg, 150 mg, 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more at a single batch. As used herein, the term "batch" refers to a quantity or amount of mRNA synthesized at one time, e.g., produced according to a single manufacturing setting. A batch may refer to an amount of mRNA synthesized in one reaction that occurs via a single aliquot of enzyme and/or a single aliquot of DNA template for continuous synthesis under one set of conditions. mRNA synthesized at a single batch would not include mRNA synthesized at different times that are combined to achieve the desired amount. Generally, a reaction mixture includes SP6 RNA polymerase, a linear DNA template, and an RNA polymerase reaction buffer (which may include ribonucleotides or may require addition of ribonucleotides).

According to the present invention, 1-100 mg of SP6 polymerase is typically used per gram (g) of mRNA produced. In some embodiments, about 1-90 mg, 1-80 mg, 1-60 mg, 1-50 mg, 1-40 mg, 10-100 mg, 10-80 mg, 10-60 mg, 10-50 mg of SP6 polymerase is used per gram of mRNA produced. In some embodiments, about 5-20 mg of SP6 polymerase is used to produce about 1 gram of mRNA. In some embodiments, about 0.5 to 2 grams of SP6 polymerase is used to produce about 100 grams of mRNA. In some embodiments, about 5 to 20 grams of SP6 polymerase is used to about 1 kilogram of mRNA. In some embodiments, at least 5 mg of SP6 polymerase is used to produce at least 1 gram of mRNA. In some embodiments, at least 500 mg of SP6 polymerase is used to produce at least 100 grams of mRNA. In some embodiments, at least 5 grams of SP6 polymerase is used to produce at least 1 kilogram of mRNA. In some embodiments, about 10 mg, 20 mg, 30 mg, 40 mg, 50 mg, 60 mg, 70 mg, 80 mg, 90 mg, or 100 mg of plasmid DNA is used per gram of mRNA produced. In some embodiments, about 10-30 mg of plasmid DNA is used to produce about 1 gram of mRNA. In some embodiments, about 1 to 3 grams of plasmid DNA is used to produce about 100 grams of mRNA. In some embodiments, about 10 to 30 grams of plasmid DNA is used to about 1 kilogram of mRNA. In some embodiments, at least 10 mg of plasmid DNA is used to produce at least 1 gram of mRNA. In some embodiments, at least 1 gram of plasmid DNA is used to produce at least 100 grams of mRNA. In some embodiments, at least 10 grams of plasmid DNA is used to produce at least 1 kilogram of mRNA.

In some embodiments, the concentration of the SP6 RNA polymerase in the reaction mixture may be from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. In certain embodiments, the concentration of the SP6 RNA polymerase is from about 10 to 50 nM, 20 to 50 nM, or 30 to 50 nM. A concentration of 100 to 10000 Units/ml of the SP6 RNA polymerase may be used, as examples, concentrations of 100 to 9000 Units/ml, 100 to 8000 Units/ml, 100 to 7000 Units/ml, 100 to 6000 Units/ml, 100 to 5000 Units/ml, 100 to 1000 Units/ml, 200 to 2000 Units/ml, 500 to 1000 Units/ml, 500 to 2000 Units/ml, 500 to 3000 Units/ml, 500 to 4000 Units/ml, 500 to 5000 Units/ml, 500 to 6000 Units/ml, 1000 to 7500 Units/ml, and 2500 to 5000 Units/ml may be used.

The concentration of each ribonucleotide (e.g., ATP, UTP, GTP, and CTP) in a reaction mixture is between about 0.1 mM and about 10 mM, e.g., between about 1 mM and about 10 mM, between about 2 mM and about 10 mM, between about 3 mM and about 10 mM, between about 1 mM and about 8 mM, between about 1 mM and about 6 mM, between about 3 mM and about 10 mM, between about 3 mM and about 8 mM, between about 3 mM and about 6 mM, between about 4 mM and about 5 mM. In some embodiments, each ribonucleotide is at about 5 mM in a reaction mixture. In some embodiments, the total concentration of rNTPs (for example, ATP, GTP, CTP and UTPs combined) used in the reaction range between 1 mM and 40 mM. In some embodiments, the total concentration of rNTPs (for example, ATP, GTP, CTP and UTPs combined) used in the reaction range between 1 mM and 30 mM, or between 1 mM and 28 mM, or between 1 mM to 25 mM, or between 1 mM and 20 mM. In some embodiments, the total rNTPs concentration is less than 30 mM. In some embodiments, the total rNTPs concentration is less than 25 mM. In some embodiments, the total rNTPs concentration is less than 20 mM. In some embodiments, the total rNTPs concentration is less than 15 mM. In some embodiments, the total rNTPs concentration is less than 10 mM.

The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride.

The pH of the reaction mixture may be between about 6 to 8.5, from 6.5 to 8.0, from 7.0 to 7.5, and in some embodiments, the pH is 7.5.

Linear or linearized DNA template (e.g., as described above and in an amount/concentration sufficient to provide a desired amount of RNA), the RNA polymerase reaction buffer, and SP6 RNA polymerase are combined to form the reaction mixture. The reaction mixture is incubated at between about 37° C. and about 42° C. for thirty minutes to six hours, e.g., about sixty to about ninety minutes.

In some embodiments, about 5 mM NTPs, about 0.05 mg/mL SP6 polymerase, and about 0.1 mg/ml DNA template in a suitable RNA polymerase reaction buffer (final reaction mixture pH of about 7.5) is incubated at about 37° C. to about 42° C. for sixty to ninety minutes.

In some embodiments, a reaction mixture contains linearized double stranded DNA template with an SP6 polymerase-specific promoter, SP6 RNA polymerase, RNase inhibitor, pyrophosphatase, 29 mM NTPs, 10 mM DTT and a reaction buffer (when at 10× is 800 mM HEPES, 20 mM spermidine, 250 mM $MgCl_2$, pH 7.7) and quantity sufficient (QS) to a desired reaction volume with RNase-free water; this reaction mixture is then incubated at 37° C. for 60 minutes. The polymerase reaction is then quenched by addition of DNase I and a DNase I buffer (when at 10× is 100 mM Tris-HCl, 5 mM $MgCl_2$ and 25 mM $CaCl_2$, pH 7.6) to facilitate digestion of the double-stranded DNA template in preparation for purification. This embodiment has been shown to be sufficient to produce 100 grams of mRNA.

In some embodiments, a reaction mixture includes NTPs at a concentration ranging from 1-10 mM, DNA template at a concentration ranging from 0.01-0.5 mg/ml, and SP6 RNA polymerase at a concentration ranging from 0.01-0.1 mg/ml, e.g., the reaction mixture comprises NTPs at a concentration of 5 mM, the DNA template at a concentration of 0.1 mg/ml, and the SP6 RNA polymerase at a concentration of 0.05 mg/ml.

Nucleotides

Various naturally-occurring or modified nucleosides may be used to product mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("ψU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination. Post-synthesis processing Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol: chloroform: isoamyl alcohol solution, well known to one of skill in the art. In some embodiments, the mRNA is purified using Tangential Flow Filtration. Suitable purification methods include those described in US 2016/0040154, US 2015/0376220, PCT application PCT/US18/19954 entitled "METHODS FOR PURIFICATION OF MESSENGER RNA" filed on Feb. 27, 2018, and PCT application PCT/US18/19978 entitled "METHODS FOR PURIFICATION OF MESSENGER RNA" filed on Feb. 27, 2018, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of mRNA

Full-length or abortive transcripts of mRNA may be detected and quantified using any methods available in the art. In some embodiments, the synthesized mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention. In some embodiments, the synthesized mRNA molecules are detected using UV absorption spectroscopy with separation by capillary electrophoresis. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

In some embodiments, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full length mRNA. The impurities include IVT contaminants, e.g., proteins, enzymes, free nucleotides and/or shortmers.

In some embodiments, mRNA produced according to the invention is substantially free of shortmers or abortive transcripts. In particular, mRNA produced according to the invention contains undetectable level of shortmers or abortive transcripts by capillary electrophoresis or Glyoxal gel electrophoresis. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

mRNA Solution

In some embodiments, mRNA may be provided in a solution to be mixed with a lipid solution such that the mRNA may be encapsulated in lipid nanoparticles. A suitable mRNA solution may be any aqueous solution containing mRNA to be encapsulated at various concentrations. For example, a suitable mRNA solution may contain an mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain an mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5., 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

Delivery Vehicles

According to the present invention, mRNA encoding a CFTR protein (e.g., a full length, fragment, or portion of a CFTR protein) as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, a delivery vehicle comprising CFTR mRNA is administered by pulmonary delivery, e.g., comprising nebulization. In these embodiments, the delivery vehicle may be in an aerosolized composition which can be inhaled. In some embodiments, the mRNA is expressed in the tissue in which the delivery vehicle was administered, e.g., nasal cavity, trachea, bronchi, bronchioles, and/or other pulmonary system-related cell or tissue. Additional teaching of pulmonary delivery and nebulization are described in the related international application PCT/US17/61100 filed Nov. 10, 2017 by Applicant entitled "NOVEL ICE-BASED LIPID NANOPARTICLE FORMULATION FOR DELIVERY OF MRNA", and the U. S. Provisional Application U.S. Ser. No. 62/507,061, each of which is incorporated by reference in its entirety.

In some embodiments, mRNAs encoding a CFTR protein may be delivered via a single delivery vehicle. In some embodiments, mRNAs encoding a CFTR protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

A delivery vehicle comprising CFTR mRNA may be administered and dosed in accordance with current medical practice, taking into account the clinical condition of the subject, the site and method of administration (e.g., local and systemic, including oral, pulmonary, and via injection), the scheduling of administration, the subject's age, sex, body weight, and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein production.

In some embodiments, delivery vehicles are formulated such that they are suitable for extended-release of the mRNA contained therein. Such extended-release compositions may be conveniently administered to a subject at extended dosing intervals.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue. In some embodiments, a nanoparticle delivery vehicle is a liposome. In some embodiments, a liposome comprises one or more cationic lipids, one or more non-cationic lipids, one or more cholesterol-based lipids and one or more PEG-modified lipids. In some embodiments, a liposome comprises no more than three distinct lipid components. In some embodiments, one distinct lipid component is a sterol-based cationic lipid.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. An example of suitable cationic lipids for use in the compositions and methods of the invention include those described in international patent publications WO 2010/053572 (for example, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g., (15Z, 18Z)—N,N-dimethyl-6-(9Z,12Z)-octadeca-9,12-dien-1-yl) tetracosa-15,18-dien-1-amine (HGT5000), (15Z,18Z)—N, N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

In some embodiments, provided liposomes include a cationic lipid described in WO 2013/063468 and in U.S. provisional application entitled "Lipid Formulations for Delivery of Messenger RNA" filed concurrently with the present application on even date, both of which are incorporated by reference herein.

In some embodiments, a cationic lipid comprises a compound of formula I-c1-a:

I-c1-a

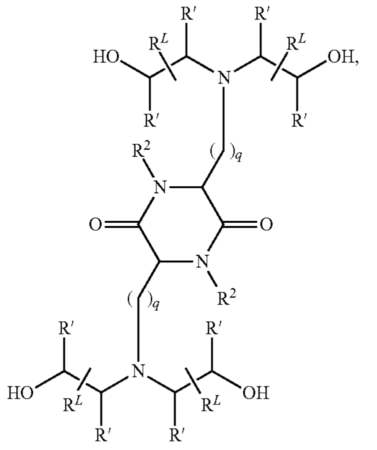

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

I-g

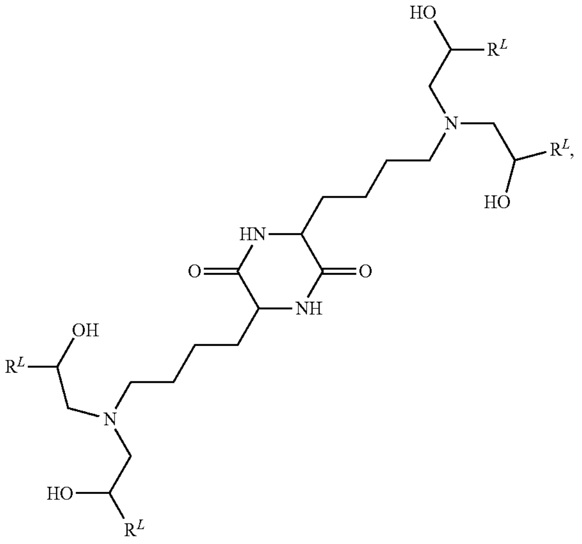

or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). The structure of cKK-E12 is shown below:

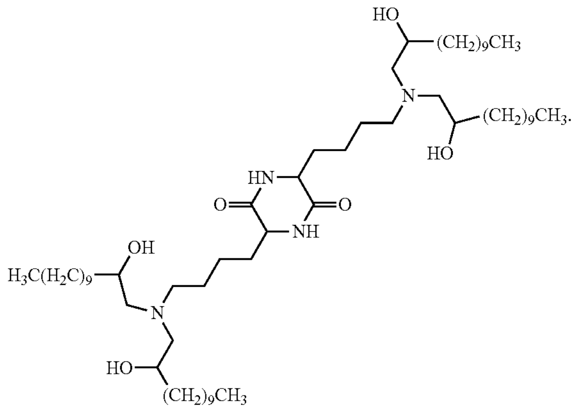

Additional exemplary cationic lipids include those of formula I:

I

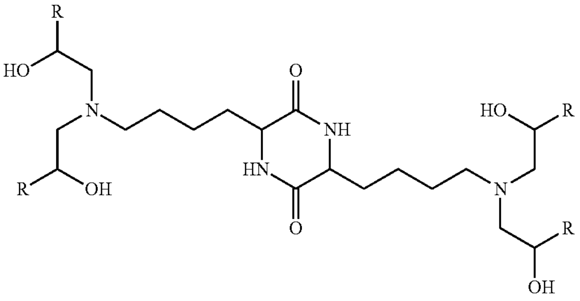

and pharmaceutically acceptable salts thereof, wherein,

R is ("OF-00")

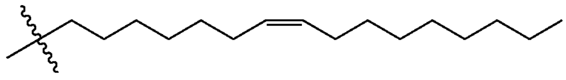
,

R is ("OF-01")

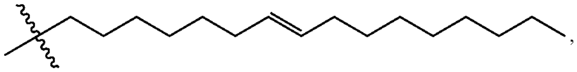
,

R is ("OF-02")

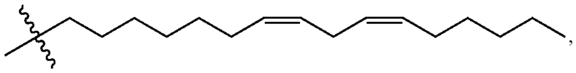
,

R is ("OF-03")

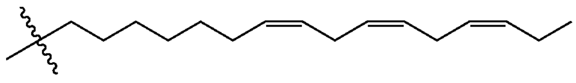

(see, e.g., Fenton, Owen S., et al. "Bioinspired Alkenyl Amino Alcohol Ionizable Lipid Materials for Highly Potent In Vivo mRNA Delivery." *Advanced materials* (2016)).

In some embodiments, the one or more cationic lipids may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin- -DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

Sterol Cationic Lipids

In some embodiments, sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate, as represented by structure (II) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate, as represented by structure (II).

(II)

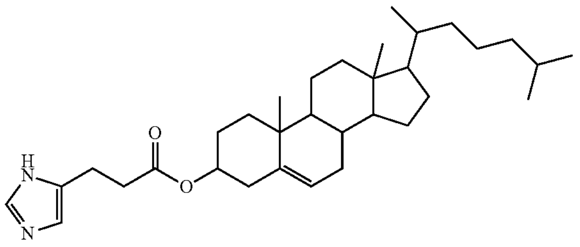

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

PEG-Modified Lipids

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the MCNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

Ratio of Distinct Lipid Components

In embodiments where a lipid nanoparticle comprises three and no more than three distinct components of lipids, the ratio of total lipid content (i.e., the ratio of lipid component (1):lipid component (2):lipid component (3)) can be represented as x:y:z, wherein $$(y+z)=100-x.$$

In some embodiments, each of "x," "y," and "z" represents molar percentages of the three distinct components of lipids, and the ratio is a molar ratio.

In some embodiments, each of "x," "y," and "z" represents weight percentages of the three distinct components of lipids, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z" is a PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "z," representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the molar percentage of lipid component (3) (e.g., a PEG lipid) is about 1%, 2%, 3%, 4%, 5%, 6%, 7%, 8%, 9%, 10%. In embodiments, variable "z," representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the weight percentage of lipid component (3) (e.g., a PEG lipid) is about 1%, 2%, 3%, 4%, 5%, 6%, 7%, 8%, 9%, 10%. In embodiments, variable "z," representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

Formation of Liposomes Encapsulating mRNA

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (zeta potential), targeting ligands and/or combinations thereof. In some embodiments, the one or more liposome may have a different composition of sterol-based cationic lipids, neutral lipid, PEG-modified lipid and/or combinations thereof. In some embodiments the one or more liposomes may have a different molar ratio of cholesterol-based cationic lipid, neutral lipid, and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of lipo some is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

EXAMPLES

While certain compounds, compositions and methods of the present invention have been described with specificity in accordance with certain embodiments, the following examples serve only to illustrate the compounds of the invention and are not intended to limit the same.

Example 1. Synthesis and Comparison of hCFTR mRNA Constructs

Codon-optimized Human Cystic Fibrosis Transmembrane Conductance Regulator (CFTR) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length as determined by gel electrophoresis. 5' and 3' untranslated regions present in each mRNA product are represented as X and Y, respectively and defined as stated (vide infra).

Exemplary Codon-Optimized Human Cystic Fibrosis Transmembrane Conductance Regulator (CFTR) mRNAs Construct Design:

X—SEQ ID NO: 1—Y

5' and 3' UTR Sequences:

```
X (5' UTR Sequence) =
                                        (SEQ ID NO: 4)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACG

Y (3' UTR Sequence) =
                                        (SEQ ID NO: 5)
CGGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAUC
AAGCU
OR

                                        (SEQ ID NO: 6)
GGGUGGCAUCCCUGUGACCCCUCCCCAGUGCCUCUCCUGGCCCUGGAAGU
UGCCACUCCAGUGCCCACCAGCCUUGUCCUAAUAAAAUUAAGUUGCAUCA
AAGCU
```

An exemplary codon-optimized human CFTR mRNA sequence includes SEQ ID NO: 1 as described in the detailed description section.

An exemplary full-length codon-optimized human CFTR mRNA sequence is shown below:

(SEQ ID NO: 7)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCAACGCU

CUCCUCUUGAAAAGGCCUCGGUGGUGUCCAAGCUCUUCUUCUCGUGGACU

AGACCCAUCCUGAGAAAGGGGUACAGACAGCGCUUGGAGCUGUCCGAUAU

CUAUCAAAUCCCUUCCGUGGACUCCGCGGACAACCUGUCCGAGAAGCUCG

AGAGAGAAUGGGACAGAGAACUCGCCUCAAAGAAGAACCCGAAGCUGAUU

AAUGCGCUUAGGCGGUGCUUUUUCUGGCGGUUCAUGUUCUACGGCAUCUU

CCUCUACCUGGGAGAGGUCACCAAGGCCGUGCAGCCCCUGUUGCUGGGAC

GGAUUAUUGCCUCCUACGACCCCGACAACAAGGAAGAAAGAAGCAUCGCU

AUCUACUUGGGCAUCGGUCUGUGCCUGCUUUUCAUCGUCCGGACCCUCUU

GUUGCAUCCUGCUAUUUUCGGCCUGCAUCACAUUGGCAUGCAGAUGAGAA

UUGCCAUGUUUUCCCUGAUCUACAAGAAAACUCUGAAGCUCUCGAGCCGC

GUGCUUGACAAGAUUUCCAUCGGCCAGCUCGUGUCCCUGCUCUCCAACAA

UCUGAACAAGUUCGACGAGGGCCUCGCCCUGGCCCACUUCGUGUGGAUCG

CCCCUCUGCAAGUGGCGCUUCUGAUGGGCCUGAUCUGGGAGCUGCUGCAA

GCCUCGGCAUUCUGUGGGCUUGGAUUCCUGAUCGUGCUGGCACUGUUCCA

GGCCGGACUGGGGCGGAUGAUGAUGAAGUACAGGGACCAGAGAGCCGGAA

-continued

AGAUUUCCGAACGGCUGGUGAUCACUUCGGAAAUGAUCGAAAACAUCCAG
UCAGUGAAGGCCUACUGCUGGGAAGAGGCCAUGGAAAAGAUGAUUGAAAA
CCUCCGGCAAACCGAGCUGAAGCUGACCCGCAAGGCCGCUUACGUGCGCU
AUUUCAACUCGUCCGCUUUCUUCUUCUCCGGGUUCUUCGUGGUGUUUCUC
UCCGUGCUCCCCUACGCCCUGAUUAAGGGAAUCAUCCUCAGGAAGAUCUU
CACCACCAUUUCCUUCUGUAUCGUGCUCCGCAUGGCCGUGACCCGGCAGU
UCCCAUGGGCCGUGCAGACUUGGUACGACUCCCUGGGAGCCAUUAACAAG
AUCCAGGACUUCCUUCAAAAGCAGGAGUACAAGACCCUCGAGUACAACCU
GACUACUACCGAGGUCGUGAUGGAAAACGUCACCGCCUUUUGGGAGGAGG
GAUUUGGCGAACUGUUCGAGAAGGCCAAGCAGAACAACAACAACCGCAAG
ACCUCGAACGGUGACGACUCCCUCUUCUUUUCAAACUUCAGCCUGCUCGG
GACGCCCGUGCUGAAGGACAUUAACUUCAAGAUCGAAAGAGGACAGCUCC
UGGCGGUGGCCGGAUCGACCGGAGCCGGAAAGACUUCCCUGCUGAUGGUG
AUCAUGGGAGAGCUUGAACCUAGCGAGGGAAAGAUCAAGCACUCCGGCCG
CAUCAGCUUCUGUAGCCAGUUUUCCUGGAUCAUGCCCGGAACCAUUAAGG
AAAACAUCAUCUUCGGCGUGUCCUACGAUGAAUACCGCUACCGGUCCGUG
AUCAAAGCCUGCCAGCUGGAAGAGGAUAUUUCAAAGUUCGCGGAGAAAGA
UAACAUCGUGCUGGGCGAAGGGGGUAUUACCUUGUCGGGGGCCAGCGGG
CUAGAAUCUCGCUGGCCAGAGCCGUGUAUAAGGACGCCGACCUGUAUCUC
CUGGACUCCCCCUUCGGAUACCUGGACGUCCUGACCGAAAAGGAGAUCUU
CGAAUCGUGCGUGUGCAAGCUGAUGGCUAACAAGACUCGCAUCCUCGUGA
CCUCCAAAAUGGAGCACCUGAAGAAGGCAGACAAGAUUCUGAUUCUGCAU
GAGGGGUCCUCCUACUUUUACGGCACCUUCUCGGAGUUGCAGAACUUGCA
GCCCGACUUCUCAUCGAAGCUGAUGGGUUGCGACAGCUUCGACCAGUUCU
CCGCCGAAAGAAGGAACUCGAUCCUGACGGAAACCUUGCACCGCUUCUCU
UUGGAAGGCGACGCCCCUGUGUCAUGGACCGAGACUAAGAAGCAGAGCUU
CAAGCAGACCGGGGAAUUCGGCGAAAAGAGGAAGAACAGCAUCUUGAACC
CCAUUAACUCCAUCCGCAAGUUCUCAAUCGUGCAAAAGACGCCACUGCAG
AUGAACGGCAUUGAGGAGGACUCCGACGAACCCCUUGAGAGGCGCCUGUC
CCUGGUGCCGGACAGCGAGCAGGGAGAAGCCAUCCUGCCUCGGAUUUCCG
UGAUCUCCACUGGUCCGACGCUCCAAGCCCGGCGGCGGCAGUCCGUGCUG
AACCUGAUGACCCACAGCGUGAACCAGGGCCAAAACAUUCACCGCAAGAC
UACCGCAUCCACCCGGAAAGUGUCCCUGGCACCUCAAGCGAAUCUUACCG
AGCUCGACAUCUACUCCCGGAGACUGUCGCAGGAAACCGGGCUCGAAAUU
UCCGAAGAAAUCAACGAGGAGGAUCUGAAAGAGUGCUUCUUCGACGAUAU
GGAGUCGAUACCCGCCGUGACGACUUGGAACACUUAUCUGCGGUACAUCA
CUGUGCACAAGUCAUUGAUCUUCGUGCUGAUUUGGUGCCUGGUGAUUUUC
CUGGCCGAGGUCGCGGCCUCACUGGUGGUGCUCUGGCUGUUGGGAAACAC
GCCUCUGCAAGACAAGGGAAACUCCACGCACUCGAGAAACAACAGCUAUG
CCGUGAUUAUCACUUCCACCUCCUCUUAUUACGUGUUCUACAUCUACGUC
GGAGUGGCGGAUACCCUGCUCGCGAUGGGUUUCUUCAGAGGACUGCCGCU

-continued

GGUCCACACCUUGAUCACCGUCAGCAAGAUUCUUCACCACAAGAUGUUGC
AUAGCGUGCUGCAGGCCCCCAUGUCCACCCUCAACACUCUGAAGGCCGGA
GGCAUUCUGAACAGAUUCUCCAAGGACAUCGCUAUCCUGGACGAUCUCCU
GCCGCUUACCAUCUUUGACUUCAUCCAGCUGCUGCUGAUCGUGAUUGGAG
CAAUCGCAGUGGUGGCGGUGCUGCAGCCUUACAUUUUCGUGGCCACUGUG
CCGGUCAUUGUGGCGUUCAUCAUGCUGCGGGCCUACUUCCUCCAAACCAG
CCAGCAGCUGAAGCAACUGGAAUCCGAGGGACGAUCCCCCAUCUUCACUC
ACCUUGUGACGUCGUUGAAGGGACUGUGGACCCUCCGGGCUUUCGGACGG
CAGCCCUACUUCGAAACCCUCUUCCACAAGGCCCUGAACCUCCACACCGC
CAAUUGGUUCCUGUACCUGUCCACCCUGCGGUGGUUCCAGAUGCGCAUCG
AGAUGAUUUUCGUCAUCUUCUUCAUCGCGGUCACAUUCAUCAGCAUCCUG
ACUACCGGAGAGGGAGAGGGACGGGUCGGAAUAAUCCUGACCCUCGCCAU
GAACAUUAUGAGCACCCUGCAGUGGGCAGUGAACAGCUCGAUCGACGUGG
ACAGCCUGAUGCGAAGCGUCAGCCGCGUGUUCAAGUUCAUCGACAUGCCU
ACUGAGGGAAAACCCACUAAGUCCACUAAGCCCUACAAAAAUGGCCAGCU
GAGCAAGGUCAUGAUCAUCGAAAACUCCCACGUGAAGAAGGACGAUAUUU
GGCCCUCCGGAGGUCAAAUGACCGUGAAGGACCUGACCGCAAAGUACACC
GAGGGAGGAAACGCCAUUCUCGAAAACAUCAGCUUCUCCAUUUCGCCGGG
ACAGCGGGUCGGCCUUCUCGGGCGGACCGGUUCCGGGAAGUCAACUCUGC
UGUCGGCUUUCCUCCGGCUGCUGAAUACCGAGGGGGAAAUCCAAAUUGAC
GGCGUGUCUUGGGAUUCCAUUACUCUGCAGCAGUGGCGGAAGGCCUCGGC
GUGAUCCCCCAGAAGGUGUUCAUCUUCUCGGGUACCUUCCGGAAGAACCU
GGAUCCUUACGAGCAGUGGAGCGACCAAGAAAUCUGGAAGGUCGCCGACG
AGGUCGGCCUGCGCUCCGUGAUUGAACAAUUUCCUGGAAAGCUGGACUUC
GUGCUCGUCGACGGGGGAUGUGUCCUGUCGCACGGACAUAAGCAGCUCAU
GUGCCUCGCACGGUCCGUGCUCUCCAAGGCCAAGAUUCUGCUGCUGGACG
AACCUUCGGCCCACCUGGAUCCGGUCACCUACCAGAUCAUCAGGAGGACC
CUGAAGCAGGCCUUUGCCGAUUGCACCGUGAUUCUCUGCGAGCACCGCAU
CGAGGCCAUGCUGGAGUGCCAGCAGUUCCUGGUCAUCGAGGAGAACAAGG
UCCGCCAAUACGACUCCAUUCAAAAGCUCCUCAACGAGCGGUCGCUGUUC
AGACAAGCUAUUUCACCGUCCGAUAGAGUGAAGCUCUUCCCGCAUCGGAA
CAGCUCAAAGUGCAAAUCGAAGCCGCAGAUCGCAGCCUUGAAGGAAGAGA
CUGAGGAAGAGGUGCAGGACACCCGGCUUUAACGGGUGGCAUCCCUGUGA
CCCCUCCCCAGUGCCUCUCCUGGCCCUGGAAGUUGCCACUCCAGUGCCCA
CCAGCCUUGUCCUAAUAAAAUUAAGUUGCAUCAAGCU

In another example, a full length codon-optimized human CFTR mRNA sequence is shown below:

(SEQ ID NO: 8)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC

-continued

GGAUUCCCCGUGCCAAGAGUGACUCACCGUCCUUGACACGAUGCAACGCU
CUCCUCUUGAAAAGGCCUCGGUGGUGUCCAAGCUCUUCUUCUCGUGGACU
AGACCCAUCCUGAGAAAGGGGUACAGACAGCGCUUGGAGCUGUCCGAUAU
CUAUCAAAUCCCUUCCGUGGACUCCGCGGACAACCUGUCCGAGAAGCUCG
AGAGAGAAUGGGACAGAGAACUCGCCUCAAAGAAGAACCCGAAGCUGAUU
AAUGCGCUUAGGCGGUGCUUUUUCUGGCGGUUCAUGUUCUACGGCAUCUU
CCUCUACCUGGGAGAGGUCACCAAGGCCGUGCAGCCCCUGUUGCUGGGAC
GGAUUAUUGCCUCCUACGACCCCGACAACAAGGAAGAAAGAAGCAUCGCU
AUCUACUUGGGCAUCGGUCUGUGCCUGCUUUUCAUCGUCCGGACCCUCUU
GUUGCAUCCUGCUAUUUUCGGCCUGCAUCACAUUGGCAUGCAGAUGAGAA
UUGCCAUGUUUUCCCUGAUCUACAAGAAAACUCUGAAGCUCUCGAGCCGC
GUGCUUGACAAGAUUUCCAUCGGCCAGCUCGUGUCCCUGCUCUCCAACAA
UCUGAACAAGUUCGACGAGGGCCUCGCCCUGGCCCACUUCGUGUGGAUCG
CCCCUCUGCAAGUGGCGCUUCUGAUGGGCCUGAUCUGGGAGCUGCUGCAA
GCCUCGGCAUUCUGUGGGCUUGGAUUCCUGAUCGUGCUGGCACUGUUCCA
GGCCGGACUGGGGCGGAUGAUGAUGAAGUACAGGGACCAGAGAGCCGGAA
AGAUUUCCGAACGGCUGGUGAUCACUUCGGAAAUGAUCGAAAACAUCCAG
UCAGUGAAGGCCUACUGCUGGGAAGAGGCCAUGGAAAAGAUGAUUGAAAA
CCUCCGGCAAACCGAGCUGAAGCUGACCCGCAAGGCCGCUUACGUGCGCU
AUUUCAACUCGUCCGCUUUCUUCUUCUCCGGGUUCUUCGUGGUGUUUCUC
UCCGUGCUCCCCUACGCCCUGAUUAAGGGAAUCAUCCUCAGGAAGAUCUU
CACCACCAUUUCCUUCUGUAUCGUGCUCCGCAUGGCCGUGACCCGGCAGU
UCCCAUGGGCCGUGCAGACUUGGUACGACUCCCUGGGAGCCAUUAACAAG
AUCCAGGACUUCCUUCAAAAGCAGGAGUACAAGACCCUCGAGUACAACCU
GACUACUACCGAGGUCGUGAUGGAAAACGUCACCGCCUUUUGGGAGGAGG
GAUUUGGCGAACUGUUCGAGAAGGCCAAGCAGAACAACAACAACCGCAAG
ACCUCGAACGGUGACGACUCCCUCUUCUUUUCAAACUUCAGCCUGCUCGG
GACGCCCGUGCUGAAGGACAUUAACUUAAGAUCGAAAGAGGACAGCUCCU
GGCGGUGGCCGGAUCGACCGGAGCCGGAAAGACUUCCCUGCUGAUGGUGA
UCAUGGGAGAGCUUGAACCUAGCGAGGGAAAGAUCAAGCACUCCGGCCGC
AUCAGCUUCUGUAGCCAGUUUUCCUGGAUCAUGCCCGGAACCAUUAAGGA
AAACAUCAUCUUCGGCGUGUCCUACGAUGAAUACCGCUACCGGUCCGUGA
UCAAAGCCUGCCAGCUGGAAGAGGAUAUUUCAAAGUUCGCGGAGAAAGAU
AACAUCGUGCUGGGCGAAGGGGGUAUUACCUUGUCGGGGGGCCAGCGGGC
UAGAAUCUCGCUGGCCAGAGCCGUGUAUAAGGACGCCGACCUGUAUCUCC
UGGACUCCCCCUUCGGAUACCUGGACGUCCUGACCGAAAAGGAGAUCUUC
GAAUCGUGCGUGUGCAAGCUGAUGGCUAACAAGACUCGCAUCCUCGUGAC
CUCCAAAAUGGAGCACCUGAAGAAGGCAGACAAGAUUCUGAUUCUGCAUG
AGGGGUCCUCCUACUUUUACGGCACCUUCUCGGAGUUGCAGAACUUGCAG
CCCGACUUCUCAUCGAAGCUGAUGGGUUGCGACAGCUUCGACCAGUUCUC
CGCCGAAAGAAGGAACUCGAUCCUGACGGAACCUUGCACCGCUUCUCUUU

-continued

GGAAGGCGACGCCCCUGUGUCAUGGACCGAGACUAAGAAGCAGAGCUUCA
AGCAGACCGGGGAAUUCGGCGAAAAGAGGAAGAACAGCAUCUUGAACCCC
AUUAACUCCAUCCGCAAGUUCUCAAUCGUGCAAAAGACGCCACUGCAGAU
GAACGGCAUUGAGGAGGACUCCGACGAACCCCUUGAGAGGCGCCUGUCCC
UGGUGCCGGACAGCGAGCAGGGAGAAGCCAUCCUGCCUCGGAUUUCCGUG
AUCUCCACUGGUCCGACGCUCCAAGCCCGGCGGCGGCAGUCCGUGCUGAA
CCUGAUGACCCACAGCGUGAACCAGGGCCAAAACAUUCACCGCAAGACUA
CCGCAUCCACCCGGAAAGUGUCCCUGGCACCUCAAGCGAAUCUUACCGAG
CUCGACAUCUACUCCCGGAGACUGUCGCAGGAAACCGGGCUCGAAAUUUC
CGAAGAAAUCAACGAGGAGGAUCUGAAAGAGUGCUUCUUCGACGAUAUGG
AGUCGAUACCCGCCGUGACGACUUGGAACACUUAUCUGCGGUACAUCACU
GUGCACAAGUCAUUGAUCUUCGUGCUGAUUUGGUGCCUGGUGAUUUUCCU
GGCCGAGGUCGCGGCCUCACUGGUGGUGCUCUGGCUGUUGGGAAACACGC
CUCUGCAAGACAAGGGAAACUCCACGCACUCGAGAAACAACAGCUAUGCC
GUGAUUAUCACUUCCACCUCCUCUUAUUACGUGUUCUACAUCUACGUCGG
AGUGGCGGAUACCCUGCUCGCGAUGGGUUUCUUCAGAGGACUGCCGCUGG
UCCACACCUUGAUCACCGUCAGCAAGAUUCUUCACCACAAGAUGUUGCAU
AGCGUGCUGCAGGCCCCCAUGUCCACCCUCAACACUCUGAAGGCCGGAGG
CAUUCUGAACAGAUUCUCCAAGGACAUCGCUAUCCUGGACGAUCUCCUGC
CGCUUACCAUCUUUGACUUCAUCCAGCUGCUGCUGAUCGUGAUUGGAGCA
AUCGCAGUGGUGGCGGUGCUGCAGCCUUACAUUUUCGUGGCCACUGUGCC
GGUCAUUGUGGCGUUCAUCAUGCUGCGGGCCUACUUCCUCCAAACCAGCC
AGCAGCUGAAGCAACUGGAAUCCGAGGGACGAUCCCCCAUCUUCACUCAC
CUUGUGACGUCGUUGAAGGGACUGUGGACCCUCCGGGCUUUCGGACGGCA
GCCCUACUUCGAAACCCUCUUCCACAAGGCCCUGAACCUCCACACCGCCA
AUUGGUUCCUGUACCUGUCCACCCUGCGGUGGUUCCAGAUGCGCAUCGAG
AUGAUUUUCGUCAUCUUCUUCAUCGCGGUCACAUUCAUCAGCAUCCUGAC
UACCGGAGAGGGAGAGGGACGGGUCGGAAUAAUCCUGACCCUCGCCAUGA
ACAUUAUGAGCACCCUGCAGUGGGCAGUGAACAGCUCGAUCGACGUGGAC
AGCCUGAUGCGAAGCGUCAGCCGCGUGUUCAAGUUCAUCGACAUGCCUAC
UGAGGGAAAACCCACUAAGUCCACUAAGCCCUACAAAAAUGGCCAGCUGA
GCAAGGUCAUGAUCAUCGAAACUCCCACGUGAAGAAGGACGAUAUUUGGC
CCUCCGGAGGUCAAAUGACCGUGAAGGACCUGACCGCAAAGUACACCGAG
GGAGGAAACGCCAUUCUCGAAAACAUCAGCUUCUCCAUUUCGCCGGGACA
GCGGGUCGGCCUUCUCGGGCGGACCGGUUCCGGGAAGUCAACUCUGCUGU
CGGCUUUCCUCCGGCUGCUGAAUACCGAGGGGGAAAUCCAAAUUGACGGC
GUGUCUUGGGAUUCCAUUACUCUGCAGCAGUGGCGGAAGGCCUUCGGCGU
GAUCCCCCAGAAGGUGUUCAUCUUCUCGGGUACCUUCCGGAAGAACCUGG
AUCCUUACGAGCAGUGGAGCGACCAAGAAAUCUGGAAGGUCGCCGACGAG
GUCGGCCUGCGCUCCGUGAUUGAACAAUUUCCUGGAAAGCUGGACUUCGU

-continued

```
GCUCGUCGACGGGGGAUGUGUCCUGUCGCACGGACAUAAGCAGCUCAUGU

GCCUCGCACGGUCCGUGCUCUCCAAGGCCAAGAUUCUGCUGCUGGACGAA

CCUUCGGCCCACCUGGAUCCGGUCACCUACCAGAUCAUCAGGAGGACCCU

GAAGCAGGCCUUUGCCGAUUGCACCGUGAUUCUCUGCGAGCACCGCAUCG

AGGCCAUGCUGGAGUGCCAGCAGUUCCUGGUCAUCGAGGAGAACAAGGUC

CGCCAAUACGACUCCAUUCAAAAGCUCCUCAACGAGCGGUCGCUGUUCAG

ACAAGCUAUUUCACCGUCCGAUAGAGUGAAGCUCUUCCCGCAUCGGAACA

GCUCAAAGUGCAAAUCGAAGCCGCAGAUCGCAGCCUUGAAGGAAGAGACU

GAGGAAGAGGUGCAGGACACCCGGCUUUAAGGGUGGCAUCCCUGUGACCC

CUCCCCAGUGCCUCUCCUGGCCCUGGAAGUUGCCACUCCAGUGCCCACCA

GCCUUGUCCUAAUAAAAUUAAGUUGCAUCAAAGCU
```

Comparison of hCFTR mRNA Constructs

A previous hCFTR sequence (SEQ ID NO: 2) was codon-optimized using a T7 promoter. Upon changing the promoter used to synthesize the hCFTR mRNA to SP6, "cleaner" mRNA was synthesized with respect to pre-aborted sequences, but a second species of approximately 1800 nt ("longmer") was being produced in low quantities. This was visualized by gel electrophoresis as depicted in FIG. 1. In FIG. 1, lane 1 contains an RNA ladder, lane 2 contains mRNA of SEQ ID NO: 1 and lane 3 contains mRNA of SEQ ID NO: 2. As indicated by the arrow, a secondary polynucleotide species approximately 1800 nucleotides in length is present in lane 3. Several new sequences (relative to SEQ ID NO: 2) were designed with site mutations to remove suspected cryptic promoters, but that did not result in the disappearance of the ~1800 nt secondary species. Complete codon-re-optimization was performed to create SEQ ID NO: 1, which successfully led to an mRNA product without the additional production of the second species at ~1800 nt (lane 1).

Thus, SEQ ID NO: 1 is particularly useful in a homogenous, safe and efficacious pharmaceutical composition.

Example 2. Additional Exemplary Codon Optimized CFTR Sequences

The following additional exemplary codon optimized sequences are used for synthesis of CFTR mRNA for safe and efficacious clinical use:

```
                                              (SEQ ID NO: 21)
ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAGCTGTTCAGCCGCTCC

TTCTTGGCCGCATCATCGCCAGCTATGACCCTGATAATAAAGAAGAAAGG

TCTATTGCTATTTATCTGGGAATTGGCCTCTGCTTGCTCTTCATCGTCGC

ACCCTTCTGCTGCACCCTGCCATTTTTGGCCTTCACCACATCGGCATGCA

AATGAGAATTGCCATGTTCTCCCTCATTTACAAAAAGACCCTGAAACTTT
```

-continued

```
CCTCAAGAGTGTTAGATAAAATATCCATTGGTCAGCTGGTCAGCCTGCTG

TCCAACAATCTTAACAAATTTGATGAAGGCTTGGCGCTGGCCCACTTCGT

GTGGATTGCACCTCTGCAGGTGGCCCTGTTGATGGGACTTATATGGGAGC

TGCTTCAAGCCTCTGCTTTCTGTGGGCTGGGCTTTTTGATTGTACTGGCA

CTTTTTCAGGCTGGGCTCGGAAGAATGATGATGAAATACAGAGATCAGCG

GGCCGGGAAGATATCAGAGCGACTTGTGATCACCAGTGAAATGATTGAAA

ATATTCAGAGCGTGAAAGCCTACTGCTGGGAAGAAGCCATGGAGAAGATG

ATTGAGAACCTGAGGCAGACAGAGCTCAAGCTCACTCGGAAGGCTGCTTA

TGTTCGCTATTTCAACAGCAGCGCCTTCTTCTTCAGTGGCTTCTTTGTTG

TCTTCCTGTCTGTTCTGCCATATGCACTGATAAAAGGCATTATTTTACGA

AAGATCTTCACCACCATCAGTTTTTGCATCGTTCTCAGGATGGCCGTCAC

AAGACAGTTCCCCTGGGCTGTGCAGACCTGGTACGATTCCTTGGGGGCCA

TCAACAAGATTCAAGATTTCTTGCAAAAACAAGAATATAAAACTTTAGAA

TACAACCTCACCACCACTGAAGTGGTCATGGAAAATGTGACAGCCTTTTG

GGAGGAGGGTTTTGGAGAATTGTTCGAGAAGGCAAAGCAGAATAACAACA

ACAGGAAGACGAGCAATGGGGACGACTCTCTCTTCTTCAGCAACTTTTCA

CTGCTCGGGACCCCTGTGTTGAAAGATATAAACTTCAAGATCGAGAGGGG

CCAGCTCTTGGCTGTGGCAGGCTCCACTGGAGCTGGTAAAACATCTCTTC

TCATGGTGATCATGGGGGAACTGGAGCCTTCCGAAGGAAAAATCAAGCAC

AGTGGGAGAATCTCATTCTGCAGCCAGTTTTCCTGGATCATGCCCGGCAC

CATTAAGGAAAACATCATATTTGGAGTGTCCTATGATGAGTACCGCTACC

GGTCAGTCATCAAAGCCTGTCAGTTGGAGGAGGACATCTCCAAGTTTGCA

GAGAAAGACAACATTGTGCTTGGAGAGGGGGGTATCACTCTTTCTGGAGG

ACAAAGAGCCAGGATCTCTTTGGCCCGGGCAGTCTACAAGGATGCAGACC

TCTACTTGTTGGACAGTCCCTTCGGCTACCTCGACGTGCTGACTGAAAAA

GAAATTTTTGAAAGCTGTGTGTGCAAACTGATGGCAAACAAGACCAGGAT

TCTTGTCACCAGCAAGATGGAACATCTGAAGAAAGCGGACAAAATTCTGA

TTCTGCATGAAGGGAGCTCCTACTTCTATGGAACATTTAGCGAGCTTCAG

AACCTACAGCCAGACTTCTCCTCCAAATTAATGGGCTGTGACTCCTTCGA

CCAGTTCTCTGCAGAAAGAAGAAACTCTATACTCACAGAGACCCTCCACC

GCTTCTCCCTTGAGGGAGATGCCCCAGTTTCTTGGACAGAAACCAAGAAG

CAGTCCTTTAAGCAGACTGGCGAGTTTGGTGAAAAGAGGAAAAATTCAAT

TCTCAATCCAATTAACAGTATTCGCAAGTTCAGCATTGTCCAGAAGACAC

CCCTCCAGATGAATGGCATCGAAGAAGATAGTGACGAGCCGCTGGAGAGA

CGGCTGAGTCTGGTGCCAGATTCAGAACAGGGGGAGGCCATCCTGCCCCG

GATCAGCGTCATTTCCACAGGCCCCACATTACAAGCACGGCGCCGGCAGA

GTGTTTTAAATCTCATGACCCATTCAGTGAACCAGGGCCAAAATATCCAC

AGGAAGACTACAGCTTCTACCCGGAAAGTGTCTCTGGCCCCTCAGGCCAA

TCTGACCGAGCTGGACATCTACAGCAGGAGGCTCTCCCAGGAAACAGGGC

TGGAAATATCTGAAGAGATTAATGAAGAGGATCTTAAAGAGTGCTTCTTT
```

-continued

GATGACATGGAGAGCATCCCCGCGGTGACCACATGGAACACCTACCTTAG

ATATATTACTGTCCACAAGAGCCTCATATTTGTCCTCATCTGGTGCCTGG

TTATTTTCCTCGCTGAGGTGGCGGCCAGTCTTGTTGTGCTCTGGCTGCTG

GGCAACACTCCTCTCCAGGACAAGGGCAATAGTACTCACAGCAGAAATAA

TTCTTATGCCGTCATCATTACAAGCACCTCCAGCTACTACGTGTTCTACA

TCTATGTGGGCGTGGCTGACACCCTCCTGGCCATGGGTTTCTTCCGGGGC

CTGCCTTTGGTGCACACCCTCATCACAGTGTCAAAAATTCTGCACCATAA

AATGCTTCATTCTGTCCTGCAGGCACCCATGAGCACTTTGAACACATTGA

AGGCTGGCGGCATCCTCAACAGATTTTCTAAAGATATTGCTATCCTGGAT

GATCTCCTCCCCCTGACAATCTTTGACTTTATCCAGCTTCTGCTGATCGT

GATTGGAGCCATAGCAGTGGTTGCTGTCCTGCAGCCCTACATTTTTGTGG

CCACCGTGCCCGTGATTGTTGCCTTTATTATGCTCAGAGCTTACTTCCTG

CAAACTTCTCAACAGCTCAAACAGCTAGAATCTGAGGGCCGGAGCCCCAT

TTTTACCCACCTGGTGACTTCCCTGAAGGGACTGTGGACTCTGAGAGCAT

TCGGGCGACAGCCTTACTTTGAGACACTGTTCCACAAGGCCCTGAACTTG

CACACTGCCAACTGGTTTCTTTACCTGAGCACACTCCGCTGGTTCCAGAT

GCGGATAGAGATGATCTTCGTCATCTTTTTTATAGCTGTAACCTTCATTT

CTATCCTTACAACAGGAGAAGGAGAGGGCAGGGTGGGAATCATCCTCACG

CTGGCTATGAACATAATGTCCACCTTGCAGTGGGCCGTGAATTCCAGTAT

AGATGTGGATTCTCTATGAGGAGTGTCTCCCGGGTGTTTAAATTCATTGA

TATGCCTACTGAGGGGAAACCCACCAAGTCAACAAAACCTTATAAGAATG

GACAGCTGAGCAAGGTGATGATAATTGAGAACAGCCACGTGAAGAAGGAT

GACATTTGGCCCAGCGGGGGCCAGATGACTGTGAAGGACCTGACGGCCAA

GTACACCGAAGGTGGAAATGCCATTTTGGAAAACATCAGCTTCTCAATCT

CTCCTGGGCAGAGAGTTGGATTGCTGGGTCGCACGGGCAGCGGCAAATCA

ACCCTGCTCAGTGCCTTCCTTCGGCTCCTGAATACAGAAGGCGAAATCCA

AATTGACGGGGTGAGCTGGGACAGCATCACCCTGCAGCAGTGGAGAAAAG

CATTTGGGGTCATTCCACAGAAAGTTTTCATCTTCTCTGGCACTTTCAGA

AAGAACCTGGACCCCTATGAGCAGTGGAGCGACCAGGAGATCTGGAAGGT

TGCAGATGAAGTTGGCCTGCGGAGTGTGATAGAACAATTTCCTGGCAAGC

TGGATTTTGTGCTGGTAGATGGAGGCTGCGTGCTGTCCCACGGCCACAAA

CAGCTGATGTGCCTCGCCCGCTCCGTTCTTTCAAAGGCCAAAATCTTGCT

TTTGGATGAGCCCAGTGCTCACCTCGACCCAGTGACCTATCAGATAATCC

GCAGGACCTTAAAGCAAGCTTTTGCCGACTGCACCGTCATACTGTGTGAG

CACCGGATTGAAGCAATGCTGGAATGCCAGCAGTTTCTGGTGATCGAGGA

GAATAAGGTCCGGCAGTACGACAGCATCCAGAAGTTGTTGAATGAGCGCA

GCCTTTTCCGCCAGGCCATCTCCCCATCTGACAGAGTCAAGCTGTTTCCA

CATAGGAACTCCTCTAAGTGCAAGTCCAAGCCCCAGATCGCTGCCCTCAA

GGAGGAAACTGAGGAAGAGGTGCAGGATACCCGCCTGTGA

-continued (SEQ ID NO: 22)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCTGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATTTCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGGA

GGACAAAGAGCCAGGATCTCTTTGGCCCGGGCAGTCTACAAGGATGCAGA

CCTCTACTTGTTGGACAGTCCCTTCGGCTACCTCGACGTGCTGACTGAAA

AAGAAATTTTTGAAAGCTGTGTGTGCAAACTGATGGCAAACAAGACCAGG

ATTCTTGTCACCAGCAAGATGGAACATCTGAAGAAAGCGGACAAAATTCT

GATTCTGCATGAAGGGAGCTCCTACTTCTATGGAACATTTAGCGAGCTTC

AGAACCTACAGCCAGACTTCTCCTCCAAATTAATGGGCTGTGACTCCTTC

GACCAGTTCTCTGCAGAAAGAAGAAACTCTATACTCACAGAGACCCTCCA

-continued

CCGCTTCTCCCTTGAGGGAGATGCCCCAGTTTCTTGGACAGAAACCAAGA

AGCAGTCCTTTAAGCAGACTGGCGAGTTTGGTGAAAAGAGGAAAAATTCA

ATTCTCAATCCAATTAACAGTATTCGCAAGTTCAGCATTGTCCAGAAGAC

ACCCCTCCAGATGAATGGCATCGAAGAAGATAGTGACGAGCCGCTGGAGA

GACGGCTGAGTCTGGTGCCAGATTCAGAACAGGGGGAGGCCATCCTGCCC

CGGATCAGCGTCATTTCCACAGGCCCCACATTACAAGCACGGCGCCGGCA

GAGTGTTTTAAATCTCATGACCCATTCAGTGAACCAGGGCCAAAATATCC

ACAGGAAGACTACAGCTTCTACCCGGAAAGTGTCTCTGGCCCCTCAGGCC

AATCTGACCGAGCTGGACATCTACAGCAGGAGGCTCTCCCAGGAAACAGG

GCTGGAAATATCTGAAGAGATTAATGAAGAGGATCTTAAAGAGTGCTTCT

TTGATGACATGGAGAGCATCCCCGCGGTGACCACATGGAACACCTACCTT

AGATATATTACTGTCCACAAGAGCCTCATATTTGTCCTCATCTGGTGCCT

GGTTATTTTCCTCGCTGAGGTGGCGGCCAGTCTTGTTGTGCTCTGGCTGC

TGGGCAACACTCCTCTCCAGGACAAGGGCAATAGTACTCACAGCAGAAAT

AATTCTTATGCCGTCATCATTACAAGCACCTCCAGCTACTACGTGTTCTA

CATCTATGTGGGCGTGGCTGACACCCTCCTGGCCATGGGTTTCTTCCGGG

GCCTGCCTTTGGTGCACACCCTCATCACAGTGTCAAAAATTCTGCACCAT

AAAATGCTTCATTCTGTCCTGCAGGCACCCATGAGCACTTTGAACACATT

GAAGGCTGGCGGCATCCTCAACAGATTTTCTAAAGATATTGCTATCCTGG

ATGATCTCCTCCCCCTGACAATCTTTGACTTTATCCAGCTTCTGCTGATC

GTGATTGGAGCCATAGCAGTGGTTGCTGTCCTGCAGCCCTACATTTTTGT

GGCCACCGTGCCCGTGATTGTTGCCTTTATTATGCTCAGAGCTTACTTCC

TGCAAACTTCTCAACAGCTCAAACAGCTAGAATCTGAGGGCCGGAGCCCC

ATTTTTACCCACCTGGTGACTTCCCTGAAGGGACTGTGGACTCTGAGAGC

ATTCGGGCGACAGCCTTACTTTGAGACACTGTTCCACAAGGCCCTGAACT

TGCACACTGCCAACTGGTTTCTTTACCTGAGCACACTCCGCTGGTTCCAG

ATGCGGATAGAGATGATCTTCGTCATCTTTTTTATAGCTGTAACCTTCAT

TTCTATCCTTACAACAGGAGAAGGAGAGGGCAGGGTGGGAATCATCCTCA

CGCTGGCTATGAACATAATGTCCACCTTGCAGTGGGCCGTGAATTCCAGT

ATAGATGTGGATTCTCTAATGAGGAGTGTCTCCCGGGTGTTTAAATTCAT

TGATATGCCTACTGAGGGGAAACCCACCAAGTCAACAAAACCTTATAAGA

ATGGACAGCTGAGCAAGGTGATGATAATTGAGAACAGCCACGTGAAGAAG

GATGACATTTGGCCCAGCGGGGGCCAGATGACTGTGAAGGACCTGACGGC

CAAGTACACCGAAGGTGGAAATGCCATTTTGGAAAACATCAGCTTCTCAA

TCTCTCCTGGGCAGAGAGTTGGATTGCTGGGTCGCACGGGCAGCGGCAAA

TCAACCCTGCTCAGTGCCTTCCTTCGGCTCCTGAATACAGAAGGCGAAAT

CCAAATTGACGGGGTGAGCTGGGACAGCATCACCCTGCAGCAGTGGAGAA

AAGCATTTGGGGTCATTCCACAGAAAGTTTTCATCTTCTCTGGCACTTTC

AGAAAGAACCTGGACCCCTAGAGCAGTGGAGCGACCAGGAGATCTGGAAG

GTTGCAGATGAAGTTGGCCTGCGGAGTGTGATAGAACAATTTCCTGGCAA

-continued

GCTGGATTTTGTGCTGGTAGATGGAGGCTGCGTGCTGTCCCACGGCCACA

AACAGCTGATGTGCCTCGCCCGCTCCGTTCTTTCAAAGGCCAAAATCTTG

CTTTTGGATGAGCCCAGTGCTCACCTTGACCCAGTGACCTATCAGATAAT

CCGCAGGACCTTAAAGCAAGCTTTTGCCGACTGCACCGTCATACTGTGTG

AGCACCGGATTGAAGCAATGCTGGAATGCCAGCAGTTTCTGGTGATCGAG

GAGAATAAGGTCCGGCAGTACGACAGCATCCAGAAGTTGTTGAATGAGCG

CAGCCTTTTCCGCCAGGCCATCTCCCCATCTGACAGAGTCAAGCTGTTTC

CACATAGGAACTCCTCTAAGTGCAAGTCCAAGCCCCAGATCGCTGCCCTC

AAGGAGGAAACTGAGGAAGAGGTGCAGGATACCCGCCTGTGA (SEQ ID NO: 23)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATATCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

-continued

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGGA

GGACAAAGAGCCAGGATCTCTTTGGCCCGGGCAGTCTACAAGGATGCAGA

CCTCTACTTGTTGGACAGTCCCTTCGGCTACCTCGACGTGCTGACTGAAA

AAGAAATTTTTGAAAGCTGTGTGTGCAAACTGATGGCAAACAAGACCAGG

ATTCTTGTCACCAGCAAGATGGAACATCTGAAGAAAGCGGACAAAATTCT

GATTCTGCATGAAGGGAGCTCCTACTTCTATGGAACATTTAGCGAGCTTC

AGAACCTACAGCCAGACTTCTCCTCCAAATTAATGGGCTGTGACTCCTTC

GACCAGTTCTCTGCAGAAAGAAGAAACTCTATACTCACAGAGACCCTCCA

CCGCTTCTCCCTTGAGGGAGATGCCCCAGTTTCTTGGACAGAAACCAAGA

AGCAGTCCTTTAAGCAGACTGGCGAGTTTGGTGAAAAGAGGAAAAATTCA

ATTCTCAATCCAATTAACAGTATTCGCAAGTTCAGCATTGTCCAGAAGAC

ACCCCTCCAGATGAATGGCATCGAAGAAGATAGTGACGAGCCGCTGGAGA

GACGGCTGAGTCTGGTGCCAGATTCAGAACAGGGGGAGGCCATCCTGCCC

CGGATCAGCGTCATTTCCACAGGCCCCACATTACAAGCACGGCGCCGGCA

GAGTGTTTTAAATCTCATGACCCATTCAGTGAACCAGGGCCAAAATATCC

ACAGGAAGACTACAGCTTCTACCCGGAAAGTGTCTCTGGCCCCTCAGGCC

AATCTGACCGAGCTGGACATCTACAGCAGGAGGCTCTCCCAGGAAACAGG

GCTTGAAATATCTGAAGAGATTAATGAAGAGGATCTTAAAGAGTGCTTCT

TTGATGACATGGAGAGCATCCCCGCGGTGACCACATGGAACACCTACCTT

AGATATATTACTGTCCACAAGAGCCTCATATTTGTCCTCATCTGGTGCCT

GGTTATTTTCCTCGCTGAGGTGGCGGCCAGTCTTGTTGTGCTCTGGCTGC

TGGGCAACACTCCTCTCCAGGACAAGGGCAATAGTACACACAGCAGAAAT

AATTCTTATGCCGTCATCATTACAAGCACCTCCAGCTACTACGTGTTCTA

CATCTATGTGGGCGTGGCTGACACCCTCCTGGCCATGGGTTTCTTCCGGG

GCCTGCCTTTGGTGCACACCCTCATCACAGTGTCAAAAATTCTGCACCAT

AAAATGCTTCATTCTGTCCTGCAGGCACCCATGAGCACTTTGAACACATT

GAAGGCTGGCGGCATCCTCAACAGATTTTCTAAAGATATTGCTATCCTGG

ATGATCTCCTCCCCCTGACAATCTTTGACTTTATCCAGCTTCTGCTGATC

GTGATTGGAGCCATAGCAGTGGTTGCTGTCCTGCAGCCCTACATTTTTGT

GGCCACCGTGCCCGTGATTGTTGCCTTTATTATGCTCAGAGCTTACTTCC

TGCAAACTTCTCAACAGCTCAAACAGCTAGAATCTGAGGGCCGGAGCCCC

ATTTTTACCCACCTGGTGACTTCCCTGAAGGGACTGTGGACTCTGAGAGC

ATTCGGGCGACAGCCTTACTTTGAGACACTGTTCCACAAGGCCCTGAACT

TGCACACTGCCAACTGGTTTCTTTACCTGAGCACACTCCGCTGGTTCCAG

ATGCGGATAGAGATGATCTTCGTCATCTTTTTTATAGCTGTAACCTTCAT

TTCTATCCTTACAACAGGAGAAGGAGAGGGCAGGGTGGGAATCATCCTCA

CGCTGGCTATGAACATAATGTCCACCTTGCAGTGGGCCGTGAATTCCAGT

ATAGATGTGGATTCTCTAATGAGGAGTGTCTCCCGGGTGTTTAAATTCAT

TGATATGCCTACTGAGGGGAAACCCACCAAGTCAACAAAACCTTATAAGA

ATGGACAGCTGAGCAAGGTGATGATAATTGAGAACAGCCACGTGAAGAAG

GATGACATTTGGCCCAGCGGGGGCCAGATGACTGTGAAGGACCTGACGGC

CAAGTACACCGAAGGTGGAAATGCCATTTTGGAAAACATCAGCTTCTCAA

TCTCTCCTGGGCAGAGAGTTGGATTGCTGGGTCGCACGGGCAGCGGCAAA

TCAACCCTGCTCAGTGCCTTCCTTCGGCTCCTGAATACAGAAGGCGAAAT

CCAAATTGACGGGGTGAGCTGGGACAGCATCACCCTGCAGCAGTGGAGAA

AAGCATTTGGGGTCATTCCACAGAAAGTTTTCATCTTCTCTGGCACTTTC

AGAAAGAACCTGGACCCCTATGAGCAGTGGAGCGACCAGGAGATCTGGAA

GGTTGCAGATGAAGTTGGCCTGCGGAGTGTGATAGAACAATTTCCTGGCA

AGCTGGATTTTGTGCTGGTAGATGGAGGCTGCGTGCTGTCCCACGGCCAC

AAACAGCTGATGTGCCTCGCCCGCTCCGTTCTTTCAAAGGCCAAAATCTT

GCTTTTGGATGAGCCCAGTGCTCACCTTGACCCAGTGACCTATCAGATAA

TCCGCAGGACCTTAAAGCAAGCTTTTGCCGACTGCACCGTCATACTGTGT

GAGCACCGGATTGAAGCAATGCTGGAATGCCAGCAGTTTCTGGTGATCGA

GGAGAATAAGGTCCGGCAGTACGACAGCATCCAGAAGTTGTTGAATGAGC

GCAGCCTTTTCCGCCAGGCCATCTCCCCATCTGACAGAGTCAAGCTGTTT

CCACATAGGAACTCCTCTAAGTGCAAGTCCAAGCCCCAGATCGCTGCCCT

CAAGGAGGAAACTGAGGAAGAGGTGCAGGATACCCGCCTGTGA (SEQ ID NO: 24)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTGATTGTACTGGC

ACTTTTTCAGGCTGGGCTCGGAAGAATGATGATGAAATACAGAGATCAGC

GGGCCGGGAAGATATCAGAGCGACTTGTGATCACCAGTGAAATGATTGAA

AATATTCAGAGCGTGAAAGCCTACTGCTGGGAAGAAGCCATGGAGAAGAT

GATTGAGAACCTGAGGCAGACAGAGCTCAAGCTCACTCGGAAGGCTGCTT

ATGTTCGCTATTTCAACAGCAGCGCCTTCTTCTTCAGTGGCTTCTTTGTT

GTCTTCCTGTCTGTTCTGCCATATGCACTGATAAAAGGCATTATTTTACG

AAAGATCTTCACCACCATCAGTTTTTGCATCGTTCTCAGGATGGCCGTCA

CAAGACAGTTCCCCTGGGCTGTGCAGACCTGGTACGATTCCTTGGGGGCC

ATCAACAAGATTCAAGATTTCTTGCAAAAACAAGAATATAAAACTTTAGA

-continued

ATACAACCTCACCACCACTGAAGTGGTCATGGAAAATGTGACAGCCTTTT
GGGAGGAGGGTTTTGGAGAATTGTTCGAGAAGGCAAAGCAGAATAACAAC
AACAGGAAGACGAGCAATGGGGACGACTCTCTCTTCTTCAGCAACTTTTC
ACTGCTCGGGACCCCTGTGTTGAAAGATATAAACTTCAAGATCGAGAGGG
GCCAGCTCTTGGCTGTGGCAGGCTCCACTGGAGCTGGTAAAACATCTCTT
CTCATGGTGATCATGGGGGAACTGGAGCCTTCCGAAGGAAAAATCAAGCA
CAGTGGGAGAATCTCATTCTGCAGCCAGTTTTCCTGGATCATGCCCGGCA
CCATTAAGGAAAACATCATATTTGGAGTGTCCTATGATGAGTACCGCTAC
CGGTCAGTCATCAAAGCCTGTCAGTTGGAGGAGGACATCTCCAAGTTTGC
AGAGAAAGACAACATTGTGCTTGGAGAGGGGGGTATCACTCTTTCTGGAG
GACAAAGAGCCAGGATCTCTTTGGCCCGGGCAGTCTACAAGGATGCAGAC
CTCTACTTGTTGGACAGTCCCTTCGGCTACCTCGACGTGCTGACTGAAAA
AGAAATTTTTGAAAGCTGTGTGTGCAAACTGATGGCAAACAAGACCAGGA
TTCTTGTCACCAGCAAGATGGAACATCTGAAGAAAGCGGACAAAATTCTG
ATTCTGCATGAAGGGAGCTCCTACTTCTATGGAACATTTAGCGAGCTTCA
GAACCTACAGCCAGACTTCTCCTCCAAATTAATGGGCTGTGACTCCTTCG
ACCAGTTCTCTGCAGAAAGAAGAAACTCTATACTCACAGAGACCCTCCAC
CGCTTCTCCCTTGAGGGAGATGCCCCAGTTTCTTGGACAGAAACCAAGAA
GCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACA
CCCCTCAGATGAATGGCATCGAAGAAGATAGTGACGAGCCGCTGGAGAGA
CGGCTGAGTCTGGTGCCAGATTCAGAACAGGGGGAGGCCATCCTGCCCCG
GATCAGCGTCATTTCCACAGGCCCCACATTACAAGCACGGCGCCGGCAGA
GTGTTTTAAATCTCATGACCCATTCAGTGAACCAGGGCCAAAATATCCAC
AGGAAGACTACAGCTTCTACCCGGAAAGTGTCTCTGGCCCCTCAGGCCAA
TCTGACCGAGCTGGACATCTACAGCAGGAGGCTCTCCAGGAAACAGGGCT
GGAAATATCTGAAGAGATTAATGAAGAGGATCTTAAAGAGTGCTTCTTTG
ATGACATGGAGAGCATCCCCGCGGTGACCACATGGAACACCTACCTTAGA
TATATTACTGTCCACAAGAGCCTCATATTTGTCCTCATCTGGTGCCTGGT
TATTTTCCTCGCTGAGGTGGCGGCCAGTCTTGTTGTGCTCTGGCTGCTGG
GCAACACTCCTCTCCAGGACAAGGGCAATAGTACTCACAGCAGAAATAAT
TCTTATGCCGTCATCATTACAAGCACCTCCAGCTACTACGTGTTCTACAT
CTATGTGGGCGTGGCTGACACCCTCCTGGCCATGGGTTTCTTCCGGGGCC
TGCCTTTGGTGCACACCCTCATCACAGTGTCAAAAATTCTGCACCATAAA
ATGCTTCATTCTGTCCTGCAGGCACCCATGAGCACTTTGAACACATTGAA
GGCTGGCGGCATCCTCAACAGATTTTCTAAAGATATTGCTATCCTGGAGA
TCTCCTCCCCCTGACAATCTTTGACTTTATCCAGCTTCTGCTGATCGTGA
TTGGAGCCATAGCAGTGGTTGCTGTCCTGCAGCCCTACATTTTTGTGGCC
ACCGTGCCCGTGATGTTGCCTTTATTATGCTCAGAGCTTACTTCCTGCAA
ACTTCTCAACAGCTCAAACAGCTAGAATCTGAGGGCCGGAGCCCCATTTT

-continued

TACCCACCTGGTGACTTCCCTGAAGGGACTGTGGACTCTGAGAGCATTCG
GGCGACAGCCTTACTTTGAGACACTGTTCCACAAGGCCCTGAACTTGCAC
ACTGCCAACTGGTTTCTTTACCTGAGCACACTCCGCTGGTTCCAGATGCG
GATAGAGATGATCTTCGTCATCTTTTTTATAGCTGTAACCTTCATTTCTA
TCCTTACAACAGGAGAAGGAGAGGGCAGGGTGGGAATCATCCTCACGCTG
GCTATGAACATAATGTCCACCTTGCAGTGGGCCGTGAATTCCAGTATAGA
TGTGGATTCTCTAATGAGGAGTGTCTCCCGGGTGTTTAAATTCATTGATA
TGCCAACTGAGGGGAAACCCACCAAGTCAACAAAACCTTATAAGAATGGA
CAGCTGAGCAAGGTGATGATAATTGAGAACAGCCACGTGAAGAAGGATGA
CATTTGGCCCAGCGGGGGCCAGATGACTGTGAAGGACCTGACGGCCAAGT
ACACCGAAGGTGGAAATGCCATTTTGGAAAACATCAGCTTCTCAATCTCT
CCTGGGCAGAGAGTTGGATTGCTGGGTCGCACGGGCAGCGGCAAATCAAC
CCTGCTCAGTGCCTTCCTTCGGCTCCTGAATACAGAAGGCGAAATCCAAA
TTGACGGGGTGAGCTGGGACAGCATCACCCTGCAGCAGTGGAGAAAAGCA
TTTGGGGTCATTCCACAGAAAGTTTTCATCTTCTCTGGCACTTTCAGAAA
GAACCTGGACCCCTATGAGCAGTGGAGCGACCAGGAGATCTGGAAGGTTG
CAGATGAAGTTGGCCTGCGGAGTGTGATAGAACAATTTCCTGGCAAGCTG
GATTTTGTGCTGGTAGATGGAGGCTGCGTGCTGTCCCACGGCCACAAACA
GCTGATGTGCCTCGCCCGCTCCGTTCTTTCAAAGGCCAAAATCTTGCTTT
TGGATGAGCCCAGTGCTCACCTCGACCCAGTGACCTATCAGATAATCCGC
AGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGA
ATAAGGTCCGGCAGTACGACAGCATCCAGAAGTTGTTGAATGAGCGCAGC
CTTTTCCGCCAGGCCATCTCCCCATCTGACAGAGTCAAGCTGTTTCCACA
TAGGAACTCCTCTAAGTGCAAGTCCAAGCCCCAGATCGCTGCCCTCAAGG
AGGAAACTGAGGAAGAGGTGCAGGATACCCGCCTGTGA (SEQ ID NO: 25)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCAGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCGCTTTTTCTGGAGGTTCATGTTTTA
TGGGATCTTCCTGTACCTGGGGGAGGTCACCAAAGCTGTTCAGCCGCTCC
TTCTTGGCCGCATCATCGCCAGCTATGACCCTGATAATAAAGAAGAAAGG
TCTATTGCTATTTATCTGGGAATTGGCCTCTGCTTGCTCTTCATCGTCCG
CACCCTTCTGCTGCACCCTGCCATTTTTGGCCTTCACCACATCGGCATGC
AAATGAGAATTGCCATGTTCTCCCTCATTTACAAAAAGACCCTGAAACTT
TCCTCAAGAGTTTAGATAAAATATCCATTGGTCAGCTGGTCAGCCTGCTG
TCCAACAATCTTAACAAATTTGATGAAGGCTTGGCGCTGGCCCACTTCGT
GTGGATTGCACCTCTGCAGGTGGCCCTGTTGATGGGACTTATATGGGAGC
TGCTTCAAGCCTCTGCTTTCTGTGGGCTGGGCTTTTTGATTGTACTGGCA

-continued

CTTTTTCAGGCTGGGCTCGGAAGAATGATGATGAAATACAGAGATCAGCG

GGCCGGGAAGATATCAGAGCGACTTGTGATCACCAGTGAAATGATTGAAA

ATATTCAGAGCGTGAAAGCCTACTGCTGGGAAGAAGCCATGGAGAAGATG

ATTGAGAACCTGAGGCAGACAGAGCTCAAGCTCACTCGGAAGGCTGCTTA

TGTTCGCTATTTCAACAGCAGCGCCTTCTTCTTCAGTGGCTTCTTTGTTG

TCTTCCTGTCTGTTCTGCCATATGCACTGATAAAAGGCATTATTTTACGA

AAGATCTTCACCACCATCAGTTTTTGCATCGTTCTCAGGATGGCCGTCAC

AAGACAGTTCCCCTGGGCTGTGCAGACCTGGTACGATTCCTTGGGGGCCA

TCAACAAGATTCAAGATTTCTTGCAAAAACAAGAATATAAAACTTTAGAA

TACAACCTCACCACCACTGAAGTGGTCATGGAAAATGTGACAGCCTTTTG

GGAGGAGGGTTTTGGAGAATTGTTCGAGAAGGCAAAGCAGAATAACAACA

ACAGGAAGACGAGCAATGGGGACGACTCTCTCTTCTTCAGCAACTTTTCA

CTGCTCGGGACCCCTGTGTTGAAAGATATAAACTTCAAGATCGAGAGGGG

CCAGCTCTTGGCTGTGGCAGGCTCCACTGGAGCTGGTAAAACATCTCTTC

TCATGGTGATCATGGGGGAACTGGAGCCTTCCGAAGGAAAAATCAAGCAC

AGTGGGAGAATCTCATTCTGCAGCCAGTTTTCCTGGATCATGCCCGGCAC

CATTAAGGAAAACATCATATTTGGAGTGTCCTATGATGAGTACCGCTACC

GGTCAGTCATCAAAGCCTGTCAGTTGGAGGAGGACATCTCCAAGTTTGCA

GAGAAAGACAACATTGTGCTTGGAGAGGGGGGTATCACTCTTTCTGGAGG

ACAAAGAGCCAGGATCTCTTTGGCCCGGGCAGTCTACAAGGATGCAGACC

TCTACTTGTTGGACAGTCCCTTCGGCTACCTCGACGTGCTGACTGAAAAA

GAAATTTTTGAAAGCTGTGTGTGCAAACTGATGGCAAACAAGACCAGGAT

TCTTGTCACCAGCAAGATGGAACATCTGAAGAAAGCGGACAAAATTCTGA

TTCTGCATGAAGGGAGCTCCTACTTCTATGGAACATTTAGCGAGCTTCAG

AACCTACAGCCAGACTTCTCCTCCAAATTAATGGGCTGTGACTCCTTCGA

CCAGTTCTCTGCAGAAAGAAGAAACTCTATACTCACAGAGACCCTCCACC

GCTTCTCCCTTGAGGGAGATGCCCCAGTTTCTTGGACAGAAACCAAGAAG

CAGTCCTTTAAGCAGACTGGCGAGTTTGGTGAAAAGAGGAAAAATTCAAT

TCTCAATCCTATTAACAGTATTCGCAAGTTCAGCATTGTCCAGAAGACAC

CCCTCCAGATGAATGGCATCGAAGAAGATAGTGACGAGCCGCTGGAGAGA

CGGCTGAGTCTGGTGCCAGATTCAGAACAGGGGGAGGCCATCCTGCCCCG

GATCAGCGTCATTTCCACAGGCCCCACATTACAAGCACGGCGCCGGCAGA

GTGTTTTAAATCTCATGACCCATTCAGTGAACCAGGGCCAAAATATCCAC

AGGAAGACTACAGCTTCTACCCGGAAAGTGTCTCTGGCCCCTCAGGCCAA

TCTGACCGAGCTGGACATCTACAGCAGGAGGCTCTCCCAGGAAACAGGGC

TTGAAATATCTGAAGAGATTAATGAAGAGGATCTTAAAGAGTGCTTCTTT

GATGACATGGAGAGCATCCCCGCGGTGACCACATGGAACACCTACCTTAG

ATATATTACTGTCCACAAGAGCCTCATATTTGTCCTCATCTGGTGCCTGG

TTATTTTCCTCGCTGAGGTGGCGGCCAGTCTTGTTGTGCTCTGGCTGCTG

GGCAACACTCCTCTCCAGGACAAGGGCAATAGTACTCACAGCAGAAATAA

TTCTTATGCCGTCATCATTACAAGCACCTCCAGCTACTACGTGTTCTACA

-continued

TCTATGTGGGCGTGGCTGACACCCTCCTGGCCATGGGTTTCTTCCGGGGC

CTGCCTTTGGTGCACACCCTCATCACAGTGTCAAAAATTCTGCACCATAA

AATGCTTCATTCTGTCCTGCAGGCACCCATGAGCACTTTGAACACATTGA

AGGCTGGCGGCATCCTCAACAGATTTTCTAAAGATATTGCTATCCTGGAT

GATCTCCTCCCCCTGACAATCTTTGACTTTATCCAGCTTCTGCTGATCGT

GATTGGAGCCATAGCAGTGGTTGCTGTCCTGCAGCCCTACATTTTTGTGG

CCACCGTGCCCGTGATTGTTGCCTTTATTATGCTCAGAGCTTACTTCCTG

CAAACTTCTCAACAGCTCAAACAGCTAGAATCTGAGGGCCGGAGCCCCAT

TTTTACCCACCTGGTGACTTCCCTGAAGGGACTGTGGACTCTGAGAGCAT

TCGGGCGACAGCCTTACTTTGAGACACTGTTCCACAAGGCCCTGAACTTG

CACACTGCCAACTGGTTTCTTTACCTGAGCACACTCCGCTGGTTCCAGAT

GCGGATAGAGATGATCTTCGTCATCTTTTTTATAGCTGTAACCTTCATTT

CTATCCTTACAACAGGAGAAGGAGAGGGCAGGGTGGGAATCATCCTCACG

CTGGCTATGAACATAATGTCCACCTTGCAGTGGGCCGTGAATTCCAGTAT

AGATGTGGATTCTCTAATGAGGAGTGTCTCCCGGGTGTTTAAATTCATTG

ATATGCCTACTGAGGGGAAACCCACCAAGTCAACAAAACCTTATAAGAAT

GGACAGCTGAGCAAGGTGATGATAATTGAGAACAGCCACGTGAAGAAGGA

TGACATTTGGCCCAGCGGGGGCCAGATGACTGTGAAGGACCTGACGGCCA

AGTACACCGAAGGTGGAAATGCCATTTTGGAAAACATCAGCTTCTCAATC

TCTCCTGGGCAGAGAGTTGGATTGCTGGGTCGCACGGGCAGCGGCAAACA

ACCCTGCTCAGTGCCTTCCTTCGGCTCCTGAATACAGAAGGCGAAATCCA

AATTGACGGGGTGAGCTGGGACAGCATCACCCTGCAGCAGTGGAGAAAAG

CATTTGGGGTCATTCCACAGAAAGTTTTCATCTTCTCTGGCACTTTCAGA

AAGAACCTGGACCCCTATGAGCAGTGGAGCGACCAGGAGATCTGGAAGGT

TGCAGATGAAGTTGGCCTGCGGAGTGTGATAGAACAATTTCCTGGCAAGC

TGGATTTTGTGCTGGTAGATGGAGGCTGCGTGCTGTCCCACGGCCACAAA

CAGCTGATGTGCCTCGCCCGCTCCGTTCTTTCAAAGGCCAAAATCTTGCT

TTTGGATGAGCCCAGTGCTCACCTCGACCCAGTGACCTATCAGATAATCC

GCAGGACCTTAAAGCAAGCTTTTGCCGACTGCACCGTCATACTGTGTGAG

CACCGGATTGAAGCAATGCTGGAATGCCAGCAGTTTCTGGTGATCGAGGA

GAATAAGGTCCGGCAGTACGACAGCATCCAGAAGTTGTTGAATGAGCGCA

GCCTTTTCCGCCAGGCCATCTCCCCATCTGACAGAGTCAAGCTGTTTCCA

CATAGGAACTCCTCTAAGTGCAAGTCCAAGCCCCAGATCGCTGCCCTCAA

GGAGGAAACTGAGGAAGAGGTGCAGGATACCCGCCTGTGA (SEQ ID NO: 26)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

-continued

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATTTCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGAG

GACAAAGAGCCAGGATCTCTTTGGCCCGGGCAGTCTACAAGGATGCAGAC

CTCTACTTGTTGGACAGTCCCTTCGGCTACCTCGACGTGCTGACTGAAAA

AGAAATTTTTGAAAGCTGTGTGTGCAAACTGATGGCAAACAAGACCAGGA

TTCTTGTCACCAGCAAGATGGAACATCTGAAGAAAGCGGACAAAATTCTG

ATTCTGCATGAAGGGAGCTCCTACTTCTATGGAACATTTAGCGAGCTTCA

GAACCTACAGCCAGACTTCTCCTCCAAATTAATGGGCTGTGACTCCTTCG

ACCAGTTCTCTGCAGAAAGAAGAAACTCTATACTCACAGAGACCCTCCAC

CGCTTCTCCCTTGAGGGAGATGCCCCAGTTTCTTGGACAGAAACCAAGAA

GCAGTCCTTTAAGCAGACTGGCGAGTTTGGTGAAAAGAGGAAAAATTCAA

TTCTCAATCCAATTAACAGTATTCGCAAGTTCAGCATTGTCCAGAAGACA

CCCCTCCAGATGAATGGCATCGAAGAAGATAGTGACGAGCCGCTGGAGAG

ACGGCTGAGTCTGGTGCCAGATTCAGAACAGGGGGAGGCCATCCTGCCCC

GGATCAGCGTCATTTCCACAGGCCCCACATTACAAGCACGGCGCCGGCAG

-continued

AGTGTTTTAAATCTCATGACCCATTCAGTGAACCAGGGCCAAAATATCCA

CAGGAAGACTACAGCTTCTACCCGGAAAGTGTCTCTGGCCCCTCAGGCCA

ATCTGACCGAGCTGGACATCTACAGCAGGAGGCTCTCCCAGGAAACAGGG

CTGGAAATATCTGAAGAGATTAATGAAGAGGATCTTAAAGAGTGCTTCTT

TGATGACATGGAGAGCATCCCCGCGGTGACCACATGGAACACCTACCTTA

GATATATTACTGTCCACAAGAGCCTCATATTTGTCCTCATCTGGTGCCTG

GTTATTTTCCTCGCTGAGGTGGCGGCCAGTCTTGTTGTGCTCTGGCTGCT

GGGCAACACTCCTCTCCAGGACAAGGGCAATAGTACTCACAGCAGAAATA

ATTCTTATGCCGTCATCATTACAAGCACCTCCAGCTACTACGTGTTCTAC

ATCTATGTGGGCGTGGCTGACACCCTCCTGGCCATGGGTTTCTTCCGGGG

CCTGCCTTTGGTGCACACCCTCATCACAGTGTCAAAATTCTGCACCATAA

AATGCTTCATTCTGTCCTGCAGGCACCCATGAGCACTTTGAACACATTGA

AGGCTGGCGGCATCCTCAACAGATTTTCTAAAGATATTGCTATCCTGGAT

GATCTCCTCCCCCTGACAATCTTTGACTTTATCCAGCTTCTGCTGATCGT

GATTGGAGCCATAGCAGTGGTTGCTGTCCTGCAGCCCTACATTTTTGTGG

CCACCGTGCCCGTGATTGTTGCCTTTATTATGCTCAGAGCTTACTTCCTG

CAAACTTCTCAACAGCTCAAACAGCTAGAATCTGAGGGCCGGAGCCCCAT

TTTTACCCACCTGGTGACTTCCCTGAAGGGACTGTGGACTCTGAGAGCAT

TCGGGCGACAGCCTTACTTTGAGACACTGTTCCACAAGGCCCTGAACTTG

CACACTGCCAACTGGTTTCTTTACCTGAGCACACTCCGCTGGTTCCAGAT

GCGGATAGAGATGATCTTCGTCATCTTTTTTATAGCTGTAACCTTCATTT

CTATCCTTACAACAGGAGAAGGAGAGGGCAGGGTGGGAATCATCCTCACG

CTGGCTATGAACATAATGTCCACCTTGCAGTGGGCCGTGAATTCCAGTAT

AGATGTGGATTCTCTAATGAGGAGTGTCTCCCGGGTGTTTAAATTCATTG

ATATGCCAACTGAGGGGAAACCCACCAAGTCAACAAAACCTTATAAGAAT

GGACAGCTGAGCAAGGTGATGATAATTGAGAACAGCCACGTGAAGAAGGA

TGACATTTGGCCCAGCGGGGGCCAGATGACTGTGAAGGACCTGACGGCCA

AGTACACCGAAGGTGGAAATGCCATTTTGGAAAACATCAGCTTCTCAATC

TCTCCTGGGCAGAGAGTTGGATTGCTGGGTCGCACGGGCAGCGGCAAATC

AACCCTGCTCAGTGCCTTCCTTCGGCTCCTGAATACAGAAGGCGAAATCC

AAATTGACGGGGTGAGCTGGGACAGCATCACCCTGCAGCAGTGGAGAAAA

GCATTTGGGGTCATTCCACAGAAAGTTTTCATCTTCTCTGGCACTTTCAG

AAAGAACCTGGACCCCTATGAGCAGTGGAGCGACCAGGAGATCTGGAAGG

TTGCAGATGAAGTTGGCCTGCGGAGTGTGATAGAACAATTTCCTGGCAAG

CTGGATTTTGTGCTGGTAGATGGAGGCTGCGTGCTGTCCCACGGCCACAA

ACAGCTGATGTGCCTCGCCCGCTCCGTTCTTTCAAAGGCCAAAATCTTGC

TTTTGGATGAGCCCAGTGCTCACCTCGACCCAGTGACCTATCAGATAATC

CGCAGGACCTTAAAGCAAGCTTTTGCCGACTGCACCGTCATACTGTGTGA

GCACCGGATTGAAGCAATGCTGGAATGCCAGCAGTTTCTGGTGATCGAGG

AGAATAAGGTCCGGCAGTACGACAGCATCCAGAAGTTGTTGAATGAGCGC

AGCCTTTTCCGCCAGGCCATCTCCCCATCTGACAGAGTCAAGCTGTTTCC

-continued

ACATAGGAACTCCTCTAAGTGCAAGTCCAAGCCCCAGATCGCTGCCCTCA

AGGAGGAAACTGAGGAAGAGGTGCAGGATACCCGCCTGTGA (SEQ ID NO: 27)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCTGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAGCTGTTCAGCCGCTCC

TTCTTGGCCGCATCATCGCCAGCTATGACCCTGATAATAAAGAAGAAAGG

TCTATTGCTATTTATCTGGGAATTGGCCTCTGCTTGCTCTTCATCGTCCG

CACCCTTCTGCTGCACCCTGCCATTTTTGGCCTTCACCACATCGGCATGC

AAATGAGAATTGCCATGTTCTCCCTCATTTACAAAAAGACCCTGAAACTT

TCCTCAAGAGTGTTAGATAAAATATCCATTGGTCAGCTGGTCAGCCTGCT

GTCCAACAATCTTAACAAATTTGATGAAGGCTTGGCGCTGGCCCACTTCG

TGTGGATTGCACCTCTGCAGGTGGCCCTGTTGATGGGACTTATATGGGAG

CTGCTTCAAGCCTCTGCTTTCTGTGGGCTGGGCTTTTTGATTGTACTGGC

ACTTTTTCAGGCTGGGCTCGGAAGAATGATGATGAAATACAGAGATCAGC

GGGCCGGGAAGATATCAGAGCGACTTGTGATCACCAGTGAAATGATTGAA

AATATTCAGAGCGTGAAAGCCTACTGCTGGGAAGAAGCCATGGAGAAGAT

GATTGAGAACCTGAGGCAGACAGAGCTCAAGCTCACTCGGAAGGCTGCTT

ATGTTCGCTATTTCAACAGCAGCGCCTTCTTCTTCAGTGGCTTCTTTGTT

GTCTTCCTGTCTGTTCTCCATATGCACTGATAAAAGGCATTATTTTACGA

AAGATCTTCACCACCATCAGTTTTTGCATCGTTCTCAGGATGGCCGTCAC

AAGACAGTTCCCCTGGGCTGTGCAGACCTGGTACGATTCCTTGGGGGCCA

TCAACAAGATTCAAGATTTCTTGCAAAAACAAGAATATAAAACTTTAGAA

TACAACCTCACCACCACTGAAGTGGTCATGGAAAATGTGACAGCCTTTTG

GGAGGAGGGTTTTGGAGAATTGTTCGAGAAGGCAAAGCAGAATAACAACA

ACAGGAAGACGAGCAATGGGGACGACTCTCTCTTCTTCAGCAACTTTTCA

CTGCTCGGGACCCCTGTGTTGAAAGATATAAACTTCAAGATCGAGAGGGG

CCAGCTCTTGGCTGTGGCAGGCTCCACTGGAGCTGGTAAAACATCTCTTC

TCATGGTGATCATGGGGGAACTGGAGCCTTCCGAAGGAAAAATCAAGCAC

AGTGGGAGAATCTCATTCTGCAGCCAGTTTTCCTGGATCATGCCCGGCAC

CATTAAGGAAAACATCATATTTGGAGTGTCCTATGATGAGTACCGCTACC

GGTCCGTCATCAAAGCCTGTCAGTTGGAGGAGGACATCTCCAAGTTTGCA

GAGAAAGACAACATTGTGCTTGGAGAGGGGGGTATCACTCTTTCTGGAGG

ACAAAGAGCCAGGATCTCTTTGGCCCGGGCAGTCTACAAGGATGCAGACC

TCTACTTGTTGGACAGTCCCTTCGGCTACCTCGACGTGCTGACTGAAAAA

GAAATTTTTGAAAGCTGTGTGTGCAAACTGATGGCAAACAAGACCAGGAT

TCTTGTCACCAGCAAGATGGAACATCTGAAGAAAGCGGACAAAATTCTGA

TTCTGCATGAAGGGAGCTCCTACTTCTATGGAACATTTAGCGAGCTTCAG

-continued

AACCTACAGCCAGACTTCTCCTCCAAATTAATGGGCTGTGACTCCTTCGA

CCAGTTCTCTGCAGAAAGAAGAAACTCTATACTCACAGAGACCCTCCACC

GCTTCTCCCTTGAGGGAGATGCCCCAGTTTCTTGGACAGAAACCAAGAAG

CAGTCCTTTAAGCAGACTGGCGAGTTTGGTGAAAAGAGGAAAAAATTCAAT

TCTCAATCCAATTAACAGTATTCGCAAGTTCAGCATTGTCCAGAAGACAC

CCCTCCAGATGAATGGCATCGAAGAAGATAGTGACGAGCCGCTGGAGAGA

CGGCTGAGTCTGGTGCCAGATTCAGAACAGGGGGAGGCCATCCTGCCCCG

GATCAGCGTCATTTCCACAGGCCCCACATTACAAGCACGGCGCCGGCAGA

GTGTTTTAAATCTCATGACCCATTCAGTGAACCAGGGCCAAAATATCCAC

AGGAAGACTACAGCTTCTACCCGGAAAGTGTCTCTGGCCCCTCAGGCCAA

TCTGACCGAGCTGGACATCTACAGCAGGAGGCTCTCCCAGGAAACAGGGC

TTGAAATATCTGAAGAGATTAATGAAGAGGATCTTAAAGAGTGCTTCTTT

GATGACATGGAGAGCATCCCCGCGGTGACCACATGGAACACCTACCTTAG

ATATATTACTGTCCACAAGAGCCTCATATTTGTCCTCATCTGGTGCCTGG

TTATTTTCCTCGCTGAGGTGGCGGCCAGTCTTGTTGTGCTCTGGCTGCTG

GGCAACACTCCTCTCCAGGACAAGGGCAATAGTACTCACAGCAGAAATAA

TTCTTATGCCGTCATCATTACAAGCACCTCCAGCTACTACGTGTTCTACA

TCTATGTGGGCGTGGCTGACACCCTCCTGGCCATGGGTTTCTTCCGGGGC

CTGCCTTTGGTGCACACCCTCATCACAGTGTCAAAAATTCTGCACCATAA

AATGCTTCATTCTGTCCTGCAGGCACCCATGAGCACTTTGAACACATTGA

AGGCTGGCGGCATCCTCAACAGATTTTCTAAAGATATTGCTATCCTGGAT

GATCTCCTCCCCCTGACAATCTTTGACTTTATCCAGCTTCTGCTGATCGT

GATTGGAGCCATAGCAGTGGTTGCTGTCCTGCAGCCCTACATTTTTGTGG

CCACCGTGCCCGTGATTGTTGCCTTTATTATGCTCAGAGCTTACTTCCTG

CAAACTTCTCAACAGCTCAAACAGCTAGAATCTGAGGGCCGGAGCCCCAT

TTTTACCCACCTGGTGACTTCCCTGAAGGGACTGTGGACTCTGAGAGCAT

TCGGGCGACAGCCTTACTTTGAGACACTGTTCCACAAGGCCCTGAACTTG

CACACTGCCAACTGGTTTCTTTACCTGAGCACACTCCGCTGGTTCCAGAT

GCGGATAGAGATGATCTTCGTCATCTTTTTTATAGCTGTAACCTTCATTT

CTATCCTTACAACAGGAGAAGGAGAGGGCAGGGTGGGAATCATCCTCACG

CTGGCTATGAACATAATGTCCACCTTGCAGTGGGCCGTGAATTCCAGTAT

AGATGTGGATTCTCTAATGAGGAGTGTCTCCCGGGTGTTTAAATTCATTG

ATATGCCTACTGAGGGGAAACCCACCAAGTCAACAAAGCCTTATAAGAAT

GGACAGCTGAGCAAGGTGATGATAATTGAGAACAGCCACGTGAAGAAGGA

TGACATTTGGCCCAGCGGGGGCCAGATGACTGTGAAGGACCTGACGGCCA

AGTACACCGAAGGTGGAAATGCCATTTTGGAAAACATCAGCTTCTCAATC

TCTCCTGGGCAGAGAGTTGGATTGCTGGGTCGCACGGGCAGCGGCAAATC

AACCCTGCTCAGTGCCTTCCTTCGGCTCCTGAATACAGAAGGCGAAATCC

AAATTGACGGGGTGAGCTGGGACAGCATCACCCTGCAGCAGTGGAGAAAA

GCATTTGGGGTCATTCCACAGAAAGTTTTCATCTTCTCTGGCACTTTCAG

-continued

AAAGAACCTGGACCCCTATGAGCAGTGGAGCGACCAGGAGATCTGGAAGG
TTGCAGATGAAGTTGGCCTGCGGAGTGTGATAGAACAATTTCCTGGCAAG
CTGGATTTTGTGCTGGTAGATGGAGGCTGCGTGCTGTCCCACGGCCACAA
ACAGCTGATGTGCCTCGCCCGCTCCGTTCTTTCAAAGGCCAAAATCTTGC
TTTTGGATGAGCCCAGTGCTCACCTCGACCCAGTGACCTATCAGATAATC
CGCAGGACCTTAAAGCAAGCTTTTGCCGACTGCACCGTCATACTGTGTGA
GCACCGGATTGAAGCAATGCTGGAATGCCAGCAGTTTCTGGTGATCGAGG
AGAATAAGGTCCGGCAGTACGACAGCATCCAGAAGTTGTTGAATGAGCGC
AGCCTTTTCCGCCAGGCCATCTCCCCATCTGACAGAGTCAAGCTGTTTCC
ACATAGGAACTCCTCTAAGTGCAAGTCCAAGCCCCAGATCGCTGCCCTCA
AGGAGGAAACTGAGGAAGAGGTGCAGGATACCCGCCTGTGA (SEQ ID NO: 28)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCAGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT
ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATATCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCTATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTTGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACACACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTACCTTACAACAGGAGAAGGAGAGGGCAGGGTGGGAATCATCCTCAC
GCTGGCTATGAACATAATGTCCACCTTGCAGTGGGCCGTGAATTCCAGTA
TAGATGTGGATTCTCTAATGAGGAGTGTCTCCCGGGTGTTTAAATTCATT

GATATGCCTACTGAGGGGAAACCCACCAAGTCAACAAAACCTTATAAGAA

TGGACAGCTGAGCAAGGTGATGATAATTGAGAACAGCCACGTGAAGAAGG

ATGACATTTGGCCCAGCGGGGGCCAGATGACTGTGAAGGACCTGACGGCC

AAGTACACCGAAGGTGGAAATGCCATTTTGGAAAACATCAGCTTCTCAAT

CTCTCCTGGGCAGAGAGTTGGATTGCTGGGTCGCACGGGCAGCGGCAAAT

CAACCCTGCTCAGTGCCTTCCTTCGGCTCCTGAATACAGAAGGCGAAATC

CAAATTGACGGGGTGAGCTGGGACAGCATCACCCTGCAGCAGTGGAGAAA

AGCATTTGGGGTCATTCCACAGAAAGTTTTCATCTTCTCTGGCACTTTCA

GAAAGAACCTGGACCCCTATGAGCAGTGGAGCGACCAGGAGATCTGGAAG

GTTGCAGATGAAGTTGGCCTGCGGAGTGTGATAGAACAATTTCCTGGCAA

GCTGGATTTTGTGCTGGTAGATGGAGGCTGCGTGCTGTCCCACGGCCACA

AACAGCTGATGTGCCTCGCCCGCTCCGTTCTTTCAAAGGCCAAAATCTTG

CTTTTGGATGAGCCCAGTGCTCACCTCGACCCAGTGACCTATCAGATAAT

CCGCAGGACCTTAAAGCAAGCTTTTGCCGACTGCACCGTCATACTGTGTG

AGCACCGGATTGAAGCAATGCTGGAATGCCAGCAGTTTCTGGTGATCGAG

GAGAATAAGGTCCGGCAGTACGACAGCATCCAGAAGTTGTTGAATGAGCG

CAGCCTTTTCCGCCAGGCCATCTCCCCATCTGACAGAGTCAAGCTGTTTC

CACATAGGAACTCCTCTAAGTGCAAGTCCAAGCCCCAGATCGCTGCCCTC

AAGGAGGAAACTGAGGAAGAGGTGCAGGATACCCGCCTGTGA (SEQ ID NO: 29)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTGATTGTACTGGC

ACTTTTTCAGGCTGGGCTCGGAAGAATGATGATGAAATACAGAGATCAGC

GGGCCGGGAAGATATCAGAGCGACTTGTGATCACCAGTGAAATGATTGAA

AATATTCAGAGCGTGAAAGCCTACTGCTGGGAAGAAGCCATGGAGAAGAT

GATTGAGAACCTGAGGCAGACAGAGCTCAAGCTCACTCGGAAGGCTGCTT

ATGTTCGCTATTTCAACAGCAGCGCCTTCTTCTTCAGTGGCTTCTTTGTT

GTCTTCCTGTCTGTTCTGCCATATGCACTGATAAAAGGCATTATTTTACG

AAAGATCTTCACCACCATCAGTTTTTGCATCGTTCTCAGGATGGCCGTCA

CAAGACAGTTCCCCTGGGCTGTGCAGACCTGGTACGATTCCTTGGGGGCC

ATCAACAAGATTCAAGATTTCTTGCAAAAACAAGAATATAAAACTTTAGA

ATACAACCTCACCACCACTGAAGTGGTCATGGAAAATGTGACAGCCTTTT

GGGAGGAGGGTTTTGGAGAATTGTTCGAGAAGGCAAAGCAGAATAACAAC

AACAGGAAGACGAGCAATGGGGACGACTCTCTCTTCTTCAGCAACTTTTC

ACTGCTCGGGACCCCTGTGTTGAAAGATATAAACTTCAAGATCGAGAGGG

GCCAGCTCTTGGCTGTGGCAGGCTCCACTGGAGCTGGTAAAACATCTCTT

CTCATGGTGATCATGGGGGAACTGGAGCCTTCCGAAGGAAAAATCAAGCA

CAGTGGGAGAATCTCATTCTGCAGCCAGTTTTCCTGGATCATGCCCGGCA

CCATTAAGGAAAACATCATATTTGGAGTGTCCTATGATGAGTACCGCTAC

CGGTCCGTCATCAAAGCCTGTCAGTTGGAGGAGGACATCTCCAAGTTTGC

AGAGAAAGACAACATTGTGCTTGGAGAGGGGGGTATCACTCTTTCTGGAG

GACAAAGAGCCAGGATCTCTTTGGCCCGGGCAGTCTACAAGGATGCAGAC

CTCTACTTGTTGGACAGTCCCTTCGGCTACCTCGACGTGCTGACTGAAAA

AGAAATTTTTGAAAGCTGTGTGTGCAAACTGATGGCAAACAAGACCAGGA

TTCTTGTCACCAGCAAGATGGAACATCTGAAGAAAGCGGACAAAATTCTG

ATTCTGCATGAAGGGAGCTCCTACTTCTATGGAACATTTAGCGAGCTTCA

GAACCTACAGCCAGACTTCTCCTCCAAATTAATGGGCTGTGACTCCTTCG

ACCAGTTCTCTGCAGAAAGAAGAAACTCTATACTCACAGAGACCCTCCAC

CGCTTCTCCCTTGAGGGAGATGCCCCAGTTTCTTGGACAGAAACCAAGAA

GCAGTCCTTTAAGCAGACTGGCGAGTTTGGTGAAAAGAGGAAAAATTCAA

TTCTCAATCCAATTAACAGTATTCGCAAGTTCAGCATTGTCCAGAAGACA

CCCCTCCAGATGAATGGCATCGAAGAAGATAGTGACGAGCCGCTGGAGAG

ACGGCTGAGTCTGTGCCAGATTCAGAACAGGGGGAGGCCATCCTGCCCCG

GATCAGCGTCATTTCCACAGGCCCCACATTACAAGCACGGCGCCGGCAGA

GTGTTTTAAATCTCATGACCCATTCAGTGAACCAGGGCCAAAATATCCAC

AGGAAGACTACAGCTTCTACCCGGAAAGTGTCTCTGGCCCCTCAGGCCAA

TCTGACCGAGCTGGACATCTACAGCAGGAGGCTCTCCCAGGAAACAGGGC

TGGAAATATCTGAAGAGATTAATGAAGAGGATCTTAAAGAGTGCTTCTTT

GATGACATGGAGAGCATCCCCGCGGTGACCACATGGAACACCTACCTTAG

ATATATTACTGTCCACAAGAGCCTCATATTTGTCCTCATCTGGTGCCTGG

TTATTTTCCTCGCTGAGGTGGCGGCCAGTCTTGTTGTGCTCTGGCTGCTG

GGCAACACTCCTCTCCAGGACAAGGGCAATAGTACTCACAGCAGAAATAA

TTCTTATGCCGTCATCATTACAAGCACCTCCAGCTACTACGTGTTCTACA

TCTATGTGGGCGTGGCTGACACCCTCCTGGCCATGGGTTTCTTCCGGGGC

CTGCCTTTGGTGCACACCCTCATCACAGTGTCAAAAATTCTGCACCATAA

AATGCTTCATTCTGTCCTGCAGGCACCCATGAGCACTTTGAACACATTGA

AGGCTGGCGGCATCCTCAACAGATTTTCTAAAGATATTGCTATCCTGGAT

GATCTCCTCCCCCTGACAATCTTTGACTTTATCCAGCTTCTGCTGATCGT

GATTGGAGCCATAGCAGTGGTTGCTGTCCTGCAGCCCTACATTTTTGTGG

-continued

CCACCGTGCCCGTGATTGTTGCCTTTATTATGCTCAGAGCTTACTTCCTG

CAAACTTCTCAACAGCTCAAACAGCTAGAGTCTGAGGGCCGGAGCCCCAT

TTTTACCCACCTGGTGACTTCCCTGAAGGGACTGTGGACTCTGAGAGCAT

TCGGGCGACAGCCTTACTTTGAGACACTGTTCCACAAGGCCCTGAACTTG

CACACTGCCAACTGGTTTCTTTACCTGAGCACACTCCGCTGGTTCAGATG

CGGATAGAGATGATCTTCGTCATCTTTTTTATAGCTGTAACCTTCATTTC

TATCCTTACAACAGGAGAAGGAGAGGGCAGGGTGGGAATCATCCTCACGC

TGGCTATGAACATAATGTCCACCTTGCAGTGGGCCGTGAATTCCAGTATA

GATGTGGATTCTCTATGAGGAGTGTCTCCCGGGTGTTTAAATTCATTGAT

ATGCCTACTGAGGGGAAACCCACCAAGTCAACAAAACCTTATAAGAATGG

ACAGCTGAGCAAGGTGATGATAATTGAGAACAGCCACGTGAAGAAGGATG

ACATTTGGCCCAGCGGGGGCCAGATGACTGTGAGGACCTGACGGCCAAGT

ACACCGAAGGTGGAAATGCCATTTTGGAAAACATCAGCTTCTCAATCTCT

CCTGGGCAGAGAGTTGGATTGCTGGGTCGCACGGGCAGCGGCAAATCAAC

CCTGCTCAGTGCCTTCCTTCGGCTCCTGAATACAGAAGGCGAAATCCAAA

TTGACGGGGTGAGCTGGGACAGCATCACCCTGCAGCAGTGGAGAAAAGCA

TTTGGGGTCATTCCACAGAAAGTTTTCATCTTCTCTGGCACTTTCAGAAA

GAACCTGGACCCCTATGAGCAGTGGAGCGACCAGGAGATCTGGAAGGTTG

CAGATGAAGTTGGCCTGCGGAGTGTGATAGAACAATTTCCTGGCAAGCTG

GATTTTGTGCTGGTAGATGGAGGCTGCGTGCTGTCCCACGGCCACAAACA

GCTGATGTGCCTCGCCCGCTCCGTTCTTTCAAAGGCCAAAATCTTGCTTT

TGGATGAGCCCAGTGCTCACCTCGACCCAGTGACCTATCAGATAATCCGC

AGGACCTTAAAGCAAGCTTTTGCCGACTGCACCGTCATACTGTGTGAGCA

CCGGATTGAAGCAATGCTGGAATGCCAGCAGTTTCTGGTGATCGAGGAGA

ATAAGGTCCGGCAGTACGACAGCATCCAGAAGTTGTTGAATGAGCGCAGC

CTTTTCCGCCAGGCCATCTCCCCATCTGACAGAGTCAAGCTGTTTCCACA

TAGGAACTCCTCTAAGTGCAAGTCCAAGCCCCAGATCGCTGCCCTCAAGG

AGGAAACTGAGGAAGAGGTGCAGGATACCCGCCTGTGA (SEQ ID NO: 30)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCTGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCTGTTGATGGGACTTATATGGGAG

CTGCTTCAAGCCTCTGCTTTCTGTGGGCTGGGCTTTTTGATTGTACTGGC

ACTTTTTCAGGCTGGGCTCGGAAGAATGATGATGAAATACAGAGATCAGC

GGGCCGGGAAGATTTCAGAGCGACTTGTGATCACCAGTGAAATGATTGAA

AATATTCAGAGCGTGAAAGCCTACTGCTGGGAAGAAGCCATGGAGAAGAT

GATTGAGAACCTGAGGCAGACAGAGCTCAAGCTCACTCGGAAGGCTGCTT

ATGTTCGCTATTTCAACAGCAGCGCCTTCTTCTTCAGTGGCTTCTTTGTT

GTCTTCCTGTCTGTTCTGCCATATGCACTGATAAAAGGCATTATTTTACG

AAAGATCTTCACCACCATCAGTTTTTGCATCGTTCTCAGGATGGCCGTCA

CAAGACAGTTCCCCTGGGCTGTGCAGACCTGGTACGATTCCTTGGGGGCC

ATCAACAAGATTCAAGATTTCTTGCAAAAACAAGAATATAAAACTTTAGA

ATACAACCTCACCACCACTGAAGTGGTCATGGAAAATGTGACAGCCTTTT

GGGAGGAGGGTTTTGGAGAATTGTTCGAGAAGGCAAAGCAGAATAACAAC

AACAGGAAGACGAGCAATGGGGACGACTCTCTCTTCTTCAGCAACTTTTC

ACTGCTCGGGACCCCTGTGTTGAAAGATATAAACTTCAAGATCGAGAGGG

GCCAGCTCTTGGCTGTGGCAGGCTCCACTGGAGCTGGTAAAACATCTCTT

CTCATGGTGATCATGGGGGAACTGGAGCCTTCCGAAGGAAAAATCAAGCA

CAGTGGGAGAATCTCATTCTGCAGCCAGTTTTCCTGGATCATGCCCGGCA

CCATTAAGGAAAACATCATATTTGGAGTGTCCTATGATGAGTACCGCTAC

CGGTCAGTCATCAAAGCCTGTCAGTTGGAGGAGGACATCTCCAAGTTTGC

AGAGAAAGACAACATTGTGCTTGGAGAGGGGGGTATCACTCTTTCTGGAG

GACAAAGAGCCAGGATCTCTTTGGCCCGGGCAGTCTACAAGGATGCAGAC

CTCTACTTGTTGGACAGTCCCTTCGGCTACCTCGACGTGCTGACTGAAAA

AGAAATTTTTGAAAGCTGTGTGTGCAAACTGATGGCAAACAAGACCAGGA

TTCTTGTCACCAGCAAGATGGAACATCTGAAGAAAGCGGACAAAATTCTG

ATTCTGCATGAAGGGAGCTCCTACTTCTATGGAACATTTAGCGAGCTTCA

GAACCTACAGCCAGACTTCTCCTCCAAATTAATGGGCTGTGACTCCTTCG

ACCAGTTCTCTGCAGAAAGAAGAAACTCTATACTCAAGAGACCCTCCACC

GCTTCTCCCTTGAGGGAGATGCCCCAGTTTCTTGGACAGAAACCAAGAAG

CAGTCCTTTAAGCAGACTGGCGAGTTTGGTGAAAAGAGGAAAAATTCAAT

TCTCAATCCTATTAACAGTATTCGCAAGTTCAGCATTGTCCAGAAGACAC

CCCTCCAGATGAATGGCATCGAAGAAGATAGTGACGAGCCGCTGGAGAGA

CGGCTGAGTCTGGTGCCAGATTCAGAACAGGGGGAGGCCATCCTGCCCCG

GATCAGCGTCATTTCCACAGGCCCCACATTACAAGCACGGCGCCGGCAGA

GTGTTTTAAATCTCATGACCCATTCAGTGAACCAGGGCCAAAATATCCAC

AGGAAGACTACAGCTTCTACCCGGAAAGTGTCTCTGGCCCCTCAGGCCAA

TCTGACCGAGCTGGACATCTACAGCAGGAGGCTCTCCAGGAAACAGGGCT

GGAAATATCTGAAGAGATTAATGAAGAGGATCTTAAAGAGTGCTTCTTTG

ATGACATGGAGAGCATCCCCGCGGTGACCACATGGAACACCTACCTTAGA

TATATTACTGTCCACAAGAGCCTCATATTTGTCCTCATCTGGTGCCTGGT

TATTTTCCTCGCTGAGGTGGCGGCCAGTCTTGTTGTGCTCTGGCTGCTGG

-continued

GCAACACTCCTCTCCAGGACAAGGGCAATAGTACACACAGCAGAAATAAT
TCTTATGCCGTCATCATTACAAGCACCTCCAGCTACTACGTGTTCTACAT
CTATGTGGGCGTGGCTGACACCCTCCTGGCCATGGGTTTCTTCCGGGGCC
TGCCTTTGGTGCACACCCTCATCACAGTGTCAAAAATTCTGCACCATAAA
ATGCTTCATTCTGTCCTGCAGGCACCCATGAGCACTTTGAACACATTGAA
GGCTGGCGGCATCCTCAACAGATTTTCTAAAGATATTGCTATCCTGGATG
ATCTCCTCCCCCTGACAATCTTTGACTTTATCCAGCTTCTGCTGATCGTG
ATTGGAGCCATAGCAGTGGTTGCTGTCCTGCAGCCCTACATTTTTGTGGC
CACCGTGCCCGTGATTGTTGCCTTTATTATGCTCAGAGCTTACTTCCTGC
AAACTTCTCAACAGCTCAAACAGCTAGAATCTGAGGGCCGGAGCCCCATT
TTTACCCACCTGGTGACTTCCCTGAAGGGACTGTGGACTCTGAGAGCATT
CGGGCGACAGCCTTACTTTGAGACACTGTTCCACAAGGCCCTGAACTTGC
ACACTGCCAACTGGTTTCTTTACCTGAGCACACTCCGCTGGTTCCAGATG
CGGATAGAGATGATCTTCGTCATCTTTTTTATAGCTGTAACCTTCATTTC
TATCCTTACAACAGGAGAAGGAGAGGGCAGGGTGGGAATCATCCTCACGC
TGGCTATGAACATAATGTCCACCTTGCAGTGGGCCGTGAATTCCAGTATA
GATGTGGATTCTCTAATGAGGAGTGTCTCCCGGGTGTTTAAATTCATTGA
TATGCCTACTGAGGGGAAACCCACCAAGTCAACAAAACCTTATAAGAATG
GACAGCTGAGCAAGGTGATGATAATTGAGAACAGCCACGTGAAGAAGGAT
GACATTTGGCCCAGCGGGGGCCAGATGACTGTGAAGGACCTGACGGCCAA
GTACACCGAAGGTGGAAATGCCATTTTGGAAAACATCAGCTTCTCAATCT
CTCCTGGGCAGAGAGTTGGATTGCTGGGTCGCACGGGCAGCGGCAAATCA
ACCCTGCTCAGTGCCTTCCTTCGGCTCCTGAATACAGAAGGCGAAATCCA
AATTGACGGGGTGAGCTGGGACAGCATCACCCTGCAGCAGTGGAGAAAAG
CATTTGGGGTCATTCCACAGAAAGTTTTCATCTTCTCTGGCACTTTCAGA
AAGAACCTGGACCCCTATGAGCAGTGGAGCGACCAGGAGATCTGGAAGGT
TGCAGATGAAGTTGGCCTGCGGAGTGTGATAGAACAATTTCCTGGCAAGC
TGGATTTTGTGCTGGTAGATGGAGGCTGCGTGCTGTCCCACGGCCACAAA
CAGCTGATGTGCCTCGCCCGCTCCGTTCTTTCAAAGGCCAAAATCTTGCT
TTTGGATGAGCCCAGTGCTCACCTCGACCCAGTGACCTATCAGATAATCC
GCAGGACCTTAAAGCAAGCTTTTGCCGACTGCACCGTCATACTGTGTGAG
CACCGGATTGAAGCAATGCTGGAATGCCAGCAGTTTCTGGTGATCGAGGA
GAATAAGGTCCGGCAGTACGACAGCATCCAGAAGTTGTTGAATGAGCGCA
GCCTTTTCCGCCAGGCCATCTCCCCATCTGACAGAGTCAAGCTGTTTCCA
CATAGGAACTCCTCTAAGTGCAAGTCCAAGCCCCAGATCGCTGCCCTCAA
GGAGGAAACTGAGGAAGAGGTGCAGGATACCCGCCTGTGA

Example 3. Additional Exemplary Codon Optimized CFTR Sequences

The following additional exemplary codon optimized sequences are used for generating human CFTR mRNA for safe and efficacious clinical use:

(SEQ ID NO: 31)

ATGCAGAGAAGCCCCCTGGAGAAGGCCTCTGTGGTGAGCAAGCTGTTCTT
CAGCTGGACCAGACCCATCCTGAGAAAGGGCTACAGACAGAGACTGGAGC
TGTCTGACATCTACCAGATCCCCTCTGTGGACTCTGCCGACAACCTGTCT
GAGAAGCTGGAGAGAGAGTGGGACAGAGAGCTGGCCAGCAAGAAGAACCC
CAAGCTGATCAATGCCCTGAGAAGATGCTTCTTCTGGAGATTCATGTTCT
ATGGCATCTTCCTGTACCTGGGAGAGGTGACCAAGGCCGTGCAGCCCCTG
CTGCTGGGCAGGATCATTGCCAGCTATGACCCTGACAACAAGGAGGAGAG
AAGCATTGCCATCTACCTGGGCATTGGCCTGTGCCTGCTGTTCATTGTGA
GAACCCTGCTGCTGCACCCTGCCATCTTTGGCCTGCACCACATTGGCATG
CAGATGAGAATTGCCATGTTCAGCCTGATCTACAAGAAGACCCTGAAGCT
GAGCAGCAGAGTGCTGGACAAGATCAGCATTGGCCAGCTGGTGAGCCTGC
TGAGCAACAACCTGAACAAGTTTGATGAGGGCCTGGCCCTGGCCCACTTT
GTGTGGATTGCCCCCCTGCAGGTGGCCCTGCTGATGGGCCTGATCTGGGA
GCTGCTGCAGGCCTCTGCCTTCTGTGGCCTGGGCTTCCTGATTGTGCTGG
CCCTGTTCCAGGCCGGCCTGGGCAGAATGATGATGAAGTACAGAGACCAG
AGAGCCGGCAAGATCTCTGAGAGACTGGTGATCACCTCTGAGATGATTGA
GAACATCCAGTCTGTGAAGGCCTACTGCTGGGAGGAGGCCATGGAGAAGA
TGATTGAGAACCTGAGACAGACAGAGCTGAAGCTGACCAGGAAGGCCGCC
TATGTGAGATACTTCAACAGCTCTGCCTTCTTCTTCTCTGGCTTCTTTGT
GGTGTTCCTGTCTGTGCTGCCCTATGCCCTGATCAAGGGCATCATCCTGA
GGAAGATCTTCACCACCATCAGCTTCTGCATTGTGCTGAGGATGGCCGTG
ACCAGGCAGTTCCCCTGGGCCGTGCAGACCTGGTATGACAGCCTGGGGGC
CATCAACAAGATCCAGGACTTCCTGCAGAAGCAGGAGTACAAGACCCTGG
AGTACAACCTGACCACCACAGAGGTGGTGATGGAGAATGTGACAGCCTTC
TGGGAGGAGGGCTTTGGAGAGCTGTTTGAGAAGGCCAAGCAGAACAACAA
CAACAGAAAGACCAGCAATGGAGATGACAGCCTGTTCTTCAGCAACTTCA
GCCTGCTGGGCACCCCTGTGCTGAAGGACATCAACTTCAAGATTGAGAGG
GGCCAGCTGCTGGCCGTGGCCGGCAGCACAGGAGCCGGCAAGACCAGCCT
GCTGATGGTGATCATGGGAGAGCTGGAGCCCTCTGAGGGCAAGATCAAGC
ACTCTGGCAGAATCAGCTTCTGCAGCCAGTTCAGCTGGATCATGCCTGGC
ACCATCAAGGAGAACATCATCTTTGGGGTGAGCTATGATGAGTACAGGTA
CAGATCTGTGATCAAGGCCTGCCAGCTGGAGGAGGACATCTCCAAGTTTG
CCGAGAAGGACAACATTGTGCTGGGGGAGGGAGGCATCACCCTGTCTGGG
GGCCAGAGAGCCAGAATCAGCCTGGCCAGAGCCGTGTACAAGGATGCCGA
CCTGTACCTGCTGGACAGCCCCTTTGGCTACCTGGATGTGCTGACAGAGA
AGGAGATCTTTGAGAGCTGTGTGTGCAAGCTGATGGCCAACAAGACCAGG

-continued

ATCCTGGTGACCAGCAAGATGGAGCACCTGAAGAAGGCCGACAAGATCCT
GATCCTGCATGAGGGCAGCAGCTACTTCTATGGCACCTTCTCTGAGCTGC
AGAACCTGCAGCCTGACTTCAGCAGCAAGCTGATGGGCTGTGACAGCTTT
GACCAGTTCTCTGCTGAGAGAAGAAACAGCATCCTGACAGAGACCCTGCA
CAGGTTCAGCCTGGAGGGGGATGCCCCTGTGAGCTGGACAGAGACCAAGA
AGCAGAGCTTCAAGCAGACAGGAGAGTTTGGGGAGAAGAGGAAGAACAGC
ATCCTGAACCCCATCAACAGCATCAGGAAGTTCAGCATTGTGCAGAAGAC
CCCCCTGCAGATGAATGGCATTGAGGAGGACTCTGATGAGCCCCTGGAGA
GAAGACTGAGCCTGGTGCCAGACTCTGAGCAGGGAGAGGCCATCCTGCCC
AGGATCTCTGTGATCAGCACAGGCCCCACCCTGCAGGCCAGAAGAAGACA
GTCTGTGCTGAACCTGATGACCCACTCTGTGAACCAGGGCCAGAATATCC
ACAGAAAGACCACAGCCAGCACCAGAAAGGTGAGCCTGGCCCCCCAGGCC
AACCTGACAGAGCTGGACATCTACAGCAGAAGGCTGAGCCAGGAGACAGG
CCTGGAGATCTCTGAGGAGATCAATGAGGAGGACCTGAAGGAGTGCTTCT
TTGATGACATGGAGAGCATCCCTGCCGTGACCACCTGGAACACCTACCTG
AGATACATCACAGTGCACAAGAGCCTGATCTTTGTGCTGATCTGGTGCCT
GGTGATCTTCCTGGCCGAGGTGGCCGCCAGCCTGGTGGTGCTGTGGCTGC
TGGGCAACACCCCCCTGCAGGACAAGGGCAACAGCACCCACAGCAGAAAC
AACAGCTATGCTGTGATCATCACCAGCACCAGCAGCTACTATGTGTTCTA
CATCTATGTGGGAGTGGCTGACACCCTGCTGGCCATGGGCTTCTTCAGAG
GCCTGCCCCTGGTGCACACCCTGATCACAGTGAGCAAGATCCTGCACCAC
AAGATGCTGCACTCTGTGCTGCAGGCCCCCATGAGCACCCTGAACACCCT
GAAGGCTGGAGGCATCCTGAACAGATTCAGCAAGGACATTGCCATCCTGG
ATGACCTGCTGCCCCTGACCATCTTTGACTTCATCCAGCTGCTGCTGATT
GTGATTGGAGCCATTGCCGTGGTGGCCGTGCTGCAGCCCTACATCTTTGT
GGCCACAGTGCCTGTGATTGTGGCCTTCATCATGCTGAGGGCCTACTTCC
TGCAGACCAGCCAGCAGCTGAAGCAGCTGGAGTCTGAGGGCAGAAGCCCC
ATCTTCACCCACCTGGTGACCAGCCTGAAGGGCCTGTGGACCCTGAGGGC
CTTTGGCAGACAGCCCTACTTTGAGACCCTGTTCCACAAGGCCCTGAACC
TGCACACAGCCAACTGGTTCCTGTACCTGAGCACCCTGAGATGGTTCCAG
ATGAGGATTGAGATGATCTTTGTGATCTTCTTCATTGCCGTGACCTTCAT
CAGCATCCTGACCACAGGGGAGGGCGAGGGCAGAGTGGGCATCATCCTGA
CCCTGGCCATGAACATCATGAGCACCCTGCAGTGGGCCGTGAACAGCAGC
ATTGATGTGGACAGCCTGATGAGATCTGTGAGCAGAGTGTTCAAGTTCAT
TGACATGCCCACAGAGGGCAAGCCCACCAAGAGCACCAAGCCCTACAAGA
ATGGCCAGCTGAGCAAGGTGATGATCATTGAGAACAGCCATGTGAAGAAG
GATGACATCTGGCCCTCTGGAGGCCAGATGACAGTGAAGGACCTGACAGC
CAAGTACACAGAGGGGGGCAATGCCATCCTGGAGAACATCAGCTTCAGCA
TCAGCCCTGGCCAGAGGGTGGGCCTGCTGGGCAGAACAGGCTCTGGCAAG
AGCACCCTGCTGTCTGCCTTCCTGAGGCTGCTGAACACAGAGGGAGAGAT

-continued

CCAGATTGATGGGGTGAGCTGGGACAGCATCACCCTGCAGCAGTGGAGGA
AGGCCTTTGGGGTGATCCCCCAGAAGGTGTTCATCTTCTCTGGCACCTTC
AGGAAGAACCTGGACCCCTATGAGCAGTGGTCTGACCAGGAGATCTGGAA
GGTGGCCGATGAGGTGGGCCTGAGATCTGTGATTGAGCAGTTCCCTGGCA
AGCTGGACTTTGTGCTGGTGGATGGAGGCTGTGTGCTGAGCCATGGCCAC
AAGCAGCTGATGTGCCTGGCCAGATCTGTGCTGAGCAAGGCCAAGATCCT
GCTGCTGGATGAGCCCTCTGCCCACCTGGACCCTGTGACCTACCAGATCA
TCAGAAGAACCCTGAAGCAGGCCTTTGCCGACTGCACAGTGATCCTGTGT
GAGCACAGAATTGAGGCCATGCTGGAGTGCCAGCAGTTCCTGGTGATTGA
GGAGAACAAGGTGAGGCAGTATGACAGCATCCAGAAGCTGCTGAATGAGA
GAAGCCTGTTCAGACAGGCCATCAGCCCCTCTGACAGAGTGAAGCTGTTC
CCCCACAGGAACAGCAGCAAGTGCAAGAGCAAGCCCCAGATTGCCGCCCT
GAAGGAGGAGACAGAGGAGGAGGTGCAGGACACCAGACTGTGA (SEQ ID NO: 32)

ATGCAGAGGAGCCCCCTGGAGAAGGCCAGCGTGGTGAGCAAGCTGTTCTT
CAGCTGGACCAGGCCCATCCTGAGGAAGGGCTACAGGCAGAGGCTGGAGC
TGAGCGACATCTACCAGATCCCCAGCGTGGACAGCGCCGACAACCTGAGC
GAGAAGCTGGAGAGGGAGTGGGACAGGGAGCTGGCCAGCAAGAAGAACCC
CAAGCTGATCAACGCCCTGAGGAGGTGCTTCTTCTGGAGGTTCATGTTCT
ACGGCATCTTCCTGTACCTGGGCGAGGTGACCAAGGCCGTGCAGCCCCTG
CTGCTGGGCAGGATCATCGCCAGCTACGACCCCGACAACAAGGAGGAGAG
GAGCATCGCCATCTACCTGGGCATCGGCCTGTGCCTGCTGTTCATCGTGA
GGACCCTGCTGCTGCACCCCGCCATCTTCGGCCTGCACCACATCGGCATG
CAGATGAGGATCGCCATGTTCAGCCTGATCTACAAGAAGACCCTGAAGCT
GAGCAGCAGGGTGCTGGACAAGATCAGCATCGGCCAGCTGGTGAGCCTGC
TGAGCAACAACCTGAACAAGTTCGACGAGGGCCTGGCCCTGGCCCACTTC
GTGTGGATCGCCCCCCTGCAGGTGGCCCTGCTGATGGGCCTGATCTGGGA
GCTGCTGCAGGCCAGCGCCTTCTGCGGCCTGGGCTTCCTGATCGTGCTGG
CCCTGTTCCAGGCCGGCCTGGGCAGGATGATGATGAAGTACAGGGACCAG
AGGGCCGGCAAGATCAGCGAGAGGCTGGTGATCACCAGCGAGATGATCGA
GAACATCCAGAGCGTGAAGGCCTACTGCTGGGAGGAGGCCATGGAGAAGA
TGATCGAGAACCTGAGGCAGACCGAGCTGAAGCTGACCAGGAAGGCCGCC
TACGTGAGGTACTTCAACAGCAGCGCCTTCTTCTTCAGCGGCTTCTTCGT
GGTGTTCCTGAGCGTGCTGCCCTACGCCCTGATCAAGGGCATCATCCTGA
GGAAGATCTTCACCACCATCAGCTTCTGCATCGTGCTGAGGATGGCCGTG
ACCAGGCAGTTCCCCTGGGCCGTGCAGACCTGGTACGACAGCCTGGGCGC
CATCAACAAGATCCAGGACTTCCTGCAGAAGCAGGAGTACAAGACCCTGG
AGTACAACCTGACCACCACCGAGGTGGTGATGGAGAACGTGACCGCCTTC
TGGGAGGAGGGCTTCGGCGAGCTGTTCGAGAAGGCCAAGCAGAACAACAA
CAACAGGAAGACCAGCAACGGCGACGACAGCCTGTTCTTCAGCAACTTCA
GCCTGCTGGGCACCCCCGTGCTGAAGGACATCAACTTCAAGATCGAGAGG

-continued

GGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGC

ACAGCGGCAGGATCAGCTTCTGCAGCCAGTTCAGCTGGATCATGCCCGGC

ACCATCAAGGAGAACATCATCTTCGGCGTGAGCTACGACGAGTACAGGTA

CAGGAGCGTGATCAAGGCCTGCCAGCTGGAGGAGGACATCAGCAAGTTCG

CCGAGAAGGACAACATCGTGCTGGGCGAGGGCGGCATCACCCTGAGCGGC

GGCCAGAGGGCCAGGATCAGCCTGGCCAGGGCCGTGTACAAGGACGCCGA

CCTGTACCTGCTGGACAGCCCCTTCGGCTACCTGGACGTGCTGACCGAGA

AGGAGATCTTCGAGAGCTGCGTGTGCAAGCTGATGGCCAACAAGACCAGG

ATCCTGGTGACCAGCAAGATGGAGCACCTGAAGAAGGCCGACAAGATCCT

GATCCTGCACGAGGGCAGCAGCTACTTCTACGGCACCTTCAGCGAGCTGC

AGAACCTGCAGCCCGACTTCAGCAGCAAGCTGATGGGCTGCGACAGCTTC

GACCAGTTCAGCGCCGAGAGGAGGAACAGCATCCTGACCGAGACCCTGCA

CAGGTTCAGCCTGGAGGGCGACGCCCCCGTGAGCTGGACCGAGACCAAGA

AGCAGAGCTTCAAGCAGACCGGCGAGTTCGGCGAGAAGAGGAAGAACAGC

ATCCTGAACCCCATCAACAGCATCAGGAAGTTCAGCATCGTGCAGAAGAC

CCCCCTGCAGATGAACGGCATCGAGGAGGACAGCGACGAGCCCCTGGAGA

GGAGGCTGAGCCTGGTGCCCGACAGCGAGCAGGGCGAGGCCATCCTGCCC

AGGATCAGCGTGATCAGCACCGGCCCCACCCTGCAGGCCAGGAGGAGGCA

GAGCGTGCTGAACCTGATGACCCACAGCGTGAACCAGGGCCAGAACATCC

ACAGGAAGACCACCGCCAGCACCAGGAAGGTGAGCCTGGCCCCCCAGGCC

AACCTGACCGAGCTGGACATCTACAGCAGGAGGCTGAGCCAGGAGACCGG

CCTGGAGATCAGCGAGGAGATCAACGAGGAGGACCTGAAGGAGTGCTTCT

TCGACGACATGGAGAGCATCCCCGCCGTGACCACCTGGAACACCTACCTG

AGGTACATCACCGTGCACAAGAGCCTGATCTTCGTGCTGATCTGGTGCCT

GGTGATCTTCCTGGCCGAGGTGGCCGCCAGCCTGGTGGTGCTGTGGCTGC

TGGGCAACACCCCCCTGCAGGACAAGGGCAACAGCACCCACAGCAGGAAC

AACAGCTACGCCGTGATCATCACCAGCACCAGCAGCTACTACGTGTTCTA

CATCTACGTGGGCGTGGCCGACACCCTGCTGGCCATGGGCTTCTTCAGGG

GCCTGCCCCTGGTGCACACCCTGATCACCGTGAGCAAGATCCTGCACCAC

AAGATGCTGCACAGCGTGCTGCAGGCCCCCATGAGCACCCTGAACACCCT

GAAGGCCGGCGGCATCCTGAACAGGTTCAGCAAGGACATCGCCATCCTGG

ACGACCTGCTGCCCCTGACCATCTTCGACTTCATCCAGCTGCTGCTGATC

GTGATCGGCGCCATCGCCGTGGTGGCCGTGCTGCAGCCCTACATCTTCGT

GGCCACCGTGCCCGTGATCGTGGCCTTCATCATGCTGAGGGCCTACTTCC

TGCAGACCAGCCAGCAGCTGAAGCAGCTGGAGAGCGAGGGCAGGAGCCCC

ATCTTCACCCACCTGGTGACCAGCCTGAAGGGCCTGTGGACCCTGAGGGC

CTTCGGCAGGCAGCCCTACTTCGAGACCCTGTTCCACAAGGCCCTGAACC

TGCACACCGCCAACTGGTTCCTGTACCTGAGCACCCTGAGGTGGTTCCAG

ATGAGGATCGAGATGATCTTCGTGATCTTCTTCATCGCCGTGACCTTCAT

CAGCATCCTGACCACCGGCGAGGGCGAGGGCAGGGTGGGCATCATCCTGA

-continued

CCCTGGCCATGAACATCATGAGCACCCTGCAGTGGGCCGTGAACAGCAGC

ATCGACGTGGACAGCCTGATGAGGAGCGTGAGCAGGGTGTTCAAGTTCAT

CGACATGCCCACCGAGGGCAAGCCCACCAAGAGCACCAAGCCCTACAAGA

ACGGCCAGCTGAGCAAGGTGATGATCATCGAGAACAGCCACGTGAAGAAG

GACGACATCTGGCCCAGCGGCGGCCAGATGACCGTGAAGGACCTGACCGC

CAAGTACACCGAGGGCGGCAACGCCATCCTGGAGAACATCAGCTTCAGCA

TCAGCCCCGGCCAGAGGGTGGGCCTGCTGGGCAGGACCGGCAGCGGCAAG

AGCACCCTGCTGAGCGCCTTCCTGAGGCTGCTGAACACCGAGGGCGAGAT

CCAGATCGACGGCGTGAGCTGGGACAGCATCACCCTGCAGCAGTGGAGGA

AGGCCTTCGGCGTGATCCCCCAGAAGGTGTTCATCTTCAGCGGCACCTTC

AGGAAGAACCTGGACCCCTACGAGCAGTGGAGCGACCAGGAGATCTGGAA

GGTGGCCGACGAGGTGGGCCTGAGGAGCGTGATCGAGCAGTTCCCCGGCA

AGCTGGACTTCGTGCTGGTGGACGGCGGCTGCGTGCTGAGCCACGGCCAC

AAGCAGCTGATGTGCCTGGCCAGGAGCGTGCTGAGCAAGGCCAAGATCCT

GCTGCTGGACGAGCCCAGCGCCCACCTGGACCCCGTGACCTACCAGATCA

TCAGGAGGACCCTGAAGCAGGCCTTCGCCGACTGCACCGTGATCCTGTGC

GAGCACAGGATCGAGGCCATGCTGGAGTGCCAGCAGTTCCTGGTGATCGA

GGAGAACAAGGTGAGGCAGTACGACAGCATCCAGAAGCTGCTGAACGAGA

GGAGCCTGTTCAGGCAGGCCATCAGCCCCAGCGACAGGGTGAAGCTGTTC

CCCCACAGGAACAGCAGCAAGTGCAAGAGCAAGCCCCAGATCGCCGCCCT

GAAGGAGGAGACCGAGGAGGAGGTGCAGGACACCAGGCTGTGA (SEQ ID NO: 33)

ATGCAGAGATCCCCTCTGGAGAAGGCCTCAGTGGTGTCCAAGCTTTTCTT

CTCCTGGACCAGGCCCATTTTAAGAAAGGGCTACAGGCAGAGACTTGAGC

TGTCTGACATCTATCAGATCCCTTCTGTGGATTCTGCTGACAATCTTAGT

GAAAAATTGGAAAGGGAGTGGGACAGAGAGCTGGCAAGTAAAAAGAACCC

CAAGCTGATTAATGCCCTGAGGCGCTGCTTTTTTTGGAGATTCATGTTCT

ATGGCATATTCCTCTACCTTGGAGAAGTAACCAAAGCTGTACAGCCTCTC

CTCCTTGGCAGAATCATTGCCTCCTATGATCCTGATAACAAGGAGGAGAG

AAGCATAGCCATCTACCTGGGCATTGGGCTGTGCCTCTTGTTTATTGTGA

GGACCCTTCTCTTGCACCCTGCCATCTTTGGCCTTCATCACATTGGCATG

CAAATGAGAATAGCAATGTTTAGTCTTATTTACAAAAAAACATTAAAACT

CTCTTCCAGGGTGTTGGACAAGATCAGTATTGGACAACTGGTCAGCCTGC

TGAGCAACAACCTGAACAAGTTTGATGAAGGACTGGCCCTGGCCCACTTT

GTCTGGATTGCCCCCCTTCAGGTGGCTCTTTTGATGGGCCTGATCTGGGA

ACTCCTGCAGGCCTCTGCCTTCTGTGGGTTAGGCTTCCTGATAGTGCTAG

CTCTCTTTCAGGCAGGGTTGGGTAGAATGATGATGAAGTACAGAGACCAG

AGGGCTGGGAAGATATCTGAGAGGCTGGTCATTACTTCTGAAATGATAGA

AAACATCCAGTCTGTTAAAGCTTACTGCTGGGAGGAGGCTATGGAAAAGA

TGATTGAGAACTTGAGGCAAACAGAGCTCAAGCTGACTAGGAAGGCAGCC

TATGTCAGGTATTTCAACAGCAGTGCTTTCTTCTTCTCAGGCTTTTTCGT

-continued

GGTCTTCTTGAGTGTTCTGCCCTATGCCCTCATCAAGGGGATAATTTTGA

GAAAGATTTTCACCACTATTTCCTTTTGCATTGTCCTGAGGATGGCTGTC

ACCAGGCAATTCCCCTGGGCTGTGCAGACATGGTATGACTCTCTGGGGGC

CATCAACAAAATCCAAGATTTCCTGCAGAAGCAGGAGTACAAGACCCTGG

AATACAACCTCACCACCACAGAAGTTGTGATGGAGAATGTGACTGCATTC

TGGGAGGAAGGATTTGGGGAGCTGTTTGAGAAAGCAAAACAAAACAATAA

TAACAGGAAAACCAGCAATGGAGATGACTCCCTGTTCTTTTCCAACTTCT

CTTTGTTGGGCACCCCTGTCCTGAAAGATATAAACTTTAAAATTGAAAGA

GGGCAGCTGTTGGCAGTTGCTGGCTCCACAGGAGCTGGAAAAACTTCACT

ACTGATGGTGATCATGGGGGAGTTAGAACCCTCTGAAGGGAAAATAAAAC

ATTCTGGGAGGATTAGTTTCTGCAGCCAGTTCAGCTGGATCATGCCTGGG

ACCATTAAAGAAAATATTATATTTGGAGTGAGCTATGATGAATATAGATA

TAGGAGTGTCATCAAAGCCTGTCAGTTGGAGGAAGACATCAGCAAATTTG

CAGAGAAAGACAACATTGTTCTGGGTGAAGGTGGCATCACCCTGTCAGGA

GGGCAAAGGGCCAGGATCAGCTTGGCCAGAGCAGTCTATAAAGATGCTGA

TCTGTACCTCCTGGATAGCCCTTTTGGCTATCTGGATGTTTTGACAGAGA

AGGAAATTTTTGAGTCCTGTGTCTGCAAGTTAATGGCAAATAAAACAAGG

ATACTTGTGACCTCAAAAATGGAACACCTGAAGAAGGCTGACAAAATTCT

GATCCTGCATGAGGGCAGCAGCTACTTTTATGGAACATTTTCTGAACTGC

AGAATTTGCAACCAGACTTTTCATCAAAGCTCATGGGATGTGACAGTTTT

GATCAGTTTTCTGCAGAAAGGAGAAACTCCATTTTGACTGAGACCCTGCA

CAGGTTCAGTCTGGAGGGGGATGCCCCAGTGAGTTGGACTGAGACAAAGA

AACAGAGCTTCAAGCAGACTGGAGAGTTTGGAGAAAAGAGGAAAAACTCA

ATTCTCAATCCCATCAATAGCATCAGGAAGTTCAGCATAGTTCAGAAGAC

TCCTTTGCAGATGAATGGGATTGAAGAGGACTCAGATGAGCCCCTGGAAA

GGAGACTCTCCTTGGTGCCAGATTCAGAGCAGGGGGAAGCCATACTGCCA

AGGATCTCTGTGATTTCTACAGGGCCCACCCTCCAAGCAAGAAGGAGACA

GTCAGTTTTAAACCTGATGACCCACTCTGTCAACCAGGGACAGAACATTC

ATAGAAAGACAACAGCATCTACAAGAAAAGTTTCACTGGCCCCTCAAGCC

AATTTAACTGAACTAGATATCTACAGCAGGAGGCTCAGCCAAGAAACAGG

CCTGGAGATCTCAGAAGAAATAAATGAGGAGGATTTGAAGGAATGCTTCT

TTGATGATATGGAGAGCATCCCAGCTGTCACAACCTGGAACACCTACCTG

AGATACATCACAGTGCACAAATCCCTCATCTTTGTACTTATATGGTGCCT

TGTCATCTTCTTAGCTGAGGTGGCTGCTTCCCTGGTGGTGCTGTGGCTGC

TGGGAAACACACCCCTCCAGGATAAAGGGAACTCTACTCACAGCAGGAAC

AACAGTTATGCTGTGATCATCACCAGTACCTCCTCCTACTATGTGTTCTA

CATTTATGTTGGAGTTGCAGACACATTGCTTGCCATGGGTTTTTTAGAG

GACTCCCCCTGGTGCATACTCTCATCACTGTTTCCAAAATCCTTCACCAC

AAGATGCTGCACAGTGTACTACAGGCTCCCATGAGCACCCTCAACACTCT

TAAAGCAGGAGGAATCTTGAACAGATTTAGCAAGGACATTGCAATTCTTG

-continued

ATGACCTGCTTCCACTGACCATCTTTGACTTCATCCAGCTTCTGCTCATT

GTAATTGGTGCCATTGCTGTGGTAGCAGTGCTCCAGCCATATATTTTTGT

GGCCACTGTGCCTGTTATTGTGGCCTTCATTATGTTGAGAGCCTACTTCC

TGCAGACCTCTCAGCAGCTCAAGCAACTTGAAAGTGAGGGCAGGAGCCCC

ATATTTACACACTTGGTCACTTCCCTCAAAGGCCTCTGGACACTCAGAGC

TTTTGGAAGACAACCTTATTTTGAAACTCTCTTCCACAAGGCTCTGAATC

TCCACACAGCCAACTGGTTTCTGTATCTTTCAACACTGCGCTGGTTCCAG

ATGAGGATTGAGATGATCTTTGTTATCTTCTTCATAGCTGTTACCTTCAT

CTCTATTCTGACAACTGGTGAGGGGGAAGGGAGAGTAGGCATCATCCTCA

CACTAGCCATGAACATAATGTCTACCTTACAATGGGCCGTGAACAGCTCC

ATAGATGTGGACAGCCTCATGAGAAGTGTGTCAAGAGTTTTCAAATTCAT

TGACATGCCCACAGAAGGCAAACCAACCAAGAGCACAAAACCCTACAAGA

ATGGCCAGCTGAGTAAGGTCATGATCATTGAAAATTCTCATGTGAAGAAG

GATGATATTTGGCCCAGTGGGGGCCAGATGACAGTCAAGGACCTCACTGC

CAAATACACAGAGGGTGGAAATGCTATCCTAGAGAACATCTCCTTCTCCA

TCTCCCCAGGCCAAAGAGTTGGCTTGCTGGGCAGGACTGGCAGTGGCAAG

TCCACCTTGCTCTCAGCATTTCTCAGGCTTTTAAATACAGAGGGAGAGAT

TCAAATTGATGGGGTGTCTTGGGATAGTATAACACTTCAACAGTGGAGGA

AAGCCTTTGGTGTGATTCCTCAGAAAGTGTTTATCTTCTCTGGCACTTTC

AGAAAAAATCTGGACCCCTATGAACAGTGGAGTGACCAGGAAATCTGGAA

GGTGGCAGATGAAGTGGGCCTAAGATCAGTCATAGAGCAGTTTCCTGGAA

AGTTGGATTTTGTGCTTGTAGATGGAGGCTGTGTGCTGTCCCATGGCCAT

AAACAGCTAATGTGCCTGGCTAGGTCAGTGCTGAGCAAGGCCAAGATCCT

GCTGTTAGATGAGCCTTCAGCCCATCTGGACCCTGTGACATACCAGATTA

TCAGAAGAACTCTGAAGCAGGCCTTTGCTGACTGCACTGTCATCCTGTGT

GAGCACAGAATTGAGGCCATGCTGGAGTGCCAGCAGTTCCTTGTTATAGA

AGAGAATAAGGTTAGGCAGTATGACAGCATTCAGAAACTGCTAAATGAAA

GATCTCTCTTCAGGCAAGCTATTTCACCATCTGATAGAGTGAAACTTTTT

CCCCACAGAAATTCCTCTAAATGTAAATCTAAGCCCCAGATAGCTGCCTT

GAAAGAGGAGACTGAAGAAGAAGTCCAGGACACCAGACTGTGA (SEQ ID NO: 34)

ATGCAGAGATCCCCGCTGGAGAAGGCATCTGTGGTGTCAAAACTGTTCTT

TAGCTGGACAAGGCCCATCCTTAGGAAAGGGTACAGACAGAGGTTGGAGC

TGTCAGACATATATCAGATCCCTTCAGTGGACTCTGCAGACAACCTCTCT

GAAAAGCTGGAGAGGGAATGGGACAGGGAACTGGCCAGCAAAAAAAACCC

TAAACTGATTAATGCCCTGAGGAGGTGCTTCTTTTGGAGATTCATGTTCT

ATGGGATCTTCCTTTACCTGGGGGAGGTGACTAAAGCTGTTCAGCCTCTT

CTTCTGGGGAGGATTATTGCCTCCTATGACCCAGACAACAAAGAAGAAAG

AAGCATAGCCATTTACTTAGGCATAGGCCTCTGCTTGCTCTTCATAGTTA

GAACCCTCCTACTCCACCCAGCCATCTTTGGTCTCCACCACATAGGTATG

CAGATGAGAATAGCAATGTTCTCCTTGATCTACAAGAAGACCCTCAAGCT

GTCCAGCAGGGTGCTGGACAAGATCTCCATAGGCCAGTTAGTCAGTCTAC
TGTCCAATAACTTAAATAAGTTTGATGAGGGACTGGCACTGGCACATTTT
GTGTGGATTGCCCCCCTCCAAGTGGCCCTTCTTATGGGCCTTATCTGGGA
GCTGTTGCAGGCCTCTGCTTTCTGTGGCCTGGGTTTCCTCATAGTCCTAG
CCTTATTCCAGGCTGGACTGGGCAGAATGATGATGAAGTATAGGGACCAA
AGAGCAGGGAAGATTTCTGAAAGGCTGGTTATAACTTCTGAGATGATTGA
GAACATTCAGTCAGTGAAAGCTTACTGCTGGGAAGAAGCTATGGAAAAAA
TGATTGAAAATCTCAGACAGACTGAATTAAAGTTGACCAGGAAAGCTGCT
TATGTCAGATACTTCAACTCCTCAGCCTTCTTTTTTTCTGGCTTCTTTGT
TGTATTCCTTTCAGTCCTCCCCTATGCCCTGATTAAGGGCATTATCTTGA
GGAAAATTTTCACAACCATCTCCTTTTGTATTGTCCTCAGGATGGCTGTT
ACAAGGCAATTTCCTTGGGCTGTGCAAACTTGGTATGATAGCCTTGGAGC
AATCAACAAGATCCAGGATTTCCTGCAAAAGCAGGAGTACAAGACATTGG
AATACAACCTTACCACCACTGAGGTGGTGATGGAAAATGTGACTGCCTTC
TGGGAGGAGGGGTTTGGAGAGCTGTTTGAGAAAGCCAAACAGAACAACAA
CAATAGAAAGACCTCTAATGGTGATGATTCCCTGTTCTTTTCTAACTTTA
GTCTTCTGGGGACCCCAGTTCTGAAAGATATTAACTTTAAAATTGAAAGG
GGACAGTTGCTGGCTGTGGCTGGGTCCACTGGGGCTGGGAAGACAAGCCT
GCTCATGGTGATCATGGGAGAGCTGGAACCCAGTGAAGGAAAGATCAAAC
ACTCAGGCAGGATCTCCTTCTGCAGCCAGTTCTCATGGATTATGCCAGGC
ACTATTAAAGAAAATATCATCTTTGGTGTAAGCTATGATGAGTACAGGTA
TAGATCTGTAATTAAAGCCTGCCAGCTGGAGGAAGACATCTCTAAGTTTG
CTGAGAAGGATAACATTGTGTTGGGGGAAGGGGGCATCACCCTTTCTGGT
GGGCAGAGGGCTAGGATCTCCCTTGCTAGGGCAGTATACAAGGATGCTGA
CTTGTACCTCTTGGATAGTCCTTTTGGCTACCTAGATGTGCTGACAGAGA
AAGAAATATTTGAAAGCTGTGTGTGTAAGCTCATGGCTAACAAGACCAGG
ATCCTGGTCACCAGTAAAATGGAACACCTCAAAAAAGCAGACAAGATCCT
TATTCTCCATGAGGGCTCCTCCTACTTCTATGGGACCTTCAGTGAGCTGC
AGAATCTGCAGCCAGACTTCTCCTCAAAACTTATGGGCTGTGACTCCTTT
GACCAATTCTCTGCAGAAAGAAGGAATAGCATACTGACAGAAACACTGCA
TAGATTCTCCCTGGAAGGAGATGCCCCAGTGAGTTGGACAGAAACCAAAA
AGCAGAGCTTCAAGCAGACTGGTGAGTTTGGTGAAAAGAGGAAGAATTCT
ATCCTGAACCCCATCAATAGCATCAGGAAATTTAGCATAGTCCAAAAGAC
CCCCCTCCAGATGAATGGAATAGAGGAGGATAGTGATGAGCCTCTTGAGA
GAAGGCTGTCCCTGGTTCCAGACAGTGAACAGGGTGAAGCCATTCTTCCG
AGGATCAGTGTCATCTCCACTGGGCCCACATTGCAGGCCAGAAGAAGACA
GTCTGTTCTGAATTTGATGACACATTCTGTGAATCAAGGCCAGAATATCC
ATAGAAAAACCACTGCCAGCACCAGAAAAGTTTCTCTAGCCCCCCAGGCT
AACCTGACTGAGTTAGACATCTACAGCAGAAGGCTGAGCCAAGAGACTGG
CTTGGAAATATCTGAGGAGATCAATGAGGAGGACCTCAAGGAGTGCTTCT
TTGATGACATGGAGTCAATCCCTGCAGTCACTACATGGAACACTTACCTA

AGGTACATCACAGTTCATAAGAGCCTCATCTTTGTCCTCATATGGTGTCT
GGTCATCTTTTTAGCAGAAGTGGCTGCCAGCCTAGTTGTGCTGTGGTTAC
TGGGCAATACACCTCTTCAGGACAAAGGCAATAGCACACACAGCAGAAAC
AACTCCTATGCAGTGATCATCACCTCTACAAGCTCTTACTATGTATTCTA
TATATATGTGGGAGTGGCAGATACTCTCCTGGCCATGGGATTCTTCAGGG
GATTACCTCTAGTTCACACATTGATCACAGTGTCAAAAATTCTCCACCAC
AAGATGTTACACAGTGTCCTGCAAGCCCCAATGTCTACTCTGAACACACT
TAAGGCAGGTGGAATTTTGAATAGGTTTAGCAAGGACATAGCTATCCTGG
ATGATCTCCTCCCTCTGACCATCTTTGACTTCATCCAGTTACTGCTCATT
GTAATTGGAGCCATTGCAGTGGTAGCAGTCCTACAGCCTTACATTTTTGT
GGCTACTGTTCCTGTTATTGTGGCCTTCATTATGCTAAGAGCTTACTTCC
TGCAAACAAGCCAACAGTTGAAACAGCTAGAAAGTGAGGGAAGGTCCCCC
ATCTTCACCCACCTGGTGACATCACTCAAGGGGCTATGGACTCTTAGGGC
TTTTGGGAGACAGCCGTACTTTGAGACCTTATTCCATAAGGCCCTTAACC
TCCATACAGCAAACTGGTTCTTATACCTGAGTACTCTGAGGTGGTTTCAA
ATGAGGATTGAAATGATTTTTGTGATCTTCTTCATTGCTGTGACCTTCAT
CTCAATCTTGACCACAGGAGAGGGGGAGGGCAGGGTGGGCATCATACTGA
CCTTGGCCATGAACATTATGTCAACCCTGCAGTGGGCTGTCAATAGCTCC
ATTGATGTGGACAGTCTGATGAGGAGTGTCTCCAGGGTCTTCAAGTTTAT
TGACATGCCAACTGAGGGCAAACCCACCAAAAGCACTAAGCCATATAAAA
ATGGCCAACTGTCCAAAGTGATGATCATTGAAAATTCACATGTAAAGAAG
GATGATATCTGGCCCTCTGGAGGACAGATGACAGTGAAAGACCTGACTGC
CAAGTACACAGAGGGTGGTAATGCCATTCTTGAGAACATTAGTTTCAGTA
TTTCCCCGGGGCAAAGGGTGGGCCTCCTTGGCAGAACAGGCTCTGGCAAG
AGTACCCTGCTGTCAGCCTTTTTAAGACTGTTGAACACTGAGGGAGAAAT
TCAGATTGATGGTGTCTCCTGGGATAGCATCACCCTCCAGCAGTGGAGAA
AAGCTTTTGGAGTGATCCCGCAAAAGGTTTTCATCTTTTCAGGCACCTTC
CGGAAGAACCTGGACCCCTATGAGCAGTGGTCTGACCAGGAAATATGGAA
GGTAGCTGATGAAGTTGGGCTTAGGTCAGTCATAGAGCAGTTCCCAGGCA
AACTGGACTTTGTCCTGGTGGATGGTGGATGTGTACTGAGTCATGGGCAC
AAACAGCTGATGTGCCTAGCCAGGTCTGTGCTCAGCAAGGCAAAGATATT
GCTGCTTGATGAACCCAGTGCCCATCTGGACCCAGTCACATATCAGATCA
TCAGAAGAACATTGAAGCAGGCCTTTGCTGATTGCACAGTTATCCTCTGT
GAGCACAGGATTGAGGCCATGCTGGAGTGCCAGCAGTTTCTGGTGATTGA
GGAGAATAAAGTAAGGCAGTATGACTCCATCCAGAAGCTGCTCAATGAAA
GAAGCCTCTTTAGACAAGCTATCTCCCCCTCAGACAGGGTCAAATTGTTC
CCTCACAGAAACAGCAGCAAGTGCAAGAGCAAGCCCCAAATTGCAGCCTT
GAAAGAGGAGACAGAGGAAGAGGTGCAGGACACCAGACTCTGA (SEQ ID NO: 35)

ATGCAGAGAAGCCCCCTGGAGAAGGCCAGCGTGGTGAGCAAGCTGTTCTT
CAGCTGGACCAGACCCATCCTGAGAAAGGGCTACAGACAGAGACTGGAGC

-continued

TGAGCGACATCTACCAGATCCCCAGCGTGGACAGCGCCGACAACCTGAGC

GAGAAGCTGGAGAGAGAGTGGGACAGAGAGCTGGCCAGCAAGAAGAACCC

CAAGCTGATCAACGCCCTGAGAAGATGCTTCTTCTGGAGATTCATGTTCT

ACGGCATCTTCCTGTACCTGGGCGAGGTGACCAAGGCCGTGCAGCCCCTG

CTGCTGGGCAGAATCATCGCCAGCTACGACCCCGACAACAAGGAGGAGAG

AAGCATCGCCATCTACCTGGGCATCGGCCTGTGCCTGCTGTTCATCGTGA

GAACCCTGCTGCTGCACCCCGCCATCTTCGGCCTGCACCACATCGGCATG

CAGATGAGAATCGCCATGTTCAGCCTGATCTACAAGAAGACCCTGAAGCT

GAGCAGCAGAGTGCTGGACAAGATCAGCATCGGCCAGCTGGTGAGCCTGC

TGAGCAACAACCTGAACAAGTTCGACGAGGGCCTGGCCCTGGCCCACTTC

GTGTGGATCGCCCCCCTGCAGGTGGCCCTGCTGATGGGCCTGATCTGGGA

GCTGCTGCAGGCCAGCGCCTTCTGCGGCCTGGGCTTCCTGATCGTGCTGG

CCCTGTTCCAGGCCGGCCTGGGCAGAATGATGATGAAGTACAGAGACCAG

AGAGCCGGCAAGATCAGCGAGAGACTGGTGATCACCAGCGAGATGATCGA

GAACATCCAGAGCGTGAAGGCCTACTGCTGGGAGGAGGCCATGGAGAAGA

TGATCGAGAACCTGAGACAGACCGAGCTGAAGCTGACCAGAAAGGCCGCC

TACGTGAGATACTTCAACAGCAGCGCCTTCTTCTTCAGCGGCTTCTTCGT

GGTGTTCCTGAGCGTGCTGCCCTACGCCCTGATCAAGGGCATCATCCTGA

GAAAGATCTTCACCACCATCAGCTTCTGCATCGTGCTGAGAATGGCCGTG

ACCAGACAGTTCCCCTGGGCCGTGCAGACCTGGTACGACAGCCTGGGCGC

CATCAACAAGATCCAGGACTTCCTGCAGAAGCAGGAGTACAAGACCCTGG

AGTACAACCTGACCACCACCGAGGTGGTGATGGAGAACGTGACCGCCTTC

TGGGAGGAGGGCTTCGGCGAGCTGTTCGAGAAGGCCAAGCAGAACAACAA

CAACAGAAAGACCAGCAACGGCGACGACAGCCTGTTCTTCAGCAACTTCA

GCCTGCTGGGCACCCCCGTGCTGAAGGACATCAACTTCAAGATCGAGAGA

GGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGC

ACAGCGGCAGAATCAGCTTCTGCAGCCAGTTCAGCTGGATCATGCCCGGC

ACCATCAAGGAGAACATCATCTTCGGCGTGAGCTACGACGAGTACAGATA

CAGAAGCGTGATCAAGGCCTGCCAGCTGGAGGAGGACATCAGCAAGTTCG

CCGAGAAGGACAACATCGTGCTGGGCGAGGGCGGCATCACCCTGAGCGGC

GGCCAGAGAGCCAGAATCAGCCTGGCCAGAGCCGTGTACAAGGACGCCGA

CCTGTACCTGCTGGACAGCCCCTTCGGCTACCTGGACGTGCTGACCGAGA

AGGAGATCTTCGAGAGCTGCGTGTGCAAGCTGATGGCCAACAAGACCAGA

ATCCTGGTGACCAGCAAGATGGAGCACCTGAAGAAGGCCGACAAGATCCT

GATCCTGCACGAGGGCAGCAGCTACTTCTACGGCACCTTCAGCGAGCTGC

AGAACCTGCAGCCCGACTTCAGCAGCAAGCTGATGGGCTGCGACAGCTTC

GACCAGTTCAGCGCCGAGAGAAGAAACAGCATCCTGACCGAGACCCTGCA

CAGATTCAGCCTGGAGGGCGACGCCCCCGTGAGCTGGACCGAGACCAAGA

AGCAGAGCTTCAAGCAGACCGGCGAGTTCGGCGAGAAGAGAAAGAACAGC

-continued

ATCCTGAACCCCATCAACAGCATCAGAAAGTTCAGCATCGTGCAGAAGAC

CCCCCTGCAGATGAACGGCATCGAGGAGGACAGCGACGAGCCCCTGGAGA

GAAGACTGAGCCTGGTGCCCGACAGCGAGCAGGGCGAGGCCATCCTGCCC

AGAATCAGCGTGATCAGCACCGGCCCCACCCTGCAGGCCAGAAGAAGACA

GAGCGTGCTGAACCTGATGACCCACAGCGTGAACCAGGGCCAGAACATCC

ACAGAAAGACCACCGCCAGCACCAGAAAGGTGAGCCTGGCCCCCCAGGCC

AACCTGACCGAGCTGGACATCTACAGCAGAAGACTGAGCCAGGAGACCGG

CCTGGAGATCAGCGAGGAGATCAACGAGGAGGACCTGAAGGAGTGCTTCT

TCGACGACATGGAGAGCATCCCCGCCGTGACCACCTGGAACACCTACCTG

AGATACATCACCGTGCACAAGAGCCTGATCTTCGTGCTGATCTGGTGCCT

GGTGATCTTCCTGGCCGAGGTGGCCGCCAGCCTGGTGGTGCTGTGGCTGC

TGGGCAACACCCCCCTGCAGGACAAGGGCAACAGCACCCACAGCAGAAAC

AACAGCTACGCCGTGATCATCACCAGCACCAGCAGCTACTACGTGTTCTA

CATCTACGTGGGCGTGGCCGACACCCTGCTGGCCATGGGCTTCTTCAGAG

GCCTGCCCCTGGTGCACACCCTGATCACCGTGAGCAAGATCCTGCACCAC

AAGATGCTGCACAGCGTGCTGCAGGCCCCCATGAGCACCCTGAACACCCT

GAAGGCCGGCGGCATCCTGAACAGATTCAGCAAGGACATCGCCATCCTGG

ACGACCTGCTGCCCCTGACCATCTTCGACTTCATCCAGCTGCTGCTGATC

GTGATCGGCGCCATCGCCGTGGTGGCCGTGCTGCAGCCCTACATCTTCGT

GGCCACCGTGCCCGTGATCGTGGCCTTCATCATGCTGAGAGCCTACTTCC

TGCAGACCAGCCAGCAGCTGAAGCAGCTGGAGAGCGAGGGCAGAAGCCCC

ATCTTCACCCACCTGGTGACCAGCCTGAAGGGCCTGTGGACCCTGAGAGC

CTTCGGCAGACAGCCCTACTTCGAGACCCTGTTCCACAAGGCCCTGAACC

TGCACACCGCCAACTGGTTCCTGTACCTGAGCACCCTGAGATGGTTCCAG

ATGAGAATCGAGATGATCTTCGTGATCTTCTTCATCGCCGTGACCTTCAT

CAGCATCCTGACCACCGGCGAGGGCGAGGGCAGAGTGGGCATCATCCTGA

CCCTGGCCATGAACATCATGAGCACCCTGCAGTGGGCCGTGAACAGCAGC

ATCGACGTGGACAGCCTGATGAGAAGCGTGAGCAGAGTGTTCAAGTTCAT

CGACATGCCCACCGAGGGCAAGCCCACCAAGAGCACCAAGCCCTACAAGA

ACGGCCAGCTGAGCAAGGTGATGATCATCGAGAACAGCCACGTGAAGAAG

GACGACATCTGGCCCAGCGGCGGCCAGATGACCGTGAAGGACCTGACCGC

CAAGTACACCGAGGGCGGCAACGCCATCCTGGAGAACATCAGCTTCAGCA

TCAGCCCCGGCCAGAGAGTGGGCCTGCTGGGCAGAACCGGCAGCGGCAAG

AGCACCCTGCTGAGCGCCTTCCTGAGACTGCTGAACACCGAGGGCGAGAT

CCAGATCGACGGCGTGAGCTGGGACAGCATCACCCTGCAGCAGTGGAGAA

AGGCCTTCGGCGTGATCCCCCAGAAGGTGTTCATCTTCAGCGGCACCTTC

AGAAAGAACCTGGACCCCTACGAGCAGTGGAGCGACCAGGAGATCTGGAA

GGTGGCCGACGAGGTGGGCCTGAGAAGCGTGATCGAGCAGTTCCCCGGCA

AGCTGGACTTCGTGCTGGTGGACGGCGGCTGCGTGCTGAGCCACGGCCAC

AAGCAGCTGATGTGCCTGGCCAGAAGCGTGCTGAGCAAGGCCAAGATCCT

GCTGCTGGACGAGCCCAGCGCCCACCTGGACCCCGTGACCTACCAGATCA

-continued

TCAGAAGAACCCTGAAGCAGGCCTTCGCCGACTGCACCGTGATCCTGTGC
GAGCACAGAATCGAGGCCATGCTGGAGTGCCAGCAGTTCCTGGTGATCGA
GGAGAACAAGGTGAGACAGTACGACAGCATCCAGAAGCTGCTGAACGAGA
GAAGCCTGTTCAGACAGGCCATCAGCCCCAGCGACAGAGTGAAGCTGTTC
CCCCACAGAAACAGCAGCAAGTGCAAGAGCAAGCCCCAGATCGCCGCCCT
GAAGGAGGAGACCGAGGAGGAGGTGCAGGACACCAGACTGTGA (SEQ ID NO: 36)
ATGCAGCGCAGCCCCCTGGAGAAGGCCAGCGTGGTGAGCAAGCTGTTCTT
CAGCTGGACCCGCCCCATCCTGCGCAAGGGCTACCGCCAGCGCCTGGAGC
TGAGCGACATCTACCAGATCCCCAGCGTGGACAGCGCCGACAACCTGAGC
GAGAAGCTGGAGCGCGAGTGGGACCGCGAGCTGGCCAGCAAGAAGAACCC
CAAGCTGATCAACGCCCTGCGCCGCTGCTTCTTCTGGCGCTTCATGTTCT
ACGGCATCTTCCTGTACCTGGGCGAGGTGACCAAGGCCGTGCAGCCCCTG
CTGCTGGGCCGCATCATCGCCAGCTACGACCCCGACAACAAGGAGGAGCG
CAGCATCGCCATCTACCTGGGCATCGGCCTGTGCCTGCTGTTCATCGTGC
GCACCCTGCTGCTGCACCCCGCCATCTTCGGCCTGCACCACATCGGCATG
CAGATGCGCATCGCCATGTTCAGCCTGATCTACAAGAAGACCCTGAAGCT
GAGCAGCCGCGTGCTGGACAAGATCAGCATCGGCCAGCTGGTGAGCCTGC
TGAGCAACAACCTGAACAAGTTCGACGAGGGCCTGGCCCTGGCCCACTTC
GTGTGGATCGCCCCCCTGCAGGTGGCCCTGCTGATGGGCCTGATCTGGGA
GCTGCTGCAGGCCAGCGCCTTCTGCGGCCTGGGCTTCCTGATCGTGCTGG
CCCTGTTCCAGGCCGGCCTGGGCCGCATGATGATGAAGTACCGCGACCAG
CGCGCCGGCAAGATCAGCGAGCGCCTGGTGATCACCAGCGAGATGATCGA
GAACATCCAGAGCGTGAAGGCCTACTGCTGGGAGGAGGCCATGGAGAAGA
TGATCGAGAACCTGCGCCAGACCGAGCTGAAGCTGACCCGCAAGGCCGCC
TACGTGCGCTACTTCAACAGCAGCGCCTTCTTCTTCAGCGGCTTCTTCGT
GGTGTTCCTGAGCGTGCTGCCCTACGCCCTGATCAAGGGCATCATCCTGC
GCAAGATCTTCACCACCATCAGCTTCTGCATCGTGCTGCGCATGGCCGTG
ACCCGCCAGTTCCCCTGGGCCGTGCAGACCTGGTACGACAGCCTGGGCGC
CATCAACAAGATCCAGGACTTCCTGCAGAAGCAGGAGTACAAGACCCTGG
AGTACAACCTGACCACCACCGAGGTGGTGATGGAGAACGTGACCGCCTTC
TGGGAGGAGGGCTTCGGCGAGCTGTTCGAGAAGGCCAAGCAGAACAACAA
CAACCGCAAGACCAGCAACGGCGACGACAGCCTGTTCTTCAGCAACTTCA
GCCTGCTGGGCACCCCCGTGCTGAAGGACATCAACTTCAAGATCGAGCGC
GGCCAGCTGCTGGCCGTGGCCGGCAGCACCGGCGCCGGCAAGACCAGCCT
GCTGATGGTGATCATGGGCGAGCTGGAGCCCAGCGAGGGCAAGATCAAGC
ACAGCGGCCGCATCAGCTTCTGCAGCCAGTTCAGCTGGATCATGCCCGGC
ACCATCAAGGAGAACATCATCTTCGGCGTGAGCTACGACGAGTACCGCTA
CCGCAGCGTGATCAAGGCCTGCCAGCTGGAGGAGGACATCAGCAAGTTCG
CCGAGAAGGACAACATCGTGCTGGGCGAGGGCGGCATCACCCTGAGCGGC
GGCCAGCGCGCCCGCATCAGCCTGGCCCGCGCCGTGTACAAGGACGCCGA

-continued

CCTGTACCTGCTGGACAGCCCCTTCGGCTACCTGGACGTGCTGACCGAGA
AGGAGATCTTCGAGAGCTGCGTGTGCAAGCTGATGGCCAACAAGACCCGC
ATCCTGGTGACCAGCAAGATGGAGCACCTGAAGAAGGCCGACAAGATCCT
GATCCTGCACGAGGGCAGCAGCTACTTCTACGGCACCTTCAGCGAGCTGC
AGAACCTGCAGCCCGACTTCAGCAGCAAGCTGATGGGCTGCGACAGCTTC
GACCAGTTCAGCGCCGAGCGCCGCAACAGCATCCTGACCGAGACCCTGCA
CCGCTTCAGCCTGGAGGGCGACGCCCCCGTGAGCTGGACCGAGACCAAGA
AGCAGAGCTTCAAGCAGACCGGCGAGTTCGGCGAGAAGCGCAAGAACAGC
ATCCTGAACCCCATCAACAGCATCCGCAAGTTCAGCATCGTGCAGAAGAC
CCCCCTGCAGATGAACGGCATCGAGGAGGACAGCGACGAGCCCCTGGAGC
GCCGCCTGAGCCTGGTGCCCGACAGCGAGCAGGGCGAGGCCATCCTGCCC
CGCATCAGCGTGATCAGCACCGGCCCCACCCTGCAGGCCCGCCGCCGCCA
GAGCGTGCTGAACCTGATGACCCACAGCGTGAACCAGGGCCAGAACATCC
ACCGCAAGACCACCGCCAGCACCCGCAAGGTGAGCCTGGCCCCCCAGGCC
AACCTGACCGAGCTGGACATCTACAGCCGCCGCCTGAGCCAGGAGACCGG
CCTGGAGATCAGCGAGGAGATCAACGAGGAGGACCTGAAGGAGTGCTTCT
TCGACGACATGGAGAGCATCCCCGCCGTGACCACCTGGAACACCTACCTG
CGCTACATCACCGTGCACAAGAGCCTGATCTTCGTGCTGATCTGGTGCCT
GGTGATCTTCCTGGCCGAGGTGGCCGCCAGCCTGGTGGTGCTGTGGCTGC
TGGGCAACACCCCCCTGCAGGACAAGGGCAACAGCACCCACAGCCGCAAC
AACAGCTACGCCGTGATCATCACCAGCACCAGCAGCTACTACGTGTTCTA
CATCTACGTGGGCGTGGCCGACACCCTGCTGGCCATGGGCTTCTTCCGCG
GCCTGCCCCTGGTGCACACCCTGATCACCGTGAGCAAGATCCTGCACCAC
AAGATGCTGCACAGCGTGCTGCAGGCCCCCATGAGCACCCTGAACACCCT
GAAGGCCGGCGGCATCCTGAACCGCTTCAGCAAGGACATCGCCATCCTGG
ACGACCTGCTGCCCCTGACCATCTTCGACTTCATCCAGCTGCTGCTGATC
GTGATCGGCGCCATCGCCGTGGTGGCCGTGCTGCAGCCCTACATCTTCGT
GGCCACCGTGCCCGTGATCGTGGCCTTCATCATGCTGCGCGCCTACTTCC
TGCAGACCAGCCAGCAGCTGAAGCAGCTGGAGAGCGAGGGCCGCAGCCCC
ATCTTCACCCACCTGGTGACCAGCCTGAAGGGCCTGTGGACCCTGCGCGC
CTTCGGCCGCCAGCCCTACTTCGAGACCCTGTTCCACAAGGCCCTGAACC
TGCACACCGCCAACTGGTTCCTGTACCTGAGCACCCTGCGCTGGTTCCAG
ATGCGCATCGAGATGATCTTCGTGATCTTCTTCATCGCCGTGACCTTCAT
CAGCATCCTGACCACCGGCGAGGGCGAGGGCCGCGTGGGCATCATCCTGA
CCCTGGCCATGAACATCATGAGCACCCTGCAGTGGGCCGTGAACAGCAGC
ATCGACGTGGACAGCCTGATGCGCAGCGTGAGCCGCGTGTTCAAGTTCAT
CGACATGCCCACCGAGGGCAAGCCCACCAAGAGCACCAAGCCCTACAAGA
ACGGCCAGCTGAGCAAGGTGATGATCATCGAGAACAGCCACGTGAAGAAG
GACGACATCTGGCCCAGCGGCGGCCAGATGACCGTGAAGGACCTGACCGC
CAAGTACACCGAGGGCGGCAACGCCATCCTGGAGAACATCAGCTTCAGCA

-continued

TCAGCCCCGGCCAGCGCGTGGGCCTGCTGGGCCGCACCGGCAGCGGCAAG

AGCACCCTGCTGAGCGCCTTCCTGCGCCTGCTGAACACCGAGGGCGAGAT

CCAGATCGACGGCGTGAGCTGGGACAGCATCACCCTGCAGCAGTGGCGCA

AGGCCTTCGGCGTGATCCCCCAGAAGGTGTTCATCTTCAGCGGCACCTTC

CGCAAGAACCTGGACCCCTACGAGCAGTGGAGCGACCAGGAGATCTGGAA

GGTGGCCGACGAGGTGGGCCTGCGCAGCGTGATCGAGCAGTTCCCCGGCA

AGCTGGACTTCGTGCTGGTGGACGGCGGCTGCGTGCTGAGCCACGGCCAC

AAGCAGCTGATGTGCCTGGCCCGCAGCGTGCTGAGCAAGGCCAAGATCCT

GCTGCTGGACGAGCCCAGCGCCCACCTGGACCCCGTGACCTACCAGATCA

TCCGCCGCACCCTGAAGCAGGCCTTCGCCGACTGCACCGTGATCCTGTGC

GAGCACCGCATCGAGGCCATGCTGGAGTGCCAGCAGTTCCTGGTGATCGA

GGAGAACAAGGTGCGCCAGTACGACAGCATCCAGAAGCTGCTGAACGAGC

GCAGCCTGTTCCGCCAGGCCATCAGCCCCAGCGACCGCGTGAAGCTGTTC

CCCCACCGCAACAGCAGCAAGTGCAAGAGCAAGCCCCAGATCGCCGCCCT

GAAGGAGGAGACCGAGGAGGAGGTGCAGGACACCCGCCTGTAA (SEQ ID NO: 37)

ATGCAGAGAAGCCCCCTGGAGAAGGCCAGCGTGGTGAGCAAGCTGTTCTT

CAGCTGGACCAGACCCATCCTGAGAAAGGGCTACAGACAGAGACTGGAGC

TGAGCGACATCTACCAGATCCCCAGCGTGGACAGCGCCGACAACCTGAGC

GAGAAGCTGGAGAGAGAGTGGGACAGAGAGCTGGCCAGCAAGAAGAACCC

CAAGCTGATCAACGCCCTGAGAAGATGCTTCTTCTGGAGATTCATGTTCT

ACGGCATCTTCCTGTACCTGGGCGAGGTGACCAAGGCCGTGCAGCCCCTG

CTGCTGGGCAGAATCATCGCCAGCTACGACCCCGACAACAAGGAGGAGAG

AAGCATCGCCATCTACCTGGGCATCGGCCTGTGCCTGCTGTTCATCGTGA

GAACCCTGCTGCTGCACCCCGCCATCTTCGGCCTGCACCACATCGGCATG

CAGATGAGAATCGCCATGTTCAGCCTGATCTACAAGAAGACCCTGAAGCT

GAGCAGCAGAGTGCTGGACAAGATCAGCATCGGCCAGCTGGTGAGCCTGC

TGAGCAACAACCTGAACAAGTTCGACGAGGGCCTGGCCCTGGCCCACTTC

GTGTGGATCGCCCCCCTGCAGGTGGCCCTGCTGATGGGCCTGATCTGGGA

GCTGCTGCAGGCCAGCGCCTTCTGCGGCCTGGGCTTCCTGATCGTGCTGG

CCCTGTTCCAGGCCGGCCTGGGCAGAATGATGATGAAGTACAGGGACCAG

AGAGCCGGCAAGATCAGCGAGAGACTGGTGATCACCAGCGAGATGATCGA

GAACATCCAGAGCGTGAAGGCCTACTGCTGGGAGGAGGCCATGGAGAAGA

TGATCGAGAACCTGAGACAGACCGAGCTGAAGCTGACCAGAAAGGCCGCC

TACGTGAGATACTTCAACAGCAGCGCCTTCTTCTTCAGCGGCTTCTTCGT

GGTGTTCCTGAGCGTGCTGCCCTACGCCCTGATCAAGGGCATCATCCTGA

GAAAGATCTTCACCACCATCAGCTTCTGCATCGTGCTGAGAATGGCCGTG

ACCAGACAGTTCCCCTGGGCCGTGCAGACCTGGTACGACAGCCTGGGCGC

CATCAACAAGATCCAGGACTTCCTGCAGAAGCAGGAGTACAAGACCCTGG

AGTACAACCTGACCACCACCGAGGTGGTGATGGAGAACGTGACCGCCTTC

TGGGAGGAGGGCTTCGGCGAGCTGTTCGAGAAGGCCAAGCAGAACAACAA

-continued

CAACAGAAAGACCAGCAACGGCGACGACAGCCTGTTCTTCAGCAACTTCA

GCCTGCTGGGCACCCCCGTGCTGAAGGACATCAACTTCAAGATCGAGAGA

GGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGC

ACAGCGGCAGAATCAGCTTCTGCAGCCAGTTCAGCTGGATCATGCCCGGC

ACCATCAAGGAGAACATCATCTTCGGCGTGAGCTACGACGAGTACAGATA

CAGAAGCGTGATCAAGGCCTGCCAGCTGGAGGAGGACATCAGCAAGTTCG

CCGAGAAGGACAACATCGTGCTGGGCGAGGGCGGCATCACCCTGAGCGGC

GGCCAGAGAGCCAGAATCAGCCTGGCCAGAGCCGTGTACAAGGACGCCGA

CCTGTACCTGCTGGACAGCCCCTTCGGCTACCTGGACGTGCTGACCGAGA

AGGAGATCTTCGAGAGCTGCGTGTGCAAGCTGATGGCCAACAAGACCAGA

ATCCTGGTGACCAGCAAGATGGAGCACCTGAAGAAGGCCGACAAGATCCT

GATCCTGCACGAGGGCAGCAGCTACTTCTACGGCACCTTCAGCGAGCTGC

AGAACCTGCAGCCCGACTTCAGCAGCAAGCTGATGGGCTGCGACAGCTTC

GACCAGTTCAGCGCCGAGAGAAGAAACAGCATCCTGACCGAGACCCTGCA

CAGATTCAGCCTGGAGGGCGACGCCCCCGTGAGCTGGACCGAGACCAAGA

AGCAGAGCTTCAAGCAGACCGGCGAGTTCGGCGAGAAGAGAAAGAACAGC

ATCCTGAACCCCATCAACAGCATCAGAAAGTTCAGCATCGTGCAGAAGAC

CCCCCTGCAGATGAACGGCATCGAGGAGGACAGCGACGAGCCCCTGGAGA

GAAGACTGAGCCTGGTGCCCGACAGCGAGCAGGGCGAGGCCATCCTGCCC

AGAATCAGCGTGATCAGCACCGGCCCCACCCTGCAGGCCAGAAGAAGACA

GAGCGTGCTGAACCTGATGACCCACAGCGTGAACCAGGGCCAGAACATCC

ACAGAAAGACCACCGCCAGCACCAGAAAGGTGAGCCTGGCCCCCCAGGCC

AACCTGACCGAGCTGGACATCTACAGCAGAAGACTGAGCCAGGAGACCGG

CCTGGAGATCAGCGAGGAGATCAACGAGGAGGACCTGAAGGAGTGCTTCT

TCGACGACATGGAGAGCATCCCCGCCGTGACCACCTGGAACACCTACCTG

AGATACATCACCGTGCACAAGAGCCTGATCTTCGTGCTGATCTGGTGCCT

GGTGATCTTCCTGGCCGAGGTGGCCGCCAGCCTGGTGGTGCTGTGGCTGC

TGGGCAACACCCCCCTGCAGGACAAGGGCAACAGCACCCACAGCAGAAAC

AACAGCTACGCCGTGATCATCACCAGCACCAGCAGCTACTACGTGTTCTA

CATCTACGTGGGCGTGGCCGACACCCTGCTGGCCATGGGCTTCTTCAGAG

GCCTGCCCCTGGTGCACACCCTGATCACCGTGAGCAAGATCCTGCACCAC

AAGATGCTGCACAGCGTGCTGCAGGCCCCCATGAGCACCCTGAACACCCT

GAAGGCCGGCGGCATCCTGAACAGATTCAGCAAGGACATCGCCATCCTGG

ACGACCTGCTGCCCCTGACCATCTTCGACTTCATCCAGCTGCTGCTGATC

GTGATCGGCGCCATCGCCGTGGTGGCCGTGCTGCAGCCCTACATCTTCGT

GGCCACCGTGCCCGTGATCGTGGCCTTCATCATGCTGAGAGCCTACTTCC

TGCAGACCAGCCAGCAGCTGAAGCAGCTGGAGAGCGAGGGCAGGAGCCCC

ATCTTCACCCACCTGGTGACCAGCCTGAAGGGCCTGTGGACCCTGAGAGC

CTTCGGCAGACAGCCCTACTTCGAGACCCTGTTCCACAAGGCCCTGAACC

TGCACACCGCCAACTGGTTCCTGTACCTGAGCACCCTGAGATGGTTCCAG

-continued

ATGAGAATCGAGATGATCTTCGTGATCTTCTTCATCGCCGTGACCTTCAT
CAGCATCCTGACCACCGGCGAGGGCGAGGGCAGAGTGGGCATCATCCTGA
CCCTGGCCATGAACATCATGAGCACCCTGCAGTGGGCCGTGAACAGCAGC
ATCGACGTGGACAGCCTGATGAGAAGCGTGAGCAGAGTGTTCAAGTTCAT
CGACATGCCCACCGAGGGCAAGCCCACCAAGAGCACCAAGCCCTACAAGA
ACGGCCAGCTGAGCAAGGTGATGATCATCGAGAACAGCCACGTGAAGAAG
GACGACATCTGGCCCAGCGGCGGCCAGATGACCGTGAAGGACCTGACCGC
CAAGTACACCGAGGGCGGCAACGCCATCCTGGAGAACATCAGCTTCAGCA
TCAGCCCCGGCCAGAGAGTGGGCCTGCTGGGCAGAACCGGCAGCGGCAAG
AGCACCCTGCTGAGCGCCTTCCTGAGACTGCTGAACACCGAGGGCGAGAT
CCAGATCGACGGCGTGAGCTGGGACAGCATCACCCTGCAGCAGTGGAGAA
AGGCCTTCGGCGTGATCCCCCAGAAGGTGTTCATCTTCAGCGGCACCTTC
AGAAAGAACCTGGACCCCTACGAGCAGTGGAGCGACCAGGAGATCTGGAA
GGTGGCCGACGAGGTGGGCCTGAGAAGCGTGATCGAGCAGTTCCCCGGCA
AGCTGGACTTCGTGCTGGTGGACGGCGGCTGCGTGCTGAGCCACGGCCAC
AAGCAGCTGATGTGCCTGGCCAGAAGCGTGCTGAGCAAGGCCAAGATCCT
GCTGCTGGACGAGCCCAGCGCCCACCTGGACCCCGTGACCTACCAGATCA
TCAGAAGAACCCTGAAGCAGGCCTTCGCCGACTGCACCGTGATCCTGTGC
GAGCACAGAATCGAGGCCATGCTGGAGTGCCAGCAGTTCCTGGTGATCGA
GGAGAACAAGGTGAGACAGTACGACAGCATCCAGAAGCTGCTGAACGAGA
GAAGCCTGTTCAGACAGGCCATCAGCCCCAGCGACAGAGTGAAGCTGTTC
CCCCACAGAAACAGCAGCAAGTGCAAGAGCAAGCCCCAGATCGCCGCCCT
GAAGGAGGAGACCGAGGAGGAGGTGCAGGACACCAGACTGTGA (SEQ ID NO: 38)
ATGCAGAGGTCACCTCTGGAAAAGGCTAGCGTGGTCAGCAAGCTATTTTT
TTCCTGGACCCGCCCGATACTCAGGAAGGGCTACCGACAGCGGCTGGAGC
TGAGTGACATTTATCAGATTCCCTCCGTCGATTCCGCTGACAACCTGTCT
GAGAAACTGGAGCGGGAATGGGATAGGGAACTGGCGTCCAAAAAAAACCC
CAAACTCATCAATGCACTCCGCAGATGCTTCTTCTGGCGGTTTATGTTTT
ATGGCATATTCCTGTATCTGGGGGAGGTGACGAAAGCCGTGCAGCCGCTG
CTGCTTGGTCGCATTATCGCGTCATACGATCCAGATAACAAGGAGGAAAG
AAGTATCGCTATCTATCTCGGGATAGGGCTGTGCCTGCTCTTCATTGTGC
GGACTCTTCTCTTGCACCCCGCCATTTTCGGTCTGCATCATATAGGTATG
CAGATGAGAATTGCGATGTTCTCATTGATTTACAAAAAAACGCTTAAGCT
AAGTTCAAGGGTGCTAGATAAGATATCGATCGGCCAGCTGGTGTCTCTGC
TTAGCAACAACCTCAATAAATTCGACGAAGGCCTTGCACTGGCCCACTTC
GTGTGGATCGCCCCTCTGCAGGTGGCTCTGCTGATGGGGTTAATATGGGA
GCTGTTGCAGGCCTCCGCTTTTTGTGGCCTGGGGTTTCTCATCGTGTTGG
CCTTGTTTCAGGCAGGGCTGGGACGTATGATGATGAAATATAGGGATCAG
AGGGCTGGCAAAATCTCTGAGCGCCTGGTTATTACGAGTGAAATGATTGA
GAACATCCAGTCAGTGAAGGCCTATTGCTGGGAGGAGGCCATGGAAAAAA
TGATTGAGAACCTACGCCAGACTGAGCTGAAGTTAACCAGAAAAGCCGCC
TATGTGCGCTACTTTAACAGTAGCGCATTTTTCTTCTCCGGTTTTTTCGT
GGTGTTTCTTAGTGTGTTGCCGTATGCCTTAATCAAGGGAATAATACTCC
GGAAGATTTTCACTACCATCAGCTTCTGTATCGTGTTGCGGATGGCCGTC
ACCCGGCAGTTTCCCTGGGCAGTACAGACTTGGTACGATTCTCTCGGAGC
AATTAACAAAATCCAAGACTTTCTACAAAAGCAGGAGTACAAGACCCTGG
AGTACAATCTGACCACCACAGAAGTCGTAATGGAGAATGTAACTGCCTTC
TGGGAAGAGGGCTTTGGCGAACTCTTTGAAAAGGCCAAGCAGAACAATAA
CAACCGGAAGACCTCCAACGGGGACGACAGCTTATTTTTCAGCAATTTTT
CTTTGCTCGGGACCCCTGTACTGAAAGATATTAACTTTAAGATCGAGCGC
GGACAACTCCTGGCTGTCGCCGGCAGCACTGGAGCTGGAAAAACATCACT
GCTTATGGTGATAATGGGAGAACTCGAACCAAGCGAGGGAAAAATAAAGC
ACTCTGGACGGATTAGTTTTTGCTCCCAGTTCTCGTGGATAATGCCTGGC
ACCATTAAGGAGAATATCATCTTTGGAGTGAGTTACGACGAATACCGGTA
CCGGTCCGTTATCAAGGCTTGTCAACTCGAGGAGGACATTTCTAAATTCG
CCGAAAAAGATAATATAGTGCTGGGCGAAGGAGGCATTACACTGAGCGGG
GGTCAGAGAGCTCGAATTAGCCTCGCCCGAGCAGTCTATAAAGACGCCGA
TCTTTACCTGCTGGATTCCCCTTTTGGGTATTTGGATGTTCTGACAGAGA
AGGAAATCTTTGAATCATGTGTCTGTAAACTGATGGCCAATAAGACTAGG
ATTCTAGTGACTTCGAAAATGGAGCACCTGAAAAAAGCGGACAAAATTCT
GATACTCCATGAAGGGTCTTCCTACTTCTACGGCACCTTCTCAGAGTTGC
AGAACTTACAACCTGATTTTTCATCTAAGCTTATGGGGTGCGACTCGTTT
GACCAGTTCTCCGCTGAAAGACGAAACAGCATCTTAACGGAAACTCTTCA
CAGGTTCTCATTAGAGGGAGATGCGCCGGTGTCCTGGACAGAGACAAAAA
AACAGTCTTTCAAACAGACAGGAGAGTTTGGCGAGAAGAGAAAAAACTCA
ATCCTCAATCCCATCAATTCTATTAGAAAGTTTAGCATCGTCCAAAAAAC
ACCATTGCAGATGAATGGGATTGAGGAGGACAGTGATGAGCCTTTGGAAC
GAAGACTGTCCCTGGTACCCGATAGCGAACAGGGTGAGGCCATCCTTCCT
AGGATCTCGGTCATAAGTACAGGGCCCACACTGCAGGCCAGGCGACGTCA
AAGTGTCCTCAATCTTATGACGCACAGTGTGAATCAGGGGCAGAACATCC
ATCGTAAGACGACAGCTTCAACTCGAAAGGTCAGTCTAGCTCCACAAGCC
AATCTTACAGAGCTGGACATTTATTCCCGCCGCCTCAGTCAGGAGACCGG
ATTGGAAATATCAGAGGAAATTAATGAAGAGGATCTGAAGGAATGCTTCT
TTGATGACATGGAATCGATCCCCGCTGTTACTACCTGGAACACATATCTG
AGATATATTACCGTCCATAAGAGCTTAATCTTTGTACTGATATGGTGCTT
GGTGATTTTCCTGGCAGAGGTTGCGGCGAGTTTGGTCGTGCTATGGCTCC
TTGGAAACACTCCCCTGCAGGATAAGGGGAACTCCACTCATAGCAGGAAT
AACAGCTATGCCGTGATCATCACCTCTACCTCCTCTTATTACGTGTTTTA
CATATACGTCGGTGTTGCGGATACCCTGTTGGCAATGGGGTTCTTTAGAG
GACTACCCCTAGTTCACACCCTGATCACCGTTTCGAAGATCTTGCACCAC

-continued

AAGATGCTTCATAGCGTTCTCCAAGCTCCTATGAGCACCCTTAATACACT
GAAAGCAGGAGGTATCCTTAACCGCTTTTCCAAAGACATCGCTATACTCG
ACGATTTGCTCCCATTGACCATCTTCGACTTCATTCAGCTGCTCCTCATT
GTGATCGGCGCCATTGCCGTGGTCGCAGTGTTACAGCCATATATTTTCGT
AGCCACCGTGCCCGTCATCGTGGCATTTATCATGCTGCGCGCATATTTCT
TACAGACATCTCAGCAACTGAAGCAGCTGGAATCTGAGGGCAGATCTCCT
ATTTTTACACACCTGGTTACCAGCCTGAAGGGCCTGTGGACCCTGCGTGC
TTTCGGTCGCCAACCCTACTTTGAGACTCTCTTCCATAAGGCTCTGAATT
TACATACTGCCAATTGGTTCCTATACCTTAGTACCCTTCGGTGGTTCCAG
ATGCGGATAGAAATGATCTTCGTGATTTTCTTCATCGCAGTCACTTTCAT
CTCTATTTTGACGACCGGTGAGGGCGAGGGCAGGGTGGGCATCATTCTGA
CTTTGGCCATGAACATTATGTCAACACTCCAGTGGGCCGTTAATTCAAGC
ATTGATGTGGATTCCTTGATGCGTTCCGTCAGCAGGGTATTTAAATTCAT
AGACATGCCCACCGAGGGCAAGCCAACAAAATCTACCAAGCCATACAAAA
ATGGCCAACTAAGCAAGGTCATGATTATCGAGAATTCTCATGTGAAAAAG
GACGACATTTGGCCTTCCGGGGGTCAAATGACTGTAAAGGACCTGACGGC
TAAATACACTGAGGGCGGTAATGCTATCTTGGAGAACATCTCTTTCAGCA
TCTCCCCTGGCCAGAGAGTGGGACTGCTCGGGCGGACAGGCTCCGGAAAG
TCTACGCTCCTTTCAGCATTCCTTAGACTTCTGAACACCGAAGGTGAGAT
TCAGATTGACGGGGTCTCTTGGGACTCCATCACACTTCAGCAATGGAGGA
AGGCATTCGGTGTAATCCCCCAAAAGGTTTTTATCTTCTCCGGAACATTT
CGTAAGAATCTGGACCCGTACGAGCAGTGGTCAGATCAGGAGATCTGGAA
AGTAGCAGACGAGGTCGGGCTACGGAGCGTTATTGAACAGTTTCCTGGCA
AACTGGACTTCGTTTTGGTGGACGGAGGCTGTGTGCTGAGTCACGGCCAT
AAACAACTGATGTGCTTAGCTAGGTCTGTTCTCAGCAAGGCAAAGATTTT
ACTGCTGGATGAACCAAGCGCCCACCTTGATCCAGTGACATATCAAATCA
TCAGAAGAACTCTTAAACAGGCGTTCGCCGACTGCACAGTGATCCTGTGT
GAGCACAGAATAGAAGCCATGCTGGAATGTCAACAGTTTCTCGTGATTGA
GGAGAACAAGGTGCGCCAGTACGATAGCATCCAGAAGTTACTCAATGAAA
GGTCACTCTTCAGGCAGGCCATCTCACCCAGCGACCGCGTTAAGCTGTTT
CCACACCGAAACAGTTCCAAGTGCAAAAGTAAGCCACAGATTGCTGCACT
GAAGGAAGAGACAGAAGAAGAAGTTCAGGACACTCGGCTCTGA (SEQ ID NO: 39)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCAGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT
ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATATCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCAATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG

-continued

GCTGGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACTCACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA

-continued (SEQ ID NO: 40)

ATGCAACGGAGTCCTCTGGAAAAAGCCTCTGTCGTATCTAAGCTTTTCTT
CAGTTGGACACGCCCGATTTTGAGAAAGGGTTATCGGCAACGCTTGGAAC
TTAGTGACATCTACCAAATTCCAAGTGTAGACTCAGCCGATAACTTGAGC
GAAAAGCTCGAACGAGAGTGGGATCGAGAACTGGCTAGCAAAAAAAATCC
CAAACTCATAAATGCCCTGCGACGCTGTTTCTTTTGGCGATTTATGTTTT
ACGGTATTTTCCTTTATTTGGGTGAGGTCACGAAGGCTGTACAGCCACTG
CTGCTGGGTCGCATCATTGCCTCTTACGACCCTGACAACAAAGAGGAGCG
GTCAATAGCTATCTACCTTGGTATAGGACTTTGCTTGCTCTTCATAGTCC
GCACGTTGCTTCTCCACCCTGCTATATTTGGTCTCCATCACATTGGGATG
CAAATGCGGATCGCGATGTTCAGTCTTATATATAAAAAGACTCTTAAACT
TTCCAGCCGGGTTCTGGATAAGATCTCTATTGGTCAACTGGTATCTCTTT
TGTCTAACAACCTGAATAAGTTCGACGAGGGCCTTGCATTGGCCCATTTT
GTATGGATTGCCCCTTTGCAAGTCGCCCTCCTGATGGGATTGATCTGGGA
ACTCCTGCAAGCTAGTGCTTTTTGCGGATTGGGATTCCTCATAGTCCTTG
CGCTCTTTCAGGCGGGACTTGGACGCATGATGATGAAGTATCGCGACCAA
CGAGCTGGCAAGATCAGTGAACGGCTTGTAATAACCAGTGAAATGATAGA
GAACATCCAGAGCGTAAAAGCTTACTGTTGGGAAGAAGCGATGGAAAAGA
TGATTGAGAACCTTCGCCAGACAGAACTTAAACTTACACGAAAGGCCGCT
TATGTCCGGTACTTCAACTCTTCAGCATTTTTTTTAGTGGCTTCTTTGT
AGTGTTCCTGTCCGTCCTTCCGTATGCACTTATCAAGGGTATAATACTTA
GGAAAATCTTCACAACAATCAGTTTTTGCATAGTCCTTCGCATGGCAGTA
ACTCGCCAATTTCCCTGGGCAGTTCAGACGTGGTACGACTCACTTGGCGC
AATTAACAAAATTCAAGATTTCCTCCAAAAGCAAGAGTATAAAACCTTGG
AATACAACCTTACCACCACAGAAGTTGTAATGGAAAATGTCACAGCCTTC
TGGGAGGAAGGTTTCGGCGAACTTTTTGAGAAGGCGAAGCAAAATAACAA
TAATCGGAAAACATCAAACGGTGACGATTCACTGTTCTTTTCTAACTTTA
GCCTTCTTGGGACGCCCGTCCTGAAGGACATAAACTTTAAGATTGAACGG
GGTCAACTTCTCGCGGTCGCAGGGAGTACTGGAGCGGGGAAAACGAGCCT
GCTGATGGTGATAATGGGGGAGTTGGAGCCCTCAGAAGGCAAGATCAAGC
ATAGTGGTAGAATTAGCTTCTGCAGTCAATTTAGTTGGATTATGCCGGGC
ACGATCAAAGAAAATATAATCTTTGGGGTATCCTACGATGAATACAGGTA
CCGATCAGTGATAAAAGCGTGCCAGCTTGAAGAAGACATTTCAAAGTTTG
CTGAGAAGGATAATATCGTACTTGGAGAAGGAGGTATCACCCTGTCTGGG
GTCAACGAGCGAGGATCTCCCTGGCACGCGCCCGTCTACAAGGACGCGGAC
CTCTATCTGTTGGATTCACCGTTCGGATATTTGGACGTGCTTACGGAGAA
AGAAATATTTGAGAGCTGTGTTTGCAAGCTCATGGCAAATAAAACCAGAA
TATTGGTTACAAGCAAGATGGAGCATCTTAAGAAAGCAGATAAAATCCTG
ATATTGCACGAGGGCTCTTCATACTTCTACGGGACGTTTTCTGAGTTGCA
GAACCTCCAGCCGGATTTCAGCTCTAAGCTGATGGGCTGTGATTCCTTTG
ATCAGTTTAGTGCGGAAAGACGAAACAGTATACTCACCGAAACACTGCAC

-continued

AGGTTCTCTCTGGAGGGCGACGCCCCGGTTTCCTGGACAGAGACGAAGAA

GCAGTCCTTCAAACAGACAGGCGAGTTTGGGGAGAAAAGGAAAAATAGCA

TACTCAACCCGATTAACAGCATTCGCAAGTTCAGTATAGTACAAAAGACC

CCGTTGCAGATGAACGGTATAGAGGAAGATTCTGATGAGCCACTGGAAAG

ACGGCTTTCTCTCGTTCCGGACAGTGAACAGGGAGAGGCAATACTGCCTC

GGATCAGCGTTATCTCTACAGGACCTACTTTGCAAGCTCGGCGCCGACAG

TCAGTCTTGAATCTTATGACTCATAGTGTTAATCAAGGCCAGAATATCCA

TCGCAAGACCACCGCAAGTACAAGGAAAGTGAGCTTGGCACCTCAAGCAA

ACCTTACTGAACTTGATATCTACTCACGGCGACTTTCACAGGAGACCGGA

CTTGAAATTAGTGAAGAAATTAACGAGGAGGACCTCAAGGAGTGCTTCTT

CGATGACATGGAATCAATCCCCGCAGTCACAACCTGGAACACTTATCTGA

GGTATATAACAGTTCACAAGAGCCTCATTTTTGTACTTATTTGGTGTTTG

GTAATTTTCCTGGCGGAGGTTGCTGCTTCTTTGGTCGTCCTTTGGCTCCT

CGGGAATACACCGCTCCAAGACAAAGGCAACTCTACCCATAGTAGGAACA

ATTCATATGCAGTGATTATAACCAGTACATCATCTTATTACGTTTTCTAT

ATTTATGTCGGGGTAGCTGACACGCTGTTGGCGATGGGCTTCTTTAGGGG

CCTCCCCTTGGTACACACCCTTATCACGGTGAGTAAAATCCTGCATCACA

AAATGCTTCATTCTGTACTCCAAGCGCCGATGAGTACGCTTAATACGCTG

AAAGCAGGAGGGATACTGAATCGGTTCAGCAAGGACATCGCCATTCTGGA

TGACCTGCTTCCATTGACAATATTTGATTTCATTCAGCTCCTTCTCATAG

TTATTGGAGCCATAGCGGTGGTGGCTGTGCTTCAGCCTTATATATTCGTT

GCCACAGTTCCCGTTATAGTGGCATTTATAATGCTCAGGGCCTACTTTCT

CCAGACTTCCCAGCAGTTGAAGCAACTCGAATCAGAAGGAAGGTCACCTA

TTTTCACACATCTTGTGACTTCCTTGAAGGGCTTGTGGACGCTGCGGGCC

TTCGGAAGACAACCATATTTTGAAACTCTCTTCCACAAAGCTTTGAATCT

TCATACTGCGAACTGGTTCCTGTATTTGAGTACTTTGCGCTGGTTCCAGA

TGAGGATAGAAATGATATTCGTTATCTTCTTTATCGCGGTTACGTTCATA

-continued

AGTATCCTCACTACGGGGGAGGGTGAGGGTAGAGTGGGCATAATACTGAC

CCTCGCCATGAACATTATGTCCACCCTGCAGTGGGCGGTAAACAGCAGCA

TAGATGTGGATTCTTTGATGCGCAGTGTGAGCAGGGTTTTTAAGTTTATC

GATATGCCGACGGAAGGAAAGCCCACTAAAAGCACGAAACCCTATAAAAA

TGGACAGCTTAGCAAAGTAATGATAATCGAGAATAGCCATGTGAAAAAGG

ATGACATATGGCCTTCCGGAGGCCAAATGACTGTTAAAGATCTGACCGCT

AAATATACCGAGGGCGGCAACGCAATACTCGAAAACATAAGCTTTTCCAT

AAGCCCCGGCCAACGCGTGGGTCTTCTGGGGAGGACTGGCTCCGGAAAAT

CAACGTTGCTTAGCGCGTTTTTGCGGCTCCTTAACACTGAAGGTGAGATC

CAAATAGATGGCGTTAGTTGGGACTCTATAACACTGCAACAATGGCGGAA

AGCTTTCGGCGTCATACCTCAGAAGGTGTTCATCTTTAGCGGAACGTTCA

GGAAGAACTTGGATCCCTACGAACAATGGAGTGATCAAGAAATATGGAAA

GTGGCAGATGAGGTAGGCTTGCGCAGTGTCATTGAACAATTCCCAGGGAA

ACTCGACTTTGTACTGGTGGACGGCGGTTGCGTCTTGTCACACGGGCACA

AACAGTTGATGTGTTTGGCCCGCAGTGTTTTGTCTAAGGCGAAGATTCTG

TTGCTCGACGAACCGAGTGCTCATCTTGATCCCGTCACCTACCAAATCAT

CAGAAGGACGTTGAAGCAAGCTTTCGCCGACTGCACTGTAATCCTTTGTG

AGCATAGGATCGAAGCAATGCTCGAGTGCCAACAGTTCTTGGTTATAGAG

GAGAATAAGGTTCGGCAATACGACTCAATACAGAAACTGCTTAATGAGCG

GTCACTCTTTCGACAAGCTATCTCTCCTAGTGACAGGGTAAAGCTTTTTC

CTCATCGGAATTCCAGCAAGTGTAAGAGTAAACCACAGATCGCCGCCCTT

AAAGAGGAGACCGAAGAAGAGGTGCAGGATACGAGACTTTAG

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A pharmaceutical composition for treating cystic fibrosis, comprising a codon optimized mRNA encoding a Cystic Fibrosis Transmembrane Conductance Regulator (CFTR) protein and wherein the codon optimized CFTR mRNA comprises a polynucleotide sequence at least 85% identical to SEQ ID NO: 1.

2. The pharmaceutical composition of claim 1, wherein the codon optimized CFTR mRNA encoding the CFTR protein is encapsulated within a nanoparticle.

3. The pharmaceutical composition of claim 2, wherein the nanoparticle is a liposome.

4. The pharmaceutical composition of claim 3, wherein the liposome comprises one or more cationic lipids, one or more non-cationic lipids, one or more cholesterol-based lipids and one or more PEG-modified lipids.

5. The pharmaceutical composition of claim 3, wherein the liposome comprises no more than three distinct lipid components.

6. A method of producing codon optimized mRNA encoding a Cystic Fibrosis Transmembrane Conductance Regulator (CFTR) protein, comprising in vitro synthesizing codon optimized CFTR mRNA using a SP6 RNA polymerase, wherein at least 80% of the synthesized codon optimized CFTR mRNA molecules are full-length and wherein at least 100 mg of codon optimized mRNA is synthesized at a single batch.

7. The method of claim 6, wherein the in vitro synthesis of codon optimized CFTR mRNA results in a secondary polynucleotide species that constitutes less than 10%, 5%, 4%, 3%, 2%, 1%, 0.5%, 0.4%, 0.3%, 0.2% or 0.1% of the total mRNA synthesized.

8. The method of claim 6, wherein at least 85%, 90%, 95%, 96%, 97%, 98%, or 99% of the synthesized codon optimized CFTR mRNA molecules are full-length.

9. The method of claim 6, wherein at least 200 mg, 300 mg, 400 mg, 500 mg, 600 mg, 700 mg, 800 mg, 900 mg, 1 g, 5 g, 10 g, 25 g, 50 g, 75 g, 100 g, 150 g, 200 g, 250 g, 500 g, 750 g, 1 kg, 5 kg, 10 kg, 50 kg, 100 kg, 1000 kg, or more of codon optimized CFTR mRNA is synthesized at a single batch.

10. The method of claim 6, wherein the codon optimized CFTR mRNA comprises a polynucleotide sequence at least 85% identical to SEQ ID NO: 1.

11. The method of claim 6, wherein the method further comprises a step of capping and/or tailing of the synthesized codon optimized CFTR mRNA.

12. A pharmaceutical composition for treating cystic fibrosis, comprising an mRNA encoding a Cystic Fibrosis Transmembrane Conductance Regulator (CFTR) protein and wherein the mRNA encoding the CFTR protein comprises a polynucleotide sequence at least 85% identical to any one of SEQ ID NO: 21-30, 33, 34, 38-40.

13. The pharmaceutical composition of claim 12, wherein the mRNA is encoded in a nanoparticle, and wherein the nanoparticle is a liposome.

14. The pharmaceutical composition of claim 13, wherein the liposome comprises one or more cationic lipids, one or more non-cationic lipids, one or more cholesterol-based lipids and one or more PEG-modified lipids.

* * * * *